US009409959B2

(12) United States Patent
Sutherland et al.

(10) Patent No.: US 9,409,959 B2
(45) Date of Patent: Aug. 9, 2016

(54) SILK PROTEINS

(75) Inventors: Tara D. Sutherland, Watson (AU);
Victoria S. Haritos, O'Connor (AU);
Holly Trueman, Frenchs Forest (AU);
Alagacone Sriskantha, Nicholls (AU);
Sarah Weisman, Griffith (AU); Peter M. Campbell, Cook (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 1736 days.

(21) Appl. No.: 12/089,045

(22) PCT Filed: Oct. 4, 2006

(86) PCT No.: PCT/AU2006/001453
§ 371 (c)(1),
(2), (4) Date: Jun. 27, 2008

(87) PCT Pub. No.: WO2007/038837
PCT Pub. Date: Apr. 12, 2007

(65) Prior Publication Data
US 2010/0100975 A1    Apr. 22, 2010

Related U.S. Application Data

(60) Provisional application No. 60/723,766, filed on Oct. 5, 2005.

(51) Int. Cl.
*C12N 5/00* (2006.01)
*C07K 14/435* (2006.01)

(52) U.S. Cl.
CPC ............................... *C07K 14/43563* (2013.01)

(58) Field of Classification Search
None
See application file for complete search history.

(56) References Cited

U.S. PATENT DOCUMENTS

| | | | |
|---|---|---|---|
| 4,515,737 A | 5/1985 | Karino et al. | |
| 4,943,674 A | 7/1990 | Houck et al. | |
| 5,232,611 A | 8/1993 | Ohashi et al. | |
| 5,856,451 A | 1/1999 | Olsen et al. | |
| 5,939,288 A | 8/1999 | Thornburg | |
| 5,981,718 A | 11/1999 | Olsen et al. | |
| 5,989,894 A | 11/1999 | Lewis et al. | |
| 6,013,250 A | 1/2000 | Cannell et al. | |
| 6,129,770 A | 10/2000 | Deutz et al. | |
| 6,139,851 A | 10/2000 | Omura et al. | |
| 6,175,053 B1 | 1/2001 | Tsubouchi | |
| 6,268,169 B1 | 7/2001 | Fahnestock | |
| 6,280,747 B1 | 8/2001 | Philippe et al. | |
| 6,284,246 B1 | 9/2001 | Weisgerber et al. | |
| 6,303,752 B1 | 10/2001 | Olsen et al. | |
| 6,358,501 B1 | 3/2002 | Dietz et al. | |
| 6,398,821 B1 | 6/2002 | Dias et al. | |
| 6,416,558 B1 | 7/2002 | Ona et al. | |
| 2003/0155670 A1 | 8/2003 | O'brien | |
| 2003/0192077 A1 | 10/2003 | Yang | |
| 2004/0005363 A1 | 1/2004 | Tsukada et al. | |
| 2004/0132978 A1 | 7/2004 | Fahnestock et al. | |
| 2004/0170590 A1 | 9/2004 | Fahnestock et al. | |
| 2004/0170827 A1 | 9/2004 | Crighton | |
| 2004/0199241 A1 | 10/2004 | Gravett et al. | |
| 2004/0210956 A1 | 10/2004 | Roth et al. | |
| 2004/0219630 A1 | 11/2004 | Tsubouchi | |
| 2004/0266992 A1 | 12/2004 | Migliaresi et al. | |
| 2005/0010035 A1 | 1/2005 | Lewis et al. | |
| 2005/0019297 A1 | 1/2005 | Philippe et al. | |
| 2005/0054830 A1 | 3/2005 | Islam et al. | |
| 2005/0055051 A1 | 3/2005 | Grafton | |
| 2005/0089552 A1 | 4/2005 | Altman et al. | |
| 2005/0161058 A1 | 7/2005 | Yerushalmy | |
| 2005/0175825 A1 | 8/2005 | Hansen et al. | |
| 2005/0268443 A1 | 12/2005 | Ramkumar | |

FOREIGN PATENT DOCUMENTS

| | | |
|---|---|---|
| EP | 0239400 | 8/1994 |
| WO | WO03020916 | 3/2003 |
| WO | WO2004016651 | 2/2004 |
| WO | WO2005017004 | 2/2005 |
| WO | WO2005045122 | 5/2005 |

OTHER PUBLICATIONS

Ngo, J. et al., "Computational Complexity, Protein Structure Prediction, and the Levinthal Paradox", in The Protein Folding Problem and Tertiary Structure Prediction, Merz et al. (eds.), Birkhauser Boston: Boston, MA, pp. 433 and 492-495, 1994.*
Rudinger, in Peptide Hormones, Parsons (ed.), University Park Press: Baltimore, MD, pp. 1-7, 1976.*
Kennell, D., Progr. Nucleic Acid Res. Mol. Biol. 11: 259-301, 1971.*
Silva-Zacarin, et al., Silk formation mechanisms in the larval salivary glands of Apis mellifera (Hymenoptera: Apidae), Journal of Biosciences, vol. 28, No. 6 / Dec. 2003, pp. 753-764.
XP002504559, Database Uniprot, Jul. 19, 2004, Database accession No. Q6F986.
XP002504560, Database Uniprot, Nov. 1, 1999, Database accession No. Q9W6J8.
XP002504561, Database Uniprot, Jul. 5, 2004, Database accession No. Q6PYY3.
XP002504562, Database Uniprot, Jun. 1, 2003, Database accession No. Q871k9.
XP002504563, Database Uniprot, Nov. 6, 2003, Database accession No. ADA15988.
XP002504564, Database EMBL, Feb. 14, 2005, Database accession No. DN048371.

(Continued)

*Primary Examiner* — Michael Burkhart
(74) *Attorney, Agent, or Firm* — Carol L. Francis; Bozicevic, Field & Francis LLP

(57) ABSTRACT

The present invention provides silk proteins, as well as nucleic acids encoding these proteins. The present invention also provides recombinant cells and/or organisms which synthesize silk proteins. Silk proteins of the invention can be used for a variety of purposes such as in the manufacture of personal care products, plastics, textiles, and biomedical products.

15 Claims, 22 Drawing Sheets

(56) References Cited

OTHER PUBLICATIONS

Figure 1:
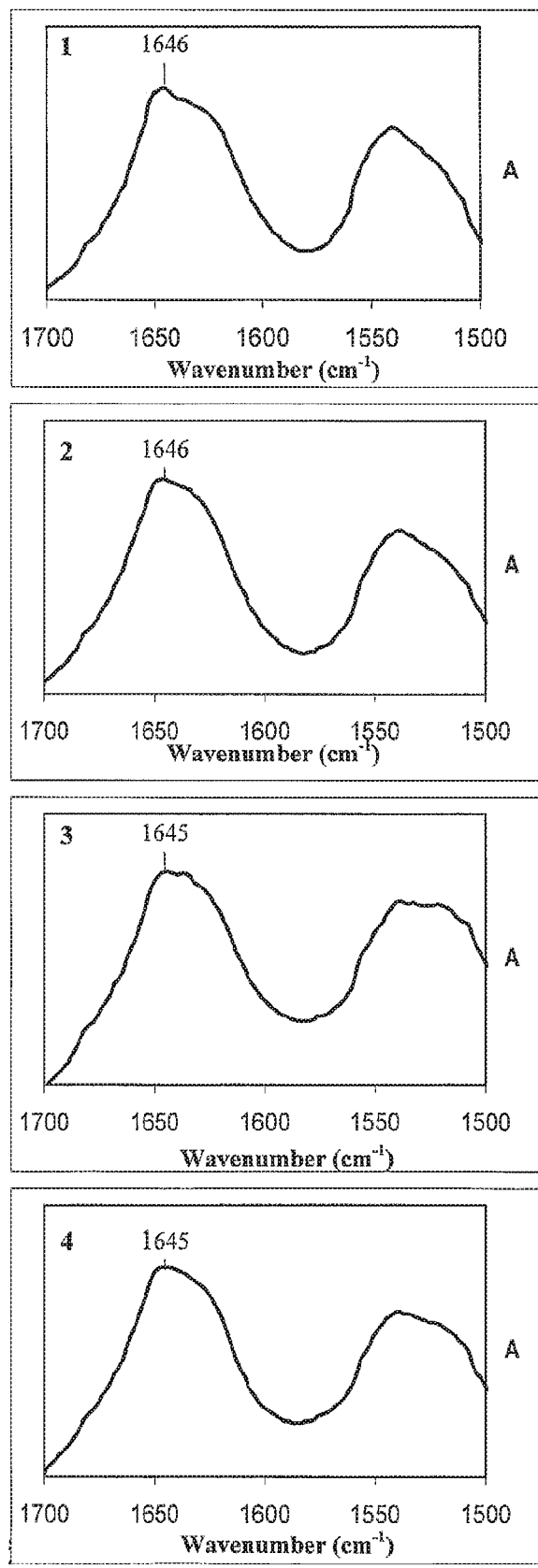
Figure 1:
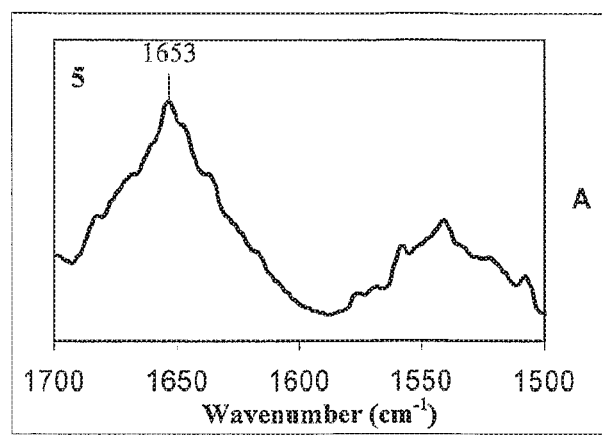

XP002504565, Database EMBL, Aug. 30, 2001, Database accession No. BI508270.
XP002504566, Database EMBL, Mar. 27, 2004, Database accession No. CK631883.
Yu, et al. (1994) "Conformation Transition of Silk Fibroin" Chemical Journal of Chinese Universities 17(2):323-325.
Atkins, E.D.T., A four-strand coiled-coil model for some insect fibrous proteins, J.Mol. Biol. (1967), 24, 139-141.
Dicko, et al.,Conformational Polymorphism, stability and aggregation in spider dragline silks proteins, International Journal of Biological Macromolecules, 36 (2005), 215-224.
Green, et al,.The influence of organic solvents and enzymatic modification on the secondary structure of fetuin, The journal of biological chemistry, vol. 238, No. 11, Nov. 1963.
Van Beek,et al., The molecular structure of spider dragline silk:Folding and orientation of the protein backbone, 10266-102871, PNAS, Aug. 6, 2002,vol. 99, No. 16.
Wilson, et al., Confrontational transitions in model silk peptides, Biophysical journal, vol. 78, May 2000, 2690-2701.
Yu, et al., Conformation transition of silk fibroin, Dept. of Macromolecular Science, Fudan University, Shanghai, (1996), 17 (2), 323-5, Abstract.
Atkins, E.D.T., A four-strand coiled-coil model for some insect fibrous proteins, The Ashbury Department of Biophysics, England, Oct. 26, 1966.
Bendtsen, et al., Improved prediction of signal peptides: SignalP 3.0., J Mol Biol. Jul. 16, 2004;340(4):783-795.
Bini, et al., Mapping domain structures in silks from insects and spiders related to protein assembly, J Mol Biol. Jan. 2, 2004;335(1):27-40.
Craig, et al., Comparative architecture of silks, fibrous proteins and their encoding genes in insects and spiders, Comparative Biochemistry and Physiology Part B: Biochemistry and Molecular Biology, vol. 133, Issue 4, Dec. 2002, pp. 493-507.
Delorenzi, et al., An HMM model for coiled-coil domains and a comparison with PSSM-based predictions, Bioinformatics vol. 18 No. 4 2002, pp. 617-625.
Deng, et al., Antiparallel Four-Stranded Coiled Coil Specified by a 3-3-1 Hydrophobic Heptad Repeat, Structure, vol. 14, Issue 2, 247-255, Feb. 2, 2006.
Flower, et al., Studies on insect fibrous proteins: the larval silk of Apis, Bombus and Vespa (Hymenoptera: Aculeata), J R Microsc Soc. Feb. 1967;86(3):297-310.
Harayama, et al., Artificial evolution by DNA shuffling, Trends in Biotechnology, vol. 16, Issue 2, 76-82, Feb. 1, 1998.
Heimburg, et al., FTIR-Spectroscopy of multistranded coiled coil proteins, Biochemistry. Sep. 28, 1999;38(39):12727-12734.
Hepburn, et al., Extensometric properties of insect fibroins: the green lacewing cross-β, honeybee α-helical and greater waxmoth parallel-β conformations. Insect Biochemistry and Molecular Biology 9:69-77, (1979).
Lamunyon, Craig, Hindgut Changes Preceding Pupation and Related Cocoon Structure in Chrysoperla Comanche Banks (Neuroptera, Chrysopidae), Psyche vol. 95 (1988), Issue 3-4, pp. 203-209.
Lamunyon, et al., Use and Effect of an Anal Defensive Secretion in Larval Chrysopidae (Neuroptera), Annals of the Entomological Society of America, vol. 80, No. 6, Nov. 1987 , pp. 804-808(5).
Lucas, et al., Comparative studies of fibroins. I. The amino acid composition of various fibroins and its significance in relation to their crystal structure and taxonomy, J Mol Biol. Dec. 1960;2:339-349.
Lupas, et al., Predicting coiled coils from protein sequences, Science. May 24, 1991;252(5010):1162-1164.
Needleman, et al., A general method applicable to the search for similarities in the amino acid sequence of two proteins, J Mol Biol. Mar. 1970;48(3):443-453.
Quicke, et al., Cocoon silk chemistry of non-cyclostome Braconidae, with remarks on phylogenetic relationships within the Microgastrinae (Hymenoptera: Braconidae), Journal of Natural History, 1464-5262, vol. 38, Issue 17, 2004, pp. 2167-2181.
Reiser, et al., Enzymatic and nonenzymatic cross-linking of collagen and elastin, The FASEB Journal, vol. 6, 2439-2449, Copyright 1992 by The Federation of American Societies for Experimental Biology.
Rost, et al., Prediction of protein secondary structure at better than 70% accuracy, J Mol Biol. Jul. 20, 1993;232(2):584-599.
Rost, et al., The PredictProtein server, Nucleic Acids Res. Jul. 1, 2004;32(Web Server issue):W321-326.
Rudall, et al., Arthropod Silks: The Problem of Fibrous Proteins in Animal Tissues, Annual Review of Entomology, vol. 16: 73-96 (Volume publication date Jan. 1971).
Silva-Zacarin, et al., Silk formation mechanisms in the larval salivary glands of Apis mellifera (Hymenoptera: Apidae), Journal of Biosciences, vol. 28, No. 6 / Dec. 2003, pp. 753-764.
Spiegler, Paul E., The Origin and Nature of the Adhesive Substance in Larvae of the Genus *Chrysopa* (Neuroptera: Chrysopidae), Annals of the Entomological Society of America, vol. 55, No. 1, Jan. 1962 , pp. 69-77(9).
Yamada, et al., A novel asparagine-rich fibrous protein (Xenofibron) from the cocoons of the parasitic wasp *Cotesia* (=*Apanteles*) *glomerata*, Int J Wild Silkmoths Silk, vol. 9;No.;p. 61-66(2004).
Database EMBL "JGI_CABJ9548.fwd NIH_XGC_tropSkil Xenopus tropicalis cDNA clone IMAGE: 7874366 5', mRNA sequence." EBI Accession No. EM_EST: DT432295, dated Aug. 27, 2005.
Database EMBL "QL1 39 Bombus terrestris larval caste mRNA Bombus terrestris cDNA clone QL1 39, mRNA sequence." EBI Accession No. EM_EST: DN048371, dated Feb. 14, 2005.
Database Uniprot "SubName: Full=Mucin-associated surface protein (MASP), putative;" EBI Accession No. UNIPROT: Q4DU48, dated Sep. 13, 2005.
Database Uniprot "SubName: Full=Mucin-associated surface protein (MASP), putative;" EBI Accession No. UNIPROT: Q4DYV1, dated Sep. 13, 2005.
Kohn et al. (1997) "α-Helical Protein Assembly Motifs" J Biol Chem 272(5):2583-2586.
Lucas & Rudall (1968) "Extracellular Fibrous Proteins: The Silks" Elsevier Publ., New York, NY, USA, pp. 475-558.
Craig et al. (2002) "Comparative architecture of silks, fibrous proteins and their encoding genes in insects and spiders", Comparative Biochemistry and Physiology Part B 133 pp. 493-507.
Delorenzi & Speed (2002) "An HMM model for coiled-coil domains and a comparison with PSSM-based predictions" Bioinformatics, 18(4):617-625.
Berger, et al., "Predicting coiled coils by use of pairwise residue correlations", Proc. Natl. Acad. Sci.,1995, 92:8259-63.
Lupas, "Predicting coiled-coil regions in proteins", Current Opinion in Structural Biology, 1997, 7:388-393.
Sutherland, et al., "Invited Review the Coiled Coil Silk of Bees, Ants, and Hornets", Biopolymers, 97:446-54.
Wolf, et al., "MultiCoil: A program for predicting two- and three-stranded coiled coils", Protein Science, 1997, 6:1179-1189.

\* cited by examiner

```
                  1          11          21          31          41          51          61          71
XENOSPIRA2   MKIPAIFVTSLLVWGLAEGRVINHES---LKTSEDIQGGYSAGIVGDGSDALGSSIENAQKVA----------RAAENVGLNL
XENOSPIRA3   MQIPTFVAICLLTSGLIVHAGVEEFKS---SATEEVISKNLEVDLLKN-VDTSAKRRENGAPVLGKN----TLQSLEKIKTSA
XENOSPIRA4   MKIPSILAVSLLIWGLASGAREEVETRDKTKTSTVVKSEKVEVVAPAKDELKLTSEPIFGRRVGTGASEVASSSGEAIAI
XENOSPIRA1   MKIPVLLATCLYLCGFASAGLEGPGN----SLPELVKGSASATASTAVTARSGLRAGQVALAS----------QKDAVLQ 81          91         101         111         121         131         141         151
                          abcdefgabcdefgabcdefgabcdefgabcdefgabcdefgabcdefg        abcdef
XENOSPIRA2   ELGAGARAAS---VAAAAQAKNTEAAEAGANAALAAAIAKREEAIKASEIANQLLTNAAKAAEATVSATKR----AAQLTA
XENOSPIRA3   SVNAKAAAVK-ASALALAEAYLRASALSAAASAKAAAALKNAQQAQLNAQEKSLAAALKAQSEEEAASAR-----ANAATA
XENOSPIRA4   SIGAGQSAAESQALAASQSKTAANAAIGASELTNKVAALVAGATGAQARATAASSSAILKASLATEEAAEE----AEAAVA
XENOSPIRA1   AQA---------AASAASEARAAADLTAKLSQESASVQSQAAAKGKETEEAAVGQARAGLESVSMAASATSAAKEAST 161         171         181         191         201         211         221         231
             gabcdefgabcdefgabcdefgabcdefgabcdefgabcdefgabcdefgabcdefgabcdefgabcdefgabcdefgab
XENOSPIRA2   AAKEATRASAAAAEAATEAQVKANADSIITKRAATAEAQAAAEAQVKAAIARKSAANFLAKAQIAAAAESEATKLAAEAV
XENOSPIRA3   ATQSALERAQASSRLATVAQNVASDLQKRTSTKAAAAEAAATLRQLQDAERTKWSANAALEVSAAAAAAETKTTASSEAAN
XENOSPIRA4   DAKAAAEKAESLAKNLASASARAALSSERANELAQAESAAAAEAQAKTAAAAKAAEIALKVAEIAVKAEADAAAAVAAA
XENOSPIRA1   AAKAAAASALSTAVVQAKIAERAAKAEAVASDEAKAKAIAAANLAAEASVAAEAAIKAEKVAEEAITARAASAKAARAAAA 241         251         261         271         281         291         301         311
             cdefgabcdefgabcdefg        abcdefgabcdefgabcdefgabcdefgabcdefg
XENOSPIRA2   VALTNAEVAVNQARNAQAN------ASTQASMAVRVDSQAANAEAAAVAQAETLLVTAEAVAAAEAEVAN--KAATFAKQI
XENOSPIRA3   AAAKTAAAIASDADGAERS------ASTEAQSAAKIESVAAAEGSANSASEDSRAAQLEASTAARANVAA--AVGDGAIIG
XENOSPIRA4   KARAVADAAAARAAAVNAI------AKAEEEASAQAENAAGVLQAAASAAAESRAAAAAAATSEAAAEAGPLAGEMKPPH
XENOSPIRA1   ALASSKEAATASARNAAESEARNEVAVLIAEIDKKSREIDAASSLNARAAAKASSRNVETATCIGANINSSKQVVSIPVE 321         331         341         351         361
XENOSPIRA2   VNEKKIHVAKLE---------
XENOSPIRA3   LGEEAGAAAQLLAQAKALAEVSSKSENIEDKKF------
XENOSPIRA4   WKWERIPVKKEEWKTISTKEEWKTTNEEWEVK-------
XENOSPIRA1   IKKFSEPEVSTSWREDEEVTKEKKEHINLNDFDLKSNVF-----
```

Figure 5

```
              1        11        21        31        41        51        61        71
         abcdefgabcdefgabcdefgabcdefgabcdefgabcdefgabcdefgabcdefgabcdefgabcdefgabc
BBF1     AVASQKDATLQADASAAAAAARASADQSASLAQQSASLQSKAAARAKSAEESAAATAKAELQAESIAASASS
AmelF1   ALASQKDAVLQAQAAASAASEARAAADLTAKLSQESASVQSQAAAKGKETEEAAVGQARAGLESVSMAASATS
BAF1     TAEEQREALEMLTLSADKNAEARILADDTAVLVQGSAEAQSVAAAKTVAVEEESASLDAAAVEAEVAAATSKS
GAF1     TVEEQREALQLLTASAEKNAEARSLADDAAVLVQGAAEAQSVAAAKTVAVEQGSNSLDAAAAEAEAAAAASRV
BBF2         ARAAAAAATKQAKDTEAAEAGAAAAIAIAIAKREEAIKASELASKLLTAAAGSSEAAVSATVRAAQLTAAASA
AmelF2   ARAASVAAAAQAKNTEAAEAGANAALAAAIAKREEAIKASEIANQLLTNAAKAAEATVSATKRAAQLTAAAKE
BAF2     ANEAEILAEAQAATSAQAGAVANSAAERAIAAMEMADRTEYIAALVTTKAAKAAEATMAATARATAAASASKI
GAF2     GNSAESLARAQASSSASAGAKANALIKQSIAAIEITEKAEYLASIVATKAAKAAEATAAATARATAVAEAAKV
BBF3     SAKVKASALALAEAFLRASAAFAAASAKAAAAVKEATQAQLLAQEKALIALKTQSEQQAASARADAAAAAAVS
AmelF3   AAVVKASALALAEAYLRASALSAAASAKAAAALKNAQQAQLNAQEKSLAALKAQSEEEAASARANAATAATQS
BAF3     LAMIKKIAMARSSAYVQAAWASAQASADALASARVAQASQEEAAEAKGRAASEALSRAIEASSRADAAAAATLD
GAF3     LAIIKKIVALLISAYVRAAEAAARASAEALATVRAAEQAQKIAEAKGRAAAAEALSELVEASQKADAAAAGTTD
BBF4     AAEAQAAAAAQAKSAAAAAANAGESSNSAAALVAAAAAAQGKAAAAAAAATKASLEAADAAEEAESAVALARA
AmelF4   AAESQALAASQSKTAANAAIGASELTNKVAALVAGATGAQARATAASSSALKASLATEEAAEEAEAAVADAKA
BAF4     AAEAQAAAAGQAEVAAKSCELADKTTAKAVAMVEAAAEAEIEVANQEVAAVKLSTWAAKAARIVEEDSAAVRA
GAF4     AAEAQAAAAGQAAIAAKSCALAAKSTAQAVALVEKVARAEVDLAESARKATRLSAEAAKAAAEVEKDLVGLRG 81        91       101       111       121       131       141
         defgabcdefgabcdefgabcdefgabcdefgabcdefgabcdef  gabcdefgabcdefgabcdefgabcd
BBF1     NAREAAASAKASASAMSSAAVQAKLAEKTAKNQALASEEAKLKAA~~AAASAAAASAAAEAALKAERIAEEA
AmelF1   AAKEASTAAKAAASALSTAVVQAKIAERAAKAEAVASDEAKAKAI~~AAANLAAEASVAAEAALKAEKVAEEA
BAF1     SAGQALQSAQTAASALRTSARSALTALKLARLQGAASSNAARMME~~KALAATQDANAAAQQAMAAESAAAEA
GAF1     SAQQALQAAQTSAAAIQTAAGSALTALKLARKQEAESNNAAEQAN~~KALALSRAASAATQRAVAAQNAAAAS
BBF2         AAKASASASEASAEAQVRANAEANIAKKASAAEAKAAAEAQVKAE~~LAKKAAAGFLAKARLAASAESEATKL
AmelF2   ATRASAAAAEAATEAQVKANADSIITKRAAIAEAQAAAEAQVKAA~~IARKSAANFLAKAQIAAAAESEATKL
BAF2     SSQESAASAANAANAEAKANAASIIANKANAVLAEAAAVLAATAA~~KAKESAMKSLSAAQAAAKAQARNAEA
GAF2     SSEQFAAEARAAADAEAKANAASIIANKANAVLAEAATGLSASAG~~KAQQSATRALQAARAAAKAQAELTQK
BBF3     ALERAQASSRAATTAQDISSDLEKRVATSAAAEAGATLRAEQSAA~~QSKWSAALAAQTAAAAAAIEAKATAS
AmelF3   ALERAQASSRLATVAQNVASDLQKRTSTKAAAEAAATLRQLQDAE~~RTKWSANAALEVSAAAAAAETKTTAS
BAF3     AMDRTMENARAANAAQTQASGQAENANRSAAAILAALLRIAEASA~~LNNEAAVNAAAAAAAASALQAKANAA
GAF3     AIERTYQDARAATSAQTKASGEAENANRNAAATLAAVLSIAKAASGQGGTRAAVDAAAAAAAAALHAKANAV
BBF4     ASAKAEALASTAAAANTRAALQAEKSNELAQAEAAAAAEAQAKAA~~AAAKATQLALKVAETAVKTEADAAAA
AmelF4   AAEKAESLAKNLASASARAALSSERANELAQAESAAAAEAQAKTA~~AAAKAAEIALKVAEIAVKAEADAAAA
BAF4     AAGKLLLAARAAAAAERRANEESEAANELAQASSAAAAEAEAKAN~~AGREAAAAALAIAEAAVAIEQEAVIL
GAF4     AAGKLNLAARAGSKAQERANEDSIEANELAQATAAAGAEAEAKAN~~AAQEAGASALAIAQAALNIEQETVKL 151       161       171       181       191       201       210
         efgabcdefgabcdefgabcdefgabcdefgabcdefgabcdefgabcdefgabcdefgabcdefg
BBF1     IAKAAAAKAAARAAAAALNSAKEAATSSARSAAEAEAKSEVAILISELDKKSREVAASASAKARAA
AmelF1   IARAASAKAAARAAAALASSKEAATASARNAAESEARNEVAVLIAEIDKKSREIDAASSLNARAA
BAF1     AAIAAAKQSEARDAGAEAKAAMAALITAQRNLVQANARAEMASEEAELDSKSRASDAKVNAVARAA
GAF1     AASAGAAQAEARNAYAKAKAAIAALTAAQRNYAAAKASASAGSVVAEQDAQSRAADAEVNAVAQAA
BBF2     AAEAEVALAKARVAVDQSQSAQATATAQAATAVQLQSQAANAEASAVAQAETLLVTAEAVSAAEAE
AmelF2   AAEAVVALTNAEVAVNQARNAQANASTQASMAVRVDSQAANAEAAAVAQAETLLVTAEAVAAAEAE
BAF2     SAEAQIKLSQARAAVARAAADQAVCSSQAQAASQIQSRASASESAAQSETNTAAAEAVATADAE
GAF2     AAQILVLIAEAKAAVSRASADQSVCTSQAQAASQIQSRASAAESAASAQSEANTIAAEAVARADAE
BBF3     SESTAAATSKAAVLTADTSSAEAAAAAEAQSASRIAGTAATEGSANWASENSRTAQLEASASAKAT
AmelF3   SEAANAAAKKAAAIASDADGAERSASTEAQSAAKIESVAAAEGSANSASEDSRAAQLEASTAARAN
BAF3     SQATARAAGQASTAAEEAQSAQEAADKNAELTTVMLEKASADQQAASARADYYTASTEAEAAAQAS
GAF3     SQATSKAAAEARVAAEEAASAQASASASAQLTAQLEEKVSADQQAASASTDTSAAIAEAEAAALAS
BBF4     AVAAAKARAVADAAASRATAVNAIAEAEERDSAQAENTAGVAQAALAAAEAQDSCIGAAATPRHSS
AmelF4   AVAAAKARAVADAAAARAAAVNAIAKAEEEASAQAENAAGVLQAAASAAAESRAAAAAAAATSEAA
BAF4     ARKAQDARLNAEAAAAAMNARVIASAESEASEDLENRASVARASAAGAEAAKAIATDAGATAEIA
GAF4     TRQAQNTRLRSENILAAASNARAIASAEAEASSDLNNRANAARSNARAAAETRAVATEAASTAEIA
```

Figure 6

A)

Xenospira1 (SEQ ID NO:2)
MKIPVLLATCLYLCGFASAGLEGPGNSLPELVKGSASATASTAVTARSGLRAGQVALASQKDAVLQAQAA
ASAASEARAAADLTAKLSQESASVQSQAAAKGKETEEAAVGQARAGLESVSMAASATSAAKEASTAAKAA
ASALSTAVVQAKIAERAAKAEAVASDEAKAKAIAAANLAAEASVAAEAALKAEKVAEEAIARAASAKAAA
RAAAAALASSKEAATASARNAAESEARNEVAVLIAEIDKKSREIDAASSLNARAAAKASSRNVETATIGA
NINSSKQVVSIPVEIKKFSEPEVSTSWREDEEVTKEKKEHINLNDFDLKSNVF Xenospira2 (SEQ ID NO:4)
MKIPAIFVTSLLVWGLAEGRVINHESLKTSEDIQGGYSAGIVGDGSDALGSSIENAQKVARAAENVGLNL
ELGAGARAASVAAAAQAKNTEAAEAGANAALAAAIAKREEAIKASEIANQLLTNAAKAAEATVSATKRAA
QLTAAAKEATRASAAAAAEAATEAQVKANADSIITKRAAIAEAQAAAEAQVKAAIARKSAANFLAKAQIAA
AAESEATKLAAEAVVALTNAEVAVNQARNAQANASTQASMAVRVDSQAANAEAAAVAQAETLLVTAEAVA
AAEAEVANKAATFAKQIVNEKKIHVAKLE Xenospira3 (SEQ ID NO:6)
MQIPTFVAICLLTSGLVHAGVEEFKSSATEEVISKNLEVDLLKNVDTSAKRRENGAPVLGKNTLQSLEKI
KTSASVNAKAAAVVKASALALAEAYLRASALSAAASAKAAAALKNAQQAQLNAQEKSLAALKAQSEEEAN
SARANAATAATQSALERAQASSRLATVAQNVASDLQKRTSTKAAAEAAATLRQLQDAERTKWSANAALEV
SAAAAAAETKTTASSEAANAAANKAAAIASDADGAERSASTEAQSAAKIESVAAAEGSANSASEDSRAAQ
LEASTAARANVAAAVGDGAIIGLGEEAGAAAQLLAQAKALAEVSSKSENIEDKKF Xenospira4 (SEQ ID NO:8)
MKIPSILAVSLLIWGLASGAREEVETRDKTKTSTVVKSEKVEVVAPAKDELKLTSEPIFGRRVGTGASEV
ASSSGEAIAISLGAGQSAAESQALAASQSKTAANAAIGASELTNKVAALVAGATGAQARATAASSSALKA
SLATEEAAEEAEAAVADAKAAAEKAESLAKNLASASARAALSSERANELAQAESAAAAEAQAKTAAAAKA
AEIALKVAEIAVKAEADAAAAAVAAAKARAVADAAAARAAAVNAIAKAEEEASAQAENAAGVLQAAASAA
AESRAAAAAAAATSEAAAEAGPLAGEMKPPHWKWERIPVKKEEWKTSTKEEWKTTNEEWEVK Xenosin (SEQ ID NO:10)
MKYMLLLLSIFICAHIVCAGVNTELKKDGELKEESYEKSESKSLKEIKEERASKSKSERLKIREEKREEE
EKSKSLNLVVVREKITKLSSWLKEEKDTSPLIEEKNGKGLLGLEDVTDELNIALKSLKEGKKFDTWKFEK
GSEDVRSLEELDTSVVELLKLIKEGKTDHGAIDLEKNGKVLVDLEKISENILETCGSQKKTVEVVDDKDK
KWNKESGWKKNLNDLDWKKDLDKDKVGGGLLGGLSGLLNSLKSEKGLLGLLNKNQIELLIPLISEIKKKN
IDFNLFDSVDSVERNLDLKLFTSSVSKVTELLNKGIDIQTILNAKNGDEFDLSGKELKNVKGIFGLIGSL
KRSLGLENILNLPFKRIPLLKI

B)

BEF1 (SEQ ID NO:23)
MKIPALLVTCLYLWGFASAGQSSPLLEIVQGSASATASTAVTARSGLRAGQVAVASQKDATLQADASAAA
AAAARASADQSASLAQQSASLQSKAAARAKSAEEESAAATAKAELQAESIAASASSNAREAAASAKASASA
MSSAAVQAKLAEKTAKNQALASEEAKLKAAAAASAAAAASAAAEAALKAERIAEEAIAKAAAAKAAARAA
AAALNSAKEAATSSARSAAEAEAKSEVAILISELDKKSREVAASASAKARAAAAASSRNAETAVIGANIN
VAKEVLAIPIEPKKLPEPELALKEENVAVASSESEVKVETSSEAWSI

BEF2 (SEQ ID NO:25)
MKIPAILVTSLLVWGGLAEGHVVKRDKELKAPALPELLGDGSDTLGASMENGIKVARASQNVGLRTELNA
AARAAAAAATKQAKDTEAAEAGAAAAIAIAIAKREEAIKASELASKLLTAAAGSSEAAVSATVRAAQLTA
AASAAAKASASASEASAEAQVRANAEANIAKKASAAEAKAAAAEAQVKAELAKKAAAGFLAKARLAASAES
EATKLAAEAEVALAKARVAVDQSQSAQATATAQAATAVQLQSQAANAEASAVAQAETLLVTAEAVSAAEA
EAATKATSWGEECHQREKVTFSEDRLNERQDNW

Figure 10

BBF3 (SEQ ID NO:27)
MQIPAIFVTCLLTWGLVHAGSVELGAPKQESVLVEQLLLKNVETSAKRKENGAPKLGESTAAALASTKAT
AAAEAKASAKVKASALALAEAFLRASAAFAAASAKAAAAVKEATQAQLLAQEKALIALKTQSEQQAASAR
ADAAAAAAVSALERAQASSRAATTAQDISSDLEKRVATSAAAEAGATLRAEQSAAQSKWSAALAAQTAAA
AAAIEAKATASSESTAAATSKAAVLTADTSSAEAAAAAEAQSASRIAGTAATEGSANWASENSRTAQLEA
SASAKATAAAAVGDGAIIGLARDASAAAQAAAEVKALAEASASLGASEKDKK

BBF4 (SEQ ID NO:29)
MKIPSILAVSLLVWGLASAGKPLIANAQIGKVKTETSSSSEIETLVSGSQTLVAGSETLASESEALASKS
EALTSEAEIASVTTKDELILKGEAITGKKLGTGASEVAAASGEAIATTLGAGQAAAEAQAAAAAQAKSAA
AAAANAGESSNSAAALVAAAAAQGKAAAAAAATKASLEAADAAEEAESAVALARAASAKAEALASTAA
AANTRAALQAEKSNELAQAEAAAAAEAQAKAAAAAKATQLALKVAETAVKTEADAAAAAVAAAKARAVAD
AAASRATAVNAIAEAEERDSAQAENTAGVAQAALAAAEAQDSCIGAAATPRHSSSYAWWKLRITSLIVIL
SPRNRRT

BBSA1 (partial) (SEQ ID NO:30)
GNSESGENWKNGESSESGKNWRNSGSSESGKNWKNGGSSESNKHWKNGGSSESGEKWKNSESSESGKNWK
NSGSSESGKNWKNGGSSESNKHWKSGGSSESGEKWKNSESGNKGKSSKSSESWKSNENSKNDGSWKSSEE
SEKWKDGKAVAEDSVSINWADVKEQISNIATSLEKGGNLEAVLKIKKGEKKISSLEEIKEKISVLLKWIQ
EGKDTSSLLDLKEGSKDIASLKEIKGKILLIVKLVNEGKDTSGLLDLEASGKVILELQSAIEKVLVKSEK
VTKVSEVSGLVKSKTVSDIKPLQAVIPLILELQKTDINLSTLNKWSTVNVNSIDKERVTKTVPVLLQSMK
GGEDIQNLLSAKGAKKLGISALDLQAVQGALGVVGKLSSGGALNSKGLLNLKDGASVLGAGKIGGLIPLP
KL

BAF1 (SEQ ID NO:41)
MKIPAIIATSLLLWGFASASGPRLLGGRSAASASASASAEASAGGWRKSGASASASAKAGSSNILSRVGA
SRAAATLVASAAVEAKAGLRAGKATAEEQREALEMLTLSADKNAEARILADDTAVLVQGSAEAQSVAAAK
TVAVEEESASLDAAAVEAEVAAATSKSSAGQALQSAQTAASALRTSARSALTALKLARLQGAASSNAARM
MEKALAATQDANAAAQQAMAAESAAAEAAAIAAAKQSEARDAGAEAKAAMAALITAQRNLVQANARAEMA
SEEEAELDSKSRASDAKVNAVARAASKSSIRRDELIEIGAEFGKASGEVISTGTRSNGGQDAIATAEASSS
ASAVGIKKTSGHWGSGKWSRVSKGKGWASSNADADASSSSIIIGGLKRGGLGSEASAAASAEAEASAGTL
LL

BAF2 (SEQ ID NO:43)
MKIPAILVISLLAWGLASGRVIESSSSASAQASASAGSRGLLGKRPIGKLEWGKEEKKLEELDEESLNEA
ALKVGIKNGGLDVAKGAAVLEAAMSDVATLTDQRSLVDLGLGPVANEAEILAEAQAATSAQAGAVANSAA
ERAIAAMEMADRTEYIAALVTTKAAKAAEATMAATARATAAASASKISSQESAASAANAANAEAKANAAS
IIANKANAVLAEAAAVLAATAAKAKESAMKSLSAAQAAAKAQARNAEASAEAQIKLSQARAAVARAAADQ
AVCSSQAQAASQIQSRASASESAASAQSETNTAAAEAVATADAEAAAQAEAWVMSLKNDLWLHLNMKGEA
KAEGEAVSISKGHRGGIRSGSISEASAEASSNVSMGGRHGRKDLVSEALAGASAGSSADSL

BAF3 (SEQ ID NO:45)
MKIPAILVISFLAWGLASGNLLKESKASASASASASASARASGKKNLHVLPLPKKSEHGIVIDKSVFDIKDV
VLSAVDEINGAPKLGLGWKKVSMGVERAEANAAAAAEALAMIKKIAMARSSAYVQAAWASAQASADALAS
ARVAQASQEAAEAKGRAASEALSRAIEASSRADAAAAATLDAMDRTMENARAANAAQTQASCQAENANRS
AAAILAALLRIAEASALNNEAAVNAAAAAAAASALQAKANAASQATARAAGQASTAAEEAQSAQEAADKN
AELTTVMLEKASADQQAASARADYYTASTEAEAAAQASAINALRDGIVVGMGNDAGASAQAMAQVEALAR
ASEHKALGEKKKGLVWGYGSKGSSSASASASASAEASSRLGKDW

Figure 10 Cont.

BAF4 (SEQ ID NO:47)
MKIPAILATSLLIWGLVGASELESEASAAASAQAEASSSGRSGKLSASQASASASASASAGSRGGSKGGW
GQLRRGDVKSEAKSAAAIAVEGAKIGTGIGNTASASAEALSRGLGIGQAAAEAQAAAAGQAEVAAKSCEL
ADKTTAKAVAMVEAAAEAEIEVANQEVAAVKLSTWAAKAARIVEEDSAAVRAAAGKLLLAARAAAAAERR
ANEESEAANELAQASSAAAAEAEAKANAGREAAAAALAIAEAAVAIEQEAVILARKAQDARLNAEAAAAA
AMNARVIASAESEASEDLENRASVARASAAGAAEAKAIATDAGATAEIAAYSWAKKGELINPGPLPKIIS
VNADLSKSEVEAMKITRGQVQEVKKISTHKGGWGWGKEGRSKVSSNASARASASANAAAGSLGSKWGRQL
SASSASADANAEADSQLLKVW

GAF1 (SEQ ID NO:57)
MKIPAIIATTLLLWGFADASKSYLLGSSASASASASASASASAGGSTGGVGVGSVISGGNNIIRGASTTSVT
LAAAAAEAKAALNAGKATVEEQREALQLLTASAEKNAEARSLADDAAVLVQGAAEAQSVAAAKTVAVEQG
SNSLDAAAAEAEAAAAASRVSAQQALQAAQTSAAAIQTAAGSALTALKLARKQEAESNNAAEQANKALAL
SRAASAATQRAVAAQNAAAASAASAGAAQAEARNAYAKAKAAIAALTAAQRNYAAAKASASAGSVVAEQD
AQSRAADAEVNAVAQAAARASVRNQEIVEIGAEFGNASGGVISTGTRSSGGKGVSVTAGAQASASASATS
SSSSSSGINKGHPRWGHNWGLGSSEASANAEAESSASSYSS*

GAF2 (SEQ ID NO:59)
MKIPAIFVTSLLAWGLASGGVIGPDTSSSQASASASASASASASASSSASIGYNELHKSINAPALAVGVKN
GGVDVAKGAAVVESAISDVSTLTDDRTLNGLAIIGNSAESLARAQASSSASAGAKANALIKQSIAAIEIT
EKAEYLASIVATKAAKAAEATAAATARATAVAEAAKVSSEQFAAEAPAAADAEAKANAASIIANKANAVL
AEAATGLSASAGKAQQSATRALQAARAAAKAQAELTQKAAQILVLIAEAKAAVSRASADQSVCTSQAQAA
SQIQSRASAAESAASAQSEANTIAAEAVARADAEAASQAQAWAESFKRELSSVVLEAEANASASASAGAL
ASGSSSSGASSSADASAGASSYGSLGGYRHGGSFSEASAAASAASRAEAA

GAF3 (SEQ ID NO:61)
MKIPAILVTSFLAWGLASGGVPKELGTSISSASASASASASATASSSSKNVHLLPLKSEHGIVIDKSKFN
IRKVVLSAIDEINGAPNIGLGLKQVSLALAKAQASAQSSAEALAIIKKIVALLISAYVRAAEAAARASAE
ALATVRAAEQAQKIAEAKGRAAAEALSELVEASQKADAAAAGTTDAIERTYQDARAATSAQTKASGEAEN
ANRNAAATLAAVLSIAKAASGQGGTRAAVDAAAAAAAAALHAKANAVSQATSKAAAEARVAAEEAASAQ
ASASASAQLTAQLEEKVSADQQAASASTDTSAAIAEAEAAALASTVNAINDGVVIGLGNTASSSAQASAQ
ASALARAKNARPKIKGWYKIGGATSASASASASASASAQSSSQGLVY

GAF4 (SEQ ID NO:63)
MKIPAILATSLFVWGLVGASELVGSDASATASAEASASSSAYGSKYGIGSGAVSGASASASASASASASA
SSAPAIEGVNVGTGVSNTASASAEALSRGLGIGQAAAEAQAAAAGQAAIAAKSCALAAKSTAQAVALVEK
VARAEVDLAESARKATRLSAEAAKAAAEVEKDLVGLRGAAGKLNLAARAGSKAQERANEDSIEANELAQA
TAAAGAEAEAKANAAQEAGASALAIAQAALNIEQETVKLTRQAQNTRLRSENILAAASNARAIASAEAEA
SSDLNNRANAARSNARAAAETRAVATEAASTAEIAAYSSSEKGEITNPGPLPKIVSVTAGLTQNEIAGSG
AAASASASALASASAGAGAGAGAGASAGAGAVAGAGAGAGAGASAGASAGANAGAGASSLLLPQSKLH
PISRSSASASASAEAEANSSAYA

MalF1 (SEQ ID NO:73)
MAASNKIIFSFLAIVLLQLATHCSSTAVLISGSAAGASSHNAAGAAAAARAALGASGAAGLGAASGAARR
NVAVGANGAAAASAAAAAARRAGAIGLNGAAGANVAVAGGKKGGAAGLNAGAGASLVSAAARRNGALGLN
GAAGANLAAAGGKKGGAIGLNAGASANVGAAAAKKNGAIGLNSAASANAAAAAAKKGGAIGLNAGASANA
AAAAAKKSGAVGLNAGASANAAAAAAKKSGAVAANSAASANAAAAAQKKAAADAANAAASESAAAAAAKK
AAAVAENAAATANAASALRKNALAIASDAAAVRADAAAAAADDAAKANNAASRGSDGLTARANAATLASD
AARRASNAATAASDAATDRLNAATAASNAATARANAATRADDAATDADNAASKASDVSAIEADNAARAAD
ADAIATNRAAEASDAAAIAADAAANAADAAAQCNNKVARVSDALALAANAAARGSDAAAEAQDAVARASD
AAAAQADGVAIAVNGATARDSAIEAAATAGAAQAKAAGRAGAAAAGLRAGAARGAAAGSARGLAGGLAAG
SNAGIAAGAASGLARGAAAEVCAARIAL

Figure 10 Cont.

Xenospira1 (SEQ ID NO:12)
ATGAAGATTCCAGTATTGCTTGCAACGTGCCTCTACCTTTGCGGATTTGCGTCCGCCGGTTTGGAGGGGCCGGGCAAC
TCGTTGCCCGAGCTCGTGAAAGGTAGCGCATCGGCCACCGCGTCGACCGCTGTGACCGCTAGATCAGGACTTAGAGCC
GGACAAGTAGCTTTAGCTTCGCAGAAGGATGCCGTACTCCAAGCTCAAGCTGCTGCATCCGCCGCGTCAGAGGCGCGC
GCTGCTGCCGATCTGACGGCTAAACTTAGCCAAGAATCGGCATCAGTGCAATCGCAGGCTGCCGCCAAAGGGAAGGAA
ACGGAGGAGGCAGCTGTTGGTCAAGCTAGGGCTGGCCTCGAGTCGGTGTCCATGGCCGCATCAGCCACATCTGCTGCC
AAAGAAGCATCGACCGCCGCCAAAGCCGCAGCATCCGCACTATCCACAGCCGTGGTGCAAGCGAAAATAGCTGAGAGG
GCAGCCAAAGCTGAAGCTGTTGCCTCGGACGAAGCCAAGGCCAAGGCGATTGCAGCAGCCAACTTGGCGGCTGAGGCC
AGTGTAGCCGCAGAAGCAGCTCTCAAGGCCGAGAAAGTGGCCGAAGAAGCCATCGCAAGAGCGGCCTCTGCAAAGGCT
GCCGCAAGAGCTGCTGCCCGCTCTAGCCTCCTCGAAGGAAGCAGCCACGGCCAGCGCAAGAAACGCCGCGGAATCC
GAGGCCAGGAACGAAGTAGCTGTATTGATCGCCGAGATTGATAAAAAGAGTAGGGAAATCGACGCAGCCAGTTCGCTT
AATGCGCGTGCCGCTGCCAAGGCAAGCTCCAGGAACGTAGAAACGGCGACAATCGGGGCCAACATCAACTCTTCGAAA
CAAGTCGTGTCAATTCCAGTGGAAATAAAGAAATTCTCGGAGCCGGAAGTGTCAACATCATGGAGAGAAGATGAAGAG
GTTACGAAAGAGAAGAAGGAGCACATAAATCTGAACGACTTCGACTTGAAGAGCAACGTATTT Xenospira2 (SEQ ID NO:14)
ATGAAGATTCCAGCAATATTCGTCACGTCTCTGCTGGTCTGGGGATTGGCCGAGGGCCGCGTGATTAATCACGAGTCC
CTGAAGACGAGCGAGGATATTCAAGGAGGATATTCAGCAGGAATAGTCGGTGATGGATCTGACGCGCTTGGCTCCTCC
ATAGAAACGCCCAAAAAGTCGCTCGAGCGGCTGAAAACGTGGGCTTGAATCTGGAATTGGGCGCAGGCGCGCGTGCT
GCCAGTGTTGCCGCTGCTGCCCAGGCCAAAAACACAGAGGCTGCGGAAGCAGGAGCAAACGCCGCTCTGGCCGCCGCC
ATTGCCAAACGGGAGGAAGCGATTAAAGCCAGCGAGATAGCAAACCAATTGTTGACCAATGCAGCAAAAGCGGCAGAA
GCGACTGTATCGGCAACGAAGAGGGCAGCACAATTGACGGCTGCAGCGAAAGAAGCAACCAGAGCTTCTGCAGCCGCT
GCTGAAGCTGCTACGGAGGCCCAGGTAAAGGCTAACGCCGATTCAATCATCACGAAGAGGGCTGCGATTGCCGAGGCT
CAAGCTGCGGCGGAAGCTCAAGTTAAGGCGGCAATCGCCAGAAAATCGGCAGCGAATTTTTTGGCTAAGGCTCAAATA
GCGGCTGCCGCGGAATCCGAGGCCACGAAACTCGCGGCCGAAGCTGTAGTGGCACTAACAAACGCCGAAGTCGCCGTG
AACCAGGCTAGAAACGCACAGGCAAACGCCTCGACTCAAGCTTCCATGGCTGTTAGGGTAGATTCTCAAGCAGCGAAC
GCTGAAGCAGCCGCTGTAGCGCAAGCCGAAACTCTCTTGGTTACGGCAGAAGCTGTCGCAGCTGCGGAGGCTGAGGTT
GCGAACAAAGCCGCCACATTTGCAAAACAGATCGTCAACGAGAAGAAAATACATGTAGCAAAGTTGGAA Xenospira3 (SEQ ID NO:16)
ATGCAGATCCCAACGTTTGTCGCCATATGCTTGCTCACATCGGGCTTGGTGCACGCAGGCGTCGAGGAATTCAAGTCC
TCGGCAACCGAGGAGGTGATCAGCAAAAACTTAGAAGTCGACCTGTTGAAAAATGTGGACACTAGCGCGAAACGAAGA
GAGAACGGCGCCCCGGTGCTCGGCAAGAACACACTTCAATCCCTGGAGAAGATCAAGACGTCGGCGAGCGTGAATGCC
AAAGCAGCAGCCGTGGTGAAAGCGTCCGCTCTGGCTCTTGCAGAGGCCTATTTGCGAGCGTCCGCATTGTCAGCCGCC
GCTTCAGCCAAGGCAGCCGCCGCCCTGAAAAATGCTCAACAAGCGCAATTAAACGCCCAGGAAAAGTCTTTGGCCGCG
TTGAAAGCTCAGTCCGAGGAAGAGGCAGCTTCTGCTCGTCGAAACGCAGCAACCGCCGCGACAGTCGGCACTGGAA
CGCGCTCAAGCCTCCTCCAGGTTAGCAACGGTCGCCCAAAACGTAGCCAGCGACTTGCAGAAACGGACCAGCACCAAG
GCCGCGGCTGAAGCCGCTGCCACCCTCAGACAATTACAGGACGCGGAACGAACGAAATGGAGTGCCAACGCTGCCTTA
GAAGTCTCCGCCGCTGCAGCTGCCGCAGAAACCAAGACCACTGCCTCCTCGGAGGCCGCCAACGCCGCCGCCAAAAAG
GCGGCCGCGATAGCTTCTGACGCGGACGGCGCGGAAAGGTCGGCATCTACCGAGGCACAATCAGCTGCGAAGATCGAG
AGTGTGGCAGCCGCCGAGGGATCCGCCAACTCGGCCTCTGAGGATTCCCGGGCCGCTCAATTGGAAGCCTCCACCGCG
GCCGAGAGCCAACGTGCCCGCAGCTGTCGGGGATGGAGCGATTATAGGACTTGGAGAGGAAGCGGGTGCCGCGGCTCAG
TTGCTTGCACAGGCGAAGGCATTGGCCGAAGTTAGCTCGAAATCCGAAAATATTGAGGATAAAAAATTTT Xenospira4 (SEQ ID NO:18)
ATGAAGATCCCATCCATACTCGCGGTTTCCCTGCTGATCTGGGCGTTTGGCAAGCGGCGCAAGGGAAGAGGTGGAGACA
CGGGACAAGACCAAGACCTCGACAGTGGTGAAAAGCGAGAAAGTGGAAGTCGTTGCTCCCGCTAAGGATGAACTTAAA
TTAACGAGCGAGCCTATCTTTGGAAGAAGAGTGGGAACTGGAGCATCCGAGGTGGCATCTAGCAGCGGTGAAGCCATC
GCGATAAGTCTTGGAGCAGGGCAGTCAGCGGCAGAGTCTCAGGCCTTGCCGCCTCGCAATCCAAAACGGCAGCGAAC
GCCGCCATAGGCGCGAGCGAGCTTACCAACAAAGTTGCTGCTCTAGTTGCTGGCGCGACTGGTGCGCAGGCGAGAGCT
ACGGCCGCCTCCTCGAGCGCGTTGAAGGCCAGCTTGGCGACCGAAGAAGCGGCGGAAGAGGCCGAGGCGGCCGTGGCT
GACGCCAAGGCTGCCGCGGAAAAAGGCCGAATCCCTGGCGAAAAATCTCGCGTCGGCGAGCGCTCGCGCGGCCCTCTCC
TCCGAAAGGGCGAACGAATTGGCTCAAGCTGAGAGCGCTGCAGCGGCCGAGGCGCAGGCCAAGACAGCAGCCGCCGCC
AAAGCAGCGGAAATCGCCCTTAAGGTCGCTGAGATAGCGGTGAAGGCGAAGCGGACGCAGCAGCTGCCGCCGTGGCA
GCTGCAAAGGCAAGAGCCGTGGCAGACGCGGCCGCTGCCCGTGCCGCAGCCGTGAACGCCATCGCCAAGGCGGAACAG
GAGGCCTCGGCCCAAGCAGAGAACGCCGCCGGTGTTTTGCAAGCAGCCGCCTCCGCCGCGGCGGAATCGCGAGCCGCT
GCAGCTGCCGCCGCTGCTACCTCGGAGGCAGCGGCTGAAGCTGGCCCGTTGGCAGGTGAGATGAAACCACCGCACTGG
AAATGGGAACGGATTCCTGTGAAGAAGGAGGAGTGGAAAACGTCAACGAAGGAAGAATGGAAAACGACGAATGAAGAA
TGGGAGGTGAAG

Figure 11

Xenosin (SEQ ID NO:20)
ATGAAATACATGCTCTTGTTGCTATCTATATTCATCTGTGCACATATTGTATGCGCAGGCGTAAATACAGAATTAAAA
AAAGATGGTGAACTAAAGGAAGAGTCTTATGAGAAAAGCGAGTCAAAGAGTTTAAAAGAAATTAAAGAAGAACGTGCT
TCAAAATCAAAAAGTGAACGTTTGAAGATTCGTGAAGAAAAACGCGAAGAGGAAGAAAAATCCAAGAGTCTGAATCTG
GTCGTGGTCAGAGAAAAGATTACCAAACTTTCTTCATGGCTCAAAGAAGAGAAAGATATCAGTCCTCTTTTGAAGAA
AAAAATGGCAAAGGTCTATTGGGTTTGGAAGATGTCACGGACGAGTTAAATATCGCTCTTAAATCGTTGAAGGAGGGC
AAAAAGTTTGATACTTGGAAATTCGAGAAAGGTAGCGAAGACGTTCGTTCTTTGGAAGAACTTGATACGAGCGTCGTT
GAACTTTTAAAATTAATAAAGGAAGGAAAAACTGACCATGGTGCTATAGATTTGGAGAAGAATGGTAAGGTACTTGTA
GATTTGGAAAAAATCTCAGAAAACATACTTGAAACTTGTGGATCACAAAAGAAGACTGTGGAAGTTGTAGATGATAAA
GACAAAAAATGGAATAAAGAATCAGGTTGGAAAAAAAATCTAAATGATCTAGATTGGAAAAAAGATTTAGATAAAGAT
AAAGTTGGTGGCGGTTTGCTTGGCGGTTTAAGTGGCCTCTTAAATAGTTTAAAATCAGAAAAAGGTCTTCTAGGTCTT
TTGAATAAGAATCAAATTGAGTTATTAATTCCTTTAATCAGTGAGATAAAAAAGAAAAATATAGATTTTAATCTCTTC
GATTCTGTTGATTCTGTCGAAAGAAATTTAGACTTGAAACTTTTCACAAGTTCTGTTTCAAAAGTTACTGAATTATTA
AATAAAGGAATCGATATTCAAACAATTTTTGAATGCGAAAAATGGAGATGAATTCGATTTAAGCGGCAAAGAATTGAAA
AACGTCAAAGGGATATTTGGTTTGATTGGAAGTTTGAAACGCTCATTAGGATTAGAAAATATATTGAACTTACCGTTT
AAACGTATACCTCTGCTTAAATTA BBF1 (SEQ ID NO:32)
ATGAAGATTCCAGCACTGCTCGTAACGTGCCTCTACCTTTGGGGCTTCGCGTCCGCCGGCCAGAGCTCACCTCTGCTC
GAGATCGTGCAGGGTAGCGCGTCGGCCACCGCATCCACCGCTGTGACCGCTAGATCCGGACTTCGTGCCGGTCAGGTA
GCCGTGGCCTCGCAGAAGGATGCCACACTTCAGGCAGATGCCTCAGCGGCCGCCGCGGCCGCTGCACGCGCTTCCGCC
GACCAGTCGGCCAGTCTAGCCCAACAGTCGGCGTCTTTGCAGTCCAAAGCTGCCGCCAGAGCAAAATCAGCCGAGGAG
TCAGCGGCAGCTACGGCCAAAGCCGAGTTGCAGGCAGAATCCATTGCTGCATCTGCCAGTTCCAATGCCAGAGAGGCT
GCAGCGTCCGCAAAAGCCTCCGCATCCGCGATGTCATCGGCTGCCGTGCAGGCGAAACTCGCTGAAAAGACGGCCAAG
AATCAAGCTCTGGCTTCCGAAGAAGCCAAACTCAAGGCTGCCGCCGCTGCCAGCGCAGCAGCAGCAGCCAGCGCCGCC
GCCGAGGCAGCCCTGAAAGCTGAGAGAATAGCGGAAGACCATCGCCAAGGCGGCCGCTGCCAAAGCAGCCGCCAGA
GCCGCTGCAGCCGCGTTAAACTCCGCGAAGGAAGCCGCCACGAGCAGCGCAAGGAGCGCCGCCGAAGCCGAAGCTAAG
AGCGAAGTCGCTATACTGATCAGCGAACTCGACAAGAAGAGCAGGGAAGTCGCCGCTTCCGCGTCCGCCAAGGCACGC
GCTGCTGCTGCGGCTAGCTCCAGAAACGCAGAAACGGCTGTTATCGGAGCTAACATCAATGTGGCCAAAGAGGTCTTG
GCGATTCCCATCGAGCCAAAGAAACTTCCGGAGCCAGAGCTGGCGTTGAAAGAAGAGAATGTCGCGGTCGCGAGCTCA
GAGAGTGAAGTGAAGGTAGAAACGAGCAGCGAAGCATGGTCAATTTAA BBF2 (SEQ ID NO:34)
ATGAAGATTCCAGCAATACTGGTTACGTCTCTGCTGGTCTGGGGTGGTCTGGCCGAGGGCCACGTGGTGAAGCGCGAC
AAGGAGCTCAAGGCCCCGGCTTTACCGGAACTACTCGGTGATGGGTCTGACACGCTCGGTGCCTCGATGGAGAACGGG
ATCAAAGTCGCCAGAGCATCGCAGAATGTGGGTCTGAGAACAGAGTTGAATGCAGCCGCGCGGGCTGCAGCCGCTGCT
GCGACCAAGCAGGCCAAAGACACAGAGGCCGCGGAAGCTGGAGCGGCCGCTGCGATTGCCATCGCTATCGCCAAGCGT
GAAGAAGCTATCAAAGCAAGCGAATTAGCCAGCAAGTTGTTGACAGCCGCGGCTGGGTCCAGCGAAGCTGCCGTGTCA
GCGACGGTGAGGGCGGCGCAATTGACGGCCGCAGCTAGCGCAGCTGCCAAAGCTTCTGCATCCGCCTCTGAGGCTTCT
GCCGAAGCCCAGGTGAGGGCCAACGCCGAAGCAAACATCGCCAAGAAAGCTTCGGCAGCTGAAGCAAAAGCCGCACCC
GAAGCCCAGGTTAAGGCGGAACTCGCCAAGAAAGCGGCCGCCGGTTTCTTAGCTAAGGCTAGACTAGCGGCCAGCGCC
GAATCCGAGGCCACTAAACTCGCAGCCGAAGCTGAAGTAGCACTGGCTAAGGCCAGAGTCGCCGTCGACCAGTCGCAG
AGCGCACAGGCAACCGCTACCGCTCAAGCTGCCACAGCCGTTCAGCTGCAGTCTCAAGCAGCTAACGCGGAAGCCTCC
GCTGTAGCACAGGCTGAAACTCTGCTGGTCACGGCGGAAGCCGTCTCTGCCGCGGAAGCCGAAGCCGCGACCAAAGCT
ACCAGTTGGGGCGAAGAATGTCATCAACGAGAAAAAGTTACGTTTAGCGAAGATCGATTAAACGAGAGACAAGACAAT
TGGTAG BBF3 (SEQ ID NO:36)
ATGCAGATCCCAGCCGATTTTCGTCACGTGCCTGCTCACATGGGGCCTGGTGCACGCAGGTAGCGTGGAACTCGGTGCC
CCCAAGCAGGAGTCTGTCCTCGTGGAGCAGCTCCTATTGAAGAACGTGGAGACTAGTGCGAAGCGAAAGGAGAACGGC
GCACCGAAACTCGGCGAGAGCACAGCTGCGGCTCTGGCTAGTACCAAGGCAACTGCAGCCGCAGAGGCTAAGGCATCC
GCCAAAGTGAAAGCTTCTGCCTTGGCCCTCGCTGAGGCTTTCTTGCGTGCGTCGGCAGCGTTTGCTGCTGCTTCAGCC
AAAGCTGCTGCCGCTGTAAAGGAAGCAACGCAGGCACAGTTGCTGGCACAGGAGAAGGCTTTGATAGCGTTGAAAACT
CAATCTGAGCAACAAGCTGCCTCTGCTCGCGCGGACGCCGCGGCTGCCGCAGCCGTATCCGCGCTAGAACGCGCCCAG
GCCTCCTCCAGAGCAGCCACGACCGCCAAGACATCTCCAGCGATCTGGAGAAACGTGTCGCCACCTCAGCCGCTGCT
GAAGCAGGTGCCACCCTCAGAGCGGAACAATCCGCCGCGCAATCGAAATGGTCCGCCGCACTGGCCTGCCCAAACCGCC
GCTGCTGCAGCCGCTATAGAAGCAAAGGCCACCGCTTCCTCAGAGCCAACCGCTGCCGCTACTAGTAAGGCCGCCGTG
TTGACCGCTGACACTAGCAGCGCAGAAGCTGCCGCTGCAGCGGAGGCACAATCCGCTTCGCGGATCGCAGGTACAGCA
GCCACCGAGGGATCCGCCAACTGGGCTAGCGAGAACTCGCGTACCGCACAACTGGAAGCTTCCGCCTCAGCGAAGGCC

Figure 11 Cont.

ACCGCAGCCGCAGCTGTCGGAGATGGAGCTATTATAGGACTTGCACGGGACGCTAGTGCCGCAGCTCAGGCAGCCGCA
GAAGTTAAAGCCTTAGCTGAAGCTAGTGCCAGCTTAGGTGCTTCAGAAAAGGACAAGAAATGA

BBF4 (SEQ ID NO:38)
ATGAAGATTCCATCGATACTCGCGGTGTCCCTGCTGGTTTGGGGTCTGGCCAGCGCAGGCAAACCACTCATTGCCAAT
GCGCAAATAGGGAAGGTCAAGACCGAAACGTCATCGTCTTCAGAGATTGAGACGTTGGTATCAGGAAGCCAGACATTG
GTGGCAGGAAGTGAGACATTGGCTTCAGAAAGCGAGGCATTGGCGTCAAAAAGCGAGGCATTGACGTCAGAAGCCGAG
ATAGCGAGCGTGACAACGAAGGACGAGCTCATACTAAAGGGCGAAGCTATCACTGGAAAGAAACTAGGAACCGGGGCG
TCGGAAGTAGCGCGGCCTCTGGGGAGGCTATCGCAACTACCCTTGGCGCGGGACAAGCTGCAGCAGAGGCACAAGCA
GCCGCCGCCGCGCAAGCAAAATCAGCAGCGGCAGCTGCCGCGAATGCAGGTGAATCCAGCAACAGTGCTGCTGCGTTG
GTTGCTGCTGCAGCTGCAGCACAAGGAAAAGCGGCTGCCGCCGCAGCAGCCGCGACGAAGGCTAGCTTAGAGGCCGCA
GACGCTGCTGAGGAAGCTGAGTCGGCCGTGGCCTTGGCTAGGGCTGCCTCCGCAAAGGCGGAAGCGCTCGCATCGACC
GCCGCTGCTGCGAATACCCGTGCTGCTCTCCAAGCGGAAAAATCGAACGAGCTGGCGCAAGCTGAGGCTGCAGCCGCC
GCCGAAGCCCAGGCTAAAGCCGCCGCTGCTGCCAAGGCAACACAACTCGCCCTTAAAGTTGCCGAAACTGCGGTGAAA
ACGAAGCAGATGCAGCAGCTGCCGCCGTTGCGGCCGCAAAAGCCAGAGCAGTCGCAGACGCAGCCGCGTCTCGTGCG
ACCGCAGTGAACGCCATTGCTGAAGCGGAAGAAAGAGACTCTGCACAGGCGGAGAACACCGCTGGTGTAGCACAAGCA
GCGCTCGCTGCTGCGGAAGCACAAGACTCCTGCATCGGCGCTGCCGCGACTCCTAGGCATTCGTCGAGCTATGCATGG
TGGAAGCTTAGGATAACATCCTTGATCGTCATTCTATCGCCACGCAATCGACGTACTTAA

BBSA1 (partial) (SEQ ID NO:39)
GGAAATTCGGAAAGCGGCGAAAATTGGAAGAACGGTGAAAGCTCCGAAAGCGGCAAAAATTGGAGGAACAGCGGAAGC
TCCGAAAGCGGCAAAAATTGGAAGAATGGCGGAAGCTCAGAAAGCAACAAACATTGGAAGAACGGTGGAAGCTCGGAA
AGCGGCGAGAAATGGAAAAACAGTGAAAGCTCCGAAAGCGGCAAAAATTGGAAGAACAGCGGAAGCTCCGAAAGCGGC
AAAAATTGGAAAAACGGCGGAAGCTCGGAAAGCAACAAACATTGGAAGAGCGGTGGAAGCTCGGAAAGTGGCGAGAAA
TGGAAAAACAGTGAAAGCGGAAATAAAGGCAAAAGCTCAGAAAGCAGCGAAAGTTGGAAGAGCAACGAAAACTCGAAG
AACGACGGCAGCTGGAAGAGCAGTGAAGAATCAGAAAAGTGGAAAGATGGTAAAGCAGTGGCGGAAGACAGCGTTAGT
ATAAACTGGGCAGATGTCAAAGAGCAGATTAGCAACATTGCTACATCCTTAGAAAAGGGTGGTAACCTCGAGGCTGTA
TTGAAAATAAAGAAAGGAGAAAAGAAAATTTCAAGTTTGAGGAAATCAAGGAGAAAATCTCTGTCCTACTGAAATGG
ATTCAAGAAGGCAAAGATACTAGCCAGCCTATTAGATTTGAAAGAGGGTAGCAAGGATATTGCGTCGTTCAAAGAAATC
AAAGGAAAGATCCTTTTGATTGTTAAATTAGTGAACGAAGGGAAAGACACTAGTGGTCTTTTAGATTTAGAAGCGAGT
GGCAAAGTAATTTTAGAATTGCAAAGCGCCATAGAAAGGTTCTCGTAAAGTCAGAAAAGGTAACCAAAGTATCTGAA
GTTTCCGGTTTAGTAAAAAGCAAAACTGTCTCGGACATAAAACCGCTTCAAGCAGTAATTCCTTTAATCCTTGAATTG
CAAAAAACAGACATTAACCTTAGTACCTTAAACAAGTGGTCCACTGTTAACGTAAATTCTATAGATAAAGAACGCGTC
ACGAAAACGGTTCCAGTGCTCCTTCAATCCATGAAAGGAGGCGAAGATATTCAGAACCTTTTGAGTGCGAAAGGTGCA
AAGAAACTTGGCATTAGTGCTTTGGACTTACAGGCAGTTCAAGGAGCTCTTGGCGTGGTTGGAAAGCTAAGTTCAGGT
GGTGCGTTGAACTCAAAAGGCTTGTTGAACTTGAAAGACGGCGCTAGTGTGTTAGGTGCAGGAAAAATCGCAGGATTA
ATTCCTTTACCGAAACTTTAAGAGATAGACCGATAAAGGCAGATATACTCTCGGAAGATTTTTTTGGAAGTTGAATAG
TCCGCAAAAAAATTATCTCTGATTATTATAATTTAGCCTAAAATATTAAATAAAATGGAGAAATAACGTTGAAATATA
TAAATAA

BAF1 (SEQ ID NO:49)
ATGAAGATCCCAGCGATAATCGCAACGTCCCTTCTCCTCTGGGGTTTCGCCAGCGCCAGCGGGCCGCGCTTACTCGGC
GGCAGATCGGCCGCGTCCGCGTCGGCTTCCGCTTCGGCTGAGGCGTCGGCGGGCGGTTGGAGGAAAAGCGGCGCATCC
GCTTCCGCTTCCGCTAAGGCTGGTAGCAGCAACATCCTCAGCCGCGTGGGAGCTTCGAGGGCGGCCGCGACGTTGGTC
GCTTCCGCCGCGGTGGAGGCCAAGGCGGGTCTCCGTGCCGGCAAGGCAACCGCCGAGGAGCAGAGGGAGGCTTTGGAA
ATGCTCACCTTGTCCGCCGACAAGAATGCCGAGGCGCGTATCCTGGCCGACGACACGGCCGTTCTGGTTCAAGGCAGC
GCCGAGGCACAGTCGGTCGCCGCCGCAGACCGTCGGCGGTCGAGGAAGAGTCCGCTTCCTTGGATGCGGCCGCAGTT
GAAGCGGAGGTCGCAGCCGCCACGTCGAAATCGTCGGCTGGCCAAGCACTCCAGTCCGCACAGACCGCCGCATCTGCT
CTCAGAACTTCCGCCAGGAGCGCCCTTGACGGCCCTCAAGCTGGCACGCCTCCAAGGCGCGGCTTCTAGCAACGCTGCC
AGGATGATGGAAAAGGCGCTGGCCGCCACCCAGGACGCAAATGCGCCGCCCAGCAAGCTATGGCGGCCGAGAGTGCA
GCCGCAGAAGCAGCGGCTATCGCGGCAGCGAAACAATCGGAGGCGAGAGACGCCGGCGCCGAGGCCAAGGCCGCCATG
GCAGCACTCATCACCGCCCAGAGGAATCTCGTGCAGGCCAATGCCAGGGCGGAAATGGCAAGCGAGGAAGCCGAATTG
GATTCGAAGTCTAGAGCGTCCGACGCCAAGGTGAACGCCGTTGCTCGTGCGGCCTCCAAGTCCAGCATACGCAGAGAT
GAACTTATCGAGATCGGCGCTGAGTTCGGCAAGGCCAGCGGCGAGGTGATTTCCACCGGCACGCGTTCCAACGGCGGT
CAAGACGCCATCGCCACCGCCGAGGCATCGAGTAGCGCGTCGCCGTCGGCATCAAGAAAACAAGCGGACACTGGGGG
AGCGGAAAATGGAGTCGTGTCTCAAGGGTAAAGGATGGGCTTCCTCGAATGCGGACGCTACGCCAGCAGCAGCAGC
ATCATCATCGGCGGTCTCAAACGCGGCGGCCTCGGTTCGGAAGCCTCTGCGGCAGCTTCCGCAGAAGCGGAAGCTTCC
GCCGGCACACTCCTGCTGTAA

Figure 11 Cont.

BAF2 (SEQ ID NO:51)
ATGAAGATTCCAGCGATACTCGTGACGTCTCTCCTCGCCTGGGGATTAGCCAGCGGCCGGGTCATCGAGTCCAGCTCG
TCGGCTTCCGCACAGGCGTCGGCATCGGCCGGCTCGAGAGGCCTGCTCGGTAAACGGCCGATTGGCAAGCTCGAGTGG
GGCAAGGAGGAGAAGAAACTCGAAGAACTCGACGAGGAATCGCTCAATGAGGCCGCTCTGAAGGTCGGCATCAAGAAC
GGCGGATTGGATGTCGCGAAGGGCGCGGCAGTCCTCGAGGCAGCGATGAGCGACGTCGCGACCCTTACGGATCAGCGT
TCTCTTGTGGATCTCGGTCTCGGCCCGGTCGCGAACGAGGCCGAGATCCTGGCGGAGGCGCAGGCCGCCACGAGCGCC
CAAGCTGCCGCTGTCGCTAATAGCGCCGCGGAGCGTGCGATCGCGGCGATGGAGATGGCCGACAGAACCGAATATATT
GCGGCACTTGTCACCACCAAAGCCGCCAAAGCTGCCGAGGCCACTATGGCCGCTACTGCCCGTGCCACCGCCGCCGCC
TCAGCCTCCAAGATATCCAGTCAGGAATCAGCCGCATCGGCCGCTAACGCCGCCAACGCCGAAGCCAAGGCCAACGCC
GCTTCCATAATCGCTAACAAGGCGAACGCCGTCCTGGCTGAGGCCGCCGCCGTACTCGCAGCCACTGCTGCCAAGGCC
AAGGAATCGGCGATGAAATCGCTTAGCGCCGCTCAGGCCGCCGCCAAGGCACAAGCCAGGAACGCCGAGGCCTCCGCC
GAAGCTCAGATCAAACTTTCCCAGGCCAGGGCCGCCGTGGCACGCGCTGCAGCCGATCAGGCCGTCTGTTCCTCCCaG
GCTCAGGCCGCAAGTCAGATACAATCGAGGGCATCCGCATCCGAATCCGCGGCATCGGCACAATCAGAGACCAACACC
GCCGCGGCCGAAGCGGTCGCCACCGCTGACGCCGAAGCGGCCGCGCAAGCTGAAGCGTGGGTCATGTCGCTGAAGAAC
GATCTGTGGCTGCATCTCAACATGAAGGGTGAGGCCAAGGCCGAAGGCGAGGCCGTTTCGATCAGCAAAGGACATCGC
GGCGGTATCAGGTCGGGCAGCATCTCGGAAGCCAGCGCCGAGGCAAGCAGCAACGTTTCCATGGGCGGACGTCATGGA
CGGAAGGACCTCGTCTCTGAAGCGTTAGCGGGAGCATCAGCGGGCAGCAGTGCCGACTCCCTTTGA

BAF3 (SEQ ID NO:53)
ATGAAGATACCAGCGATACTCGTGACGTCCTTCCTCGCCTGGGGACTGGCCAGCGGGAATCTCCTTAAGGAGTCGAAA
GCTTCCGCGTCCGCGTCCGCGTCCGCTTCCGCGAGGGCCAGCGGCAAGAAGAATCTTCACGTGTTGCCATTACCGAAG
AAAAGCGAGCATGGCATCGTGATCGACAAGTCGGTGTTCGACATCAAGGATGTAGTGCTGAGCGCGGTCGACGAGATC
AACGGCGCCCCGAAACTCGGCCTGGGATGGAAGAAGGTCAGCATGGGGGTGGAGCGCGCCGAGGCGAACGCAGCCGCT
GCCGCCGAGGCATTGGCGATGATCAAGAAGATTGCCATGGCCCGCAGCAGTGCATACGTCCAGGCGGCCTGGGCATCG
GCCCAGGCATCAGCTGACGCATTGGCTAGCGCCAGGGTGGCACAGGCGTCTCAGGAGGCTGCGGAGGCAAAGGGTAGA
GCGGCTTCCGAGGCGCTCTCCAGAGCCATCGAAGCATCCTCGCGGGCCGATGCGGCAGCCGCTGCGACGCTGGACGCG
ATGGACCGCACCATGGAGAACGCGAGCGCCGCCAAATGCCGCGCAAACGCAGGCCACCGGCCCAAGCTGAGAACGCAAAT
CGCAGCGCTGCTGCCATCCTCGCAGCTCTGCTACGTATCGCGGAGGCATCCGCGTTGAACAACGAGGCCGCGGTCAAC
GCGGCCGCGGCCGCAGCCGCAGCGTCTGCCCTTCAGGCCAAGGCTAACGCGGCTTCTCAAGCAACCGCCAGAGCCGCA
GGACAGGCGTCGACGGCCGCCGAAGAGGCGCAATCCGCCCAAGAAGCCGCCGATAAGAACGCGGAGCTGACCACGGTC
ATGCTCGAAAAGGCTAGTGCTGATCAACAGGCGGCATCCGCTAGGGCTGACTACTACACCGCCTCAACCGAGGCCGAA
GCCGCTGCACAGGCGTCTGCTATCAACGCACTCAGGGACGGAATAGTTGTCGGAaTGGGAAATGACGCTGGCGCATCG
GCCCAAGCGATGGCACAGGTAGAAGCTCTCGCTCGCGCCAGCGAGCACAAGGCGTTAGGCGAGAAGAAGAAGGGCCTG
GTTTGGGGCTACGGAAGCAAGGGCAGTAGCTCCGCCAGCGCATCCGCCAGCGCCTCCGCCGAAGCATCCTCGAGACTC
GGAAAGGACTGGTAG

BAF4 (SEQ ID NO:55)
ATGAAGATTCCAGCGATACTTGCGACGTCCCTCCTCATCTGGGGTCTTGTCGGCGCCAGCGAGCTCGAATCGGAAGCG
AGTGCGGCGGCGTCTGCGCAAGCGGAAGCGTCCTCGTCTGGTCGCTCCGGCAAACTGTCCGCGTCTCAGGCTTCCGCC
AGCGCGTCCGCCAGCGCGTCAGCCGGCAGCAGAGGTGGCAGCAAAGGTGGCTGGGGCCAGCTCCGCCGTGGTGATGTT
AAGAGCGAGGCGAAGAGCGCCGCCGCGATCGCGGTCGAAGGAGCTAAAATCGGCACCGGAATCGGAAATACCGCGTCC
GCATCCGCGGAGGCGCTCTCACGAGGACTCGGCATCGGACAGGCGGCCGCGGAGGCGCAAGCCGCAGCCGCCAGGTCAG
GCAGAGGTCGCCGCGAAATCGTGCGAACTTGCCGACAAGACCACCGCCAAAGCGGTCGCCATGGTCGAAGCGGCAGCC
GAGGCCGAAATCGAGGTGGCCAATCAGGAGGTCGCAGCCGTCAAATTATCGACTTGGGCCGCTAAAGCAGCAAGGATA
GTCGAGGAAGACAGCGCCGCCGTGAGGGCGGCTGCCGGCAAATTGCTTTTGGCCGCGAGAGCTGCCGCCGCCGCCGAG
AGACGCGCCAACGAGGAATCCGAGGCGGCCAACGAACTTGCTCAAGCGTCATCTGCCGCTGCCGCCGAGGCCGAAGCC
AAAGCGAACGCCGGCCGTGAGGCCGCTGCCGCTGCCTTGGCTATCGCCGAGGCCGCCGTCGCCATCGAACAAGAAGCC
GTCATTTTGGCTCGCAAGGCACAAGATGCCCGTTTGAATGCTGAAGCCGCAGCCGCCGCTGCGATGAACGCCCGTGTC
ATCGCTTCCGCCGAATCCGAGGCCAGTGAAGATCTGGAGAATCGCGCTAGTGTGGCGCGTGCCAGTGCGGCCGGTGCC
GCTGAGGCAAAGGCTATCGCCACCGATGCCGGCGCCACTGCCGAGATCGCGGCCTACAGTTGGGCCAAGAAGGGCGAA
CTGATCAACCCCGGCCCGTTGCCGAAGATCATCAGCGTCAACGCCGATCTGTCCAAGAGCGAGGTCGAGGCCATGAAG
ATCACCCGGGGTCAAGTACAGGAAGTCAAGAAAATCAGCACTCACAAAGGTGGCTGGGGATGGGAAAGGAAGGAAGG
TCGAAGGTATCTTCCAACGCTAGTGCCAGAGCTAGTGCCAGCGCCAATGCAGCCGCCGGTAGCCTCGGCAGCAAATGG
GGAAGACAACTATCCGCATCATCCGCGTCGGCTGACGCCAACGCCGAAGCCGACAGCCAGTTGCTGAAAGTGTGGTGA

GAF1 (SEQ ID NO:65)
ATGAAGATCCCAGCGATAATCGCAACGACCCTCCTTCTCTGGGGTTTCGCCGACGCCAGCAAGTCGTACCTCTTAGGC
TCATCCGCGTCTGCTTCCGCTTCCGCTTCCGCCTCGGCATCAGCGGGAGGAAGCACCGGCGGCGTCGGCGTCGGATCT
GTAATATCCGGTGGCAACAACATCATCAGAGGAGCTTCGACCACATCCGTGACATTGGCAGCCGCCGCAGCGGAGGCC

Figure 11 Cont.

AAGGCAGCTCTGAATGCTGGAAAAGCGACTGTCGAAGAGCAAAGGGAAGCGTTACAGTTGCTCACCGCGTCCGCTGAA
AAAAACGCCGAGGCGCGTTCCTTGGCCGACGATGCGGCCGTTCTAGTTCAGGGTGCCGCTGAGGCGCAATCGGTCGCC
gCCGCGAAGACGGTCGCGGTCGAGCAAGGATCCAACTCTCTGGATGCAGCTGCAGCCGAAGCGGAAGCCGCCGCCGCC
GCATCCAGGGTATCGGCCCAGCAGGCACTCCAGGCCGCGCAGACCTCCGCCGCCGCTATTCAAACCGCTGCCGGTAGC
GCCCTGACGGCTCTCAAATTGGCACGCAAACAGGAAGCGGAATCCAATAATGCCGCCGAACAGGCAAATAAAGCATTG
GCCTTAAGTCGCGCAGCCAGCGCTGCCACTCAACGAGCCGTGGCAGCTCAGAACGCGGCTGCCGCCATCAGCGGCTTCG
GCTGGAGCCGCACAAGCTGAGGCAAGGAACGCCTACGCCAAAGCCAAAGCAGCGATAGCTGCTCTTACGGCCGCCCAA
AGAAATTACGCCGCGGCCAAGGCTAGCGCAAGCGCGGGTAGCGTGGTGGCCGAACAAGATGCTCAATCTAGAGCGGCC
GATGCCGAGGTGAACGCCGTTGCCCAAGCCGCTGCCCGAGCCAGCGTTCGCAATCAGGAGATCGTTGAAATCGGCGCG
GAATTCGGCAACGCCAGCGGCGGAGTGATCTCGACCGGCACACGTTCTTCCGGAGGCAAGGGTGTCTCCGTTACCGCT
GGAGCTCAGGCTAGCGCGTCCGCTTCCGCGACCTCCTCCTCCTCCTCCTCCGGCATCAACAAAGGACATCCCAGA
TGGGGGCACAATTGGGGTTTAGGTTCTTCGGAAGCGTCAGCAAACGCTGAAGCCGAAAGCAGCGCTTCCTCTTATTCA
TCTTAA

GAF2 (SEQ ID NO:67)
ATGAAGATTCCAGCGATATTCGTGACGTCTCTGCTCGCCTGGGGACTCGCCAGCGGCGGAGTCATAGGTCCCGACACG
TCCTCATCGTCCCAGGCATCGGCATCGGCATCGGCGTCAGCATCGGCGTCGGCATCATCGTCGGCATCGATCGGTTAC
AACGAACTCCATAAATCGATCAATGCGCCCGCCTTGGCGGTCGGCGTCAAGAACGGCGGAGTGGATGTCGCCAAGGGC
GCGGCCGTTGTCGAaTCAGCGATATCCGACGTATCGACTCTAACCGATGATCGTACGTTGAACGGTCTCGCTATCATC
GGGAATAGCGCCGAGAGTCTGGCAAGAGCACAGGCTTCCTCGAGCGCCAGCGCCGGCGCAAAAGCCAATGCTCTCATC
AAACAATCGATAGCGGCTATAGAGATCACCGAAAAGGCAGAGTACCTTGCGTCGATCGTCGCCACCAAGGCAGCGAAG
GCCGCCGAGGCCACAGCGGCCGCGACCGCTCGCGCCACTGCCGTCGCCGAGGCTGCCAAGGTTTCCAGCGAGCAATTC
GCGGCCGAGGCACGCGCGGCCGCCGACGCCGAAGCCAAGGCCAACGCCGCTTCCATCATCGCCAACAAAGCGAACGCC
GTCCTCGCGGAGGCAGCCACCGGACTTAGCGCCAGCGCTGGCAAAGCCCAACAATCGGCGACCAGGGCGTTGCAAGCC
GCACGAGCTGCCGCTAAGGCTCAAGCCGAACTTACCCAGAAAGCCGCTCAAATCTTAGTCCTCATTGCTGAAGCCAAA
GCCGCCGTGAGCCGAGCAAGCGCCGATCAATCCGTCTGTACGTCCCAGGCACAAGCCGCCAGTCAGATTCAATCGAGA
GCCTCCGCGGCCGAATCCGCGGCATCGGCTCAATCGGAAGCCAACACCATTGCGGCCGAGGCGGTCGCTAGAGCTGAC
GCCGAGGCGCCCAGTCAAGCTCAAGCGTGGGCCGAATCCTTCAAACGCGAACTCTCGAGTGTCGTTTTGGAGGCCGAG
GCCAATGCCTCGGCTAGTGCCTCGGCTGGTGCCCTGGCCAGTGGTAGCAGCAGCTCGGGCGCGAGTTCCAGCGCGGAT
GCCAGCGCCGGAGCGAGCAGCTATGGATCCTTGGGCGGATATCGACACGGCGGAAGCTTCAGCGAGGCATCGGCAGCC
GCGTCAGCGGCCAGTCGCGCCGAGGCTGCGTAA

GAF3 (SEQ ID NO:69)
ATGAAGATTCCAGCGATACTCGTGACGTCCTTCCTCGCCTGGGGACTGGCCAGCGGGGGTGTCCCTAAAGAGTTGGGA
ACTTCCATTTCTTCCGCGTCCGCATCCGCATCCGCATCCGCATCCGCGACCGCGTCCTCCAGTAGCAAGAATGTTCAC
TTATTACCATTGAAAAGCGAGCATCGCATCGTAATTGACAAGTCAAAATTCAACATCAGAAAGGTAGTGTTGAGCGCA
ATCGATGAGATCAACGGCGCGCCCAACATCGGTCTGGGATTGAAACAGGTCAGTTTGGCGCTCGCAAAAGCCCAGGCT
AGTGCTCAATCGAGCGCCGAGGCATTGGCAATCATCAAGAAAATCGTCGCGCTCCTCATCTCGGCCTACGTCAGAGCA
GCCGAGGCCGCGGCTCGAGCATCCGCCGAAGCTTTAGCTACCGTTAGGGCTGCGGAACAAGCGCAAAAAATTGCTGAA
GCGAAGGGTAGAGCGGCTGCTGAGGCGCTCTCCGAGTTAGTCGAGGCGTCCCAGAAGGCCGATGCGGCGGCCGCGGGA
ACGACGGACGCGATCGAACGCACCTACCAGGATGCCAGAGCGGCCACTTCCGCACAGACCAAGGCCAGCGGCGAAGCC
GAGAATGCTAATCGCAATGCTGCCGCCACCCTCGCGGCGGTCTTGAGCATCGCTAAGGCCGCCTCCGGTCAAGGAGGC
ACTCGAGCCGCTGTCGATGCAGCTGCTGCCGCTGCCGCGCCAGCCGCTCTCGCATGCTAAAGCTAACGCGGTTTCGCAA
GCTACCAGCAAAGCAGCCGCTGAAGCTAGAGTCGCGGCTGAGGAGGCAGCATCCGCCCAGGCATCCGCCTCAGCAAGC
GCACAGCTGACCGCACAATTAGAGGAGAAAGTCAGCGCCGATCAACAAGCAGCCTCCGCCAGTACTGATACCTCCGCT
GCTATAGCCGAGGCTGAAGCTGCCGCGTTAGCGTCCACCGTCAACGCGATCAACGACGGAGTGGTCATCGGATTAGGA
AATACCGCCAGTTCTTCTGCCCAAGCTTCCGCACAGGCCAGTGCTCTCGCTCGCGCAAAAAATGCGCGCCCTAAAATA
AAGGGCTGGTACAAAATCGGAGGCGCGACTTCCGCTTCTGCAAGCGCATCGGCCAGCGCTTCCGCCCAGTCATCCTCG
CAAGGACTGGTATACTAG

GAF4 (SEQ ID NO:71)
ATGAAGATTCCAGCGATACTTGCGACGTCCCTTTTCGTCTGGGGTCTTGTCGGCGCCAGCGAACTCGTCGGATCGGAC
GCGAGCGCGACGGCATCTGCTGAAGCGTCAGCATCGTCATCGCATACGGTAGCAAGTATGGTATTGGTAGTGGTGCT
GTCTCCGGTGCATCAGCCAGCGCCTCTGCCAGCGCGTCTGCTAGCGCATCAGCCAGCAGTGCTCCCGCGATCGAAGGA
GTAAACGTTGGCACCGGAGTCAGTAACACCGCTTCCGCGTCCGCAGAAGCTCTCTCCCGTGGACTCGGCATCGGACaA
GCGGCTGCCGAAGCGCAAGCCGCTGCCGCTGGCCAAGCGGCGATCGCTGCGAAATCGTGCGCGCTAGCGGCCAAGAGC
ACCGCTCAAGCGGTTGCCCTGGTTGAGAAAGTGGCCCGCGCCGAGGTAGATCTGGCCGAAAGCGCGAGAAAGGCTACA
AGATTATCGGCAGAAGCAGCCAAGGCAGCGGCGAAGTCGAGAAGGACCTCGTCGGTCTGAGAGGGGCTGCCGGTAAA
CTGAATCTGGCTGCGAGAGCCGGTTCTAAAGCCCAAGAACGCGCAACGAAGACTCTATAGAGGCTAACGAACTTGCC
CAAGCAACGGCCGCCGCCGGTGCCGAGGCTGAAGCCAAGGCGAATGCCGCCCAGGAGGCAGGCGCCTCCGCTTTGGCC

```
ATCGCCCAAGCCGCCCTTAACATCGAGCAAGAGACTGTTAAATTGACCCGCCAGGCCCAGAATACTCGTCTCAGATCT
GAAAATATTCTCGCCGCGGCCAGCAATGCCCGCGCCATCGCTTCCGCTGAGGCCGAGGCCAGTAGTGATTTGAATAAT
CGTGCGAATGCAGCGCGTTCCAATGCCCGAGCTGCTGCCGAGACCAGAGCCGTAGCTACCGAAGCCGCTTCTACCGCC
GAGATCGCAGCTTATAGTTCATCCGAGAAAGGCGagATCACCAATCCCGGTCCTCTGCCCAAGATCGTCAGTGTTACC
GCAGGTCTGACCCagAACGAAATAGCGGGATCAGGAGCGGCCGCTAGTGCTAGTGCCAGTGCTCTTGCCAGTGCCAGT
GCCGGTGCCGGTGCCGGTGCAGGTGCAGGAGCCGGTGCAAGTGCAGGAGCCGGTGCAGTTGCAGGTgCAGGAGCCGGT
GCAGGAGCCGGTGCTAGTGCCGGAGCGAGTGCCGGAGCGAATGCCGGTGCCGGTGCCAGCAGTTTACTCTTGCCGCAG
AGTAAACTCCATCCAATCTCCAGGTCTTCCGCCTCTGCCTCCGCTTCCGCCGAGGCCGAAGCTAACAGTTCGGCGTAT
GCGTAA

MalFl (SEQ ID NO:75)
ATGGCAGCGTCGAACAAAATCATCTTCAGCTTTTTAGCTATTGTTCTATTACAACTTGCCACACACTGTTCATCAACA
GCTGTATTGATTTCTGGTTCGGCTGCTGGTGCTTCCTCACACAATGCTGCTGGTGCAGCTGCAGCAGCCAGAGCTGCC
TTAGGCGCTTCTGGGGCTGCAGGTTTAGGTGCTGCATCTGGTGCTGCAAGAAGAAACGTAGCAGTTGGTGCTAACGGT
GCCGCCGCCGCTAGTGCTGCAGCTGCAGCTGCCAGACGAGCTGGCGCTATTGGCCTAAATGGAGCAGCTGGAGCTAAT
GTAGCTGTCGCTGGTGGCAAAAAAGGAGGTGCTGCTGGATTAAATGCTGGCGCTGGTGCTTCTTTAGTATCTGCAGCT
GCAAGACGAAATGGAGCCCTTGGACTTAACGGTGCAGCTGGAGCAAATCTCGCAGCAGCTGGTGGCAAAAAAGGAGGT
GCTATTGGATTAAACGCTGGAGCATCAGCCAATGTTGGTGCCGCTGCTGCCAAGAAAAATGGAGCCATAGGACTTAAC
TCAGCTGCTTCAGCTAATGCTGCCGCTGCCGCTGCTAAAAAAGGTGGAGCCATTGGATTGAATGCTGGAGCTTCAGCA
AATGCTGCTGCTGCCGCTGCCAAGAAGAGTGGAGCTGTTGGATTAAATGCTGGAGCTTCTGCTAACGCTGCTGCTGCT
GCTGCCAAGAAAAGTGGAGCTGTTGCTGCCAATTCCGCTGCTTCAGCAAATGCAGCTGCTGCTGCACAAAAGAAAGCC
GCTGCTGATGCCGCAAATGCTGCTGCTTCTGAAAGTGCTGCTGCTGCTGCAGCCAAGAAAGCCGCCGCTGTTGCTGAA
AATGCAGCTGCCACCGCCAATGCCGCTTCAGCTTTACGTAAAAATGCATTAGCCATTGCCAGTGATGCAGCAGCTGTC
CGTGCTGATGCCGCTGCCGCCGCCGCTGACGATGCTGCTAAAGCTAACAACGCTGCTTCCCGTGGAAGTGATGGTTTA
ACTGCCCGCGCCAATGCCGCCACTTTAGCCAGTGATGCTGCCCGTAGAGCTAGCAATGCAGCAACAGCTGCCAGCGAT
GCTGCCACTGACCGATTGAACGCCGCCACCGCTGCTAGCAACGCTGCCACTGCTCGTGCAAATGCCGCCACACGTGCC
GATGATGCCGCCACTGATGCCGACAATGCTGCTTCAAAGGCCAGTGATGTATCAGCTATTGAAGCCGACAACGCTGCA
CGAGCTGCTGATGCTGATGCTATCGCTACCAACCGTGCCGCTGAAGCAAGCGATGCTGCTGCTATTGCCGCTGATGCC
GCTGCCAATGCTGCTGATGCCGCTGCCCAATGTAATAACAAAGTTGCCCGAGTAAGTGATGCCTTAGCTCTCGCCGCT
AATGCTGCTGCCCGAGGATCTGATGCCGCCGCTGAAGCTCAAGATGCTGTTGCCAGAGCAAGTGACGCTGCCGCTGCC
CAAGCTGATGGTGTTGCCATTGCCGTAAATGGAGCTACTGCGAGAGACTCAGCAATTGAAGCCGCTGCTACTGCTGGA
GCTGCCCAAGCTAAAGCCGCTGGACGTGCTGGAGCTGCTGCAGCTGGTTTAAGAGCTGGTGCCGCTAGAGGTGCTGCC
GCTGGTAGTGCCCGCGGTCTAGCTGGAGGATTAGCTGCAGGTTCCAATGCTGGAATCGCGGCTGGTGCAGCTTCTGGA
TTAGCAAGAGGCGCAGCTGCTGAAGTTTGCGCAGCTAGAATAGCATTGTAA
```

Figure 11 Cont.

Xenosin - Inclusion of intron
ATGAAATACATGCTCTTGTTGCTATCTATATTCATCTGTGCACATATTGTATGCGCAGGCGTAAATACAG
AATTAAAAAAAGATGGTGAACTAAAGGAAGAGTCTTATGAGAAAAGCGAGTCAAAGAGTTTAAAAGAAAT
TAAAGAAGAACGTGCTTCAAAATCAAAAAGTGAACGTTTGAAGATTCGTGAAGGTAATTCGTGAGATTCA
AGATTCAAATCAATTAAATTTGAAAATTATGAAAGTAGTATTGTTAAATTATAAGATAGAAGATTTTATC
TAAAAAATAATAAATTAAGCTTTTTGTATTTTTGGATATTGTAGATATTTTTAATATAGAATTCTTATAA
AGTTAAAAAATATTTTATAAATTAAACAACTTTTTATTATTTTTATGATCTAAAAATTAAAAATTTCAAG
TTAAAGTTCAAATTAAAAATTTGTAAAAAATATGGAAAAAACATAAAAATTGAATTTGTTGTAATTTAAA
AAGGATTTTTATTATTTATTGATTAATTATGAATATAAGTTCGAAAAATCCTAAATATTAATGTTTAAAA
TTTTAATTCTTAACAAAATATATTTAATTTAATTCTTAACAAAGATACATTTAAAGAATTTCGCAAATTT
AAAAATTAGGTTTTTAATTTTAAGAATCAAATGGTAAAAAACATTTTAAATTTGAAATATATAAAAGTAA
ATCTTTTAATCGACAAACGGATGAATTTATTGATTAGAAAAACGCGAAGAGGAAGAAAAATCCAAGAGTC
TGAATCTGGTCGTGGTCAGAGAAAAGATTACCAAACTTTCTTCATGGCTCAAAGAAGAGAAAGATATCAG
TCCTCTTTTGGAAGAAAAAAATGGCAAAGGTCTATTGGGTTTGGAAGATGTCACGGACGAGTTAAATATC
GCTCTTAAATCGTTGAAGGAGGGCAAAAAGTTTGATACTTGGAAATTCGAGAAAGGTAGCGAAGACGTTC
GTTCTTTGGAAGAACTTGATACGAGCGTCGTTGAACTTTTAAAATTAATAAAGGAAGGAAAAACTGACCA
TGGTGCTATAGATTTGGAGAAGAATGGTAAGGTACTTGTAGATTTGGAAAAAATCTCAGAAAACATACTT
GAAACTTGTGGATCACAAAAGAAGACTGTGGAAGTTGTAGATGATAAAGACAAAAAATGGAATAAAGAAT
CAGGTTGGAAAAAAAATCTAAATGATCTAGATTGGAAAAAAGATTTAGATAAAGATAAAGTTGGTGGCGG
TTTGCTTGGCGGTTTAAGTGGCCTCTTAAATAGTTTAAAATCAGAAAAAGGTCTTCTAGGTCTTTTGAAT
AAGAATCAAATTGAGTTATTAATTCCTTTAATCAGTGAGATAAAAAAGAAAAATATAGATTTTAATCTCT
TCGATTCTGTTGATTCTGTCGAAAGAAATTTAGACTTGAAACTTTTCACAAGTTCTGTTTCAAAAGTTAC
TGAATTATTAAATAAAGGAATCGATATTCAAACAATTTTGAATGCGAAAAATGGAGATGAATTCGATTTA
AGCGGCAAAGAATTGAAAAACGTCAAAGGGATATTTGGTTTGATTGGAAGTTTGAAACGCTCATTAGGAT
TAGAAAATATATTGAACTTACCGTTTAAACGTATACCTCTGCTTAAATTA

Figure 12

SILK PROTEINS

FIELD OF THE INVENTION

The present invention relates to silk proteins, as well as nucleic acids encoding such proteins. The present invention also relates to recombinant cells and/or organisms which synthesize silk proteins. Silk proteins of the invention can be used for a variety of purposes such as in the production of personal care products, plastics, textiles, and biomedical products.

BACKGROUND OF THE INVENTION

Silks are fibrous protein secretions that exhibit exceptional strength and toughness and as such have been the target of extensive study. Silks are produced by over 30,000 species of spiders and by many insects. Very few of these silks have been characterised, with most research concentrating on the cocoon silk of the domesticated silkworm, *Bombyx mori* and on the dragline silk of the orb-weaving spider *Nephila clavipes*.

In the Lepidoptera and spider, the fibroin silk genes code for proteins that are generally large with prominent hydrophilic terminal domains at either end spanning an extensive region of alternating hydrophobic and hydrophilic blocks (Bini et al., 2004). Generally these proteins comprise different combinations of crystalline arrays of β-pleated sheets loosely associated with β-sheets, β-spirals, α-helices and amorphous regions (see Craig and Riekel, 2002 for review).

As silk fibres represent some of the strongest natural fibres known, they have been subject to extensive research in attempts to reproduce their synthesis. However, a recurrent problem with expression of Lepidopteran and spider fibroin genes has been low expression rates in various recombinant expression systems due to the combination of the repeating nucleotide motifs in the silk gene that lead to deleterious recombination events, the large gene size and the small number of codons used for each amino acid in the gene which leads to depletion of tRNA pools in the host cells. Recombinant expression leads to difficulties during translation such as translational pauses as a result of codon preferences and codon demands and extensive recombination rates leading to truncation of the genes. Shorter, less repetitive sequences would avoid many of the problems associated with silk gene expression to date.

In contrast to the extensive knowledge that has accumulated about the Lepidopteran (in particular the cocoon silk of *Bombyx mori*) and spider (in particular the dragline silk of *Nephila clavipes*) little is known about the chemical composition and molecular organisation of other insect silks.

In the early 1960s, the silk of the aculeate Hymenopteran was shown to have an alpha-helical structure by X-ray diffraction patterns obtained from silk fibres drawn from the salivary gland of honeybee larvae (Rudall, 1962). As well as demonstrating that this silk was helical, the patterns obtained were indicative of a coiled-coil system of alpha-helical chains (Atkins, 1967). Similar X-ray diffraction patterns have been obtained for cocoon silks from other Aculeata species including the wasp *Pseudopompilus humbolti* (Rudall, 1962) and the bumblebee, *Bombus lucorum* (Lucas and Rudall, 1967).

In contrast to the alpha-helical structure described in the Aculeata silks, the silks characterised from a related Glade to the aculeata, the Ichneumonoidea, have parallel-β structures. X-ray diagrams for four examples of this structure have been described in the Braconidae (*Cotesia*(=*Apenteles*) *glomerate*; *Cotesia*(=*Apenteles*) *gonopterygis*; *Apenteles bignelli*) and three in Ichneumonidae (*Dusona* sp.; *Phytodietris* sp.; *Branchus femoralis*) (Lucas and Rudall, 1967). In addition the sequence of a single Braconidae (*Cotesia glomerate*) silk has been described (Genbank database accession number AB188680; Yamada et al., 2004). This partial protein sequence consists of a highly conserved 28 X-asparagine repeat (where X is alanine or serine) and is not predicted to contain coiled coil forming heptad repeats. Extensive analysis of the amino acid composition of the cocoon silks of the Braconidae has shown that the silks from the subfamily Microgastrinae are unique in their high asparagine and serine content (Lucas et al., 1960; Quicke et al., 2004). Related subfamilies produce silks with significantly different amino acid compositions suggesting that the Microgastrinae silks have evolved specifically in this subfamily (Yamada et al., 2004). The partial cDNA of *Cotesia glomerata* was isolated using PCR primers designed from sequence obtained from internal peptides derived from isolated cocoon silk proteins. The predicted amino acid composition of this partial sequence closely resembles the amino acid composition of the extensively washed silk from this species.

The structure of many of the silks within other non aculeate Apocrita and within the rest of the Hymenoptera (Symphata) are most commonly parallel-β sheets, with both collagen-like and polyglycine silks produced by the Tenthredimidae (Lucas and Rudall, 1967).

Honeybee silk proteins are synthesised in the middle of the final instar and can be imaged as a mix of depolymerised silk proteins (Silva-Zacarin et al., 2003). As the instar progresses, water is removed from the gland and dehydration results in the polymerisation of the silk protein to form well-organised and insoluble silk filaments labelled tactoids (Silva-Zacarin et al., 2003). Progressive dehydration leads to further reorganisation of the tactoids (Silva-Zacarin et al., 2003) and possibly new inter-filamentary bonding between filaments (Rudall, 1962). Electron microscope images of fibrils isolated from the honeybee silk gland show structures of approximately 20-25 angstroms diameter (Flower and Kenchington, 1967). This value is consistent with three-, four-, or five-stranded coiled coils.

The amino acid composition of the silks of various aculeate Hymenopteran species was determined by Lucas and Rudall (1967) and found to contain high contents of alanine, serine, the acid residues, aspartic acid and glutamic acids, and reduced amounts of glycine in comparison to classical fibroins. It was considered that the helical content of the aculeate Hymenoptera silk was a consequence of a reduced glycine content and increased content of acidic residues (Rudall and Kenchington, 1971).

Little is known about the larval silk of the lacewings (Order: Neuroptera). The cocoon is comprised of two layers, an inner solid layer and an outer fibrous layer. Previously the cocoon was described as being comprised of a cuticulin silk (Rudall and Kenchington, 1971), a description that only related to the inner solid layer. LaMunyon (1988) described a substance excreted from the malphigian tubules that made up the outer fibres. After deposition of this layer, the solid inner wall was constructed from secretions from the epithelial cells in the highly villous lumen (LaMunyon, 1988).

It is also known that lacewing larva produce a proteinaceous adhesive substance from the malpighian tubules throughout all instars to stick the larvae to substrates, to glue items of camouflage on to the larvae's back or to entrap prey (Speilger, 1962). In the genus *Lomamyia* (Bethothidae), the larvae produce the silk and adhesive substance at the same time and it has been postulated that these two substances may well be the same product (Speilger, 1962). The adhesive secretion is highly soluble and is also thought to be associated with defense against predators (LaMunyon & Adams, 1987).

Considering the unique properties of silks produced by insects such as Hymenopterans and Neuropterans, there is a need for the identification of novel nucleic acids encoding silk proteins from these organisms.

SUMMARY OF THE INVENTION

The present inventors have identified numerous silk proteins from insects. These silk proteins are surprisingly different to other known silk proteins in their primary sequence, secondary structure and/or amino acid content.

Thus, in a first aspect the present invention provides a substantially purified and/or recombinant silk polypeptide, wherein at least a portion of the polypeptide has a coiled coil structure.

As known in the art, coiled coil structures of polypeptides are characterized by heptad repeats represented by the consensus sequence (abcdefg)$_n$, with generally hydrophobic residues in position a and d, and generally polar residues at the remaining positions. Surprisingly, the heptads of the polypeptides of the present invention have a novel composition when viewed collectively—with an unusually high abundance of alanine in the 'hydrophobic' heptad positions a and d. Additionally, there are high levels of small polar residues in these positions. Furthermore, the e position also has high levels of alanine and small hydrophobic residues.

Accordingly, in a particularly preferred embodiment, the portion of the polypeptide that has a coiled coil structure comprises at least 10 copies of the heptad sequence abcdefg, and at least 25% of the amino acids at positions a and d are alanine residues.

In a further preferred embodiment, the portion of the polypeptide that has a coiled coil structure comprises at least 10 copies of the heptad sequence abcdefg, and at least 25% of the amino acids at positions a, d and e are alanine residues.

In a further preferred embodiment, the portion of the polypeptide that has a coiled coil structure comprises at least 10 copies of the heptad sequence abcdefg, and at least 25% of the amino acids at position a are alanine residues.

In a further preferred embodiment, the portion of the polypeptide that has a coiled coil structure comprises at least 10 copies of the heptad sequence abcdefg, and at least 25% of the amino acids at position d are alanine residues.

In a further preferred embodiment, the portion of the polypeptide that has a coiled coil structure comprises at least 10 copies of the heptad sequence abcdefg, and at least 25% of the amino acids at position e are alanine residues.

In a particularly preferred embodiment, the at least 10 copies of the heptad sequence are contiguous.

In a further preferred embodiment, the portion of the polypeptide that has a coiled coil structure comprises at least 5 copies of the heptad sequence abcdefg, and at least 15% of the amino acids at positions a and d are alanine residues.

In a further preferred embodiment, the portion of the polypeptide that has a coiled coil structure comprises at least 5 copies of the heptad sequence abcdefg, and at least 15% of the amino acids at positions a, d and e are alanine residues.

In a further preferred embodiment, the portion of the polypeptide that has a coiled coil structure comprises at least 5 copies of the heptad sequence abcdefg, and at least 15% of the amino acids at position a are alanine residues.

In a further preferred embodiment, the portion of the polypeptide that has a coiled coil structure comprises at least 5 copies of the heptad sequence abcdefg, and at least 15% of the amino acids at position d are alanine residues.

In a further preferred embodiment, the portion of the polypeptide that has a coiled coil structure comprises at least 5 copies of the heptad sequence abcdefg, and at least 15% of the amino acids at position e are alanine residues.

In a particularly preferred embodiment, the at least 5 copies of the heptad sequence are contiguous.

In one embodiment, the polypeptide comprises a sequence selected from:
i) an amino acid sequence as provided in any one of SEQ ID NO:1, SEQ ID NO:2, SEQ ID NO:22, SEQ ID NO:23, SEQ ID NO:40, SEQ ID NO:41, SEQ ID NO:56, and SEQ ID NO:57;
ii) an amino acid sequence which is at least 30% identical to any one or more of SEQ ID NO:1, SEQ ID NO:2, SEQ ID NO:22, SEQ ID NO:23, SEQ ID NO:40, SEQ ID NO:41, SEQ ID NO:56, and SEQ ID NO:57; and
iii) a biologically active fragment of i) or ii).

In another embodiment, the polypeptide comprises a sequence selected from:
i) an amino acid sequence as provided in any one of SEQ ID NO:3, SEQ ID NO:4, SEQ ID NO:24, SEQ ID NO:25, SEQ ID NO:42, SEQ ID NO:43, SEQ ID NO:58, and SEQ ID NO:59;
ii) an amino acid sequence which is at least 30% identical to any one or more of SEQ ID NO:3, SEQ ID NO:4, SEQ ID NO:24, SEQ ID NO:25, SEQ ID NO:42, SEQ ID NO:43, SEQ ID NO:58, and SEQ ID NO:59; and
iii) a biologically active fragment of i) or ii).

In another embodiment, the polypeptide comprises a sequence selected from:
i) an amino acid sequence as provided in any one of SEQ ID NO:5, SEQ ID NO:6, SEQ ID NO:26, SEQ ID NO:27, SEQ ID NO:44, SEQ ID NO:45, SEQ ID NO:60, and SEQ ID NO:61;
ii) an amino acid sequence which is at least 30% identical to any one or more of SEQ ID NO:5, SEQ ID NO:6, SEQ ID NO:26, SEQ ID NO:27, SEQ ID NO:44, SEQ ID NO:45, SEQ ID NO:60, and SEQ ID NO:61; and
iii) a biologically active fragment of i) or ii).

In another embodiment, the polypeptide comprises a sequence selected from:
i) an amino acid sequence as provided in any one of SEQ ID NO:7, SEQ ID NO:8, SEQ ID NO:28, SEQ ID NO:29, SEQ ID NO:46, SEQ ID NO:47, SEQ ID NO:62, and SEQ ID NO:63;
ii) an amino acid sequence which is at least 30% identical to any one or more of SEQ ID NO:7, SEQ ID NO:8, SEQ ID NO:28, SEQ ID NO:29, SEQ ID NO:46, SEQ ID NO:47, SEQ ID NO:62, and SEQ ID NO:63; and
iii) a biologically active fragment of i) or ii).

In a further embodiment, the polypeptide comprises a sequence selected from:
i) an amino acid sequence as provided in SEQ ID NO:72 or SEQ ID NO:73;
ii) an amino acid sequence which is at least 30% identical to SEQ ID NO:72 and/or SEQ ID NO:73; and
iii) a biologically active fragment of i) or ii).

Further silk proteins which co-associate with proteins of the first aspect have been identified. One of these proteins (SEQ ID NO:10) is predicted to have 41% alpha-helical, 8% beta-sheet and 50% loop secondary structure by PROFsec, and therefore is classified as a mixed structure protein. MARCOIL analysis of this protein predicted only a short region of heptad repeats characteristic of proteins with a coiled coil structure.

Accordingly, in a second aspect, the present invention provides a substantially purified and/or recombinant silk polypeptide which comprises a sequence selected from:

i) an amino acid sequence as provided in any one of SEQ ID NO:9, SEQ ID NO:10 and SEQ ID NO:30;

ii) an amino acid sequence which is at least 30% identical to any one or more of SEQ ID NO:9, SEQ ID NO:10 and SEQ ID NO:30; and iii) a biologically active fragment of i) or ii).

Without wishing to be limited by theory, it appears that four proteins of the first aspect become intertwined to form a bundle with helical axes almost parallel to each other, and this bundle extends axially into a fibril. Furthermore, it is predicted that in at least some species such as the honeybee and bumblebee the proteins of the second aspect act as a "glue" assisting in binding various bundles of coiled coil proteins of the first aspect together to form a fibrous protein complex. However, silk fibers and copolymers can still be formed without a polypeptide of second aspect.

In a preferred embodiment, a polypeptide of the invention can be purified from, or is a mutant of a polypeptide purified from, a species of Hymenoptera or Neuroptera. Preferably, the species of Hymenoptera is *Apis mellifera, Oecophylla smaragdina, Myrmecia foricata* or *Bombus terrestris*. Preferably, the species of Neuroptera is *Mallada signata*.

In another aspect, the present invention provides a polypeptide of the invention fused to at least one other polypeptide.

In a preferred embodiment, the at least one other polypeptide is selected from the group consisting of: a polypeptide that enhances the stability of a polypeptide of the present invention, a polypeptide that assists in the purification of the fusion protein, and a polypeptide which assists in the polypeptide of the invention being secreted from a cell (for example secreted from a plant cell).

In another aspect, the present invention provides an isolated and/or exogenous polynucleotide which encodes a silk polypeptide, wherein at least a portion of the polypeptide has a coiled coil structure.

In one embodiment, the polynucleotide comprises a sequence selected from:

i) a sequence of nucleotides as provided in any one of SEQ ID NO:11, SEQ ID NO:12, SEQ ID NO:31, SEQ ID NO:32, SEQ ID NO:48, SEQ ID NO:49, SEQ ID NO:64, and SEQ ID NO:65;

ii) a sequence of nucleotides encoding a polypeptide of the invention, iii) a sequence of nucleotides which is at least 30% identical to any one or more of SEQ ID NO:11, SEQ ID NO:12, SEQ ID NO:31, SEQ ID NO:32, SEQ ID NO:48, SEQ ID NO:49, SEQ ID NO:64, and SEQ ID NO:65, and iv) a sequence which hybridizes to any one of i) to iii) under stringent conditions.

In another embodiment, the polynucleotide comprises a sequence selected from:

i) a sequence of nucleotides as provided in any one of SEQ ID NO:13, SEQ ID NO:14, SEQ ID NO:33, SEQ ID NO:34, SEQ ID NO:50, SEQ ID NO:51, SEQ ID NO:66, and SEQ ID NO:67;

ii) a sequence of nucleotides encoding a polypeptide of the invention, iii) a sequence of nucleotides which is at least 30% identical to any one or more of SEQ ID NO:13, SEQ ID NO:14, SEQ ID NO:33, SEQ ID NO:34, SEQ ID NO:50, SEQ ID NO:51, SEQ ID NO:66, and SEQ ID NO:67, and iv) a sequence which hybridizes to any one of i) to iii) under stringent conditions.

In another embodiment, the polynucleotide comprises a sequence selected from:

i) a sequence of nucleotides as provided in any one of SEQ ID NO:15, SEQ ID NO:16, SEQ ID NO:35, SEQ ID NO:36, SEQ ID NO:52, SEQ ID NO:53, SEQ ID NO:68, and SEQ ID NO:69;

ii) a sequence of nucleotides encoding a polypeptide of the invention, iii) a sequence of nucleotides which is at least 30% identical to any one or more of SEQ ID NO:15, SEQ ID NO:16, SEQ ID NO:35, SEQ ID NO:36, SEQ ID NO:52, SEQ ID NO:53, SEQ ID NO:68, and SEQ ID NO:69, and iv) a sequence which hybridizes to any one of i) to iii) under stringent conditions.

In a further embodiment, the polynucleotide comprises a sequence selected from:

i) a sequence of nucleotides as provided in any one of SEQ ID NO:17, SEQ ID NO:18, SEQ ID NO:37, SEQ ID NO:38, SEQ ID NO:54, SEQ ID NO:55, SEQ ID NO:70, SEQ ID NO:71 and SEQ ID NO:76;

ii) a sequence of nucleotides encoding a polypeptide of the invention, iii) a sequence of nucleotides which is at least 30% identical to any one or more of SEQ ID NO:17, SEQ ID NO:18, SEQ ID NO:37, SEQ ID NO:38, SEQ ID NO:54, SEQ ID NO:55, SEQ ID NO:70, SEQ ID NO:71 and SEQ ID NO:76, and iv) a sequence which hybridizes to any one of i) to iii) under stringent conditions.

In another embodiment, the polynucleotide comprises a sequence selected from:

i) a sequence of nucleotides as provided in SEQ ID NO:74 or SEQ ID NO:75;

ii) a sequence of nucleotides encoding a polypeptide of the invention, iii) a sequence of nucleotides which is at least 30% identical to SEQ ID NO:74 and/or SEQ ID NO:75, and iv) a sequence which hybridizes to any one of i) to iii) under stringent conditions.

In a further aspect, the present invention provides an isolated and/or exogenous polynucleotide, the polynucleotide comprising a sequence selected from:

i) a sequence of nucleotides as provided in any one of SEQ ID NO:19, SEQ ID NO:20, SEQ ID NO:21, and SEQ ID NO:39;

ii) a sequence of nucleotides encoding a polypeptide of the invention, iii) a sequence of nucleotides which is at least 30% identical to any one or more of SEQ ID NO:19, SEQ ID NO:20, SEQ ID NO:21, and SEQ ID NO:39, and iv) a sequence which hybridizes to any one of i) to iii) under stringent conditions.

In a preferred embodiment, a polynucleotide can be isolated from, or is a mutant of a polynucleotide isolated from, a species of Hymenoptera or Neuroptera. Preferably, the species of Hymenoptera is *Apis mellifera, Oecophylla smaragdina, Myrmecia foricata* or *Bombus terrestris*. Preferably, the species of Neuroptera is *Mallada signata*.

In a further aspect, the present invention provides a vector comprising at least one polynucleotide of the invention.

Preferably, the vector is an expression vector.

In another aspect, the present invention provides a host cell comprising at least one polynucleotide of the invention, and/or at least one vector of the invention.

The host cell can be any type of cell. Examples include, but are not limited to, a bacterial, yeast or plant cell.

Also provided is a process for preparing a polypeptide according to the invention, the process comprising cultivating a host cell of the invention, or a vector of the invention, under conditions which allow expression of the polynucleotide encoding the polypeptide, and recovering the expressed polypeptide.

It is envisaged that transgenic plants will be particularly useful for the production of polypeptides of the invention. Thus, in yet another aspect, the present provides a transgenic plant comprising an exogenous polynucleotide, the polynucleotide encoding at least one polypeptide of the invention.

In another aspect, the present invention provides a transgenic non-human animal comprising an exogenous polynucleotide, the polynucleotide encoding at least one polypeptide of the invention.

In yet another aspect, the present invention provides an antibody which specifically binds a polypeptide of the invention.

In a further aspect, the present invention provides a silk fiber comprising at least one polypeptide of the invention.

Preferably, the polypeptide is a recombinant polypeptide.

In an embodiment, at least some of the polypeptides are crosslinked. In an embodiment, at least some of the lysine residues of the polypeptides are crosslinked.

In another aspect, the present invention provides a copolymer comprising at least two polypeptides of the invention.

Preferably, the polypeptides are recombinant polypeptides.

In an embodiment, the copolymer comprises at least four different polypeptide of the first aspect. In another embodiment, the copolymer further comprises a polypeptide of the second aspect.

In an embodiment, at least some of the polypeptides are crosslinked. In an embodiment, at least some of the lysine residues of the polypeptides are crosslinked.

As the skilled addressee will appreciate, the polypeptides of the invention have a wide variety of uses as is known in the art for other types of silk proteins. Thus, in a further aspect, the present invention provides a product comprising at least one polypeptide of the invention, a silk fiber of the invention and/or a copolymer of the invention.

Examples of products include, but are not limited to, personal care products, textiles, plastics, and biomedical products.

In yet a further aspect, the present invention provides a composition comprising at least one polypeptide of the invention, a silk fiber of the invention and/or a copolymer of the invention, and one or more acceptable carriers.

In one embodiment, the composition further comprises a drug.

In another embodiment, the composition is used as a medicine, in a medical device or a cosmetic.

In another aspect, the present invention provides a composition comprising at least one polynucleotide of the invention, and one or more acceptable carriers.

In a preferred embodiment, a composition, silk fiber, copolymer and/or product of the invention does not comprise a royal jelly protein produced by an insect.

In a further aspect, the present invention provides a method of treating or preventing a disease, the method comprising administering a composition comprising a drug for treating or preventing the disease and a pharmaceutically acceptable carrier, wherein the pharmaceutically acceptable carrier is selected from at least one polypeptide of the invention, a silk fiber of the invention and/or a copolymer of the invention.

In yet another aspect, the present invention provides for the use of at least one polypeptide of the invention, a silk fiber of the invention and/or a copolymer of the invention, and a drug, for the manufacture of a medicament for treating or preventing a disease.

In a further aspect, the present invention provides a kit comprising at least one polypeptide of the invention, at least one polynucleotide of the invention, at least one vector of the invention, at least one silk fiber of the invention and/or a copolymer of the invention.

Preferably, the kit further comprises information and/or instructions for use of the kit.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Fourier transform infrared spectra of the amide I and II regions of the silks: 1) honeybee silk, 2) bumblebee silk, 3) bulldog ant silk, 4) weaver ant silk 5) lacewing larval silk. All the silks have spectra expected of helical proteins. The Hymenopteran silks (ants and bees) have spectral maxima at 1645-1646 $cm^{-1}$ (labelled), shifted approximately 10 $cm^{-1}$ lower than a classical alpha-helical signal and broadened, as is typical of coiled-coil proteins (Heimburg et al., 1999).

Figure 2:
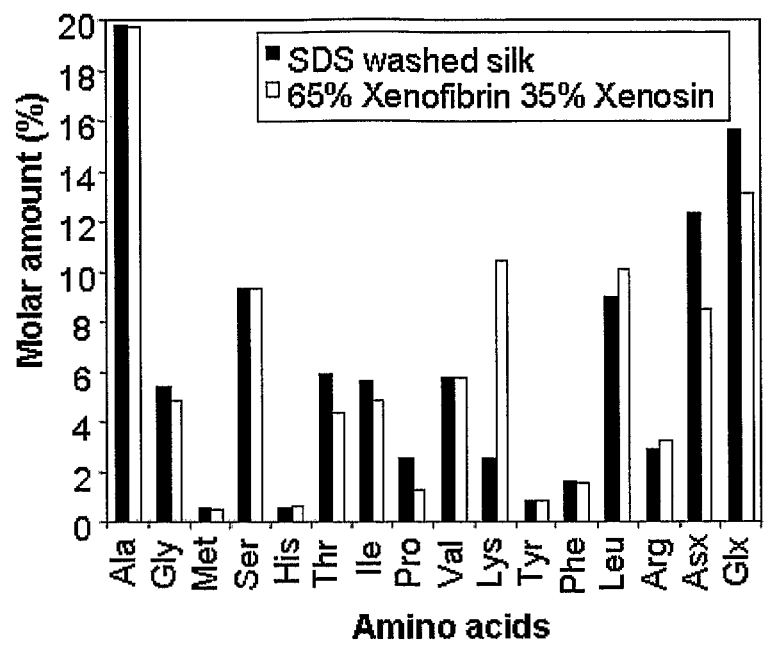

FIG. 2. Comparison of amino acid composition of SDS washed honeybee brood comb silk with amino acid composition of Xenospira proteins (namely, Xenospira1, Xenospira2, Xenospira3 and Xenospira4) (equimolar amounts totaling 65%) and Xenosin (35%).

Figure 3:
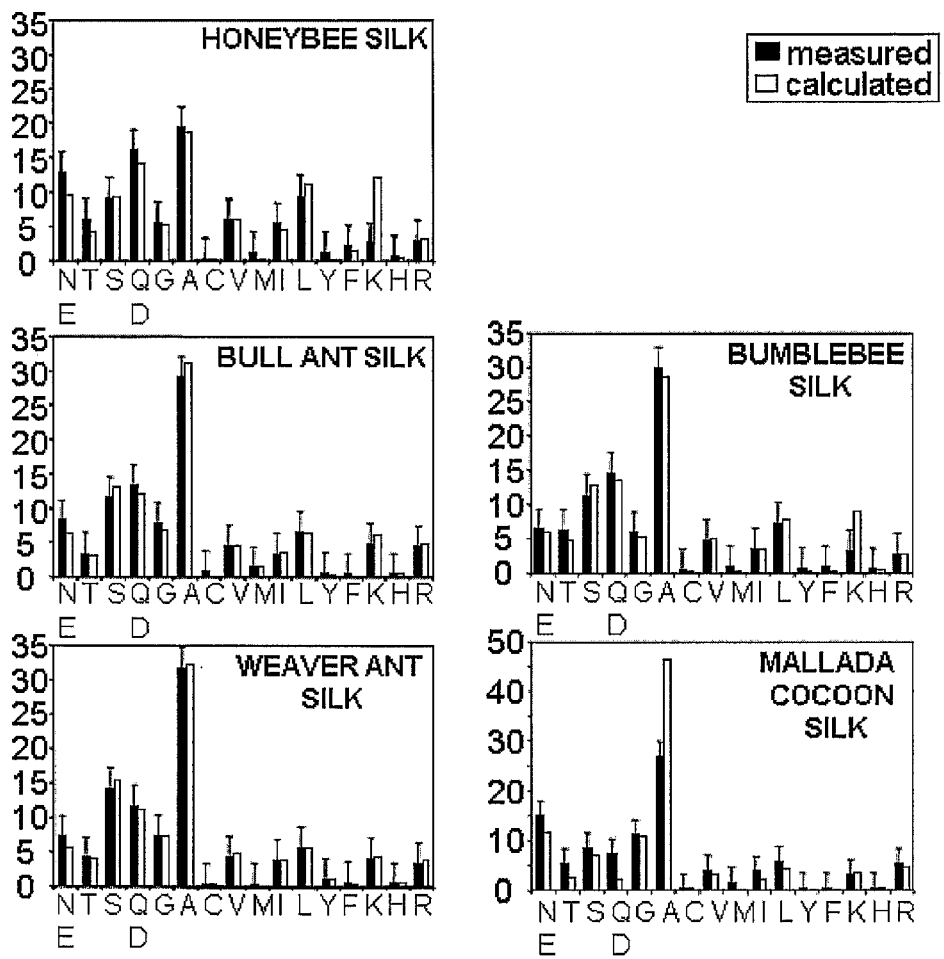

FIG. 3. Comparison of amino acid composition of silk with amino acid composition predicted from proteins encoded by silk genes.

Figure 4:
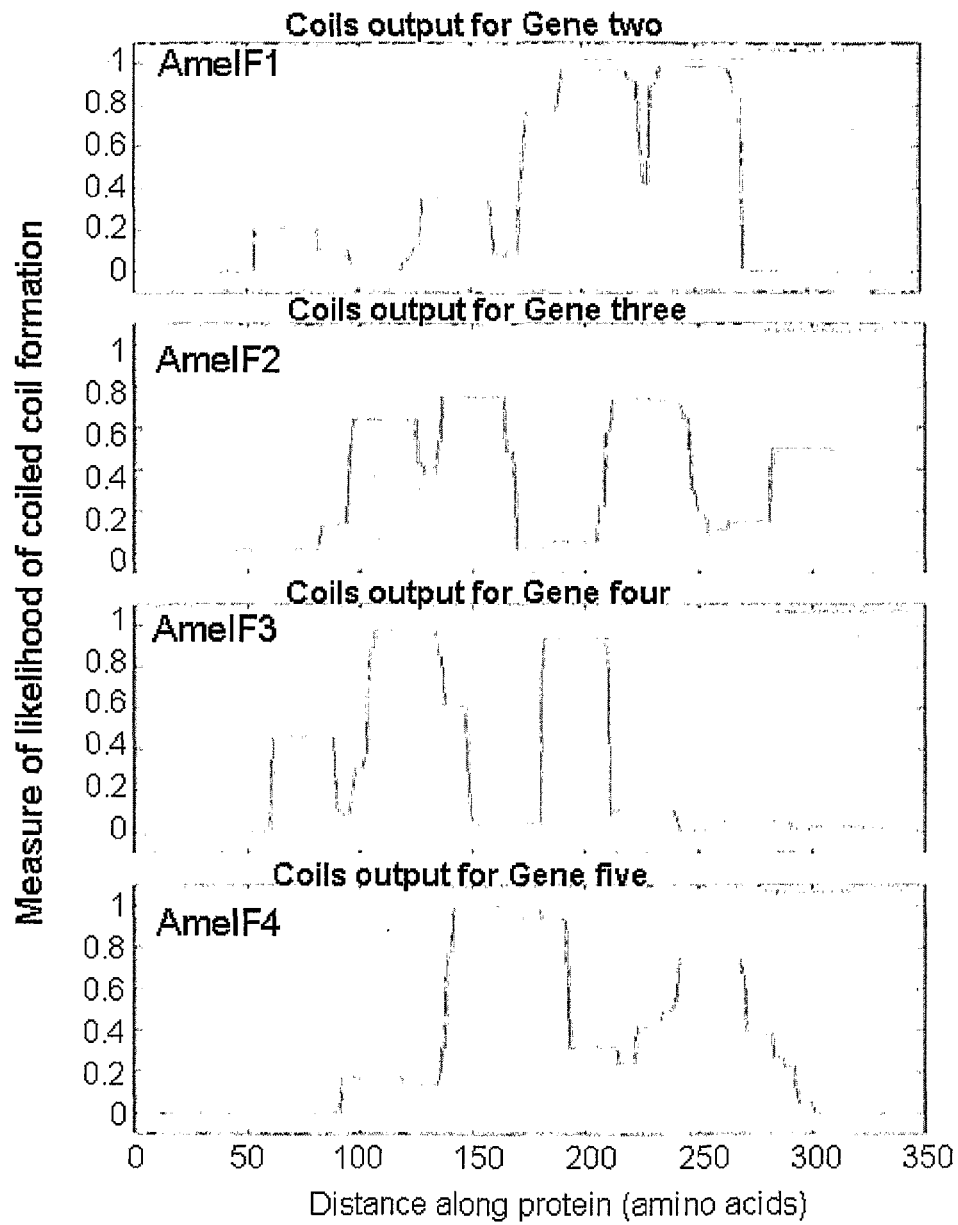

FIG. 4. Prediction of coiled coil regions in honeybee silk proteins. COILS is a program that compares a sequence to a database of known parallel two-stranded coiled-coils and derives a similarity score. By comparing this score to the distribution of scores in globular and coiled-coil proteins, the program then calculates the probability that the sequence will adopt a coiled-coil conformation as described in Lupas et al. (1991). Using a window size of 28 this program predicts the following numbers of residues exist in each protein in coiled coil domains: Xenospira3: 77; Xenospira4: 35; Xenospira1: 28; Xenospira2: 80.

FIG. 5. Alignment of honey bee silk proteins showing MARCOIL prediction of major heptads that form a coiled-coil structure. Heptad sequences are shown above the amino acids, and alanine residues in positions a and d are highlighted.

FIG. 6. Alignment of Marciol predicted coiled coil regions of hymenopteran (bees and ants) silk proteins showing the heptad position assignment. Amel, honeybee; BB, bumblebee; BA, bulldog ant; WA, weaver ant; F1-4, silk fibroins 1-4. Heptad sequences are shown above the amino acids, and alanine residues in positions a, d and e are highlighted.

Figure 7:
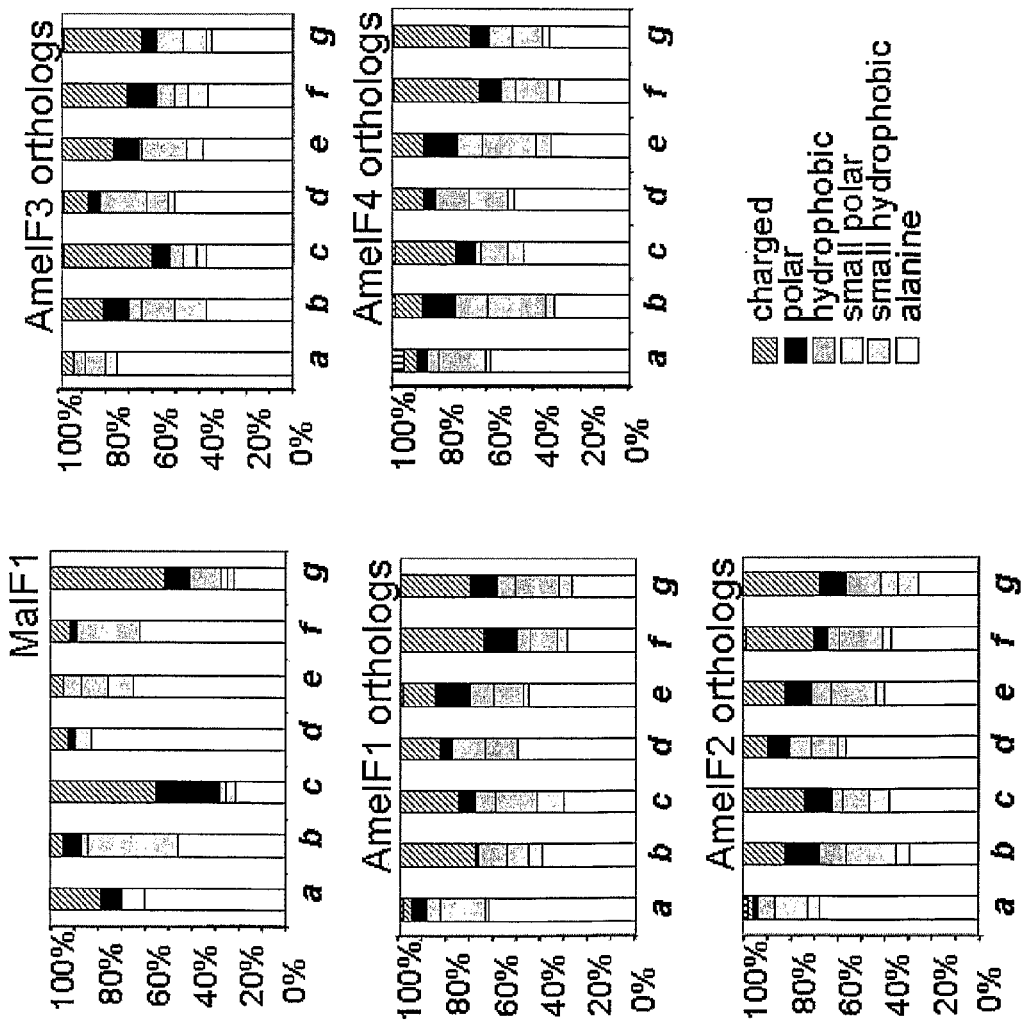

FIG. 7. The amino acid character of heptad positions in the predicted coiled coil regions of the *Mallada signata* larval silk protein and the orthologous clusters of the Hymenopteran silk proteins.

Figure 8:
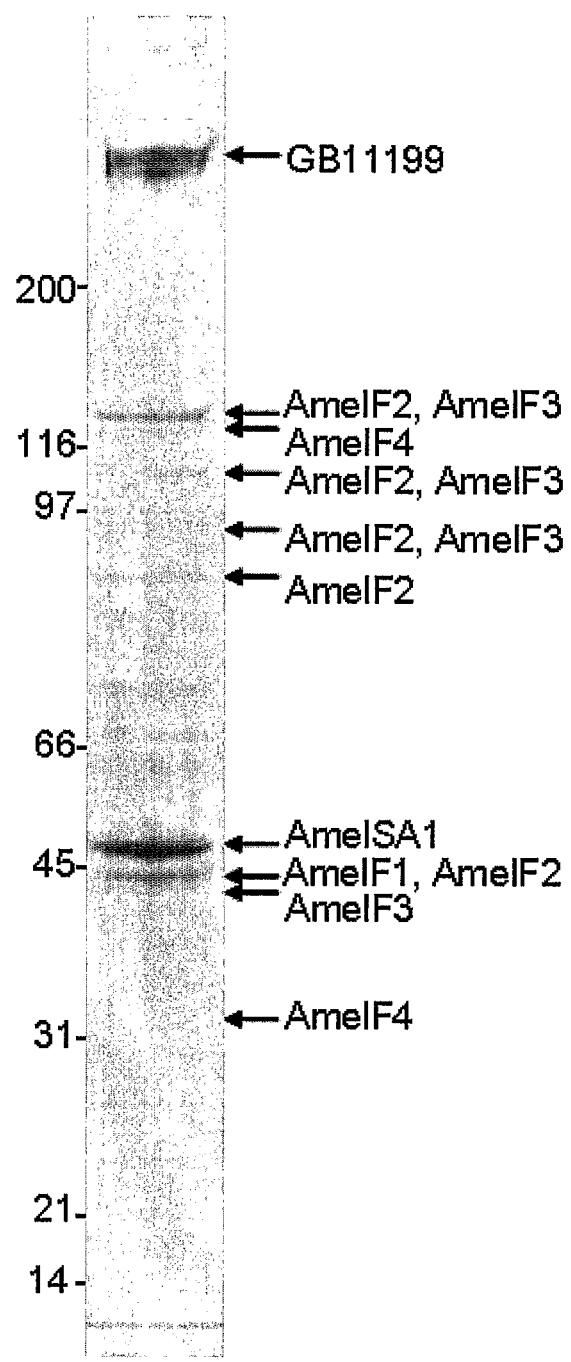

FIG. 8. SDS polyacrylamide gel electrophoresis of late last instar salivary gland proteins. Proteins were identified after tryptic digest and analysis of mass spectral data set using Agilent's Spectrum Mill software to match the data with predictions of protein sequences from proteins identified from cDNA sequences. The software generated scores for the quality of each match between experimentally observed sets of masses of fragments of peptides and the predictions of fragments that might be generated according to the sequences of proteins in a provided database. All the sequence matches shown here received scores greater than 20 by the Spectrum Mill software, where a score of 20 would be sufficient for automatic, confident acceptance of a valid match.

Figure 9:
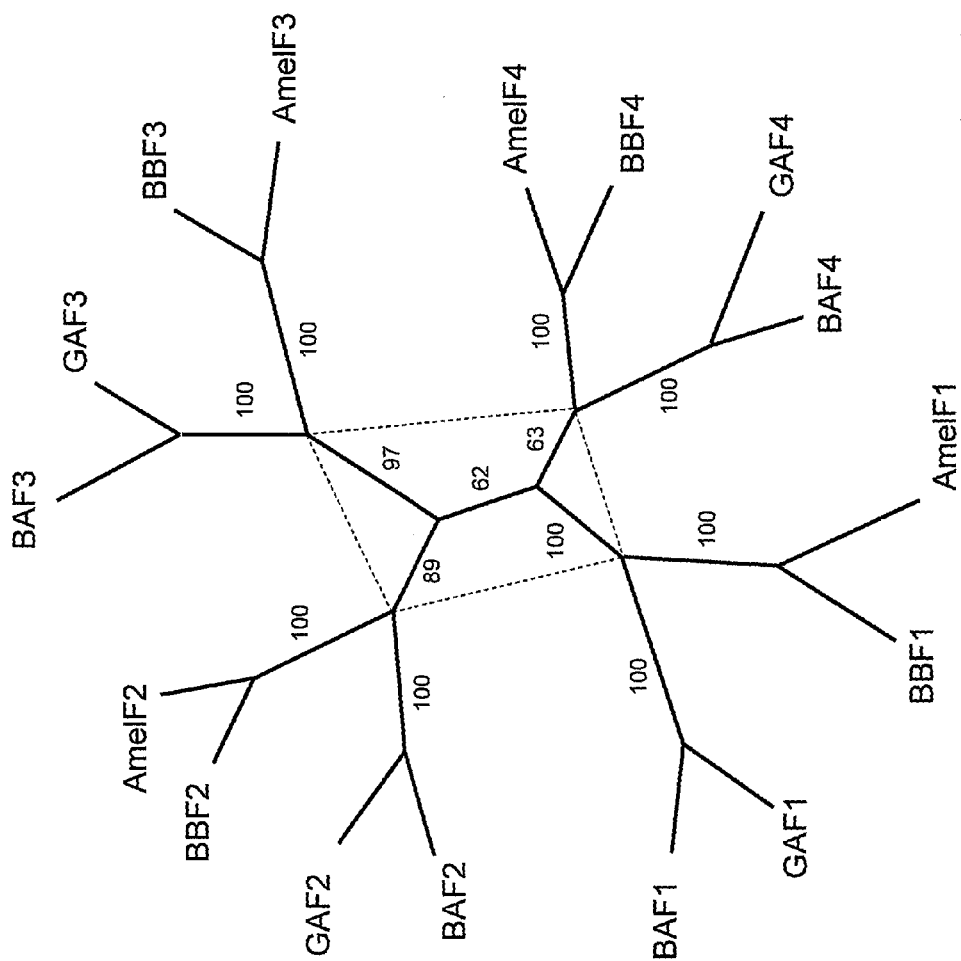

FIG. 9. Parsimony analysis of the coiled coil region of silk proteins. The relatedness of the four coiled-coil proteins suggests that the genes evolved from a common ancestor predating the divergence of the Euaculeata. The area bound by the dashed line indicates variation that occurred before the ants and wasps (Vespoidea) diverged from the bees (Apoidea) in the Late Jurassic (155 myrs; Grimaldi and Engel, 2005). Numbers indicating bootstrap values from 1000 iterations are shown.

FIG. 10. A) *Apis mellifera* silk proteins identified by mass spectral analysis of peptides generated from bee silk after digestion with trypsin. Shading indicates peptides identified by the mass spectral analysis. All the sequence matches shown here received scores greater than 20 by the Spectrum Mill software, where a score of 20 would be sufficient for automatic, confident acceptance of a valid match.

B) Full length amino sequences of bumblebee, bulldog ant, weaver and lacewing silk proteins.

FIG. 11. Open reading frames encoding honeybee, bumblebee, bulldog ant, weaver ant and lacewing silk proteins.

FIG. 12. Sequence of gene encoding Xenosin. Entire coding sequence provided which is interrupted by a single intron (highlighted).

Figure 13:
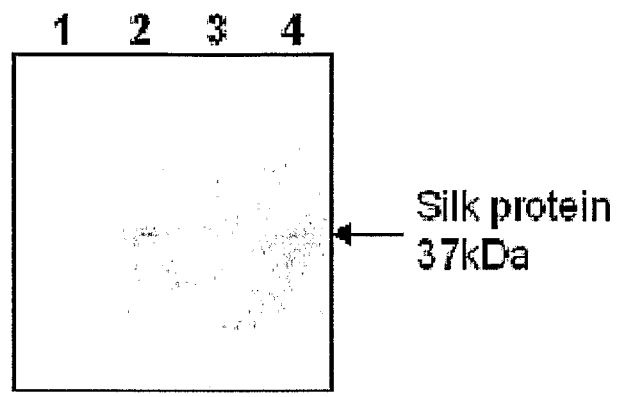

FIG. 13. Expression of silk protein in tobacco. Detection of histidine tagged proteins after western blot analysis of proteins from: 1. *E. coli* transformed with empty expression vector, 2. *E. coli* transformed with expression vector containing AmelF4 (Xenospira4) coding region, 3. tobacco transformed with empty expression vector, 4. tobacco transformed with expression vector containing AmelF4 coding region.

Figure 14:
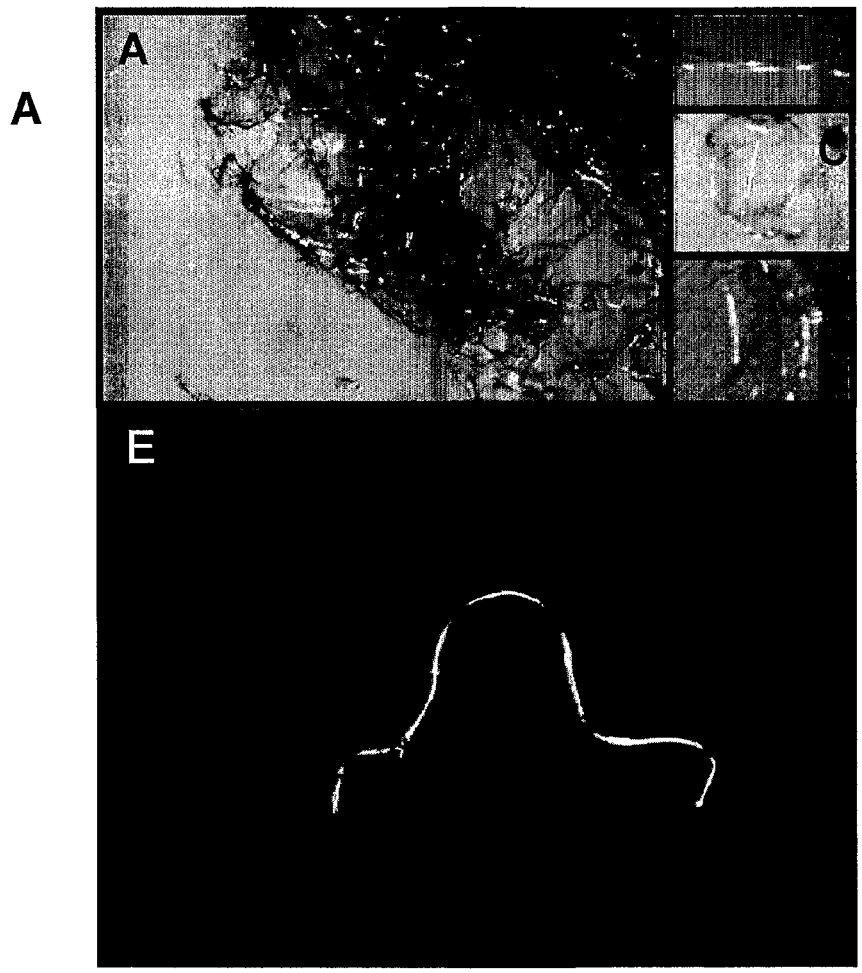

FIG. 14. Fibres made from recombinant honeybee silk proteins showing birefringent threads. Biorefringence indicates structure is present in the threads. Different recombinant honeybee threads are shown in each panel A-D, and recombinant lacewing thread is shown in panel E.

KEY TO THE SEQUENCE LISTING

SEQ ID NO:1—Honeybee silk protein termed herein Xenospira1 (also termed herein AmelF1) (minus signal peptide).
SEQ ID NO:2—Honeybee silk protein termed herein Xenospira1.
SEQ ID NO:3—Honeybee silk protein termed herein Xenospira2 (also termed herein AmelF2) (minus signal peptide).
SEQ ID NO:4—Honeybee silk protein termed herein Xenospira2.
SEQ ID NO:5—Honeybee silk protein termed herein Xenospira3 (also termed herein AmelF3) (minus signal peptide).
SEQ ID NO:6—Honeybee silk protein termed herein Xenospira3.
SEQ ID NO:7—Honeybee silk protein termed herein Xenospira4 (also termed herein AmelF4) (minus signal peptide).
SEQ ID NO:8—Honeybee silk protein termed herein Xenospira4.
SEQ ID NO:9—Honeybee silk protein termed herein Xenosin (also termed herein Ame1SA1) (minus signal peptide).
SEQ ID NO:10—Honeybee silk protein termed herein Xenosin.
SEQ ID NO:11—Nucleotide sequence encoding honeybee silk protein Xenospira1 (minus region encoding signal peptide).
SEQ ID NO:12—Nucleotide sequence encoding honeybee silk protein Xenospira1.
SEQ ID NO:13—Nucleotide sequence encoding honeybee silk protein Xenospira2 (minus region encoding signal peptide).
SEQ ID NO:14—Nucleotide sequence encoding honeybee silk protein Xenospira2.
SEQ ID NO:15—Nucleotide sequence encoding honeybee silk protein Xenospira3 (minus region encoding signal peptide).
SEQ ID NO:16—Nucleotide sequence encoding honeybee silk protein Xenospira3.
SEQ ID NO:17—Nucleotide sequence encoding honeybee silk protein Xenospira4 (minus region encoding signal peptide).
SEQ ID NO:18—Nucleotide sequence encoding honeybee silk protein Xenospira4.
SEQ ID NO:19—Nucleotide sequence encoding honeybee silk protein Xenosin (minus region encoding signal peptide).
SEQ ID NO:20—Nucleotide sequence encoding honeybee silk protein Xenosin.
SEQ ID NO:21—Gene sequence encoding honeybee silk protein Xenosin.
SEQ ID NO:22—Bumblebee silk protein termed herein BBF1 (minus signal peptide).
SEQ ID NO:23—Bumblebee silk protein termed herein BBF1.
SEQ ID NO:24—Bumblebee silk protein termed herein BBF2 (minus signal peptide).
SEQ ID NO:25—Bumblebee silk protein termed herein BBF2.
SEQ ID NO:26—Bumblebee silk protein termed herein BBF3 (minus signal peptide).
SEQ ID NO:27—Bumblebee silk protein termed herein BBF3.
SEQ ID NO:28—Bumblebee silk protein termed herein BBF4 (minus signal peptide).
SEQ ID NO:29—Bumblebee silk protein termed herein BBF4.
SEQ ID NO:30—Partial amino acid sequence of bumblebee silk protein termed herein BBSA1.
SEQ ID NO:31—Nucleotide sequence encoding bumblebee silk protein BBF1 (minus region encoding signal peptide).
SEQ ID NO:32—Nucleotide sequence encoding bumblebee silk protein BBF1.
SEQ ID NO:33—Nucleotide sequence encoding bumblebee silk protein BBF2 (minus region encoding signal peptide).
SEQ ID NO:34—Nucleotide sequence encoding bumblebee silk protein BBF2.
SEQ ID NO:35—Nucleotide sequence encoding bumblebee silk protein BBF3 (minus region encoding signal peptide).

SEQ ID NO:36—Nucleotide sequence encoding bumblebee silk protein BBF3.
SEQ ID NO:37—Nucleotide sequence encoding bumblebee silk protein BBF4 (minus region encoding signal peptide).
SEQ ID NO:38—Nucleotide sequence encoding bumblebee silk protein BBF4.
SEQ ID NO:39—Partial nucleotide sequence encoding bumblebee silk protein BBSA1.
SEQ ID NO:40—Bulldog ant silk protein termed herein BAF1 (minus signal peptide).
SEQ ID NO:41—Bulldog ant silk protein termed herein BAF1.
SEQ ID NO:42—Bulldog ant silk protein termed herein BAF2 (minus signal peptide).
SEQ ID NO:43—Bulldog ant silk protein termed herein BAF2.
SEQ ID NO:44—Bulldog ant silk protein termed herein BAF3 (minus signal peptide).
SEQ ID NO:45—Bulldog ant silk protein termed herein BAF3.
SEQ ID NO:46—Bulldog ant silk protein termed herein BAF4 (minus signal peptide).
SEQ ID NO:47—Bulldog ant silk protein termed herein BAF4.
SEQ ID NO:48—Nucleotide sequence encoding bulldog ant silk protein BAF1 (minus region encoding signal peptide).
SEQ ID NO:49—Nucleotide sequence encoding bulldog ant silk protein BAF1.
SEQ ID NO:50—Nucleotide sequence encoding bulldog ant silk protein BAF2 (minus region encoding signal peptide).
SEQ ID NO:51—Nucleotide sequence encoding bulldog ant silk protein BAF2.
SEQ ID NO:52—Nucleotide sequence encoding bulldog ant silk protein BAF3 (minus region encoding signal peptide).
SEQ ID NO:53—Nucleotide sequence encoding bulldog ant silk protein BAF3.
SEQ ID NO:54—Nucleotide sequence encoding bulldog ant silk protein BAF4 (minus region encoding signal peptide).
SEQ ID NO:55—Nucleotide sequence encoding bulldog ant silk protein BAF4.
SEQ ID NO:56—Weaver ant silk protein termed herein GAF1 (minus signal peptide).
SEQ ID NO:57—Weaver ant silk protein termed herein GAF1.
SEQ ID NO:58—Weaver ant silk protein termed herein GAF2 (minus signal peptide).
SEQ ID NO:59—Weaver ant silk protein termed herein GAF2.
SEQ ID NO:60—Weaver ant silk protein termed herein GAF3 (minus signal peptide).
SEQ ID NO:61—Weaver ant silk protein termed herein GAF3.
SEQ ID NO:62—Weaver ant silk protein termed herein GAF4 (minus signal peptide).
SEQ ID NO:63—Weaver ant silk protein termed herein GAF4.
SEQ ID NO:64—Nucleotide sequence encoding weaver ant silk protein GAF1 (minus region encoding signal peptide).
SEQ ID NO:65—Nucleotide sequence encoding weaver ant silk protein GAF1.
SEQ ID NO:66—Nucleotide sequence encoding weaver ant silk protein GAF2 (minus region encoding signal peptide).
SEQ ID NO:67—Nucleotide sequence encoding weaver ant silk protein GAF2,
SEQ ID NO:68—Nucleotide sequence encoding weaver ant silk protein GAF3 (minus region encoding signal peptide).
SEQ ID NO:69—Nucleotide sequence encoding weaver ant silk protein GAF3.
SEQ ID NO:70—Nucleotide sequence encoding weaver ant silk protein GAF4 (minus region encoding signal peptide).
SEQ ID NO:71—Nucleotide sequence encoding weaver ant silk protein GAF4.
SEQ ID NO:72—Lacewing silk protein termed herein MalF1 (minus signal peptide).
SEQ ID NO:73—Lacewing silk protein termed herein MalF1.
SEQ ID NO:74—Nucleotide sequence encoding lacewing silk protein MalF1 (minus region encoding signal peptide).
SEQ ID NO:75—Nucleotide sequence encoding lacewing silk protein MalF1.
SEQ ID NO:76—Nucleotide sequence encoding honeybee silk protein termed herein Xenospira4 codon-optimized for plant expression (before subcloning into pET14b and pVEC8).
SEQ ID NO:77—Honeybee silk protein (Xenospira4) open reading frame optimized for plant expression (without translational fusion).

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

As used herein, the terms "silk protein" and "silk polypeptide" refer to a fibrous protein/polypeptide that can be used to produce a silk fibre, and/or a fibrous protein complex. Naturally occurring silk proteins of the invention form part of the brood comb silk of insects such as honeybees, however, as described herein variants of these proteins could readily be produced which would perform the same function if expressed within an appropriate insect.

As used herein, a "silk fibre" refers to filaments comprising proteins of the invention which can be woven into various items such as textiles.

As used herein, a "copolymer" is composition comprising two or more silk proteins of the invention. This term excludes naturally occurring copolymers such as the brood comb of insects.

The term "plant" includes whole plants, vegetative structures (for example, leaves, stems), roots, floral organs/structures, seed (including embryo, endosperm, and seed coat), plant tissue (for example, vascular tissue, ground tissue, and the like), cells and progeny of the same.

A "transgenic plant" refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

"Polynucleotide" refers to an oligonucleotide, nucleic acid molecule or any fragment thereof. It may be DNA or RNA of genomic or synthetic origin, double-stranded or single-stranded, and combined with carbohydrate, lipids, protein, or other materials to perform a particular activity defined herein.

"Operably linked" as used herein refers to a functional relationship between two or more nucleic acid (e.g., DNA) segments. Typically, it refers to the functional relationship of transcriptional regulatory element to a transcribed sequence. For example, a promoter is operably linked to a coding sequence, such as a polynucleotide defined herein, if it stimulates or modulates the transcription of the coding sequence in an appropriate host cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

The term "signal peptide" refers to an amino terminal polypeptide preceding a secreted mature protein. The signal peptide is cleaved from and is therefore not present in the mature protein. Signal peptides have the function of directing and trans-locating secreted proteins across cell membranes. The signal peptide is also referred to as signal sequence.

As used herein, "transformation" is the acquisition of new genes in a cell by the incorporation of a polynucleotide.

As used herein, the term "drug" refers to any compound that can be used to treat or prevent a particular disease, examples of drugs which can be formulated with a silk protein of the invention include, but are not limited to, proteins, nucleic acids, anti-tumor agents, analgesics, antibiotics, anti-inflammatory compounds (both steroidal and non-steroidal), hormones, vaccines, labeled substances, and the like.

Polypeptides

By "substantially purified polypeptide" we mean a polypeptide that has generally been separated from the lipids, nucleic acids, other polypeptides, and other contaminating molecules such as wax with which it is associated in its native state. With the exception of other proteins of the invention, it is preferred that the substantially purified polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment the cell is a cell that does not naturally produce the polypeptide. However, the cell may be a cell which comprises a non-endogenous gene that causes an altered, preferably increased, amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The terms "polypeptide" and "protein" are generally used interchangeably and refer to a single polypeptide chain which may or may not be modified by addition of non-amino acid groups. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

As used herein a "biologically active" fragment is a portion of a polypeptide of the invention which maintains a defined activity of the full-length polypeptide, namely the ability to be used to produce silk. Biologically active fragments can be any size as long as they maintain the defined activity.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the E. coli XL-1 red (Stratagene) and propagating the transformed bacteria for a suitable number of generations. In another example, the polynucleotides of the invention are subjected to DNA shuffling techniques as broadly described by Harayama (1998). These DNA shuffling techniques may include genes of the invention possibly in addition to genes related to those of the present invention, such as silk genes from Hymenopteran or Neuroptean species other than the specific species characterized herein. Products derived from mutated/altered DNA can readily be screened using techniques described herein to determine if they can be used as silk proteins.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as important for function. Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

As outlined above, a portion of some of the polypeptides of the invention have a coiled coil structure. Coiled coil structures of polypeptides are characterized by heptad repeats represented by the consensus sequence (abcdefg)$_n$. In a preferred embodiment, the portion of the polypeptide that has a coiled coil structure comprises at least 10 copies of the heptad sequence abcdefg, and at least 25% of the amino acids at positions a and d are alanine residues.

TABLE 1

| Exemplary substitutions | |
| --- | --- |
| Original Residue | Exemplary Substitutions |
| Ala (A) | val; leu; ile; gly; cys; ser; thr |
| Arg (R) | lys |
| Asn (N) | gln; his |
| Asp (D) | glu |
| Cys (C) | Ser; thr; ala; gly; val |
| Gln (Q) | asn; his |
| Glu (E) | asp |
| Gly (G) | pro; ala; ser; val; thr |
| His (H) | asn; gln |
| Ile (I) | leu; val; ala; met |
| Leu (L) | ile; val; met; ala; phe |
| Lys (K) | arg |
| Met (M) | leu; phe |
| Phe (F) | leu; val; ala |

TABLE 1-continued

| Exemplary substitutions | |
| --- | --- |
| Original Residue | Exemplary Substitutions |
| Pro (P) | gly |
| Ser (S) | thr; ala; gly; val; gln |
| Thr (T) | ser; gln; ala |
| Trp (W) | tyr |
| Tyr (Y) | trp; phe |
| Val (V) | ile; leu; met; phe; ala; ser; thr |

In a preferred embodiment, the polypeptide that has a coiled coil structure comprises at least 12 consecutive copies, more preferably at least 15 consecutive copies, and even more preferably at least 18 consecutive copies of the heptad. In further embodiments, the polypeptide that has a coiled coil structure can have up to at least 28 copies of the heptad. Typically, the copies of the heptad will be tandemly repeated. However, they do not necessarily have to be perfect tandem repeats, for example, as shown in FIGS. 5 and 6 a few amino acids may be found between two heptads, or a few truncated heptads may be found (see, for example, Xenospira1 in FIG. 5).

Guidance regarding amino acid substitutions which can be made to the polypeptides of the invention which have a coiled coil structure is provided in FIGS. 5 and 6, as well as Tables 6 to 10. Where a predicted useful amino acid substitution based on the experimental data provided herein is in anyway in conflict with the exemplary substitutions provided in Table 1 it is preferred that a substitution based on the experimental data is used.

Coiled coil structures of polypeptides of the invention have a high content of alanine residues, particularly at amino acid positions a, d and e of the heptad. However, positions b, c, f and g also have a high frequency of alanine residues. In a preferred embodiment, at least 15% of the amino acids at positions a, d and/or e of the heptads are alanine residues, more preferably at least 25%, more preferably at least 30%, more preferably at least 40%, and even more preferably at least 50%. In a further preferred embodiment, at least 25% of the amino acids at both positions a and d of the heptads are alanine residues, more preferably at least 30%, more preferably at least 40%, and even more preferably at least 50%. Furthermore, it is preferred that at least 15% of the amino acids at positions b, c, f and g of the heptads are alanine residues, more preferably at least 20%, and even more preferably at least 25%.

Typically, the heptads will not comprise any proline or histidine residues. Furthermore, the heptads will comprise few (1 or 2), if any, phenylalanine, methionine, tyrosine, cysteine, glycine or tryptophan residues. Apart from alanine, common (for example greater than 5%, more preferably greater than 10%) amino acids in the heptads include leucine (particularly at positions b and d), serine (particularly at positions b, e and f), glutamic acid (particularly at positions c, e and f), lysine (particularly at positions b, c, d, f and g) as well as arginine at position g.

Polypeptides (and polynucleotides) of the invention can be purified (isolated) from a wide variety of Hymenopteran and Neuropteran species. Examples of Hymenopterans include, but are not limited to, any species of the Suborder Apocrita (bees, ants and wasps), which include the following Families of insects; Chrysididae (cuckoo wasps), Formicidae (ants), Mutillidae (velvet ants), Pompilidae (spider wasps), Scoliidae, Vespidae (paper wasps, potter wasps, hornets), Agaonidae (fig wasps), Chalcididae (chalcidids), Eucharitidae (eucharitids), Eupelmidae (eupelmids), Pteromalidae (pteromalids), Evamidae (ensign wasps), Braconidae, Ichneumonidae (ichneumons), Megachilidae, Apidae, Colletidae, Halictidae, and Melittidae (oil collecting bees). Examples of Neuropterans include species from the following insect Families: Mantispidae, Chrysopidae (lacewings), Myrmeleontidae (antlions), and Ascalaphidae (owlflies). Such further polypeptides (and polynucleotides) can be characterized using the same procedures described herein for silks from *Bombus terrestris, Myrmecia forficata, Oecophylla smaragdina* and *Mallada signata*.

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated.

Furthermore, the term "polynucleotide" is used interchangeably herein with the term "nucleic acid".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

With regard to the defined polynucleotides, it will be appreciated that % identity figures higher than those provided above will encompass preferred embodiments. Thus, where applicable, in light of the minimum % identity figures, it is preferred that a polynucleotide of the invention comprises a sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Oligonucleotides and/or polynucleotides of the invention hybridize to a silk gene of the present invention, or a region flanking said gene, under stringent conditions. The term "stringent hybridization conditions" and the like as used herein refers to parameters with which the art is familiar, including the variation of the hybridization temperature with length of an oligonucleotide. Nucleic acid hybridization parameters may be found in references which compile such methods, Sambrook, et al. (supra), and Ausubel, et al. (supra). For example, stringent hybridization conditions, as used herein, can refer to hybridization at 65° C. in hybridization buffer (3.5×SSC, 0.02% Ficoll, 0.02% polyvinyl pyrrolidone, 0.02% Bovine Serum Albumin (BSA), 2.5 mM $NaH_2PO_4$ (pH7), 0.5% SDS, 2 mM EDTA), followed by one or more washes in 0.2.×SSC, 0.01% BSA at 50° C. Alternatively, the nucleic acid and/or oligonucleotides (which may also be referred to as "primers" or "probes") hybridize to the region of the an insect genome of interest, such as the genome of a honeybee, under conditions used in nucleic acid amplification techniques such as PCR.

Oligonucleotides of the present invention can be RNA, DNA, or derivatives of either. Although the terms polynucleotide and oligonucleotide have overlapping meaning, oligonucleotides are typically relatively short single stranded molecules. The minimum size of such oligonucleotides is the size required for the formation of a stable hybrid between an oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Usually, monomers of a polynucleotide or oligonucleotide are linked by phosphodiester bonds or analogs thereof to form oligonucleotides ranging in size from a relatively short monomeric units, e.g., 12-18, to several hundreds of monomeric units. Analogs of phosphodiester linkages include: phosphorothioate, phosphorodithioate, phosphoroselenoate, phosphorodiselenoate, phosphoroanilothioate, phosphoranilidate, phosphoramidate.

The present invention includes oligonucleotides that can be used as, for example, probes to identify nucleic acid molecules, or primers to produce nucleic acid molecules. Oligonucleotides of the present invention used as a probe are typically conjugated with a detectable label such as a radioisotope, an enzyme, biotin, a fluorescent molecule or a chemiluminescent molecule.

Recombinant Vectors

One embodiment of the present invention includes a recombinant vector, which comprises at least one isolated polynucleotide molecule of the present invention, inserted into any vector capable of delivering the polynucleotide molecule into a host cell. Such a vector contains heterologous polynucleotide sequences, that is polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and typically is a transposon (such as described in U.S. Pat. No. 5,792,294), a virus or a plasmid.

One type of recombinant vector comprises a polynucleotide molecule of the present invention operatively linked to an expression vector. The phrase operatively linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, animal, and plant cells. Particularly preferred expression vectors of the present invention can direct gene expression in plants cells. Vectors of the invention can also be used to produce the polypeptide in a cell-free expression system, such systems are well known in the art.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, arthropod, plant or mammalian cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells.

Particularly preferred transcription control sequences are promoters active in directing transcription in plants, either constitutively or stage and/or tissue specific, depending on the use of the plant or parts thereof. These plant promoters include, but are not limited to, promoters showing constitutive expression, such as the 35S promoter of Cauliflower Mosaic Virus (CaMV), those for leaf-specific expression, such as the promoter of the ribulose bisphosphate carboxylase small subunit gene, those for root-specific expression, such as the promoter from the glutamine synthase gene, those for seed-specific expression, such as the cruciferin A promoter from *Brassica napus*, those for tuber-specific expression, such as the class-I patatin promoter from potato or those for fruit-specific expression, such as the polygalacturonase (PG) promoter from tomato.

Recombinant molecules of the present invention may also (a) contain secretory signals (i.e., signal segment nucleic acid sequences) to enable an expressed polypeptide of the present invention to be secreted from the cell that produces the polypeptide and/or (b) contain fusion sequences which lead to the expression of nucleic acid molecules of the present invention as fusion proteins. Examples of suitable signal segments include any signal segment capable of directing the secretion of a polypeptide of the present invention. Preferred signal segments include, but are not limited to, tissue plasminogen activator (t-PA), interferon, interleukin, growth hormone, viral envelope glycoprotein signal segments, *Nicotiana nectarin* signal peptide (U.S. Pat. No. 5,939,288), tobacco extensin signal, the soy oleosin oil body binding protein signal, *Arabidopsis thaliana* vacuolar basic chitinase signal peptide, as well as native signal sequences of a polypeptide of the invention. In addition, a nucleic acid molecule of the present invention can be joined to a fusion segment that directs the encoded polypeptide to the proteosome, such as a ubiquitin fusion segment. Recombinant molecules may also include intervening and/or untranslated sequences surrounding and/or within the nucleic acid sequences of the present invention.

Host Cells

Another embodiment of the present invention includes a recombinant cell comprising a host cell transformed with one or more recombinant molecules of the present invention, or progeny cells thereof. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing polypeptides of the present invention or can be capable of producing such polypeptides after being transformed with at least one polynucleotide molecule of the present invention. Host cells of the present invention can be any cell capable of producing at least one protein of the present invention, and include bacterial, fungal (including yeast), parasite, arthropod, animal and plant cells. Examples of host cells include *Salmonella, Escherichia, Bacillus, Listeria, Saccharomyces, Spodoptera, Mycobacteria, Trichoplusia*, BHK (baby hamster kidney) cells, MDCK cells, CRFK cells, CV-1 cells, COS (e.g., COS-7) cells, and Vero cells. Further examples of host cells are *E. coli*, including *E. coli* K-12 derivatives; *Salmonella typhi; Salmonella typhimurium*, including attenuated strains; *Spodoptera frugiperda; Trichoplusia ni*; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK cells and/or HeLa cells. Particularly preferred host cells are plant cells such as those available from Deutsche Sammlung von Mikroorganismen und Zellkulturen GmbH (German Collection of Microorganisms and Cell Cultures).

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Transgenic Plants

The term "plant" refers to whole plants, plant organs (e.g. leaves, stems roots, etc), seeds, plant cells and the like. Plants contemplated for use in the practice of the present invention include both monocotyledons and dicotyledons. Target plants include, but are not limited to, the following: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers).

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

A polynucleotide of the present invention may be expressed constitutively in the transgenic plants during all stages of development. Depending on the use of the plant or plant organs, the polypeptides may be expressed in a stage-specific manner. Furthermore, the polynucleotides may be expressed tissue-specifically.

Regulatory sequences which are known or are found to cause expression of a gene encoding a polypeptide of interest in plants may be used in the present invention. The choice of the regulatory sequences used depends on the target plant and/or target organ of interest. Such regulatory sequences may be obtained from plants or plant viruses, or may be chemically synthesized. Such regulatory sequences are well known to those skilled in the art.

Constitutive plant promoters are well known. Further to previously mentioned promoters, some other suitable promoters include but are not limited to the nopaline synthase promoter, the octopine synthase promoter, CaMV 35S promoter, the ribulose-1,5-bisphosphate carboxylase promoter, Adh1-based pEmu, Act1, the SAM synthase promoter and Ubi promoters and the promoter of the chlorophyll a/b binding protein. Alternatively it may be desired to have the transgene(s) expressed in a regulated fashion. Regulated expression of the polypeptides is possible by placing the coding sequence of the silk protein under the control of promoters that are tissue-specific, developmental-specific, or inducible. Several tissue-specific regulated genes and/or promoters have been reported in plants. These include genes encoding the seed storage proteins (such as napin, cruciferin, β-conglycinin, glycinin and phaseolin), zein or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4). Particularly useful for seed-specific expression is the pea vicilin promoter. Other useful promoters for expression in mature leaves are those that are switched on at the onset of senescence, such as the SAG promoter from *Arabidopsis*). A class of fruit-specific promoters expressed at or during anthesis through fruit development, at least until the beginning of ripening, is discussed in U.S. Pat. No. 4,943,674. Other examples of tissue-specific promoters include those that direct expression in tubers (for example, patatin gene promoter), and in fiber cells (an example of a developmentally-regulated fiber cell protein is E6 fiber).

Other regulatory sequences such as terminator sequences and polyadenylation signals include any such sequence functioning as such in plants, the choice of which would be obvious to the skilled addressee. The termination region used in the expression cassette will be chosen primarily for convenience, since the termination regions appear to be relatively interchangeable. The termination region which is used may be native with the transcriptional initiation region, may be native with the polynucleotide sequence of interest, or may be derived from another source. The termination region may be naturally occurring, or wholly or partially synthetic. Convenient termination regions are available from the Ti-plasmid of *A. tumefaciens*, such as the octopine synthase and nopaline synthase termination regions or from the genes for β-phaseolin, the chemically inducible lant gene, pIN.

Several techniques are available for the introduction of an expression construct containing a nucleic acid sequence encoding a polypeptide of interest into the target plants. Such techniques include but are not limited to transformation of protoplasts using the calcium/polyethylene glycol method, electroporation and microinjection or (coated) particle bombardment. In addition to these so-called direct DNA transformation methods, transformation systems involving vectors are widely available, such as viral and bacterial vectors (e.g. from the genus *Agrobacterium*). After selection and/or screening, the protoplasts, cells or plant parts that have been transformed can be regenerated into whole plants, using methods known in the art. The choice of the transformation and/or regeneration techniques is not critical for this invention.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Transgenic Hon-Human Animals

Techniques for producing transgenic animals are well known in the art. A useful general textbook on this subject is Houdebine, Transgenic animals—Generation and Use (Harwood Academic, 1997).

Heterologous DNA can be introduced, for example, into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals.

Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology. Using this method, fibroblasts from donor animals are stably transfected with a plasmid incorporating the coding sequences for a binding domain or binding partner of interest under the control of regulatory sequences. Stable transfectants are then fused to enucleated oocytes, cultured and transferred into female recipients.

Recovery Methods and Production of Silk

The silk proteins of the present invention may be extracted and purified from recombinant cells, such as plant, bacteria or yeast cells, producing said protein by a variety of methods. In one embodiment, the method involves removal of native cell proteins from homogenized cells/tissues/plants etc. by lowering pH and heating, followed by ammonium sulfate fractionation. Briefly, total soluble proteins are extracted by homogenizing cells/tissues/plants. Native proteins are removed by precipitation at pH 4.7 and then at 60° C. The resulting supernatant is then fractionated with ammonium sulfate at 40% saturation. The resulting protein will be of the order of 95% pure. Additional purification may be achieved with conventional gel or affinity chromatography.

In another example, cell lysates are treated with high concentrations of acid e.g. HCl or propionic acid to reduce pH to ~1-2 for 1 hour or more which will solubilise the silk proteins but precipitate other proteins.

Fibrillar aggregates will form from solutions by spontaneous self-assembly of silk proteins of the invention when the protein concentration exceeds a critical value. The aggregates may be gathered and mechanically spun into macroscopic fibers according to the method of O'Brien et al. (I. O'Brien et al., "Design, Synthesis and Fabrication of Novel Self-Assembling Fibrillar Proteins", in Silk Polymers: Materials Science and Biotechnology, pp. 104-117, Kaplan, Adams, Farmer and Viney, eds., c. 1994 by American Chemical Society, Washington, D.C.).

By nature of the inherent coiled coil secondary structure, proteins such as Xenospira1-4, BBF1-4, BAF1-4 and GAF1-4 will spontaneously form the coiled coil secondary structure upon dehydration. As described below, the strength of the coiled coil can be enhanced through enzymatic or chemical cross-linking of lysine residues in close proximity.

Silk fibres and/or copolymers of the invention have a low processing requirement. The silk proteins of the invention require minimal processing e.g. spinning to form a strong fibre as they spontaneously forms strong coiled coils which can be reinforced with crosslinks such as lysine crosslinks. This contrasts with *B. mori* and spider recombinant silk polypeptides which require sophisticated spinning techniques in order to obtain the secondary structure (β-sheet) and strength of the fibre.

However, fibers may be spun from solutions having properties characteristic of a liquid crystal phase. The fiber concentration at which phase transition can occur is dependent on the composition of a protein or combination of proteins present in the solution. Phase transition, however, can be detected by monitoring the clarity and birefringence of the solution. Onset of a liquid crystal phase can be detected when the solution acquires a translucent appearance and registers birefringence when viewed through crossed polarizing filters.

In one fiber-forming technique, fibers can first be extruded from the protein solution through an orifice into methanol, until a length sufficient to be picked up by a mechanical means is produced. Then a fiber can be pulled by such mechanical means through a methanol solution, collected, and dried. Methods for drawing fibers are considered well-known in the art.

Further examples of methods which may be used for producing silk fibres and/or copolymers of the present are described in US 2004/0170827 and US 2005/0054830.

In a preferred embodiment, silk fibres and/or copolymers of the invention are crosslinked. In one embodiment, the silk fibres and/or copolymers are crosslinked to a surface/article/product etc of interest using techniques known in the art. In another embodiment (or in combination with the previous embodiment), at least some silk proteins in the silk fibres and/or copolymers are crosslinked to each other. Preferably, the silk proteins are crosslinked via lysine residues in the proteins. Such crosslinking can be performed using chemical and/or enzymatic techniques known in the art. For example, enzymatic cross links can be catalysed by lysyl oxidase, whereas nonenzymatic cross links can be generated from glycated lysine residues (Reiser et al., 1992).

Antibodies

The invention also provides monoclonal or polyclonal antibodies to polypeptides of the invention or fragments thereof. Thus, the present invention further provides a process for the production of monoclonal or polyclonal antibodies to polypeptides of the invention.

The term "binds specifically" refers to the ability of the antibody to bind to at least one polypeptide of the present invention but not other known silk proteins.

As used herein, the term "epitope" refers to a region of a polypeptide of the invention which is bound by the antibody. An epitope can be administered to an animal to generate antibodies against the epitope, however, antibodies of the present invention preferably specifically bind the epitope region in the context of the entire polypeptide.

If polyclonal antibodies are desired, a selected mammal (e.g., mouse, rabbit, goat, horse, etc.) is immunised with an immunogenic polypeptide of the invention. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals.

Monoclonal antibodies directed against polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Antibodies of the invention may be bound to a solid support and/or packaged into kits in a suitable container along with suitable reagents, controls, instructions and the like.

Preferably, antibodies of the present invention are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, e.g., biotin. Such labeled antibodies can be used in techniques known in the art to detect polypeptides of the invention.

Compositions

Compositions of the present invention may include an "acceptable carrier".

Examples of such acceptable carriers include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used.

In one embodiment, the "acceptable carrier" is a "pharmaceutically acceptable carrier". The term pharmaceutically acceptable carrier refers to molecular entities and compositions that do not produce an allergic, toxic or otherwise adverse reaction when administered to an animal, particularly a mammal, and more particularly a human. Useful examples of pharmaceutically acceptable carriers or diluents include, but are not limited to, solvents, dispersion media, coatings, stabilizers, protective colloids, adhesives, thickeners, thixotropic agents, penetration agents, sequestering agents and isotonic and absorption delaying agents that do not affect the activity of the polypeptides of the invention. The proper fluidity can be maintained, for example, by the use of a coating, such as lecithin, by the maintenance of the required particle size in the case of dispersion and by the use of surfactants. More generally, the polypeptides of the invention can be combined with any non-toxic solid or liquid additive corresponding to the usual formulating techniques.

As outlined herein, in some embodiments a polypeptide, a silk fiber and/or a copolymer of the invention is used as a pharmaceutically acceptable carrier.

Other suitable compositions are described below with specific reference to specific uses of the polypeptides of the invention.

Uses

Silk proteins are useful for the creation of new biomaterials because of their exceptional toughness and strength. However, to date the fibrous proteins of spiders and insects are large proteins (over 100 kDa) and consist of highly repetitive amino acid sequences. These proteins are encoded by large genes containing highly biased codons making them particularly difficult to produce in recombinant systems. By comparison, the silk proteins of the invention are short and non-repetitive. These properties make the genes encoding these proteins particularly attractive for recombinant production of new biomaterials.

The silk proteins, silk fibers and/or copolymers of the invention can be used for a broad and diverse array of medical, military, industrial and commercial applications. The fibers can be used in the manufacture of medical devices such as sutures, skin grafts, cellular growth matrices, replacement ligaments, and surgical mesh, and in a wide range of industrial and commercial products, such as, for example, cable, rope, netting, fishing line, clothing fabric, bullet-proof vest lining, container fabric, backpacks, knapsacks, bag or purse straps, adhesive binding material, non-adhesive binding material, strapping material, tent fabric, tarpaulins, pool covers, vehicle covers, fencing material, sealant, construction material, weatherproofing material, flexible partition material, sports equipment; and, in fact, in nearly any use of fiber or fabric for which high tensile strength and elasticity are desired characteristics. The silk proteins, silk fibers and/or copolymers of the present invention also have applications in compositions for personal care products such as cosmetics, skin care, hair care and hair colouring; and in coating of particles, such as pigments.

The silk proteins may be used in their native form or they may be modified to form derivatives, which provide a more beneficial effect. For example, the silk protein may be modified by conjugation to a polymer to reduce allergenicity as described in U.S. Pat. Nos. 5,981,718 and 5,856,451. Suitable modifying polymers include, but are not limited to, polyalkylene oxides, polyvinyl alcohol, poly-carboxylates, poly(vinylpyrrolidone), and dextrans. In another example, the silk proteins may be modified by selective digestion and splicing of other protein modifiers. For example, the silk proteins may be cleaved into smaller peptide units by treatment with acid at an elevated temperature of about 60° C. The useful acids include, but are not limited to, dilute hydrochloric, sulfuric or phosphoric acids. Alternatively, digestion of the silk proteins may be done by treatment with a base, such as sodium hydroxide, or enzymatic digestion using a suitable protease may be used.

The proteins may be further modified to provide performance characteristics that are beneficial in specific applications for personal care products. The modification of proteins for use in personal care products is well known in the art. For example, commonly used methods are described in U.S. Pat. Nos. 6,303,752, 6,284,246, and 6,358,501. Examples of modifications include, but are not limited to, ethoxylation to promote water-oil emulsion enhancement, siloxylation to provide lipophilic compatibility, and esterification to aid in compatibility with soap and detergent compositions. Additionally, the silk proteins may be derivatized with functional groups including, but not limited to, amines, oxiranes, cyanates, carboxylic acid esters, silicone copolyols, siloxane esters, quaternized amine aliphatics, urethanes, polyacrylamides, dicarboxylic acid esters, and halogenated esters. The silk proteins may also be derivatized by reaction with diimines and by the formation of metal salts.

Consistent with the above definitions of "polypeptide" (and "protein"), such derivatized and/or modified molecules are also referred to herein broadly as "polypeptides" and "proteins".

Silk proteins of the invention can be spun together and/or bundled or braided with other fiber types. Examples include, but are not limited to, polymeric fibers (e.g., polypropylene, nylon, polyester), fibers and silks of other plant and animal sources (e.g., cotton, wool, Bombyx mori or spider silk), and glass fibers. A preferred embodiment is silk fiber braided with 10% polypropylene fiber. The present invention contemplates that the production of such combinations of fibers can be readily practiced to enhance any desired characteristics, e.g., appearance, softness, weight, durability, water-repellant properties, improved cost-of-manufacture, that may be generally sought in the manufacture and production of fibers for medical, industrial, or commercial applications.

Personal Care Products

Cosmetic and skin care compositions may be anhydrous compositions comprising an effective amount of silk protein in a cosmetically acceptable medium. The uses of these compositions include, but are not limited to, skin care, skin cleansing, make-up, and anti-wrinkle products. An effective amount of a silk protein for cosmetic and skin care compositions is herein defined as a proportion of from about $10^{-4}$ to about 30% by weight, but preferably from about $10^{-3}$ to 15% by weight, relative to the total weight of the composition. This proportion may vary as a function of the type of cosmetic or skin care composition. Suitable compositions for a cosmetically acceptable medium are described in U.S. Pat. No. 6,280,747. For example, the cosmetically acceptable medium may contain a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants, including but not limited to, antioxidants, preserving agents, fillers, surfactants, UVA and/or UVB sunscreens, fragrances, thickeners, wetting agents and anionic, nonionic or amphoteric polymers, and dyes or pigments.

Emulsified cosmetics and quasi drugs which are producible with the use of emulsified materials comprising at least one silk protein of the present invention include, for example, cleansing cosmetics (beauty soap, facial wash, shampoo, rinse, and the like), hair care products (hair dye, hair cosmetics, and the like), basic cosmetics (general cream, emulsion, shaving cream, conditioner, cologne, shaving lotion, cosmetic oil, facial mask, and the like), make-up cosmetics (foundation, eyebrow pencil, eye cream, eye shadow, mascara, and the like), aromatic cosmetics (perfume and the like), tanning and sunscreen cosmetics (tanning and sunscreen cream, tanning and sunscreen lotion, tanning and sunscreen oil, and the like), nail cosmetics (nail cream and the like), eyeliner cosmetics (eyeliner and the like), lip cosmetics (lipstick, lip cream, and the like), oral care products (tooth paste and the like) bath cosmetics (bath products and the like), and the like.

The cosmetic composition may also be in the form of products for nail care, such as a nail varnish. Nail varnishes are herein defined as compositions for the treatment and colouring of nails, comprising an effective amount of silk protein in a cosmetically acceptable medium. An effective amount of a silk protein for use in a nail varnish composition is herein defined as a proportion of from about $10^{-4}$ to about 30% by weight relative to the total weight of the varnish. Components of a cosmetically acceptable medium for nail varnishes are described in U.S. Pat. No. 6,280,747. The nail varnish typically contains a solvent and a film forming substance, such as cellulose derivatives, polyvinyl derivatives, acrylic polymers or copolymers, vinyl copolymers and polyester polymers. The composition may also contain an organic or inorganic pigment.

Hair care compositions are herein defined as compositions for the treatment of hair, including but not limited to shampoos, conditioners, lotions, aerosols, gels, and mousses, comprising an effective amount of silk protein in a cosmetically acceptable medium. An effective amount of a silk protein for use in a hair care composition is herein defined as a proportion of from about $10^{-2}$ to about 90% by weight relative to the total weight of the composition. Components of a cosmetically acceptable medium for hair care compositions are described in US 2004/0170590, U.S. Pat. Nos. 6,280,747, 6,139,851, and 6,013,250. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hair care compositions may contain one or more conventional cosmetic or dermatological additives or adjuvants, as given above.

Hair colouring compositions are herein defined as compositions for the colouring, dyeing, or bleaching of hair, comprising an effective amount of silk protein in a cosmetically acceptable medium. An effective amount of a silk protein for use in a hair colouring composition is herein defined as a proportion of from about $10^{-4}$ to about 60% by weight relative to the total weight of the composition. Components of a cosmetically acceptable medium for hair colouring compositions are described in US 2004/0170590, U.S. Pat. Nos. 6,398,821 and 6,129,770. For example, hair colouring compositions generally contain a mixture of inorganic peroxygen-based dye oxidizing agent and an oxidizable coloring agent. The peroxygen-based dye oxidizing agent is most commonly hydrogen peroxide. The oxidative hair coloring agents are formed by oxidative coupling of primary intermediates (for example p-phenylenediamines, p-aminophenols, p-diaminopyridines, hydroxyindoles, aminoindoles, aminothymidines, or cyanophenols) with secondary intermediates (for example phenols, resorcinols, m-aminophenols, m-phenylenediamines, naphthols, pyrazolones, hydroxyindoles, catechols or pyrazoles). Additionally, hair colouring compositions may contain oxidizing acids, sequestrants, stabilizers, thickeners, buffers carriers, surfactants, solvents, antioxidants, polymers, non-oxidative dyes and conditioners.

The silk proteins can also be used to coat pigments and cosmetic particles in order to improve dispersibility of the particles for use in cosmetics and coating compositions. Cosmetic particles are herein defined as particulate materials such as pigments or inert particles that are used in cosmetic compositions. Suitable pigments and cosmetic particles, include, but are not limited to, inorganic color pigments, organic pigments, and inert particles. The inorganic color pigments include, but are not limited to, titanium dioxide, zinc oxide, and oxides of iron, magnesium, cobalt, and aluminium. Organic pigments include, but are not limited to, D&C Red No. 36, D&C Orange No. 17, the calcium lakes of D&C Red Nos. 7, 11, 31 and 34, the barium lake of D&C Red No. 12, the strontium lake D&C Red No. 13, the aluminium lake of FD&C Yellow No. 5 and carbon black particles. Inert particles include, but are not limited to, calcium carbonate, aluminium silicate, calcium silicate, magnesium silicate, mica, talc, barium sulfate, calcium sulfate, powdered Nylon™, perfluorinated alkanes, and other inert plastics.

The silk proteins may also be used in dental floss (see, for example, US 2005/0161058). The floss may be monofilament yarn or multifilament yarn, and the fibers may or may not be twisted. The dental floss may be packaged as individual pieces or in a roll with a cutter for cutting pieces to any desired length. The dental floss may be provided in a variety of shapes other than filaments, such as but not limited to, strips and sheets and the like. The floss may be coated with different materials, such as but not limited to, wax, polytetrafluoroethylene monofilament yarn for floss.

The silk proteins may also be used in soap (see, for example, US 2005/0130857).

Pigment and Cosmetic Particle Coating

The effective amount of a silk protein for use in pigment and cosmetic particle coating is herein defined as a proportion of from about $10^{-4}$ to about 50%, but preferably from about 0.25 to about 15% by weight relative to the dry weight of particle. The optimum amount of the silk protein to be used depends on the type of pigment or cosmetic particle being coated. For example, the amount of silk protein used with inorganic color pigments is preferably between about 0.01% and 20% by weight. In the case of organic pigments, the preferred amount of silk protein is between about 1% to about 15% by weight, while for inert particles, the preferred amount is between about 0.25% to about 3% by weight. Methods for the preparation of coated pigments and particles are described in U.S. Pat. No. 5,643,672. These methods include: adding an aqueous solution of the silk protein to the particles while tumbling or mixing, forming a slurry of the silk protein and the particles and drying, spray drying a solution of the silk protein onto the particles or lyophilizing a slurry of the silk protein and the particles. These coated pigments and cosmetic particles may be used in cosmetic formulations, paints, inks and the like.

Biomedical

The silk proteins may be used as a coating on a bandage to promote wound healing. For this application, the bandage material is coated with an effective amount of the silk protein. For the purpose of a wound-healing bandage, an effective amount of silk protein is herein defined as a proportion of from about $10^{-4}$ about 30% by weight relative to the weight of the bandage material. The material to be coated may be any soft, biologically inert, porous cloth or fiber. Examples include, but are not limited to, cotton, silk, rayon, acetate, acrylic, polyethylene, polyester, and combinations thereof. The coating of the cloth or fiber may be accomplished by a number of methods known in the art. For example, the material to be coated may be dipped into an aqueous solution containing the silk protein. Alternatively, the solution containing the silk protein may be sprayed onto the surface of the material to be coated using a spray gun. Additionally, the solution containing the silk protein may be coated onto the surface using a roller coat printing process. The wound bandage may include other additives including, but not limited to, disinfectants such as iodine, potassium iodide, povidon iodine, acrinol, hydrogen peroxide, benzalkonium chloride, and chlorohexidine; cure accelerating agents such as allantoin, dibucaine hydrochloride, and chlorophenylamine malate; vasoconstrictor agents such as naphazoline hydrochloride; astringent agents such as zinc oxide; and crust generating agents such as boric acid.

The silk proteins of the present invention may also be used in the form of a film as a wound dressing material. The use of silk proteins, in the form of an amorphous film, as a wound dressing material is described in U.S. Pat. No. 6,175,053. The amorphous film comprises a dense and nonporous film of a crystallinity below 10% which contains an effective amount of silk protein. For a film for wound care, an effective amount of silk protein is herein defined as between about 1 to 99% by weight. The film may also contain other components including but not limited to other proteins such as sericin, and disinfectants, cure accelerating agents, vasoconstrictor agents, astringent agents, and crust generating agents, as described above. Other proteins such as sericin may comprise 1 to 99% by weight of the composition. The amount of the other ingredients listed is preferably below a total of about 30% by weight, more preferably between about 0.5 to 20% by weight of the composition. The wound dressing film may be prepared by dissolving the above mentioned materials in an aqueous solution, removing insolubles by filtration or centrifugation, and casting the solution on a smooth solid surface such as an acrylic plate, followed by drying.

The silk proteins of the present invention may also be used in sutures (see, for example, US 2005/0055051). Such sutures can feature a braided jacket made of ultrahigh molecular weight fibers and silk fibers. The polyethylene provides strength. Polyester fibers may be woven with the high molecular weight polyethylene to provide improved tie down properties. The silk may be provided in a contrasting color to provide a trace for improved suture recognition and identification. Silk also is more tissue compliant than other fibers, allowing the ends to be cut close to the knot without concern for deleterious interaction between the ends of the suture and surrounding tissue. Handling properties of the high strength suture also can be enhanced using various materials to coat the suture. The suture advantageously has the strength of Ethibond No. 5 suture, yet has the diameter, feel and tieability of No. 2 suture. As a result, the suture is ideal for most orthopedic procedures such as rotator cuff repair, Achilles tendon repair, patellar tendon repair, ACL/PCL reconstruction, hip and shoulder reconstruction procedures, and replacement for suture used in or with suture anchors. The suture can be uncoated, or coated with wax (beeswax, petroleum wax, polyethylene wax, or others), silicone (Dow Corning silicone fluid 202A or others), silicone rubbers, PBA (polybutylate acid), ethyl cellulose (Filodel) or other coatings, to improve lubricity of the braid, knot security, or abrasion resistance, for example.

The silk proteins of the present invention may also be used in stents (see, for example, US 2004/0199241). For example, a stent graft is provided that includes an endoluminal stent and a graft, wherein the stent graft includes silk. The silk induces a response in a host who receives the stent graft, where the response can lead to enhanced adhesion between the silk stent graft and the host's tissue that is adjacent to the silk of the silk stent graft. The silk may be attached to the graft by any of various means, e.g., by interweaving the silk into the graft or by adhering the silk to the graft (e.g., by means of an adhesive or by means of suture). The silk may be in the form of a thread, a braid, a sheet, powder, etc. As for the location of the silk on the stent graft, the silk may be attached only the exterior of the stent, and/or the silk may be attached to distal regions of the stent graft, in order to assist in securing those distal regions to neighbouring tissue in the host. A wide variety of stent grafts may be utilized within the context of the present invention, depending on the site and nature of treatment desired. Stent grafts may be, for example, bifurcated or tube grafts, cylindrical or tapered, self-expandable or balloon-expandable, unibody or, modular, etc.

In addition to silk, the stent graft may contain a coating on some or all of the silk, where the coating degrades upon insertion of the stent graft into a host, the coating thereby delaying contact between the silk and the host. Suitable coatings include, without limitation, gelatin, degradable polyesters (e.g., PLGA, PLA, MePEG-PLGA, PLGA-PEG-PLGA, and copolymers and blends thereof), cellulose and cellulose derivatives (e.g., hydroxypropyl cellulose), polysaccharides (e.g., hyaluronic acid, dextran, dextran sulfate, chitosan), lipids, fatty acids, sugar esters, nucleic acid esters, polyanhydrides, polyorthoesters and polyvinylalcohol (PVA). The silk-containing stent grafts may contain a biologically active agent (drug), where the agent is released from the stent graft and then induces an enhanced cellular response (e.g., cellular or extracellular matrix deposition) and/or fibrotic response in a host into which the stent graft has been inserted.

The silk proteins of the present invention may also be used in a matrix for producing ligaments and tendons ex vivo (see, for example, US 2005/0089552). A silk-fiber-based matrix can be seeded with pluripotent cells, such as bone marrow stromal cells (BMSCs). The bioengineered ligament or tendon is advantageously characterized by a cellular orientation and/or matrix crimp pattern in the direction of applied mechanical forces, and also by the production of ligament and tendon specific markers including collagen type I, collagen type III, and fibronectin proteins along the axis of mechanical load produced by the mechanical forces or stimulation, if such forces are applied. In a preferred embodiment, the ligament or tendon is characterized by the presence of fiber bundles which are arranged into a helical organization. Some examples of ligaments or tendons that can be produced include anterior cruciate ligament, posterior cruciate ligament, rotator cuff tendons, medial collateral ligament of the elbow and knee, flexor tendons of the hand, lateral ligaments of the ankle and tendons and ligaments of the jaw or temporomandibular joint. Other tissues that may be produced by methods of the present invention include cartilage (both articular and meniscal), bone, muscle, skin and blood vessels.

The silk proteins of the present invention may also be used in hydrogels (see, for example, US 2005/0266992). Silk fibroin hydrogels can be characterized by an open pore structure which allows their use as tissue engineering scaffolds, substrate for cell culture, wound and burn dressing, soft tissue substitutes, bone filler, and as well as support for pharmaceutical or biologically active compounds.

The silk proteins may also be used in dermatological compositions (see, for example, US 2005/0019297). Furthermore, the silk proteins of the invention and derivatives thereof may also be used in sustained release compositions (see, for example, US 2004/0005363).

Textiles

The silk proteins of the present invention may also be applied to the surface of fibers for subsequent use in textiles. This provides a monolayer of the protein film on the fiber, resulting in a smooth finish. U.S. Pat. Nos. 6,416,558 and 5,232,611 describe the addition of a finishing coat to fibers. The methods described in these disclosures provide examples of the versatility of finishing the fiber to provide a good feel and a smooth surface. For this application, the fiber is coated with an effective amount of the silk protein. For the purpose of fiber coating for use in textiles, an effective amount of silk protein is herein defined as a proportion of from about 1 to about 99% by weight relative to the weight of the fiber material. The fiber materials include, but are not limited to textile fibers of cotton, polyesters such as rayon and Lycra™, nylon, wool, and other natural fibers including native silk. Compositions suitable for applying the silk protein onto the fiber may include co-solvents such as ethanol, isopropanol, hexafluoranols, isothiocyanouranates, and other polar solvents that can be mixed with water to form solutions or microemulsions. The silk protein-containing solution may be sprayed onto the fiber or the fiber may be dipped into the solution. While not necessary, flash drying of the coated material is preferred. An alternative protocol is to apply the silk protein composition onto woven fibers. An ideal embodiment of this application is the use of silk proteins to coat stretchable weaves such as used for stockings.

Composite Materials

Silk fibres can be added to polyurethane, other resins or thermoplastic fillers to prepare panel boards and other construction material or as moulded furniture and benchtops that replace wood and particle board. The composites can be also be used in building and automotive construction especially rooftops and door panels. The silk fibres re-enforce the resin making the material much stronger and allowing lighter-weight construction which is of equal or superior strength to other particle boards and composite materials. Silk fibres may be isolated and added to a synthetic composite-forming resin or be used in combination with plant-derived proteins, starch and oils to produce a biologically-based composite materials. Processes for the production of such materials are described in JP 2004284246, US 2005175825, U.S. Pat. No. 4,515,737, JP 47020312 and WO 2005/017004.

Paper Additives

The fibre properties of the silk of the invention can add strength and quality texture to paper making. Silk papers are made by mottling silk threads in cotton pulp to prepare extra smooth handmade papers is used for gift wrapping, notebook covers, carry bags. Processes for production of paper products which can include silk proteins of the invention are generally described in JP 2000139755.

Advanced Materials

Silks of the invention have considerable toughness and stands out among other silks in maintaining these properties when wet (Hepburn et al., 1979).

Areas of substantial growth in the clothing textile industry are the technical and intelligent textiles. There is a rising demand for healthy, high value functional, environmentally friendly and personalized textile products. Fibers, such as those of the invention, that do not change properties when wet and in particular maintain their strength and extensibility are useful for functional clothing for sports and leisure wear as well as work wear and protective clothing.

Developments in the weapons and surveillance technologies are prompting innovations in individual protection equipments and battle-field related systems and structures. Besides conventional requirements such as material durability to prolonged exposure, heavy wear and protection from external environment, silk textiles of the invention can be processed to resist ballistic projectiles, fire and chemicals. Processes for the production of such materials are described in WO 2005/045122 and US 2005268443.

EXAMPLES

Example 1

Preparation and Analysis of Late Last Instar Salivary Gland cDNAs

The proteins that are found in euaculeatan and neuropteran (*Apis mellifera, Bombus terrestris, Myrmecia forficata, Oecophylla smaragdina, Mallada signata*) silks were identified by matching ion trap consecutive mass spectral (MS/MS) fragmentation patterns of peptides obtained by trypsin digestion of the silk with the predicted mass spectral data of proteins encoded by cDNAs isolated from the salivary gland of late final instar larvae. For confirmation that no proteins were missed by this analysis for the honeybee, the peptide mass spectral data were also compared to virtual tryptic digests of *Apis mellifera* proteins predicted by the bee genome project and translations of the Ame13 honeybee genomic sequences in all six reading frames.

Honeybee

*Apis mellifera* larvae were obtained from domestic hives. Previously it was shown that silk production in *Apis mellifera* is confined to the salivary gland during the latter half of the final instar (Silva-Zacarin et al., 2003). During this period, RNA is more abundant in the posterior end of the gland (Flower and Kenchington, 1967). The cubical cell regions of 50 salivary glands were dissected from late fifth instar *Apis mellifera* immersed in phosphate buffered saline. The posterior end of the dissected gland was immediately placed into RNAlater® (Ambion, Austin, Tex., USA), to stabilise the mRNA, and subsequently stored at 4° C.

Total RNA (35 µg) was isolated from the late final instar salivary glands using the RNAqueous for PCR kit from Ambion (Austin, Tex., USA). Message RNA was isolated from the total RNA using the Micro-FastTrack™ 2.0 mRNA Isolation kit from Invitrogen (Calsbad, Calif., USA) according to the manufacturer's directions with the isolated mRNA being eluted into 10 ul RNAse free water.

A cDNA library was constructed from the mRNA isolated from *Apis mellifera* larvae using the CloneMiner™ cDNA library construction kit of Invitrogen (Calsbad, Calif., USA) with the following modifications from the standard protocol: For the first strand synthesis, 0.5 µl of Biotin-attB2-Oligo(dT) primer at 6 pmol.µl$^{-1}$ and 0.5 µl of dNTPs at 2 mM each was added to the 10 µl mRNA. After incubation at 65° C. for 5 min then 45° C. for 2 min, 2 µl 5× First strand buffer, 1 µl of 0.1M DTT, and 0.5 µl SuperScript™ II RT at 200 U.µl$^{-1}$ were added. For second strand synthesis, the total volume of all reagents was halved and after ethanol precipitation, the cDNA was resuspended in 5 µl of DEPC-treated water. The aatB1 adapter (1 µl) was ligated in a total volume of 10 µl to the 5 µl cDNA with 2 µl 5× Adapter buffer, 1 µl 0.1M DTT and 1 µl T4 DNA ligase (1 U.µl$^{-1}$) at 16° C. for 48 hrs with an additional 0.5 µl T4 DNA ligase (1 U.µl$^{-1}$) added after 16 hrs. The cDNA was size fractionated according, to the manufactures instructions with samples eluting between 300-500 µl being precipitated with ethanol, resuspended and transformed into the provided *E. coli* DH10B™ T1 phage resistant cells as recommended. The cDNA library comprised approximately 1,200,000 colony forming units (cfu) with approximately 1% the original vector. The average insert size was 1.3±1.4 kbp.

Eighty two clones were randomly selected and sequenced using the GenomeLab™ DTCS Quick start kit (Beckman-Coulter, Fullerton Calif. USA) and run on a CEQ8000 Biorad sequencer. These clustered into fifty four groups (Table 2). Identification of the cDNAs that encoded the silk proteins is described below.

Other Species

Total RNA was isolated from 4 bumblebee (Bombus terrestris) (2 µg RNA), 4 bulldog ant (*Myrmecia forficata*) (3 µg RNA), approximately 100 Weaver ants (*Oecophylla smaragdina*) (0.4 µg RNA) and approximately 50 green lacewing (*Mallada signata*) late larval labial glands using the RNAqueous for PCR kit from Ambion (Austin, Tex., USA). mRNA was isolated from the total RNA using the Micro-FastTrack™

2.0 mRNA Isolation kit from Invitrogen (Calsbad, Calif., USA) into a final volume of 10 μl water. cDNA libraries were constructed from the mRNA using the CloneMiner™ cDNA kit of Invitrogen (Calsbad, Calif., USA) with the following modifications from the standard protocol: For the first strand synthesis, 3 pmol of Biotin-attB2-Oligo(dT) primer and 1 nmol each dNTPs were added to the 10 μl mRNA. After 5 min at 65° C. followed by 2 min at 45° C., 2 μl 5× First strand buffer, 50 nmol DTT, and 100 U SuperScript™ II RT were added.

TABLE 2

*A. mellifera* final instar salivary gland cDNAs and MS ion trap fragmentation patterns of peptides from trypsin digestion of SDS treated brood comb silk.

| Number of cDNA's in cluster | Abundance in salivary gland library (%) | Protein or gene synonyms | Number of tryptic peptides identified in the silk | Distinct summed MS/MS search score | Coverage of protein sequence (% protein) | Protein identification |
|---|---|---|---|---|---|---|
| Proteins identified in cDNA library and in honeybee silk ||||||||
| 10 | 13 | Xenosin; GB15233-PA | 9 | 143.89 | 25 | AC004701 |
| 8 | 11 | Xenospira1; GB12184-PA | 10 | 165.13 | 37 | No matches |
| 6 | 7 | Xenospira4; GB19585-PA | 8 | 142.16 | 35 | No matches |
| 6 | 7 | Xenospira2; GB12348-PA | 9 | 145.91 | 28 | No matches |
| 5 | 6 | Xenospira3; GB17818-PA | 9 | 147.02 | 31 | No matches |
| Proteins identified in cDNA library only ||||||||
| 4 | 4 | GB14261-PA | 0 | | | |
| 2 | 2 | Contig 2504 | 0 | | | |
| 2 | 2 | GB17108-PA | 0 | | | |
| 1 | 1 | Contig 68 | 0 | | | |
| 1 | 1 | Contig 110 | 0 | | | |
| 1 | 1 | Contig 487 | 0 | | | |
| 1 | 1 | GB14199-PA | 0 | | | |
| 1 | 1 | GB10847-PA | 0 | | | |
| 1 | 1 | Contig 1047 | 0 | | | |
| 1 | 1 | GB17558-PA | 0 | | | |
| 1 | 1 | Contig 1471 | 0 | | | |
| 1 | 1 | GB16480-PA | 0 | | | |
| 1 | 1 | Contig 1818 | 0 | | | |
| 1 | 1 | GB16911-PA | 0 | | | |
| 1 | 1 | Contig 2046 | 0 | | | |
| 1 | 1 | Contig 2136 | 0 | | | |
| 1 | 1 | Contig 2196 | 0 | | | |
| 1 | 1 | GB11234-PA | 0 | | | |
| 1 | 1 | GB11199-PA | 0 | | | |
| 1 | 1 | GB18183-PA | 0 | | | |
| 1 | 1 | Contig 2938 | 0 | | | |
| 1 | 1 | Contig 2976 | 0 | | | |
| 1 | 1 | Contig 3263 | 0 | | | |
| 1 | 1 | Contig 3527 | 0 | | | |
| 1 | 1 | GB16412-PA | 0 | | | |
| 1 | 1 | GB18750-PA | 0 | | | |
| 1 | 1 | GB16132-PA | 0 | | | |
| 1 | 1 | Contig 4536 | 0 | | | |
| 1 | 1 | GB19431-PA | 0 | | | |
| 1 | 1 | Contig 4704 | 0 | | | |
| 1 | 1 | Contig 4758 | 0 | | | |
| 1 | 1 | Contig 4830 | 0 | | | |
| 1 | 1 | Contig 4968 | 0 | | | |
| 1 | 1 | Contig 5402 | 0 | | | |
| 1 | 1 | Contig 5971 | 0 | | | |
| 1 | 1 | GB11274-PA | 0 | | | |
| 1 | 1 | GB14693-PA | 0 | | | |
| 1 | 1 | GB19585-PA | 0 | | | |
| 1 | 1 | GB15606-PA | 0 | | | |
| 1 | 1 | GB16801-PA | 0 | | | |
| 1 | 1 | GB12085-PA | 0 | | | |
| 1 | 1 | Contig 7704 | 0 | | | |
| 1 | 1 | Contig 8630 | 0 | | | |
| 1 | 1 | Contig 9774 | 0 | | | |
| 1 | 1 | GB16452-PA | 0 | | | |
| 1 | 1 | GB10420-PA | 0 | | | |
| 1 | 1 | GB14724-PA | 0 | | | |

For second strand synthesis, the total volume of all reagents was halved from the manufacturer's recommended amounts and after ethanol precipitation, the cDNA was resuspended in 5 μl of DEPC-treated water. The aatB1 adapter (1 μl) was ligated in a total volume of 10 μl to the 5 μl cDNA with 2 μl 5× Adapter buffer, 50 nmol DTT and 1 U T4 DNA ligase at 16° C. for 12 hrs. The cDNA libraries comprised approximately $2.4 \times 10^7$ (bumblebee), $5.0 \times 10^7$ (bulldog ant) and 6000 (green ant) colony forming units (cfu) with less than 1% the original vector for the bulldog ant and bumblebee libraries and greater than 80% original vector in the green ant library. The average insert size within the libraries was 1.3 Kbp.

Sequence data was obtained from more than 100 random clones from the cDNA libraries from bumblebee and bulldog ant, 82 clones from the honeybee and 60 clones from the lacewing. The technical difficulties of obtaining salivary glands from the minute green ants (approximately 1 mm in length) reduced the efficiency of the library from this species and as such only 40 sequences were examined. A summary of the silk proteins identified is provided in Table 3.

A subset of the honeybee material was soaked overnight in 2% SDS at 95° C., followed by three washes in distilled water. Extraction in hot SDS solution solubilises most proteins, but in this case the silk sheets retained their conformation.

The clean silks were analysed by liquid chromatography followed by tandem mass spectrometry (LCMS) as described below.

Pieces of cleaned silk were placed in a well of a Millipore 'zipplate', a 96 well microtitre tray containing a plug of C18 reversed phase chromatography medium through the bottom of each well to which was added 20 μl 25 mM ammonium bicarbonate containing 160 ng of sequencing grade trypsin (Promega). Then the tray was incubated overnight in a humidified plastic bag at 30° C.

The C18 material was wetted by pipetting acetonitrile (10 μl) to the sides of each well and incubating the plate at 37° C. for 15 min. Formic acid solution (130 μl, 1% v/v) was added to each well and after 30 min peptides from the digested bee proteins were captured on the C18 material by slowly drawing the solutions from each well through the base of the plate

TABLE 3

Identification and properties of the euacuieatan silk proteins.

| Species | Protein name | Length of protein (amino acids) | % cDNA library clones | Distinct summed MS/MS identification score | % helical structure** | MARCOIL predicted coiled coil length*** (amino acids) |
|---|---|---|---|---|---|---|
| Honeybee | AmelF1* | 333 | 6 | 52 | 76 | 117 |
| Honeybee | AmelF2* | 290 | 7 | 51 | 88 | 175 |
| Honeybee | AmelF3* | 335 | 11 | 107 | 81 | 154 |
| Honeybee | AmelF4* | 342 | 7 | 88 | 76 | 174 |
| Honeybee | AmelSA1* | 578 | 13 | 40 | 41 | 45 |
| Bumblebee | BBF1 | 327 | 4 | 180 | 86 | 147 |
| Bumblebee | BBF2 | 313 | 14 | 100 | 84 | 199 |
| Bumblebee | BBF3 | 332 | 20 | 218 | 86 | 146 |
| Bumblebee | BBF4 | 357 | 32 | 137 | 80 | 188 |
| Bumblebee | BBSA1 | >501 | 3 | 138 | 21 | 0 |
| Bulldog ant | BAF1 | 422 | 16 | 99 | 69 | 121 |
| Bulldog ant | BAF2 | 411 | 30 | 90 | 76 | 132 |
| Bulldog ant | BAF3 | 394 | 26 | 88 | 79 | 131 |
| Bulldog ant | BAF4 | 441 | 24 | 116 | 76 | 157 |
| Weaver ant | GAF1 | 391 | 35 | 228 | 74 | 177 |
| Weaver ant | GAF2 | 400 | 22 | 191 | 79 | 158 |
| Weaver ant | GAF3 | 395 | 13 | 156 | 72 | 103 |
| Weaver ant | GAF4 | 443 | 17 | 148 | 74 | 166 |
| Lacewing | MalF1 | 596 | 23 | 45 | 89 | 151 |

*also referred to herein as Xenospira1-4 and Xenosin respectively,
**predicted by PROFsec,
***predicted by MARCOIL at 90% threshold Example 2

Preparation and Proteomic Analysis of Native Silk

Honeybee brood comb after the removal of larvae, bumblebee cocoons after the removal of larvae, bulldog ant cocoons after the removal of larvae, or weaver ant silk sheets were washed extensively three times in warm water to remove water soluble contaminants and then washed extensively three times in chloroform to remove wax. Chloroform was removed by rinsing in distilled water and a subset of this silk was retained for analysis. A subset of the Hymenopteran (ants and bees) silk samples was further washed by boiling for 30 minutes in 0.05% sodium carbonate solution, a standard procedure for degumming silkworm silk, then rinsed in distilled water. Lacewing silk was rinsed in distilled water only. A subset of the lacewing silk samples was degummed by boiling for 30 minutes in 0.05% sodium carbonate solution.

under a reduced vacuum. The C18 material was washed twice by drawing through 100 μl of formic acid solution. Peptides were eluted with 6 μl of 1% formic acid in 70% methanol pipetted directly onto the C18 material and promptly centrifuged through the C18 plug to an underlying microtitre tray. This tray was placed under vacuum till the volume in each well was reduced about 2-fold by evaporation. Formic acid solution (10 μl) was added to each well and the tray was transferred to the well plate sampler of an Agilent 1100 capillary liquid chromatography system.

Peptides (8 μl) from the silk extract were bound to an Agilent Zorbax SB-C18 5 μm 150×0.5 mm column with a flow rate of 0.1% formic acid/5% acetonitrile at 20 μl.min$^{-1}$ for one min then eluted with gradients of increasing acetonitrile concentration to 0.1% formic acid/20% acetonitrile over one minute at 5 μl.min$^{-1}$, then to 0.1% formic acid/50% acetonitrile over 28 minutes, then to 0.1% formic acid/95% acetonitrile over one minute. The column was washed with 0.1% formic acid/95%-100% acetonitrile over 5 mins at 20 µl.min$^{-1}$ and reequilibrated with 0.1% formic acid/5% acetonitrile for 7 mins before peptides from the next well were sampled.

Eluate from the column was introduced to an Agilent XCT ion trap mass spectrometer through the instrument's electrospray ion source fitted with a micronebuliser. Briefly, as peptides were eluting from the column, the ion trap collected full spectrum positive ion scans (100-2200 m/z) followed by two MS/MS scans of ions observed in the full spectrum avoiding the selection of ions that carried only a single charge. When an ion was selected for MS/MS analysis all others were excluded from the ion trap, the selected ion was fragmented according to the instrument's recommended "SmartFrag" and "Peptide Scan" settings. Once two fragmentation spectra were collected for any particular m/z value it was excluded from selection for analysis for a further 30 seconds to avoid collecting redundant data.

Mass spectral data sets from the entire experiment were analysed using Agilent's Spectrum Mill software to match the data with predictions of protein sequences from the cDNA libraries. The software generated scores for the quality of each match between experimentally observed sets of masses of fragments of peptides and the predictions of fragments that might be generated according to the sequences of proteins in a provided database. All the sequence matches reported here received scores greater than 20, the default setting for automatic, confident acceptance of valid matches.

This analysis identified that five proteins expressed at high levels in the labial gland matched the silk from each of the cognate bee species (shown in Tables 2 and 3) and four proteins expressed at high levels in the labial gland matched the silk from each of the cognate ant species (shown in Table 3). The abundance of message RNA encoding these proteins in the labial gland of the larvae was consistent with the proteins being abundantly produced (abundance of message shown in Table 3).

To ensure that none of the honeybee silk proteins were missed by this identification process, we also compared the honeybee silk trypsin peptide mass spectral data to a set of publicly available predicted protein sequences from the honeybee genome project, generated by a computer algorithm that tries to recognise transcribed genes in the complete genomic DNA sequences of the bee. Additionally, we generated a database of translations in the six possible reading frames of each contiguous genomic DNA sequence provided by the bee genome project (Amel3 release). These translated DNA sequences were presented to the Spectrum Mill software as if they were the sequences of very large proteins. Matching MS/MS peptide data identified open reading frames within the genomic sequences that had encoded parts of the isolated bee proteins without the need to first predict the organisation of genes. No additional proteins were identified in the silk by this analysis.

Example 3

Structural Analysis of the Native Silk

Native silk samples were prepared as described in Example 2. Silk samples were examined using a Bruker Tensor 37 Fourier transform infrared spectrometer with a Pike Miracle diamond attenuated total reflection accessory. Analysis of the amide I and II regions of the spectra of honeybee, bumblebee, green ant, bulldog ant silks and lacewing larval silk (FIG. 1) shows that all these silks have a predominantly alpha-helical secondary structure. The silks of the Euaculeatan species have dominant peaks in the FT-IR spectra at 1645-1646 cm$^{-1}$, shifted approximately 10 cm$^{-1}$ lower than a classical α-helical signal and broadened. This shift in the α-helical signal is typical of coiled-coil proteins (Heimburg et al., 1999). Spectra from samples that were degummed were unchanged.

Example 4

The Amino Acid Composition of Native Silks Closely Resembles that Of the Identified Silk Proteins The amino acid composition of the native silks was determined after 24 hr gas phase hydrolysis at 110° C. using the Waters AccQTag chemistry by Australian Proteome Analysis Facility Ltd (Macquarie University, Sydney).

The measured amino acid composition of the SDS washed silk was similar to that predicted from the identified silks protein sequences (FIGS. 2 and 3).

Example 5

Structural Analysis of the Silk Proteins

Predicted Secretory Peptides

As expected for silk proteins, the SignalP 3.0 signal prediction program (Bendtsen et al., 2004), which uses two models to identify signal peptides predicted that all the identified silk genes encoded proteins which contain signal peptides that targeted them for secretion from a cell (data not shown). The predicted cleavage sites of the polypeptides are as follows:

Xenospira1 (AmelF1)—between pos 19 and 20 (ASA-GL),
Xenospira2 (AmelF2)—between pos 19 and 20 (AEG-RV),
Xenospira3 (AmelF3)—between pos 19 and 20 (VHA-GV),
Xenospira4 (AmelF4)—between pos 19 and 20 (ASG-AR),
Xenosin (AmelSA1)—between pos 19 and 20 (VCA-GV),
BBF1—between pos 19 and 20 (ASA-GQ),
BBF2—between pos 20 and 21 (AEG-HV),
BBF3—between pos 19 and 20 (VHA-GS),
BBF4—between pos 19 and 20 (ASA-GK),
BAF1—between pos 19 and 20 (ASA-SG),
BAF2—between pos 19 and 20 (ASG-RV),
BAF3—between pos 19 and 20 (ASG-NL),
BAF4—between pos 19 and 20 (VGA-SE),
GAF1—between pos 19 and 20 (ADA-SK),
GAF2—between pos 19 and 20 (ASG-GV),
GAF3—between pos 19 and 20 (ASG-GV),
GAF4—between pos 19 and 20 (VGA-SE),
MalF1 between pos 26 and 27 (SST-AV).

All Four of the Ant and Four of the Five Bee Silk Proteins are Helical and Formed Coiled Coils Protein modelling and results from pattern recognition algorithms confirmed that the majority of the identified honeybee silk proteins were helical proteins that formed coiled coils.

PROFsec (Rost and Sander, 1993) and NNPredict (McClelland and Rumelhart, 1988; Kneller et al., 1990), algorithms were used to investigate the secondary structure of the identified silk genes. These algorithms identified Xenospira1 [GB 12184-PA] (SEQ ID NO:1), Xenospira2 [GB12348-PA] (SEQ ID NO:3), Xenospira3 [GB17818-PA] (SEQ ID NO:5), and Xenospira4 [GB19585-PA] (SEQ ID NO:7), as highly helical proteins, with between 76-85% helical structure (Table 4). Xenosin [GB15233-PA] (SEQ ID NO:10) had significantly less helical structure.

TABLE 4

The secondary structure of *Apis mellifera* silk proteins predicted by PROFsec (Rost and Sander, 1993) showing percentages of helices, extended sheets and loops.

| Protein | helical | | extended | | loop | |
|---|---|---|---|---|---|---|
| | PROFsec | NNPredict | PROFsec | NNPredict | PROFsec | NNPredict |
| Xenospira3 | 77 | 70 | 3 | 6 | 20 | 27 |
| Xenospira4 | 85 | 82 | 2 | 6 | 14 | 16 |
| Xenospira1 | 80 | 73 | 1 | 4 | 19 | 26 |
| Xenospira2 | 77 | 69 | 2 | 5 | 21 | 29 |
| Xenosin | 41 | 41 | 8 | 9 | 51 | 50 |

Further protein modelling and results from pattern recognition algorithms confirmed that the majority of the identified silk proteins were helical proteins that formed coiled coils. PredictProtein (Rost et al., 2004) algorithms were used to investigate the secondary structure of the identified silk genes. These algorithms identified Xenospira1 (SEQ ID NO:1), Xenospira2 (SEQ ID NO:3), Xenospira3 (SEQ ID NO:5), Xenospira4 (SEQ ID NO:7), BBF1 (SEQ ID NO:22), BBF2 (SEQ ID NO:24), BBF3 (SEQ ID NO:26), BBF4 (SEQ ID NO:28), BAF1 (SEQ ID NO:40), BAF2 (SEQ ID NO:42), BAF3 (SEQ ID NO:44), BAF4 (SEQ ID NO:46), GAF1 (SEQ ID NO:56), GAF2 (SEQ ID NO:58), GAF3 (SEQ ID NO:60), GAF4 (SEQ ID NO:62), and MalF1 (SEQ ID NO:72) as highly helical proteins, with between 69-88% helical structure (Table 3). Ame1SA1 [GB15233-PA] (Xenosin) (SEQ ID NO:10) and BBSA1 (SEQ ID NO:30) had significantly less helical structure.

Super-coiling of helical proteins (coiled coils) arises from a characteristic heptad repeat sequence normally denoted as (abcdefg)$_n$ with generally hydrophobic residues in position a and d, and generally charged or polar residues at the remaining positions. The pattern recognition programs (MARCOIL (Delorenzi and Speed, 2002), COILS (Lupas et al., 1991)) identified numerous heptad repeats typical of coiled-coils in Xenospira1 [GB12184-PA] (SEQ ID NO:1), Xenospira2 [GB12348-PA] (SEQ ID NO:3), Xenospira3 [GB17818-PA] (SEQ ID NO:5), and Xenospira4 [GB19585-PA] (SEQ ID NO:7) (MARCOIL: Table 5; COILS: FIG. 4), as well as BBF1 (SEQ ID NO:22), BBF2 (SEQ ID NO:24), BBF3 (SEQ ID NO:26), BBF4 (SEQ ID NO:28), BAF1 (SEQ ID NO:40), BAF2 (SEQ ID NO:42), BAF3 (SEQ ID NO:44), BAF4 (SEQ ID NO:46), GAF1 (SEQ ID NO:56), GAF2 (SEQ ID NO:58), GAF3 (SEQ ID NO:60), GAF4 (SEQ ID NO:62), and MalF1 (SEQ ID NO:72) (MARCOIL: Table 3).

Identification of a Novel Coiled Coil Sequence in the Honeybee Silk Proteins

The heptad repeats of amino acid residues identified in the sequences of Xenospira1 [GB 12184-PA], Xenospira2 [GB 12348-PA], Xenospira3 [GB 17818-PA], Xenospira4 [GB19585-PA], were each highly indicative of a coiled coil secondary structure (FIG. 5) (see Table 5 for confidence levels). The fact that the heptads are found consecutively and numerously suggests the proteins adopt a very regular structure. Overlapping heptads were identified in two of the honeybee proteins: the major coiled coil region of Xenospira1 contained overlapping heptads with a 3 residue offset followed by a space of 5 residues and then four consecutive heptads; and the entire coiled coil region of Xenospira2 had multiple overlapping heptads with a single offset and 4 residue offset (equivalent to 3 residue offset). The composition of amino acids in the various positions of the major heptad are shown in the first column in Table 6, with the positions of the overlapping heptads indicated in adjacent columns.

TABLE 5

Percent of residues in the identified silk proteins predicted to exist as coiled coil by the MARCOIL (Delorenzi and Speed, 2002) pattern recognition algorithm.

| Protein | Lenght of mature protein (amino acids) | Percent protein that exists as coiled coil | | |
|---|---|---|---|---|
| | | 50% threshold | 90% threshold | 99% threshold |
| Xenospira3 | 315 | 64% (residues 68 to 268) | 34% (residues 128-223 and 235-246) | 20% (residues 149-211) |
| Xenospira4 | 290 | 73% (residues 83-293) | 60% (residues 98-168 and 182-285) | 27% (residues 113-154 and 212-247) |
| Xenospira1 | 316 | 69% (residues 67-282) | 49% (residues 103-256) | 18% (residues 113-169) |
| Xenospira2 | 328 | 65% (residues 89-298) | 54% (residues 110-283) | 45% (residues 127-270) |
| Xenosin | 350 | 26% (residues 32-127) | 9% (residues 42-75) | 2% (residues 59-67) |

Surprisingly the major heptads have a novel composition when viewed collectively—with an unusually high abundance of alanine in the 'hydrophobic' heptad positions a and d (see Table 6 and FIG. 5). Additionally, a high proportion of heptads have alanine at both a and d positions within the same heptad (33% in Xenospira1 [GB12184-PA]; 36% in Xenospira2 [GB 12348-PA]; 27% in Xenospira3 [GB17818-PA]; and 38% in Xenospira4 [GB19585-PA]; see Tables 6 and 7).

The composition of amino acids in the various heptad positions in the coiled coil region of the hymenopteran silks are summarised in FIGS. 6 and 7. As noted above, the positions within the heptads have a novel composition—the 'hydrophobic' heptad positions a and d of the bee and ant silks contain very high levels of alanine (average 58%) and high levels of small polar residues (average 21%) in comparison to other coiled coils. Additionally, position e is unusually small

TABLE 6

Summary of the number of each amino acid residues in the various heptad positions in coiled coil regions of honeybee silk proteins.

|   | A | I | R | L | K | T | E | V | F | S | Q | N | D | G | M | Y | W | Total |
|---|---|---|---|---|---|---|---|---|---|---|---|---|---|---|---|---|---|---|
| Xenospira4 ||||||||||||||||||
| a | 23 | 0 | 1 | 1 | 0 | 1 | 1 | 1 | 0 | 1 | 0 | 0 | 0 | 0 | 0 | 0 | 0 | 29 |
| b | 12 | 0 | 0 | 2 | 2 | 2 | 3 | 1 | 0 | 3 | 1 | 1 | 1 | 1 | 0 | 0 | 0 | 29 |
| c | 12 | 0 | 0 | 1 | 5 | 1 | 3 | 1 | 0 | 3 | 1 | 1 | 0 | 1 | 0 | 0 | 0 | 29 |
| d | 17 | 0 | 0 | 5 | 1 | 0 | 1 | 2 | 0 | 2 | 1 | 0 | 0 | 0 | 0 | 0 | 0 | 29 |
| e | 12 | 0 | 1 | 0 | 0 | 2 | 4 | 2 | 0 | 5 | 2 | 1 | 0 | 0 | 0 | 0 | 0 | 29 |
| f | 13 | 1 | 0 | 1 | 2 | 0 | 7 | 1 | 0 | 1 | 1 | 2 | 0 | 0 | 0 | 0 | 0 | 29 |
| g | 9 | 3 | 4 | 0 | 2 | 1 | 2 | 1 | 0 | 2 | 0 | 1 | 2 | 2 | 0 | 0 | 0 | 29 |
| Xenospira3 ||||||||||||||||||
| a | 19 | 0 | 0 | 1 | 0 | 4 | 2 | 0 | 0 | 1 | 1 | 1 | 0 | 0 | 0 | 1 | 0 | 30 |
| b | 8 | 0 | 0 | 5 | 1 | 2 | 2 | 0 | 0 | 5 | 4 | 2 | 1 | 0 | 0 | 0 | 0 | 30 |
| c | 13 | 0 | 1 | 0 | 3 | 2 | 2 | 3 | 0 | 1 | 2 | 0 | 1 | 1 | 0 | 0 | 1 | 30 |
| d | 13 | 3 | 0 | 2 | 2 | 0 | 2 | 2 | 0 | 4 | 0 | 1 | 1 | 0 | 0 | 0 | 0 | 30 |
| e | 8 | 0 | 0 | 2 | 2 | 2 | 4 | 0 | 0 | 7 | 4 | 0 | 0 | 1 | 0 | 0 | 0 | 30 |
| f | 7 | 0 | 2 | 3 | 4 | 2 | 4 | 0 | 0 | 4 | 1 | 2 | 1 | 0 | 0 | 0 | 0 | 30 |
| g | 9 | 0 | 5 | 2 | 2 | 3 | 0 | 1 | 2 | 0 | 5 | 0 | 2 | 1 | 0 | 0 | 0 | 30 |
| Xenospira2 ||||||||||||||||||
| a | 20 | 0 | 0 | 1 | 0 | 3 | 1 | 1 | 1 | 1 | 0 | 0 | 0 | 0 | 0 | 0 | 0 | 28 |
| b | 7 | 2 | 2 | 2 | 2 | 2 | 2 | 4 | 0 | 1 | 1 | 3 | 0 | 0 | 0 | 0 | 0 | 28 |
| c | 9 | 0 | 2 | 0 | 4 | 1 | 2 | 4 | 0 | 1 | 3 | 2 | 0 | 0 | 1 | 1 | 1 | 28 |
| d | 16 | 0 | 0 | 3 | 3 | 1 | 0 | 1 | 0 | 1 | 2 | 0 | 1 | 0 | 0 | 0 | 0 | 28 |
| e | 11 | 0 | 1 | 3 | 0 | 3 | 4 | 1 | 0 | 2 | 2 | 0 | 1 | 0 | 0 | 0 | 0 | 28 |
| f | 10 | 2 | 1 | 0 | 1 | 2 | 6 | 1 | 0 | 3 | 1 | 1 | 0 | 0 | 0 | 0 | 0 | 28 |
| g | 8 | 4 | 1 | 0 | 1 | 1 | 5 | 0 | 0 | 0 | 2 | 4 | 0 | 1 | 1 | 0 | 0 | 28 |
| Xenospira1 ||||||||||||||||||
| a | 13 | 3 | 0 | 1 | 2 | 0 | 1 | 1 | 0 | 2 | 1 | 1 | 0 | 2 | 0 | 0 | 0 | 27 |
| b | 7 | 1 | 1 | 1 | 6 | 0 | 2 | 1 | 0 | 3 | 1 | 0 | 4 | 0 | 0 | 0 | 0 | 27 |
| c | 8 | 1 | 2 | 1 | 1 | 1 | 7 | 2 | 0 | 1 | 1 | 1 | 0 | 1 | 0 | 0 | 0 | 27 |
| d | 18 | 0 | 0 | 2 | 1 | 2 | 1 |   | 0 | 2 | 1 | 0 | 0 | 0 | 0 | 0 | 0 | 27 |
| e | 11 | 1 | 2 | 1 | 1 | 2 | 3 | 2 | 0 | 4 | 0 | 0 | 0 | 0 | 0 | 0 | 0 | 27 |
| f | 7 | 0 | 3 | 0 | 2 | 1 | 3 | 3 | 0 | 7 | 0 | 1 | 0 | 0 | 0 | 0 | 0 | 27 |
| g | 13 | 0 | 0 | 3 | 3 | 0 | 2 | 1 | 0 | 3 | 1 | 0 | 0 | 0 | 1 | 0 | 0 | 27 |

TABLE 7

Summary of alanine residues in heptads of honeybee silk proteins.

| Protein | Amount of helical structure (%)[1] | Number of major heptads | Amount of protein in major heptad (%) | Amount of Ala in major heptads (%) | Amount of Ala in position a of major heptads (%) | Amount of Ala in position d of major heptads (%) | Amount of Ala in position a and d of major heptads (%) |
|---|---|---|---|---|---|---|---|
| Xenospira1 | 77 (70) | 27 |   | 41 | 44 | 74 | 33 |
| Xenospira2 | 85 (82) | 28 |   | 37 | 71 | 57 | 36 |
| Xenospira3 | 80 (73) | 30 |   | 37 | 63 | 43 | 27 |
| Xenospira4 | 77 (69) | 29 |   | 48 | 79 | 58 | 38 |
| Xenosin | 41 (41) |   |   | n/a | n/a | n/a | n/a |

[1]PROFsec predictions with NNPredict predictions shown in brackets.

and hydrophobic (Table 8, FIG. 7). Topographically this position is located adjacent to the a residues within the helices. Its compositional similarity with the a and d residues suggest that the silks adopt a coiled coil structure with three core residues per α-helix. Three residue cores contribute a larger hydrophobic interface than two residues in the core (Deng et al., 2006)—a feature that would assist coiled coil formation and stability.

In addition, when viewed collectively the positions b, c, e, f and g within the heptad are generally more hydrophobic, less polar and less charged than protein coiled coil regions previously characterised (see FIG. 7, and Tables 8 and 9). Therefore, although historically it was regarded that the helical content of the aculeate Hymenopteran silk was a consequence of a reduced glycine content and increased content of acidic residues (Rudall and Kenchington, 1971), we have discovered that it is not the glycine/acid residues that are responsible for the novel silk structure but rather the position of the alanine residues within the polypeptide chains.

TABLE 8

Average size and hydrophobicity at each heptad position of the orthologous hymenopteran silk proteins and of the green lacewing silk protein (MalF1) showing that a, d, and e positions (core) are smaller and more hydrophobic than other positions. In some cases the b position (partially submerged) is also small and hydrophobic.

| | Heptad position | | | | | | |
|---|---|---|---|---|---|---|---|
| | a | b | c | d | e | f | g |
| Amel F1 orthologs | | | | | | | |
| Average residue side chain hydrophobicity | 0.36 | 0.20 | 0.20 | 0.30 | 0.26 | −0.16 | 0.03 |
| Average residue side chain length | 1.7 | 2.5 | 2.5 | 2.1 | 2.3 | 3.0 | 2.6 |
| Amel F2 orthologs | | | | | | | |
| Average residue side chain hydrophobicity | 0.53 | 0.20 | 0.03 | 0.36 | 0.24 | 0.05 | 0.12 |
| Average residue side chain length | 1.5 | 2.6 | 2.6 | 2.0 | 2.2 | 2.5 | 3.0 |
| Amel F3 orthologs | | | | | | | |
| Average residue side chain hydrophobicity | 0.44 | 0.36 | 0.06 | 0.41 | 0.27 | −0.10 | 0.00 |
| Average residue side chain length | 1.9 | 2.3 | 2.4 | 2.1 | 2.3 | 2.8 | 2.8 |
| Amel F4 orthologs | | | | | | | |
| Average residue side chain hydrophobicity | 0.46 | 0.17 | −0.13 | 0.61 | 0.04 | 0.06 | 0.06 |
| Average residue side chain length | 1.4 | 2.2 | 2.6 | 2.04 | 2.3 | 2.6 | 2.7 |
| MalF1 | | | | | | | |
| Average residue side chain hydrophobicity | −0.05 | 0.14 | −0.61 | 0.27 | 0.59 | 0.23 | −0.22 |
| Average residue side chain length | 2.1 | 1.7 | 2.5 | 1.4 | 1.5 | 1.7 | 3.5 |

Example 6

The Bee Silk Proteins are Likely to be Extensively Cross-Linked

The bee silk proteins all contain a high proportion of lysine (6.5%-16.3%). A comparison between the measured amino acid composition of bee silk and the sequences of the identified silk proteins reveals a substantial mismatch in the number of lysine residues, with much less lysine detected in the silk than expected (FIGS. 2 and 3). This suggests that lysine residues in the silk have been modified, so are not being identified by standard amino acid analysis. Lysine is known to form a variety of cross-links: either enzymatic cross links catalysed by lysyl oxidase or nonenzymatic cross links generated from glycated lysine residues (Reiser et al., 1992). The under-representation of lysine in the honeybee and bumblebee silk amino acid analysis is consistent with the presence of lysine cross-linking

TABLE 9

Number of residues in each class of amino acids at various heptad positions in coiled coil regions of silk proteins.

| Nonpolar | Polar | Charged | Small | Medium | Large | Heptad position |
|---|---|---|---|---|---|---|
| Xenospira4 | | | | | | |
| 25 | 2 | 2 | 26 | 2 | 1 | a |
| 16 | 7 | 6 | 19 | 10 | 0 | b |
| 15 | 6 | 8 | 18 | 11 | 0 | c |
| 24 | 3 | 2 | 21 | 8 | 0 | d |
| 14 | 10 | 5 | 21 | 7 | 1 | e |
| 16 | 4 | 9 | 15 | 14 | 0 | f |
| 15 | 4 | 10 | 15 | 10 | 4 | g |
| Xenospira3 | | | | | | |
| 20 | 8 | 2 | 24 | 5 | 1 | a |
| 13 | 13 | 4 | 15 | 15 | 0 | b |
| 17 | 6 | 7 | 20 | 8 | 2 | c |
| 20 | 5 | 5 | 19 | 11 | 0 | d |
| 11 | 13 | 6 | 18 | 12 | 0 | e |
| 10 | 9 | 11 | 13 | 15 | 2 | f |
| 13 | 7 | 10 | 16 | 9 | 5 | g |
| Xenospira2 | | | | | | |
| 23 | 4 | 1 | 25 | 2 | 1 | a |
| 15 | 7 | 6 | 14 | 12 | 2 | b |
| 13 | 7 | 8 | 15 | 11 | 2 | c |
| 20 | 4 | 4 | 19 | 9 | 0 | d |
| 15 | 7 | 6 | 17 | 10 | 1 | e |
| 13 | 7 | 8 | 16 | 11 | 1 | f |
| 14 | 7 | 7 | 10 | 17 | 1 | g |
| Xenospira1 | | | | | | |
| 20 | 4 | 3 | 18 | 9 | 0 | a |
| 10 | 4 | 13 | 11 | 15 | 1 | b |
| 13 | 4 | 10 | 13 | 12 | 2 | c |
| 20 | 5 | 2 | 22 | 5 | 0 | d |
| 15 | 6 | 6 | 19 | 6 | 2 | e |
| 10 | 9 | 8 | 18 | 6 | 3 | f |
| 18 | 4 | 5 | 17 | 10 | 0 | g |

Covalently cross-linked proteins subjected to SDS polyacrylamide gel electrophoresis (PAGE) are expected to migrate according to the molecular weight of the cross-linked complex. We subjected late last instar honeybee labial gland proteins to SDS PAGE and measured the migration of the silk proteins in relation to standard protein markers. Bands were observed corresponding to monomers of each of the identified silk proteins, however higher molecular weight bands containing these proteins were also present, as expected in a cross-linked system (FIG. 8).

As described above, the honeybee labial gland contains a mixture of organised and disorganised silk proteins. The cross-linked proteins observed probably correspond to the protein population of the anterior region of the gland, where the silk is prepared for extrusion. It is reasonable to assume that extracellular honeybee silk contains a substantially higher proportion of cross-linked proteins than is observed in a heterogenous mixture of all stages of salivary gland silk proteins. The bonds are unlikely to be cysteine cross-links, as the silk was unaffected by reductive treatment, and the identified silk proteins contain few or no cysteine residues.

Example 7

The Euaculeatan Silk Proteins Differ Significantly from the Other Silk Proteins The euaculeatan silk is significantly different from other described silk genes in relation to amino acid composition (Table 10), molecular weight of the proteins involved, secondary structure and physical properties (Tables 11 and 12). The lepidopteran silks are primarily composed of the small amino acid residues alanine, serine and glycine (for example the silk of *Bombyx mori*, Table 10) and are dominated by extended beta sheet secondary structure. The *Cotesia glomerata* silk protein is high in asparagine and serine—the abundance of the latter residue being characteristic of Lepidopteran silk sericins (glues) (Table 10). Modelling of the *Cotesia glomerata* silk protein does not identify helices or coiled coils in the secondary structure. In contrast, the bee, ant and lacewing silks are high in alanine (Table 10) and are comprised of a high level of helical secondary structure that forms coiled coils.

TABLE 10

Amino acid composition of silk from various Insects with most abundant residues shown in boldface.

| | Honey-bee | Euaculeatan silk | Mallada silk | *Cotesia glomerata* | *Bombyx mori* |
|---|---|---|---|---|---|
| Alanine | 22.6 | 27.5 | 26.9 | 12.5 | 29.3 |
| Glutamic acid + Glutamine | 16.1 | 13.9 | 7.4 | 0.6 | 0.9 |
| Aspartic acid + Asparagine | 13.2 | 8.6 | 15.0 | 37.6 (Asn 33.7) | 1.2 |
| Serine | 10.4 | 11.5 | 8.5 | 37.1 | 11.3 |
| Leucine | 9.0 | 7.2 | 5.9 | 0.4 | 0.4 |
| Valine | 6.6 | 4.8 | 4.1 | 0.3 | 2.1 |
| Glycine | 5.7 | 6.6 | 11.2 | 5.5 | 46.0 |
| Isoleucine | 5.6 | 4.0 | 3.9 | 0.4 | 0.6 |
| Threonine | 5.1 | 4.9 | 5.3 | 0.5 | 0.8 |
| Lysine | 3.7 | 3.7 | 3.2 | 0.1 | 0.3 |
| Phenylalanine | 2.0 | 1.0 | 0.5 | 0.5 | 0.6 |
| Tyrosine | 0 | 0.9 | 0.5 | 3.1 | 5.3 |
| Proline | 0 | 0 | 0 | 0.7 | 0.4 |
| Histidine | 0 | 0.5 | 0.5 | 0.4 | 0.2 |
| Arginine | 0 | 3.3 | 5.4 | 0.2 | 0.4 |
| Methionine | 0 | 1.0 | 1.6 | 0 | 0.1 |
| Tryptophan | 0 | Not reported | Not reported | Not reported | 0.2 |
| Cysteine | 0 | 0.4 | 0.3 | Not reported | 0.1 |

TABLE 11

Differences between insect silks.

| | Ant and bee silk | Mallada silk | *Cotesia* sp. | Lepidoptera For example *Bombyx mori* |
|---|---|---|---|---|
| Most abundant amino acids | Ala | Ala | Ser, Asn | Gly, Ala |
| Size of fibroin proteins | 25-35 kDa | 57 KDa | Approx 500 KDa | >100 KDa |
| Secondary structure | Coiled coil | Coiled coil | Most likely beta sheets. Secondary structure prediction programs PROFsec and MARCOIL do not recognise any helical structure or coiled coil regions. | beta-pleated sheets loosely associated with beta-sheets, beta-spirals, alpha helices and amorphous regions |

TABLE 12

Solubility of insect silks.

| | Ant and bee silk | | Mallada silk | | *Cotesia* sp. | | *Bombyx mori* | |
|---|---|---|---|---|---|---|---|---|
| Solvent | 20° C. | 95° C. | 20° C. | 95° C. | 20° C. | 95° C. | 20° C. | 95° C. |
| LiBr 54% | — | — | — | — | — | part | — | ✓ |
| LiSCN saturated | — | — | — | — | — | part | — | ✓ |
| 8M urea | — | — | — | — | — | — | — | part |
| 6M guanidine HCl | — | — | — | — | — | — | — | part |
| 1M NaOH | — | part | ? | ? | — | part | part | ✓ |
| 6M HCl | — | part | part | ✓ | — | part | — | ✓ |
| 3M HCl/50% propanoic acid | — | part | ? | ? | — | part | part | ✓ |

Cladistic analysis of the coiled coil regions of the silk proteins of the four Hymenopteran species (FIG. 9) suggests that the genes evolved in a common ancestor that predates the divergence of the Euaculeata from the parasitic wasps. The sequences of the silk have diverged extensively and we were only able to align the 210 amino acids that comprise the coiled coil region of each protein. The amino acid sequence identity between the coiled coil regions of each of the silk proteins provided herein is shown in Table 13 and DNA identity in the corresponding region is shown in Table 14. Whilst the proteins have similar amino acid contents (especially high levels of alanine) and tertiary structure, the primary amino acid sequence identity is very low. In fact, the gene encoding the *Mallada* silk protein has evolved independently and as such the silk protein sequence cannot be aligned to the Hymenopteran sequences. This indicates that considerable variety in the identity of the amino acids can occur, whilst not affecting the biological function of the proteins.

The cladistic analysis predicts that silk of euaculeatan wasps is comprised of related proteins to the silk of ants and bees and that although these proteins will have similar composition and architecture to the proteins described here, they will have highly diverged primary sequence.

The amino acid sequences of the silk proteins provided herein (FIG. 10) were subjected to comparisons with protein databases, however, no prior art proteins were identified with any reasonable level of sequence identity (for example, none greater than 30% identical over the length of the silk protein sequence).

TABLE 13

Percent identity between protein sequences of the coiled coil region of the fibre proteins in ants and bees.

| | Honeybee | | | | Bumblebee | | | | Bulldog ant | | | | Green ant | | | |
|---|---|---|---|---|---|---|---|---|---|---|---|---|---|---|---|---|
| | F1 | F2 | F3 | F4 | F1 | F2 | F3 | F4 | F1 | F2 | F3 | F4 | F1 | F2 | F3 | F4 |
| beeF1 | 100 | | | | | | | | | | | | | | | |
| beeF2 | 26.7 | 100 | | | | | | | | | | | | | | |
| beeF3 | 23.3 | 31.4 | 100 | | | | | | | | | | | | | |
| beeF4 | 34.8 | 32.4 | 30.0 | 100 | | | | | | | | | | | | |
| BBF1 | 65.7 | 28.1 | 24.8 | 35.7 | 100 | | | | | | | | | | | |
| BBF2 | 28.6 | 71.4 | 28.6 | 31.9 | 31.0 | 100 | | | | | | | | | | |
| BBF3 | 25.2 | 31.0 | 65.7 | 27.6 | 27.1 | 29.5 | 100 | | | | | | | | | |
| BBF4 | 33.3 | 31.0 | 29.5 | 64.8 | 34.8 | 31.4 | 28.1 | 100 | | | | | | | | |
| BAF1 | 37.1 | 20.0 | 20.0 | 32.4 | 39.5 | 21.4 | 21.4 | 29.1 | 100 | | | | | | | |
| BAF2 | 25.2 | 44.3 | 29.5 | 33.8 | 28.1 | 38.1 | 28.6 | 27.6 | 27.1 | 100 | | | | | | |
| BAF3 | 23.8 | 26.2 | 36.7 | 28.1 | 24.8 | 25.2 | 36.7 | 28.1 | 21.0 | 27.6 | 100 | | | | | |
| BAF4 | 28.1 | 33.8 | 24.8 | 45.2 | 28.6 | 33.8 | 23.3 | 43.8 | 26.1 | 27.6 | 25.2 | 100 | | | | |
| GAF1 | 33.8 | 20.0 | 23.8 | 32.9 | 36.2 | 22.9 | 23.8 | 29.1 | 66.7 | 28.1 | 25.2 | 28.6 | 100 | | | |
| GAF2 | 24.8 | 41.9 | 27.6 | 29.5 | 28.1 | 39.5 | 29.0 | 26.7 | 21.9 | 66.2 | 23.8 | 26.7 | 23.8 | 100 | | |
| GAF3 | 26.9 | 28.8 | 40.1 | 31.6 | 25.5 | 28.3 | 38.2 | 30.2 | 24.0 | 28.3 | 62.7 | 27.4 | 27.4 | 26.4 | 100 | |
| GAF4 | 24.7 | 32.4 | 24.3 | 37.6 | 27.1 | 32.4 | 24.8 | 38.1 | 23.9 | 29.5 | 21.0 | 63.3 | 24.8 | 27.6 | 24.1 | 100 |

TABLE 14

Percent identity between nucleotide sequences encoding coiled coil region of the fibre proteins in ants and bees.

| | Honeybee | | | | Bumblebee | | | | Bulldog ant | | | | Green ant | | | |
|---|---|---|---|---|---|---|---|---|---|---|---|---|---|---|---|---|
| | F1 | F2 | F3 | F4 | F1 | F2 | F3 | F4 | F1 | F2 | F3 | F4 | F1 | F2 | F3 | F4 |
| beeF1 | 100 | | | | | | | | | | | | | | | |
| beeF2 | 39.4 | 100 | | | | | | | | | | | | | | |
| beeF3 | 37.0 | 40.2 | 100 | | | | | | | | | | | | | |
| beeF4 | 45.1 | 44.8 | 41.0 | 100 | | | | | | | | | | | | |
| BBF1 | 68.9 | 40.9 | 37.5 | 45.2 | 100 | | | | | | | | | | | |
| BBF2 | 42.5 | 72.9 | 42.5 | 44.9 | 42.2 | 100 | | | | | | | | | | |
| BBF3 | 40.6 | 40.0 | 67.6 | 40.5 | 38.4 | 41.0 | 100 | | | | | | | | | |
| BBF4 | 45.4 | 41.0 | 41.7 | 66.0 | 45.9 | 43.6 | 40.0 | 100 | | | | | | | | |
| BAF1 | 45.7 | 35.1 | 35.9 | 41.1 | 47.9 | 36.5 | 36.0 | 38.7 | 100 | | | | | | | |
| BAF2 | 38.1 | 49.8 | 41.4 | 44.6 | 38.7 | 47.3 | 40.0 | 41.0 | 40.6 | 100 | | | | | | |
| BAF3 | 33.3 | 36.7 | 45.4 | 40.3 | 36.3 | 36.8 | 46.2 | 39.4 | 36.0 | 40.5 | 100 | | | | | |
| BAF4 | 39.5 | 43.3 | 41.4 | 46.8 | 43.0 | 47.6 | 39.8 | 49.4 | 42.5 | 41.7 | 40.3 | 100 | | | | |
| GAF1 | 45.6 | 35.1 | 37.3 | 42.4 | 47.6 | 38.5 | 37.8 | 41.4 | 68.9 | 41.7 | 36.7 | 43.0 | 100 | | | |
| GAF2 | 38.5 | 47.8 | 38.4 | 43.2 | 38.1 | 46.5 | 41.4 | 40.0 | 37.5 | 69.7 | 38.9 | 40.6 | 39.4 | 100 | | |
| GAF3 | 39.0 | 40.1 | 46.1 | 41.8 | 37.7 | 39.3 | 46.1 | 40.0 | 37.7 | 41.7 | 65.1 | 41.2 | 40.0 | 41.7 | 100 | |
| GAF4 | 38.9 | 42.4 | 38.1 | 44.9 | 38.9 | 43.8 | 38.4 | 44.3 | 37.3 | 42.7 | 36.7 | 67.8 | 38.2 | 40.3 | 37.7 | 100 |

The open reading frames encoding the silk proteins (provided on FIG. 11) were subjected to similar database searching as that described above. The only related molecules that were identified have been published as part of the honeybee genome project (www.ncbi.nlm.nih.gov/genome/guide/bee). The open reading frames had been predicted by the bee genome project, however, the function of the encoded proteins had not been suggested. Furthermore, there is no evidence that a polynucleotide comprising the open reading frame of the mRNA had ever been produced for any of these molecules.

The genes encoding Xenospira1, Xenospira2, Xenospira3 and Xenospira4 comprise an exon covering the entire single open reading frame, whereas the gene encoding Xenosin comprises at least one intron (see FIG. 12).

Example 8

Expression of Silk Proteins in Transgenic Plants

A plant expression vector encoding a silk protein of the invention may consist of a recombinant nucleic acid molecule coding for said protein (for example a polynucleotide provided in any one of SEQ ID NO's:11 to 21, 31 to 39, 48 to 55, 64 to 71, 74 or 75) placed downstream of the CaMV 35S promoter in a binary vector backbone containing a kanamycin-resistance gene (NptII).

For the polynucleotides comprising any one of SEQ ID NO's 11, 13, 15, 17, 19, 31, 33, 35, 37, 48, 50, 52, 54, 64, 66, 68, 70 or 74 the construct further may comprise a signal peptide encoding region such as *Arabidopsis thaliana* vacuolar basic chitinase signal peptide, which is placed in-frame and upstream of the sequence encoding the silk protein.

The construct carrying a silk protein encoding polypeptide is transformed separately into *Agrobacterium tumefaciens* by electroporation prior to transformation into *Arabidopsis thaliana*. The hypocotyl method of transformation can be used to transform *A. thaliana* which can be selected for survival on selective media comprising kanamycin media. After roots are formed on the regenerates they are transferred to soil to establish primary transgenic plants.

Verification of the transformation process can be achieved via PCR screening. Incorporation and expression of polynucleotide can be measured using PCR, Southern blot analysis and/or LC/MS of trypsin-digested expressed proteins.

Two or more different silk protein encoding constructs can be provided in the same vector, or numerous different vectors can be transformed into the plant each encoding a different protein.

As an experimental example of plant expression, a codon-optimised version of AmelF4 (Xenospira4) (SEQ ID NO:76) was cloned into pET14b (Novagen), generating pET14b-6×His:F4op, forming an in-frame translational fusion with a 6× histidine at the N-terminal of the protein. The sequence encoding the protein "6× Histidine:F4op" was cloned into pVEC8 (Wang et al., 1992) under the control of the CaMV 35S promoter and ocs polyadenylation regulatory apparatus, generating pVEC8-35S-6×His:F4op-ocs. pET14b-6×His: F4op was transformed into chemically-competent *E. coli* and pVEC8-35S-6×His:F4op was transformed into tobacco leaf discs by *Agrobacterium* mediated transformation. Proteins from antibiotic resistant *E. coli* (induced expression) and tobacco leaves were isolated and subjected to western blot analysis using the Tetra-Histidine antibody (Qiagen, Karlsrule, Germany) for detection. The empty vectors pET14b and pVEC8-35S-ocs were used as negative controls in there respective host backgrounds. As shown in FIG. 13, these experiments resulted in the plant producing the Xenospira4 (AmelF4) protein.

Example 9

Fermentation and Purification of Silk Proteins

Expression constructs were constructed after the silk coding regions of honeybee genes AmelF1-F4 (Xenospira1 to 4 respectively) and lacewing MalF1 genes were amplified by PCR and cloned into pET14b expression vectors (Novagen, Madison, Wis.). The resultant expression plasmids were then electroporated into *E. coli* BL21 (DE3) Rosetta cells and grown overnight on LB agar containing ampicillin. A single colony was then used to inoculate LB broth containing ampicilin then grown at 37° C. overnight. Cells were harvested by centrifugation and lysed with detergent (Bugbuster, Novagen). Inclusion bodies were washed extensively and re-solubilised in 6M guanidinium.

This procedure yielded proteins mixtures with greater than 95% purity of the honeybee proteins and greater than 50% purity of the lacewing MalF1 protein. Yields of up to 50% of the wet weight of the *E. coli* cell pellet were regularly obtained, indicating that the proteins are easy to express in this manner.

The solubilised honeybee recombinant proteins were applied to a Talon resin column prepared according to manufactures directions. They were then eluted off the column in 100 mM Tris.HCL, 150 mM imidazole pH 8.

Example 10

Processing of Silk Proteins into Threads

The honeybee and lacewing silk proteins have been readily made into threads using a variety of methods (see FIG. 14) using the following procedure.

The anterior segment of the salivary gland from late final instar *Apis mellifera* was dissected under phosphate buffered saline and removed to a flat surface in a droplet of buffer. Forceps were used to grasp either end of the segment. One end was raised out of the droplet and away from the other at a steady rate. This enabled the drawing of a fine thread that rapidly solidified in air.

The honeybee and lacewing larval recombinant silk proteins formed threads or sheets after dehydration or concentration. For example, by dropping soluble protein into a butanol solution or by concentrating proteins on the Talon resin column.

Threads were also obtained after honeybee or lacewing recombinant silk proteins were mixed with an organic solvent (such as hexane) to concentrate them at the interface in the correct conformation, and then addition of a reagent to exclude them from the interface (such as butanol). The threads formed by this procedure had similar FT-IR spectra to the native silk indicating that they were comprised of the same coiled coil structure.

Silk proteins from other species described herein can also be processed by this procedure.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Atkins E. D. T. (1967) J Mol Biol 24:139-141.
Bendtsen J. D., Nielsen H., von Heijne G. and Brunak S. (2004) J. Mol. Biol. 340:783-795.
Bini E., Knight D. P. and Kaplan D. L. (2004) J. Mol. Biol. 335:27-40.
Craig C. L. and Riekel C. (2002) Comparative Biochemistry and Physiology Part B 133:493-507.
Delorenzi M. and Speed T. (2002) Bioinformatics 18:617-625.
Deng Y., Liu J., Zheng Q., Eliezer D., Kallenbach N. R. and Lu M. (2006) Structure 14:247-255.
Flower N. E. and Kenchington W. R. (1967) Journal of the Royal Microscopical Society 86:297.
Grimaldi D. and Engel M. S. (2005) Evolution of insects. Cambridge University Press, New York.
Harayama S. (1998) Trends Biotech., 16; 76-82.
Heimburg T, Schunemann J., Weber K., and Geisler N. (1999) Biochemistry 38:12727-12734.
Hepburn H. R., Chandler H. D. and Davidoff M. R. (1979) Insect Biochem. 9:66.
Kneller D. G., Cohen F. E. and Langridge R. (1990) J. Mol. Biol. 214:171-182.
LaMunyon C. W. (1988) Psyche 95:203-209.
LaMunyon C. W. and Adams P. A. (1987) Annals of the Entomological Society of America 80:804-808.
Lucas F. Shaw J. T. B. and Smith S. G. (1960) J. Mol. Biol. 2:339-349.
Lucas F. and Rudall K. M. (1967) In Comprehensive Biochemistry (Ed. Florkin M and Stotz H) Vol 26B pp 475-559 Elsevier Amsterdam.
Lupas A., Van Dyke M. and Stock J. (1991) Science 252: 1162-1164.
McClelland J. L. and Rumelhart D. E. (1988) Explorations in Parallel Distributed Processing vol 13. pp 318-362. MIT-Press, Cambridge Mass.
Needleman, S. B. and Wunsch, C. D. (1970) J. Mol. Biol., 48; 443-453.
Quicke D. L. J., Shaw M. R., Takahashi M. and Yanechin B. (2004) Journal of Natural History 38:2167-2181.
Reiser K., McCormick, Rucker R. B. (1992) The FASEB Journal 6:2439-2449.
Rost B. and Sander C. (1993) J. Molecular Biology 232:584-599.
Rost B., Yachdav G. and Liu J. (2004) Nucleic Acids Research 32 (Web Server issue):W321-W326.
Rudall K. M. (1962) In Comparative Biochemistry (Ed. By Florkin M and Mason HS) Vol 4, pp. 297-435. Academic Press, New York.
Rudall K. M. and Kenchington W. (1971) Annual Reviews in Entomology 16:73-96.
Silva-Zacarin E. C. M., Silva De Moraes R. L. M. and Taboga S. R. (2003) J. Biosci. 6:753-764.
Speilger P. E. (1962) Annals of the Entomological Society of America. 55: 69-77.
Wang M. B., Li Z. Y. et al. (1998). Acta Hort. 461: 401-407.
Yamada H., Shigesada K., Igarashi Y., Takasu Y., Tsubouchi K. and Kato Y. (2004) Int. J. Wild Silkmoth and Silk 9:61-66.

The invention claimed is:

1. A recombinant host cell comprising a polynucleotide which encodes a silk polypeptide, wherein at least a portion of the polypeptide has a coiled coil structure, and wherein the silk polypeptide comprises an amino acid sequence which is at least 90% identical to at least any one or more of SEQ ID NO:1, SEQ ID NO:2, SEQ ID NO:22, SEQ ID NO:23, SEQ ID NO:40, SEQ ID NO:41, SEQ ID NO:56, SEQ ID NO:57, SEQ ID NO:3, SEQ ID NO:4, SEQ ID NO:24, SEQ ID NO:25,SEQ ID NO:42, SEQ ID NO:43, SEQ ID NO:58, SEQ ID NO:59, SEQ ID NO:5, SEQ ID NO:6, SEQ ID NO:26, SEQ ID NO:27, SEQ ID NO:44, SEQ ID NO:45, SEQ ID NO:60, SEQ ID NO:61, SEQ ID NO:7, SEQ ID NO:8, SEQ ID NO:28, SEQ ID NO:29, SEQ ID NO:46, SEQ ID NO:47, SEQ ID NO:62,or SEQ ID NO:63; and
wherein
   a) the polynucleotide is operably linked to a heterologous promoter, and/or
   b) the recombinant host cell is a bacterial, yeast or plant cell.

2. The recombinant host cell of claim 1, wherein the silk polypeptide comprises an amino acid sequence which is at least 95% identical to at least any one or more of SEQ ID NO:1, SEQ ID NO:2, SEQ ID NO:22, SEQ ID NO:23, SEQ ID NO:40, SEQ ID NO:41, SEQ ID NO:56,SEQ ID NO:57; SEQ ID NO:3, SEQ ID NO:4, SEQ ID NO:24, SEQ ID NO:25, SEQ ID NO:42, SEQ ID NO:43, SEQ ID NO:58, SEQ ID NO:59, SEQ ID NO:5, SEQ ID NO:6, SEQ ID NO:26, SEQ ID NO:27, SEQ ID NO:44, SEQ ID NO:45, SEQ ID NO:60, SEQ ID NO:61, SEQ ID NO:7, SEQ ID NO:8,SEQ ID NO:28, SEQ ID NO:29, SEQ ID NO:46, SEQ ID NO:47, SEQ ID NO:62, or SEQ ID NO:63.

3. The recombinant host cell of claim 1, wherein the silk polypeptide comprises an amino acid sequence which is at least 97% identical to at least any one or more of SEQ ID NO:1, SEQ ID NO:2, SEQ ID NO:22, SEQ ID NO:23, SEQ ID NO:40, SEQ ID NO:41, SEQ ID NO:56,SEQ ID NO:57; SEQ ID NO:3, SEQ ID NO:4, SEQ ID NO:24, SEQ ID NO:25, SEQ ID NO:42, SEQ ID NO:43, SEQ ID NO:58, SEQ ID NO:59, SEQ ID NO:5, SEQ ID NO:6, SEQ ID NO:26, SEQ ID NO:27, SEQ ID NO:44, SEQ ID NO:45, SEQ ID NO:60, SEQ ID NO:61, SEQ ID NO:7, SEQ ID NO:8,SEQ ID NO:28, SEQ ID NO:29, SEQ ID NO:46, SEQ ID NO:47, SEQ ID NO:62, or SEQ ID NO:63.

4. The recombinant host cell of claim 1, wherein the silk polypeptide comprises an amino acid sequence which is at least 99% identical to at least any one or more of SEQ ID NO:1, SEQ ID NO:2, SEQ ID NO:22, SEQ ID NO:23, SEQ ID NO:40, SEQ ID NO:41, SEQ ID NO:56,SEQ ID NO:57; SEQ ID NO:3, SEQ ID NO:4, SEQ ID NO:24, SEQ ID NO:25, SEQ ID NO:42, SEQ ID NO:43, SEQ ID NO:58, SEQ ID NO:59, SEQ ID NO:5, SEQ ID NO:6, SEQ ID NO:26, SEQ ID NO:27, SEQ ID NO:44, SEQ ID NO:45, SEQ ID NO:60, SEQ ID NO:61, SEQ ID NO:7, SEQ ID NO:8,SEQ ID NO:28, SEQ ID NO:29, SEQ ID NO:46, SEQ ID NO:47, SEQ ID NO:62, or SEQ ID NO:63.

5. The recombinant host cell of claim 1, wherein the silk polypeptide comprises an amino acid sequence of any one of SEQ ID NO:1, SEQ ID NO:2, SEQ ID NO:22, SEQ ID NO:23, SEQ ID NO:40, SEQ ID NO:41, SEQ ID NO:56, SEQ ID NO:57; SEQ ID NO:3, SEQ ID NO:4,SEQ ID NO:24, SEQ ID NO:25, SEQ ID NO:42, SEQ ID NO:43, SEQ ID NO:58, SEQ ID NO:59, SEQ ID NO:5, SEQ ID NO:6,SEQ ID NO:26, SEQ ID NO:27, SEQ ID NO:44, SEQ ID NO:45, SEQ ID NO:60, SEQ ID NO:61, SEQ ID NO:7, SEQ ID NO:8, SEQ ID NO:28, SEQ ID NO:29, SEQ ID NO:46,SEQ ID NO:47, SEQ ID NO:62, or SEQ ID NO:63.

6. The recombinant host cell of claim 1, wherein the silk polypeptide comprises an amino acid sequence which is at least 90% identical to at least any one or more of SEQ ID NO:1, SEQ ID NO:2, SEQ ID NO:22, SEQ ID NO:23, SEQ ID NO:40, SEQ ID NO:41, SEQ ID NO:56,SEQ ID NO:57; SEQ ID NO:3, SEQ ID NO:4, SEQ ID NO:24, SEQ ID NO:25, SEQ ID NO:42, SEQ ID NO:43, SEQ ID NO:58, SEQ ID NO:59, SEQ ID NO:5, SEQ ID NO:6, SEQ ID NO:26, SEQ ID NO:27, SEQ ID NO:44, SEQ ID NO:45, SEQ ID NO:60, SEQ ID NO:61, SEQ ID NO:7, SEQ ID NO:8,SEQ ID NO:28, SEQ ID NO:29, SEQ ID NO:46, SEQ ID NO:47, SEQ ID NO:62, or SEQ ID NO:63.

7. The recombinant host cell of claim 1, wherein the polynucleotide comprises a nucleic acid sequence which is at least 95% identical to any one or more of SEQ ID NO:11,SEQ ID NO:12, SEQ ID NO:31, SEQ ID NO:32, SEQ ID NO:48, SEQ ID NO:49, SEQ ID NO:64, SEQ ID NO:65, SEQ ID NO:13, SEQ ID NO:14, SEQ ID NO:33, SEQ ID NO:34, SEQ ID NO:50, SEQ ID NO:51, SEQ ID NO:66, SEQ ID NO:67, SEQ ID NO:15, SEQ ID NO:16, SEQ ID NO:35, SEQ ID NO:36, SEQ ID NO:52, SEQ ID NO:53, SEQ ID NO:68, SEQ ID NO:69, SEQ ID NO:17, SEQ ID NO:18, SEQ ID NO:37, SEQ ID NO:38, SEQ ID NO:54, SEQ ID NO:55, SEQ ID NO:70, SEQ ID NO:71, or SEQ ID NO:76.

8. The recombinant host cell of claim 1, wherein the polynucleotide comprises a nucleic acid sequence which is at least 97% identical to any one or more of SEQ ID NO:11,SEQ ID NO:12, SEQ ID NO:31, SEQ ID NO:32, SEQ ID NO:48, SEQ ID NO:49, SEQ ID NO:64, SEQ ID NO:65, SEQ ID NO:13, SEQ ID NO:14, SEQ ID NO:33, SEQ ID NO:34, SEQ ID NO:50, SEQ ID NO:51, SEQ ID NO:66, SEQ ID NO:67, SEQ ID NO:15, SEQ ID NO:16, SEQ ID NO:35, SEQ ID NO:36, SEQ ID NO:52, SEQ ID NO:53, SEQ ID NO:68, SEQ ID NO:69, SEQ ID NO:17, SEQ ID NO:18, SEQ ID NO:37, SEQ ID NO:38, SEQ ID NO:54, SEQ ID NO:55, SEQ ID NO:70, SEQ ID NO:71, or SEQ ID NO:76.

9. The recombinant host cell of claim 1, wherein the polynucleotide comprises a nucleic acid sequence which is at least 99% identical to any one or more of SEQ ID NO:11, SEQ ID NO:12, SEQ ID NO:31, SEQ ID NO:32, SEQ ID NO:48, SEQ ID NO:49, SEQ ID NO:64, SEQ ID NO:65, SEQ ID NO:13, SEQ ID NO:14, SEQ ID NO:33, SEQ ID NO:34, SEQ ID NO:50, SEQ ID NO:51, SEQ ID NO:66, SEQ ID NO:67, SEQ ID NO:15, SEQ ID NO:16, SEQ ID NO:35, SEQ ID NO:36, SEQ ID NO:52, SEQ ID NO:53, SEQ ID NO:68, SEQ ID NO:69, SEQ ID NO:17, SEQ ID NO:18, SEQ ID NO:37, SEQ ID NO:38, SEQ ID NO:54, SEQ ID NO:55, SEQ ID NO:70, SEQ ID NO:71, or SEQ ID NO:76.

10. The recombinant host cell of claim 1, wherein the polynucleotide comprises a nucleic acid sequence of any one of SEQ ID NO:11, SEQ ID NO:12, SEQ ID NO:31, SEQ ID NO:32, SEQ ID NO:48, SEQ ID NO:49, SEQ ID NO:64, SEQ ID NO:65, SEQ ID NO:13, SEQ ID NO:14, SEQ ID NO:33, SEQ ID NO:34, SEQ ID NO:50, SEQ ID NO:51, SEQ ID NO:66, SEQ ID NO:67, SEQ ID NO:15, SEQ ID NO:16, SEQ ID NO:35, SEQ ID NO:36, SEQ ID NO:52, SEQ ID NO:53, SEQ ID NO:68, SEQ ID NO:69, SEQ ID NO:17, SEQ ID NO:18, SEQ ID NO:37, SEQ ID NO:38, SEQ ID NO:54, SEQ ID NO:55, SEQ ID NO:70, SEQ ID NO:71, or SEQ ID NO:76.

11. The recombinant host cell of claim 1, wherein the portion of the silk polypeptide that has a coiled coil structure comprises at least 10 copies of the heptad sequence abcdefg, and wherein at least 25% of the amino acids at positions a and d are alanine residues.

12. The recombinant host cell of claim 11, wherein the portion of the silk polypeptide that has a coiled coil structure comprises at least 10 copies of the heptad sequence abcdefg, and at least 25% of the amino acids at positions a, d and e are alanine residues.

13. The recombinant host cell of claim 1, wherein the portion of the silk polypeptide that has a coiled coil structure comprises at least 18 copies of the heptad sequence abcdefg, and wherein at least 25% of the amino acids at positions a and d are alanine residues.

14. The recombinant host cell of claim 13, wherein the portion of the silk polypeptide that has a coiled coil structure comprises at least 18 copies of the heptad sequence abcdefg, and at least 25% of the amino acids at positions a, d and e are alanine residues.

15. A process for preparing a silk polypeptide comprising cultivating the recombinant host cell of claim 1, under conditions which allow expression of the polynucleotide encoding the polypeptide, and recovering the expressed polypeptide.

* * * * *

SEQUENCE LISTING

```
<160> NUMBER OF SEQ ID NOS: 77

<210> SEQ ID NO 1
<211> LENGTH: 314
<212> TYPE: PRT
<213> ORGANISM: Apis mellifera

<400> SEQUENCE: 1

Gly Leu Glu Gly Pro Gly Asn Ser Leu Pro Glu Leu Val Lys Gly Ser
1               5                   10                  15

Ala Ser Ala Thr Ala Ser Thr Ala Val Thr Ala Arg Ser Gly Leu Arg
            20                  25                  30

Ala Gly Gln Val Ala Leu Ala Ser Gln Lys Asp Ala Val Leu Gln Ala
        35                  40                  45

Gln Ala Ala Ala Ser Ala Ala Ser Glu Ala Arg Ala Ala Ala Asp Leu
    50                  55                  60

Thr Ala Lys Leu Ser Gln Glu Ser Ala Ser Val Gln Ser Gln Ala Ala
65                  70                  75                  80

Ala Lys Gly Lys Glu Thr Glu Glu Ala Ala Val Gly Gln Ala Arg Ala
                85                  90                  95

Gly Leu Glu Ser Val Ser Met Ala Ala Ser Ala Thr Ser Ala Ala Lys
            100                 105                 110

Glu Ala Ser Thr Ala Ala Lys Ala Ala Ala Ser Ala Leu Ser Thr Ala
        115                 120                 125
```

```
Val Val Gln Ala Lys Ile Ala Glu Arg Ala Ala Lys Ala Glu Ala Val
            130                 135                 140

Ala Ser Asp Glu Ala Lys Ala Lys Ala Ile Ala Ala Asn Leu Ala
145                 150                 155                 160

Ala Glu Ala Ser Val Ala Ala Glu Ala Ala Leu Lys Ala Glu Lys Val
                165                 170                 175

Ala Glu Glu Ala Ile Ala Arg Ala Ala Ser Ala Lys Ala Ala Ala Arg
                180                 185                 190

Ala Ala Ala Ala Ala Leu Ala Ser Ser Lys Glu Ala Ala Thr Ala Ser
                195                 200                 205

Ala Arg Asn Ala Ala Glu Ser Glu Ala Arg Asn Glu Val Ala Val Leu
                210                 215                 220

Ile Ala Glu Ile Asp Lys Lys Ser Arg Glu Ile Asp Ala Ala Ser Ser
225                 230                 235                 240

Leu Asn Ala Arg Ala Ala Lys Ala Ser Ser Arg Asn Val Glu Thr
                245                 250                 255

Ala Thr Ile Gly Ala Asn Ile Asn Ser Ser Lys Gln Val Val Ser Ile
                260                 265                 270

Pro Val Glu Ile Lys Lys Phe Ser Glu Pro Glu Val Ser Thr Ser Trp
                275                 280                 285

Arg Glu Asp Glu Glu Val Thr Lys Glu Lys Lys Glu His Ile Asn Leu
                290                 295                 300

Asn Asp Phe Asp Leu Lys Ser Asn Val Phe
305                 310

<210> SEQ ID NO 2
<211> LENGTH: 333
<212> TYPE: PRT
<213> ORGANISM: Apis mellifera

<400> SEQUENCE: 2

Met Lys Ile Pro Val Leu Leu Ala Thr Cys Leu Tyr Leu Cys Gly Phe
1               5                   10                  15

Ala Ser Ala Gly Leu Glu Gly Pro Gly Asn Ser Leu Pro Glu Leu Val
                20                  25                  30

Lys Gly Ser Ala Ser Ala Thr Ala Ser Thr Ala Val Thr Ala Arg Ser
            35                  40                  45

Gly Leu Arg Ala Gly Gln Val Ala Leu Ala Ser Gln Lys Asp Ala Val
        50                  55                  60

Leu Gln Ala Gln Ala Ala Ser Ala Ala Ser Glu Ala Arg Ala Ala
65                  70                  75                  80

Ala Asp Leu Thr Ala Lys Leu Ser Gln Glu Ser Ala Ser Val Gln Ser
                85                  90                  95

Gln Ala Ala Lys Gly Lys Glu Thr Glu Glu Ala Ala Val Gly Gln
            100                 105                 110

Ala Arg Ala Gly Leu Glu Ser Val Ser Met Ala Ala Ser Ala Thr Ser
            115                 120                 125

Ala Ala Lys Glu Ala Ser Thr Ala Ala Lys Ala Ala Ser Ala Leu
            130                 135                 140

Ser Thr Ala Val Val Gln Ala Lys Ile Ala Glu Arg Ala Ala Lys Ala
145                 150                 155                 160

Glu Ala Val Ala Ser Asp Glu Ala Lys Ala Lys Ala Ile Ala Ala Ala
                165                 170                 175

Asn Leu Ala Ala Glu Ala Ser Val Ala Ala Glu Ala Ala Leu Lys Ala
```

```
            180                 185                 190
Glu Lys Val Ala Glu Ala Ile Ala Arg Ala Ser Ala Lys Ala
        195                 200                 205

Ala Ala Arg Ala Ala Ala Ala Leu Ala Ser Ser Lys Glu Ala Ala
    210                 215                 220

Thr Ala Ser Ala Arg Asn Ala Ala Glu Ser Glu Ala Arg Asn Glu Val
225                 230                 235                 240

Ala Val Leu Ile Ala Glu Ile Asp Lys Lys Ser Arg Glu Ile Asp Ala
                245                 250                 255

Ala Ser Ser Leu Asn Ala Arg Ala Ala Lys Ala Ser Ser Arg Asn
            260                 265                 270

Val Glu Thr Ala Thr Ile Gly Ala Asn Ile Asn Ser Ser Lys Gln Val
        275                 280                 285

Val Ser Ile Pro Val Glu Ile Lys Lys Phe Ser Glu Pro Glu Val Ser
    290                 295                 300

Thr Ser Trp Arg Glu Asp Glu Glu Val Thr Lys Glu Lys Lys Glu His
305                 310                 315                 320

Ile Asn Leu Asn Asp Phe Asp Leu Lys Ser Asn Val Phe
                325                 330

<210> SEQ ID NO 3
<211> LENGTH: 290
<212> TYPE: PRT
<213> ORGANISM: Apis mellifera

<400> SEQUENCE: 3

Arg Val Ile Asn His Glu Ser Leu Lys Thr Ser Glu Asp Ile Gln Gly
1               5                   10                  15

Gly Tyr Ser Ala Gly Ile Val Gly Asp Gly Ser Asp Ala Leu Gly Ser
            20                  25                  30

Ser Ile Glu Asn Ala Gln Lys Val Ala Arg Ala Ala Glu Asn Val Gly
        35                  40                  45

Leu Asn Leu Glu Leu Gly Ala Gly Ala Arg Ala Ala Ser Val Ala Ala
    50                  55                  60

Ala Ala Gln Ala Lys Asn Thr Glu Ala Ala Glu Ala Gly Ala Asn Ala
65                  70                  75                  80

Ala Leu Ala Ala Ala Ile Ala Lys Arg Glu Glu Ala Ile Lys Ala Ser
                85                  90                  95

Glu Ile Ala Asn Gln Leu Leu Thr Asn Ala Lys Ala Ala Glu Ala
            100                 105                 110

Thr Val Ser Ala Thr Lys Arg Ala Ala Gln Leu Thr Ala Ala Lys
        115                 120                 125

Glu Ala Thr Arg Ala Ser Ala Ala Ala Glu Ala Ala Thr Glu Ala
    130                 135                 140

Gln Val Lys Ala Asn Ala Asp Ser Ile Ile Thr Lys Arg Ala Ala Ile
145                 150                 155                 160

Ala Glu Ala Gln Ala Ala Ala Glu Ala Gln Val Lys Ala Ala Ile Ala
                165                 170                 175

Arg Lys Ser Ala Ala Asn Phe Leu Ala Lys Ala Gln Ile Ala Ala Ala
            180                 185                 190

Ala Glu Ser Glu Ala Thr Lys Leu Ala Ala Glu Ala Val Val Ala Leu
        195                 200                 205

Thr Asn Ala Glu Val Ala Val Asn Gln Ala Arg Asn Ala Gln Ala Asn
    210                 215                 220
```

```
Ala Ser Thr Gln Ala Ser Met Ala Val Arg Val Asp Ser Gln Ala Ala
225                 230                 235                 240

Asn Ala Glu Ala Ala Val Ala Gln Ala Glu Thr Leu Leu Val Thr
            245                 250                 255

Ala Glu Ala Val Ala Ala Glu Ala Glu Val Ala Asn Lys Ala Ala
            260                 265                 270

Thr Phe Ala Lys Gln Ile Val Asn Glu Lys Lys Ile His Val Ala Lys
        275                 280                 285

Leu Glu
    290

<210> SEQ ID NO 4
<211> LENGTH: 309
<212> TYPE: PRT
<213> ORGANISM: Apis mellifera

<400> SEQUENCE: 4

Met Lys Ile Pro Ala Ile Phe Val Thr Ser Leu Leu Val Trp Gly Leu
1               5                   10                  15

Ala Glu Gly Arg Val Ile Asn His Glu Ser Leu Lys Thr Ser Glu Asp
            20                  25                  30

Ile Gln Gly Gly Tyr Ser Ala Gly Ile Val Gly Asp Gly Ser Asp Ala
        35                  40                  45

Leu Gly Ser Ser Ile Glu Asn Ala Gln Lys Val Ala Arg Ala Ala Glu
    50                  55                  60

Asn Val Gly Leu Asn Leu Glu Leu Gly Ala Gly Ala Arg Ala Ala Ser
65                  70                  75                  80

Val Ala Ala Ala Gln Ala Lys Asn Thr Glu Ala Ala Glu Ala Gly
                85                  90                  95

Ala Asn Ala Ala Leu Ala Ala Ile Ala Lys Arg Glu Glu Ala Ile
            100                 105                 110

Lys Ala Ser Glu Ile Ala Asn Gln Leu Leu Thr Asn Ala Ala Lys Ala
        115                 120                 125

Ala Glu Ala Thr Val Ser Ala Thr Lys Arg Ala Ala Gln Leu Thr Ala
    130                 135                 140

Ala Ala Lys Glu Ala Thr Arg Ala Ser Ala Ala Ala Glu Ala Ala
145                 150                 155                 160

Thr Glu Ala Gln Val Lys Ala Asn Ala Asp Ser Ile Ile Thr Lys Arg
                165                 170                 175

Ala Ala Ile Ala Glu Ala Gln Ala Ala Ala Glu Ala Gln Val Lys Ala
            180                 185                 190

Ala Ile Ala Arg Lys Ser Ala Ala Asn Phe Leu Ala Lys Ala Gln Ile
        195                 200                 205

Ala Ala Ala Glu Ser Glu Ala Thr Lys Leu Ala Ala Glu Ala Val
    210                 215                 220

Val Ala Leu Thr Asn Ala Glu Val Ala Val Asn Gln Ala Arg Asn Ala
225                 230                 235                 240

Gln Ala Asn Ala Ser Thr Gln Ala Ser Met Ala Val Arg Val Asp Ser
                245                 250                 255

Gln Ala Ala Asn Ala Glu Ala Ala Val Ala Gln Ala Glu Thr Leu
            260                 265                 270

Leu Val Thr Ala Glu Ala Val Ala Ala Glu Ala Glu Val Ala Asn
        275                 280                 285

Lys Ala Ala Thr Phe Ala Lys Gln Ile Val Asn Glu Lys Lys Ile His
    290                 295                 300
```

Val Ala Lys Leu Glu
305

<210> SEQ ID NO 5
<211> LENGTH: 316
<212> TYPE: PRT
<213> ORGANISM: Apis mellifera

<400> SEQUENCE: 5

Gly Val Glu Glu Phe Lys Ser Ser Ala Thr Glu Val Ile Ser Lys
1               5                   10                  15

Asn Leu Glu Val Asp Leu Leu Lys Asn Val Asp Thr Ser Ala Lys Arg
            20                  25                  30

Arg Glu Asn Gly Ala Pro Val Leu Gly Lys Asn Thr Leu Gln Ser Leu
                35                  40                  45

Glu Lys Ile Lys Thr Ser Ala Ser Val Asn Ala Lys Ala Ala Ala Val
        50                  55                  60

Val Lys Ala Ser Ala Leu Ala Leu Ala Glu Ala Tyr Leu Arg Ala Ser
65                  70                  75                  80

Ala Leu Ser Ala Ala Ala Ser Ala Lys Ala Ala Ala Leu Lys Asn
                85                  90                  95

Ala Gln Gln Ala Gln Leu Asn Ala Gln Glu Lys Ser Leu Ala Ala Leu
            100                 105                 110

Lys Ala Gln Ser Glu Glu Glu Ala Ser Ala Arg Ala Asn Ala Ala
            115                 120                 125

Thr Ala Thr Gln Ser Ala Leu Glu Arg Ala Gln Ala Ser Ser Arg
130                 135                 140

Leu Ala Thr Val Ala Gln Asn Val Ala Ser Asp Leu Gln Lys Arg Thr
145                 150                 155                 160

Ser Thr Lys Ala Ala Ala Glu Ala Ala Ala Thr Leu Arg Gln Leu Gln
                165                 170                 175

Asp Ala Glu Arg Thr Lys Trp Ser Ala Asn Ala Ala Leu Glu Val Ser
            180                 185                 190

Ala Ala Ala Ala Ala Ala Glu Thr Lys Thr Thr Ala Ser Ser Glu Ala
        195                 200                 205

Ala Asn Ala Ala Ala Lys Lys Ala Ala Ile Ala Ser Asp Ala Asp
210                 215                 220

Gly Ala Glu Arg Ser Ala Ser Thr Glu Ala Gln Ser Ala Ala Lys Ile
225                 230                 235                 240

Glu Ser Val Ala Ala Ala Glu Gly Ser Ala Asn Ser Ala Ser Glu Asp
                245                 250                 255

Ser Arg Ala Ala Gln Leu Glu Ala Ser Thr Ala Ala Arg Ala Asn Val
            260                 265                 270

Ala Ala Ala Val Gly Asp Gly Ala Ile Ile Gly Leu Gly Glu Glu Ala
        275                 280                 285

Gly Ala Ala Ala Gln Leu Leu Ala Gln Ala Lys Ala Leu Ala Glu Val
    290                 295                 300

Ser Ser Lys Ser Glu Asn Ile Glu Asp Lys Lys Phe
305                 310                 315

<210> SEQ ID NO 6
<211> LENGTH: 335
<212> TYPE: PRT
<213> ORGANISM: Apis mellifera

<400> SEQUENCE: 6

```
Met Gln Ile Pro Thr Phe Val Ala Ile Cys Leu Leu Thr Ser Gly Leu
1               5                   10                  15

Val His Ala Gly Val Glu Glu Phe Lys Ser Ser Ala Thr Glu Val
            20                  25                  30

Ile Ser Lys Asn Leu Glu Val Asp Leu Leu Lys Asn Val Asp Thr Ser
            35                  40                  45

Ala Lys Arg Arg Glu Asn Gly Ala Pro Val Leu Gly Lys Asn Thr Leu
    50                  55                  60

Gln Ser Leu Glu Lys Ile Lys Thr Ser Ala Ser Val Asn Ala Lys Ala
65                  70                  75                  80

Ala Ala Val Val Lys Ala Ser Ala Leu Ala Leu Ala Glu Ala Tyr Leu
                85                  90                  95

Arg Ala Ser Ala Leu Ser Ala Ala Ser Ala Lys Ala Ala Ala
            100                 105                 110

Leu Lys Asn Ala Gln Gln Ala Gln Leu Asn Gln Glu Lys Ser Leu
        115                 120                 125

Ala Ala Leu Lys Ala Gln Ser Glu Glu Ala Ala Ser Ala Arg Ala
        130                 135                 140

Asn Ala Ala Thr Ala Ala Thr Gln Ser Ala Leu Glu Arg Ala Gln Ala
145                 150                 155                 160

Ser Ser Arg Leu Ala Thr Val Ala Gln Asn Val Ala Ser Asp Leu Gln
            165                 170                 175

Lys Arg Thr Ser Thr Lys Ala Ala Glu Ala Ala Thr Leu Arg
            180                 185                 190

Gln Leu Gln Asp Ala Glu Arg Thr Lys Trp Ser Ala Asn Ala Ala Leu
        195                 200                 205

Glu Val Ser Ala Ala Ala Ala Ala Glu Thr Lys Thr Thr Ala Ser
    210                 215                 220

Ser Glu Ala Ala Asn Ala Ala Lys Lys Ala Ala Ala Ile Ala Ser
225                 230                 235                 240

Asp Ala Asp Gly Ala Glu Arg Ser Ala Ser Thr Glu Ala Gln Ser Ala
            245                 250                 255

Ala Lys Ile Glu Ser Val Ala Ala Glu Gly Ser Ala Asn Ser Ala
        260                 265                 270

Ser Glu Asp Ser Arg Ala Ala Gln Leu Glu Ala Ser Thr Ala Ala Arg
    275                 280                 285

Ala Asn Val Ala Ala Val Gly Asp Gly Ala Ile Ile Gly Leu Gly
        290                 295                 300

Glu Glu Ala Gly Ala Ala Gln Leu Leu Ala Gln Ala Lys Ala Leu
305                 310                 315                 320

Ala Glu Val Ser Ser Lys Ser Glu Asn Ile Glu Asp Lys Lys Phe
            325                 330                 335

<210> SEQ ID NO 7
<211> LENGTH: 323
<212> TYPE: PRT
<213> ORGANISM: Apis mellifera

<400> SEQUENCE: 7

Ala Arg Glu Glu Val Glu Thr Arg Asp Lys Thr Lys Thr Ser Thr Val
1               5                   10                  15

Val Lys Ser Glu Lys Val Glu Val Ala Pro Ala Lys Asp Glu Leu
            20                  25                  30

Lys Leu Thr Ser Glu Pro Ile Phe Gly Arg Arg Val Gly Thr Gly Ala
```

```
                35                  40                  45
Ser Glu Val Ala Ser Ser Gly Glu Ala Ile Ala Ile Ser Leu Gly
 50                  55                  60
Ala Gly Gln Ser Ala Ala Glu Ser Gln Ala Leu Ala Ala Ser Gln Ser
 65                  70                  75                  80
Lys Thr Ala Ala Asn Ala Ala Ile Gly Ala Ser Glu Leu Thr Asn Lys
                 85                  90                  95
Val Ala Ala Leu Val Ala Gly Thr Gly Ala Gln Ala Arg Ala Thr
                100                 105                 110
Ala Ala Ser Ser Ser Ala Leu Lys Ala Ser Leu Ala Thr Glu Glu Ala
            115                 120                 125
Ala Glu Glu Ala Glu Ala Ala Val Ala Asp Ala Lys Ala Ala Ala Glu
            130                 135                 140
Lys Ala Glu Ser Leu Ala Lys Asn Leu Ala Ser Ala Ser Ala Arg Ala
145                 150                 155                 160
Ala Leu Ser Ser Glu Arg Ala Asn Glu Leu Ala Gln Ala Glu Ser Ala
                165                 170                 175
Ala Ala Ala Glu Ala Gln Ala Lys Thr Ala Ala Ala Lys Ala Ala
            180                 185                 190
Glu Ile Ala Leu Lys Val Ala Glu Ile Ala Val Lys Ala Glu Ala Asp
            195                 200                 205
Ala Ala Ala Ala Val Ala Ala Ala Lys Ala Arg Ala Val Ala Asp
            210                 215                 220
Ala Ala Ala Ala Arg Ala Ala Val Asn Ala Ile Ala Lys Ala Glu
225                 230                 235                 240
Glu Glu Ala Ser Ala Gln Ala Glu Asn Ala Ala Gly Val Leu Gln Ala
                245                 250                 255
Ala Ala Ser Ala Ala Ala Glu Ser Arg Ala Ala Ala Ala Ala Ala
            260                 265                 270
Ala Thr Ser Glu Ala Ala Ala Glu Ala Gly Pro Leu Ala Gly Glu Met
            275                 280                 285
Lys Pro Pro His Trp Lys Trp Glu Arg Ile Pro Val Lys Lys Glu Glu
            290                 295                 300
Trp Lys Thr Ser Thr Lys Glu Glu Trp Lys Thr Thr Asn Glu Glu Trp
305                 310                 315                 320
Glu Val Lys

<210> SEQ ID NO 8
<211> LENGTH: 342
<212> TYPE: PRT
<213> ORGANISM: Apis mellifera

<400> SEQUENCE: 8

Met Lys Ile Pro Ser Ile Leu Ala Val Ser Leu Leu Ile Trp Gly Leu
1               5                   10                  15
Ala Ser Gly Ala Arg Glu Glu Val Glu Thr Arg Asp Lys Thr Lys Thr
                20                  25                  30
Ser Thr Val Val Lys Ser Glu Lys Val Glu Val Ala Pro Ala Lys
            35                  40                  45
Asp Glu Leu Lys Leu Thr Ser Glu Pro Ile Phe Gly Arg Arg Val Gly
 50                  55                  60
Thr Gly Ala Ser Glu Val Ala Ser Ser Gly Glu Ala Ile Ala Ile
 65                  70                  75                  80
Ser Leu Gly Ala Gly Gln Ser Ala Ala Glu Ser Gln Ala Leu Ala Ala
```

```
            85                  90                  95
Ser Gln Ser Lys Thr Ala Ala Asn Ala Ala Ile Gly Ala Ser Glu Leu
            100                 105                 110

Thr Asn Lys Val Ala Ala Leu Val Ala Gly Ala Thr Gly Ala Gln Ala
            115                 120                 125

Arg Ala Thr Ala Ala Ser Ser Ser Ala Leu Lys Ala Ser Leu Ala Thr
            130                 135                 140

Glu Glu Ala Ala Glu Ala Glu Ala Val Ala Asp Ala Lys Ala
145                 150                 155                 160

Ala Ala Glu Lys Ala Glu Ser Leu Ala Lys Asn Leu Ala Ser Ala Ser
            165                 170                 175

Ala Arg Ala Ala Leu Ser Ser Glu Arg Ala Asn Glu Leu Ala Gln Ala
            180                 185                 190

Glu Ser Ala Ala Ala Glu Ala Gln Ala Lys Thr Ala Ala Ala Ala
            195                 200                 205

Lys Ala Ala Glu Ile Ala Leu Lys Val Ala Glu Ile Ala Val Lys Ala
            210                 215                 220

Glu Ala Asp Ala Ala Ala Ala Val Ala Ala Ala Lys Ala Arg Ala
225                 230                 235                 240

Val Ala Asp Ala Ala Ala Arg Ala Ala Val Asn Ala Ile Ala
            245                 250                 255

Lys Ala Glu Glu Ala Ser Ala Gln Ala Glu Asn Ala Ala Gly Val
            260                 265                 270

Leu Gln Ala Ala Ser Ala Ala Glu Ser Arg Ala Ala Ala
            275                 280                 285

Ala Ala Ala Ala Thr Ser Glu Ala Ala Glu Ala Gly Pro Leu Ala
            290                 295                 300

Gly Glu Met Lys Pro Pro His Trp Lys Trp Arg Ile Pro Val Lys
305                 310                 315                 320

Lys Glu Glu Trp Lys Thr Ser Thr Lys Glu Glu Trp Lys Thr Thr Asn
            325                 330                 335

Glu Glu Trp Glu Val Lys
            340

<210> SEQ ID NO 9
<211> LENGTH: 353
<212> TYPE: PRT
<213> ORGANISM: Apis mellifera

<400> SEQUENCE: 9

Gly Val Asn Thr Glu Leu Lys Lys Asp Gly Glu Leu Lys Glu Glu Ser
1               5                   10                  15

Tyr Glu Lys Ser Glu Ser Lys Ser Leu Lys Glu Ile Lys Glu Glu Arg
            20                  25                  30

Ala Ser Lys Ser Lys Ser Glu Arg Leu Lys Ile Arg Glu Glu Lys Arg
            35                  40                  45

Glu Glu Glu Lys Ser Lys Ser Leu Asn Leu Val Val Arg Glu
            50                  55                  60

Lys Ile Thr Lys Leu Ser Ser Trp Leu Lys Glu Glu Lys Asp Ile Ser
65                  70                  75                  80

Pro Leu Leu Glu Glu Lys Asn Gly Lys Gly Leu Leu Gly Leu Glu Asp
            85                  90                  95

Val Thr Asp Glu Leu Asn Ile Ala Leu Lys Ser Leu Lys Glu Gly Lys
            100                 105                 110
```

```
Lys Phe Asp Thr Trp Lys Phe Glu Lys Gly Ser Glu Asp Val Arg Ser
            115                 120                 125

Leu Glu Glu Leu Asp Thr Ser Val Val Glu Leu Leu Lys Leu Ile Lys
130                 135                 140

Glu Gly Lys Thr Asp His Gly Ala Ile Asp Leu Glu Lys Asn Gly Lys
145                 150                 155                 160

Val Leu Val Asp Leu Glu Lys Ile Ser Glu Asn Ile Leu Glu Thr Cys
                165                 170                 175

Gly Ser Gln Lys Lys Thr Val Glu Val Asp Lys Asp Lys Lys
            180                 185                 190

Trp Asn Lys Glu Ser Gly Trp Lys Lys Asn Leu Asn Asp Leu Asp Trp
            195                 200                 205

Lys Lys Asp Leu Asp Lys Asp Lys Val Gly Gly Leu Gly Gly
210                 215                 220

Leu Ser Gly Leu Leu Asn Ser Leu Lys Ser Glu Lys Gly Leu Leu Gly
225                 230                 235                 240

Leu Leu Asn Lys Asn Gln Ile Glu Leu Ile Pro Leu Ile Ser Glu
                245                 250                 255

Ile Lys Lys Lys Asn Ile Asp Phe Asn Leu Phe Asp Ser Val Asp Ser
            260                 265                 270

Val Glu Arg Asn Leu Asp Leu Lys Leu Phe Thr Ser Ser Val Ser Lys
            275                 280                 285

Val Thr Glu Leu Leu Asn Lys Gly Ile Asp Ile Gln Thr Ile Leu Asn
            290                 295                 300

Ala Lys Asn Gly Asp Glu Phe Asp Leu Ser Gly Lys Glu Leu Lys Asn
305                 310                 315                 320

Val Lys Gly Ile Phe Gly Leu Ile Gly Ser Leu Lys Arg Ser Leu Gly
                325                 330                 335

Leu Glu Asn Ile Leu Asn Leu Pro Phe Lys Arg Ile Pro Leu Leu Lys
                340                 345                 350

Leu

<210> SEQ ID NO 10
<211> LENGTH: 372
<212> TYPE: PRT
<213> ORGANISM: Apis mellifera

<400> SEQUENCE: 10

Met Lys Tyr Met Leu Leu Leu Ser Ile Phe Ile Cys Ala His Ile
1               5                   10                  15

Val Cys Ala Gly Val Asn Thr Glu Leu Lys Lys Asp Gly Glu Leu Lys
                20                  25                  30

Glu Glu Ser Tyr Glu Lys Ser Glu Ser Lys Ser Leu Lys Glu Ile Lys
            35                  40                  45

Glu Glu Arg Ala Ser Lys Ser Lys Ser Glu Arg Leu Lys Ile Arg Glu
        50                  55                  60

Glu Lys Arg Glu Glu Glu Lys Ser Lys Ser Leu Asn Leu Val Val
65                  70                  75                  80

Val Arg Glu Lys Ile Thr Lys Leu Ser Ser Trp Leu Lys Glu Lys
                85                  90                  95

Asp Ile Ser Pro Leu Leu Glu Glu Lys Asn Gly Lys Gly Leu Leu Gly
            100                 105                 110

Leu Glu Asp Val Thr Asp Glu Leu Asn Ile Ala Leu Lys Ser Leu Lys
            115                 120                 125
```

Glu Gly Lys Lys Phe Asp Thr Trp Lys Phe Glu Lys Gly Ser Glu Asp
130                 135                 140

Val Arg Ser Leu Glu Glu Leu Asp Thr Ser Val Val Glu Leu Leu Lys
145                 150                 155                 160

Leu Ile Lys Glu Gly Lys Thr Asp His Gly Ala Ile Asp Leu Glu Lys
            165                 170                 175

Asn Gly Lys Val Leu Val Asp Leu Glu Lys Ile Ser Glu Asn Ile Leu
        180                 185                 190

Glu Thr Cys Gly Ser Gln Lys Lys Thr Val Glu Val Val Asp Asp Lys
    195                 200                 205

Asp Lys Lys Trp Asn Lys Glu Ser Gly Trp Lys Lys Asn Leu Asn Asp
210                 215                 220

Leu Asp Trp Lys Lys Asp Leu Asp Lys Asp Lys Val Gly Gly Gly Leu
225                 230                 235                 240

Leu Gly Gly Leu Ser Gly Leu Leu Asn Ser Leu Lys Ser Glu Lys Gly
            245                 250                 255

Leu Leu Gly Leu Leu Asn Lys Asn Gln Ile Glu Leu Leu Ile Pro Leu
        260                 265                 270

Ile Ser Glu Ile Lys Lys Lys Asn Ile Asp Phe Asn Leu Phe Asp Ser
    275                 280                 285

Val Asp Ser Val Glu Arg Asn Leu Asp Leu Lys Leu Phe Thr Ser Ser
290                 295                 300

Val Ser Lys Val Thr Glu Leu Leu Asn Lys Gly Ile Asp Ile Gln Thr
305                 310                 315                 320

Ile Leu Asn Ala Lys Asn Gly Asp Glu Phe Asp Leu Ser Gly Lys Glu
            325                 330                 335

Leu Lys Asn Val Lys Gly Ile Phe Gly Leu Ile Gly Ser Leu Lys Arg
        340                 345                 350

Ser Leu Gly Leu Glu Asn Ile Leu Asn Leu Pro Phe Lys Arg Ile Pro
    355                 360                 365

Leu Leu Lys Leu
    370

<210> SEQ ID NO 11
<211> LENGTH: 942
<212> TYPE: DNA
<213> ORGANISM: Apis mellifera

<400> SEQUENCE: 11
ggtttggagg ggccgggcaa ctcgttgccc gagctcgtga aaggtagcgc atcggccacc    60
gcgtcgaccg ctgtgaccgc tagatcagga cttagagccg acaagtagc tttagcttcg    120 cagaaggatg ccgtactcca agctcaagct gctgcatccg ccgcgtcaga ggcgcgcgct    180
gctgccgatc tgacggctaa acttagccaa gaatcggcat cagtgcaatc gcaggctgcc    240
gccaaaggga aggaaacgga ggaggcagct gttggtcaag ctagggctgg cctcgagtcg    300
gtgtccatgg ccgcatcagc cacatctgct gccaagaag catcgaccgc cgccaaagcc    360
gcagcatccg cactatccac agccgtggtg caagcgaaaa tagctgagag gcagccaaa    420 gctgaagctg ttgcctcgga cgaagccaag gccaaggcga ttgcagcagc caacttggcg    480
gctgaggcca gtgtagccgc agaagcagct ctcaaggccg agaaagtggc cgaagaagcc    540
atcgcaagag cggcctctgc aaaggctgcc gcaagagctg ctgctgccgc tctagcctcc    600
tcgaaggaag cagccacggc cagcgcaaga acgccgcgg aatccgaggc caggaacgaa    660
gtagctgtat tgatcgccga gattgataaa aagagtaggg aaatcgacgc agccagttcg    720

```
cttaatgcgc gtgccgctgc caaggcaagc tccaggaacg tagaaacggc gacaatcggg    780
gccaacatca actcttcgaa acaagtcgtg tcaattccag tggaaataaa gaaattctcg    840
gagccggaag tgtcaacatc atggagagaa gatgaagagg ttacgaaaga gaagaaggag    900
cacataaatc tgaacgactt cgacttgaag agcaacgtat tt                      942
```

<210> SEQ ID NO 12
<211> LENGTH: 999
<212> TYPE: DNA
<213> ORGANISM: Apis mellifera

<400> SEQUENCE: 12

```
atgaagattc cagtattgct tgcaacgtgc ctctacccttt gcggatttgc gtccgccggt    60 ttggagggggc cgggcaactc gttgcccgag ctcgtgaaag gtagcgcatc ggccaccgcg   120
tcgaccgctg tgaccgctag atcaggactt agagccggac aagtagcttt agcttcgcag   180
aaggatgccg tactccaagc tcaagctgct gcatccgccg cgtcagaggc gcgcgctgct   240
gccgatctga cggctaaaact tagccaagaa tcggcatcag tgcaatcgca ggctgccgcc   300
aaagggaagg aaacggagga ggcagctgtt ggtcaagcta gggctggcct cgagtcggtg   360
tccatggccg catcagccac atctgctgcc aaagaagcat cgaccgccgc caaagccgca   420
gcatccgcac tatccacagc cgtggtgcaa gcgaaaatag ctgagagggc agccaaagct   480
gaagctgttg cctcggacga agccaaggcc aaggcgattg cagcagccaa cttggcggct   540
gaggccagtg tagccgcaga agcagctctc aaggccgaga agtggccga agaagccatc    600 gcaagagcgg cctctgcaaa ggctgccgca agagctgctg ctgccgctct agcctcctcg   660
aaggaagcag ccacggccag cgcaagaaac gccgcggaat ccgaggccag gaacgaagta   720
gctgtattga tcgccgagat tgataaaaag agtagggaaa tcgacgcagc cagttcgctt   780
aatgcgcgtg ccgctgccaa ggcaagctcc aggaacgtag aaacggcgac aatcggggcc   840
aacatcaact cttcgaaaca agtcgtgtca attccagtgg aaataaagaa attctcggag   900
ccggaagtgt caacatcatg gagagaagat gaagaggtta cgaaagagaa gaaggagcac   960
ataaatctga acgacttcga cttgaagagc aacgtattt                          999
```

<210> SEQ ID NO 13
<211> LENGTH: 870
<212> TYPE: DNA
<213> ORGANISM: Apis mellifera

<400> SEQUENCE: 13

```
cgcgtgatta atcacgagtc cctgaagacg agcgaggata ttcaaggagg atattcagca    60
ggaatagtcg gtgatggatc tgacgcgctt ggctcctcca tagaaaacgc ccaaaaagtc   120
gctcgagcgg ctgaaaacgt gggcttgaat ctggaattgg gcgcaggcgc gcgtgctgcc   180
agtgttgccg ctgctgccca ggccaaaaac acagaggctg cggaagcagg agcaaacgcc   240
gctctggccg ccgccattgc caaacgggag gaagcgatta agccagcga gatagcaaac   300 caattgttga ccaatgcagc aaaagcggca gaagcgactg tatcggcaac gaagagggca   360
gcacaattga cggctgcagc gaaagaagca accagagctt ctgcagccgc tgctgaagct   420
gctacggagg cccaggtaaa ggctaacgcc gattcaatca tcacgaagag ggctgcgatt   480
gccgaggctc aagctgcggc ggaagctcaa gttaaggcgg caatcgccag aaaatcggca   540
gcgaattttt tggctaaggc tcaaatagcg gctgccgcgg aatccgaggc cacgaaactc   600
```

```
gcggccgaag ctgtagtggc actaacaaac gccgaagtcg ccgtgaacca ggctagaaac    660
gcacaggcaa acgcctcgac tcaagcttcc atgctgttta gggtagattc tcaagcagcg    720
aacgctgaag cagccgctgt agcgcaagcc gaaactctct tggttacggc agaagctgtc    780
gcagctgcgg aggctgaggt tgcgaacaaa gccgccacat ttgcaaaaca gatcgtcaac    840
gagaagaaaa tacatgtagc aaagttggaa                                    870

<210> SEQ ID NO 14
<211> LENGTH: 927
<212> TYPE: DNA
<213> ORGANISM: Apis mellifera

<400> SEQUENCE: 14
atgaagattc cagcaatatt cgtcacgtct ctgctggtct ggggattggc cgagggccgc     60
gtgattaatc acgagtccct gaagacgagc gaggatattc aaggaggata ttcagcagga    120
atagtcggtg atggatctga cgcgcttggc tcctccatag aaaacgccca aaaagtcgct    180
cgagcggctg aaaacgtggg cttgaatctg gaattgggcg caggcgcgcg tgctgccagt    240
gttgccgctg ctgcccaggc caaaaacaca gaggctgcgg aagcaggagc aaacgccgct    300
ctggccgccg ccattgccaa cggggaggaa gcgattaaag ccagcgagat agcaaaccaa    360
ttgttgacca atgcagcaaa agcggcagaa gcgactgtat cggcaacgaa gagggcagca    420
caattgacgc tgcagcgaa agaagcaacc agagcttctg cagccgctgc tgaagctgct    480
acggaggccc aggtaaaggc taacgccgat tcaatcatca cgaagagggc tgcgattgcc    540
gaggctcaag ctgcggcgga agctcaagtt aaggcggcaa tcgccagaaa atcggcagcg    600 aatttttttgg ctaaggctca aatagcggct gccgcggaat ccgaggccac gaaactcgcg    660
gccgaagctg tagtggcact aacaaacgcc gaagtcgccg tgaaccaggc tagaaacgca    720
caggcaaacg cctcgactca agcttccatg ctgttaggg tagattctca gcagcgaac     780 gctgaagcag ccgctgtagc gcaagccgaa actctcttgg ttacggcaga agctgtcgca    840
gctgcggagg ctgaggttgc gaacaaagcc gccacatttg caaaacagat cgtcaacgag    900
aagaaaatac atgtagcaaa gttggaa                                       927

<210> SEQ ID NO 15
<211> LENGTH: 949
<212> TYPE: DNA
<213> ORGANISM: Apis mellifera

<400> SEQUENCE: 15
ggcgtcgagg aattcaagtc ctcggcaacc gaggaggtga tcagcaaaaa cttagaagtc     60
gacctgttga aaatgtggac actagcgcg aaacgaagag agaacggcgc cccggtgctc    120
ggcaagaaca cacttcaatc cctggagaag atcaagacgt cggcgagcgt gaatgccaaa    180
gcagcagccg tggtgaaagc gtccgctctg ctcttgcag aggcctattt gcgagcgtcc    240
gcattgtcag ccgccgcttc agccaaggca gccgccgccc tgaaaaatgc tcaacaagcg    300
caattaaacg cccaggaaaa gtctttggcc gcgttgaaag ctcagtccga ggaagaggca    360
gcttctgctc gtgcaaacgc agcaaccgcc gcgacacagt cggcactgga acgcgctcaa    420
gcctcctcca ggttagcaac ggtcgcccaa acgtagccaa gcgacttgca gaaacggacc    480
agcaccaagg ccgggctga gccgctgcc accctcagac aattacagga cgcggaacga    540
acgaaatgga gtgccaacgc tgccttagaa gtctccgccg ctgcagctgc gcagaaacc    600 aagaccactg cctcctcgga ggccgccaac gccgccgcca aaaaggcggc cgcgatagct    660
```

```
tctgacgcgg acggcgcgga aaggtcggca tctaccgagg cacaatcagc tgcgaagatc    720
gagagtgtgg cagccgccga gggatccgcc aactcggcct ctgaggattc ccgggccgct    780
caattggaag cctccaccgc ggcgagagcc aacgtggccg cagctgtcgg ggatggagcg    840
attataggac ttggagagga agcgggtgcc gcggctcagt tgcttgcaca ggcgaaggca    900
ttggccgaag ttagctcgaa atccgaaaat attgaggata aaaaattt                949

<210> SEQ ID NO 16
<211> LENGTH: 1006
<212> TYPE: DNA
<213> ORGANISM: Apis mellifera

<400> SEQUENCE: 16
atgcagatcc caacgtttgt cgccatatgc ttgctcacat cgggcttggt gcacgcaggc     60
gtcgaggaat tcaagtcctc ggcaaccgag gaggtgatca gcaaaaactt agaagtcgac    120
ctgttgaaaa atgtggacac tagcgcgaaa cgaagagaga acggcgcccc ggtgctcggc    180
aagaacacac ttcaatccct ggagaagatc aagacgtcgg cgagcgtgaa tgccaaagca    240
gcagccgtgg tgaaagcgtc cgctctggct cttgcagagg cctatttgcg agcgtccgca    300 tgtcagccg ccgcttcagc caaggcagcc gccgccctga aaatgctcaa caagcgcaa     360 ttaaacgccc aggaaaagtc tttggccgcg ttgaaagctc agtccgagga gaggcagct    420 tctgctcgtg caaacgcagc aaccgccgcg acacagtcgg cactggaacg cgctcaagcc    480
tcctccaggt tagcaacggt cgcccaaaac gtagccagcg acttgcagaa acggaccagc    540
accaaggccg cggctgaagc cgctgccacc ctcagacaat tacaggacgc ggaacgaacg    600
aaatggagtg ccaacgctgc cttagaagtc tccgccgctg cagctgccgc agaaaccaag    660
accactgcct cctcggaggc cgccaacgcc gccgccaaaa aggcggccgc gatagcttct    720
gacgcggacg gcgcggaaag gtcggcatct accgaggcac aatcagctgc gaagatcgag    780
agtgtggcag ccgccgaggg atccgccaac tcggcctctg aggattcccg ggccgctcaa    840
ttggaagcct ccaccgcggc gagagccaac gtggccgcag ctgtcgggga tggagcgatt    900
ataggacttg gagaggaagc gggtgccgcg gctcagttgc ttgcacaggc gaaggcattg    960
gccgaagtta gctcgaaatc gaaaatatt gaggataaaa aatttt                   1006

<210> SEQ ID NO 17
<211> LENGTH: 969
<212> TYPE: DNA
<213> ORGANISM: Apis mellifera

<400> SEQUENCE: 17
gcaagggaag aggtggagac acgggacaag accaagacct cgacagtggt gaaaagcgag     60
aaagtggaag tcgttgctcc cgctaaggat gaacttaaat taacgagcga gcctatcttt    120
ggaagaagag tgggaactgg agcatccgag gtggcatcta gcagcggtga agccatcgcg    180
ataagtcttg gagcagggca gtcagcggca gagtctcagg ccttggccgc ctcgcaatcc    240
aaaacggcag cgaacgccgc cataggcgcg agcgagctta ccaacaaagt tgctgctcta    300
gttgctggcg cgactggtgc gcaggcgaga gctacggccg cctcctcgag cgcgttgaag    360
gccagcttgg cgaccgaaga agcggcggaa gaggccgagg cggccgtggc tgacgccaag    420
gctgccgcga aaaggccgga atccctggcg aaaaatctcg cgtcggcgag cgctcgcgcg    480
gccctctcct ccgaaagggc gaacgaattg gctcaagctg agagcgctgc agcggccgag    540
```

-continued

```
gcgcaggcca agacagcagc cgccgccaaa gcagcggaaa tcgcccttaa ggtcgctgag      600
atagcggtga aggcggaagc ggacgcagca gctgccgccg tggcagctgc aaaggcaaga      660
gccgtggcag acgcggccgc tgcccgtgcc gcagccgtga acgccatcgc caaggcggaa      720
gaggaggcct cggcccaagc agagaacgcc gccggtgttt tgcaagcagc cgcctccgcc      780
gcggcggaat cgcgagccgc tgcagctgcc gccgctgcta cctcggaggc agcggctgaa      840
gctggcccgt tggcaggtga gatgaaacca ccgcactgga aatgggaacg gattcctgtg      900
aagaaggagg agtggaaaac gtcaacgaag gaagaatgga aaacgacgaa tgaagaatgg      960
gaggtgaag                                                             969
```

```
<210> SEQ ID NO 18
<211> LENGTH: 1026
<212> TYPE: DNA
<213> ORGANISM: Apis mellifera

<400> SEQUENCE: 18
atgaagatcc catccatact cgcggtttcc ctgctgatct ggggtttggc aagcggcgca       60
agggaagagg tggagacacg ggacaagacc aagacctcga cagtggtgaa aagcgagaaa      120
gtggaagtcg ttgctcccgc taaggatgaa cttaaattaa cgagcgagcc tatctttgga      180
agaagagtgg gaactggagc atccgaggtg gcatctagca gcggtgaagc catcgcgata      240
agtcttggag cagggcagtc agcggcagag tctcaggcct tggccgcctc gcaatccaaa      300
acggcagcga acgccgccat aggcgcgagc gagcttacca caaagttgc tgctctagtt       360
gctggcgcga ctggtgcgca ggcgagagct acggccgcct cctcgagcgc gttgaaggcc      420
agcttggcga ccgaagaagc ggcggaagag gccgaggcgg ccgtggctga cgccaaggct      480
gccgcgaaa aggccgaatc cctggcgaaa aatctcgcgt cggcgagcgc tcgcgcggcc      540
ctctcctccg aaagggcgaa cgaattggct caagctgaga gcgctgcagc ggccgaggcg      600
caggccaaga cagcagccgc cgccaaagca gcggaaatcg cccttaaggt cgctgagata      660
gcggtgaagg cggaagcgga cgcagcagct gccgccgtgg cagctgcaaa ggcaagagcc      720
gtggcagacg cggccgctgc ccgtgccgca gccgtgaacg ccatcgccaa gcggaagag      780
gaggcctcgg cccaagcaga gaacgccgcc ggtgttttgc aagcagccgc tccgccgcg      840
gcggaatcgc gagccgctgc agctgccgcc gctgctacct cggaggcagc ggctgaagct      900
ggcccgttgg caggtgagat gaaaccaccg cactggaaat gggaacggat tcctgtgaag      960
aaggaggagt ggaaaacgtc aacgaaggaa gaatggaaaa cgacgaatga agaatgggag     1020
gtgaag                                                               1026
```

```
<210> SEQ ID NO 19
<211> LENGTH: 1059
<212> TYPE: DNA
<213> ORGANISM: Apis mellifera

<400> SEQUENCE: 19
ggcgtaaata cagaattaaa aaaagatggt gaactaaagg aagagtctta tgagaaaagc       60
gagtcaaaga gtttaaaaga aattaaagaa gaacgtgctt caaaatcaaa aagtgaacgt      120
ttgaagattc gtgaagaaaa acgcgaagag gaagaaaaat ccaagagtct gaatctggtc      180
gtggtcagag aaaagattac caaactttct tcatggctca agaagagaa agatatcagt      240
cctctttttgg aagaaaaaaa tggcaaaggt ctattgggtt tggaagatgt cacggacgag      300
ttaaatatcg ctcttaaatc gttgaaggag ggcaaaaagt ttgatacttg gaaattcgag      360
```

```
aaaggtagcg aagacgttcg ttctttggaa gaacttgata cgagcgtcgt tgaactttta      420
aaattaataa aggaaggaaa aactgaccat ggtgctatag atttggagaa gaatggtaag      480
gtacttgtag atttggaaaa aatctcagaa aacatacttg aaacttgtgg atcacaaaag      540
aagactgtgg aagttgtaga tgataaagac aaaaaatgga ataaagaatc aggttggaaa      600
aaaaatctaa atgatctaga ttggaaaaaa gatttagata agataaagt tggtggcggt       660 ttgcttggcg gtttaagtgg cctcttaaat agtttaaaat cagaaaaagg tcttctaggt      720
cttttgaata agaatcaaat tgagttatta attcctttaa tcagtgagat aaaaaagaaa      780
aatatagatt ttaatctctt cgattctgtt gattctgtcg aaagaaattt agacttgaaa      840
cttttcacaa gttctgtttc aaaagttact gaattattaa ataaaggaat cgatattcaa      900
acaattttga atgcgaaaaa tggagatgaa ttcgatttaa gcggcaaaga attgaaaaac      960
gtcaaaggga tatttggttt gattggaagt ttgaaacgct cattaggatt agaaaatata     1020
ttgaacttac cgtttaaacg tatacctctg cttaaatta                            1059

<210> SEQ ID NO 20
<211> LENGTH: 1116
<212> TYPE: DNA
<213> ORGANISM: Apis mellifera

<400> SEQUENCE: 20
atgaaataca tgctcttgtt gctatctata ttcatctgtg cacatattgt atgcgcaggc       60
gtaaatacag aattaaaaaa agatggtgaa ctaaaggaag agtcttatga gaaaagcgag      120
tcaaagagtt taaagaaat taagaagaa cgtgcttcaa aatcaaaaag tgaacgtttg       180
aagattcgtg aagaaaaacg cgaagaggaa gaaaaatcca agagtctgaa tctggtcgtg      240
gtcagagaaa agattaccaa actttcttca tggctcaaag aagagaaaga tatcagtcct      300
cttttggaag aaaaaaatgg caaaggtcta ttgggtttgg aagatgtcac ggacgagtta      360
aatatcgctc ttaaatcgtt gaaggagggc aaaaagtttg atacttggaa attcgagaaa      420
ggtagcgaag acgttcgttc tttggaagaa cttgatacga gcgtcgttga acttttaaaa      480
ttaataaagg aaggaaaaac tgaccatggt gctatagatt tggagaagaa tggtaaggta      540
cttgtagatt tggaaaaaat ctcagaaaac atacttgaaa cttgtggatc acaaagaag       600 actgtgaag ttgtagatga taaagacaaa aaatggaata agaatcagg ttggaaaaaa       660 aatctaaatg atctagattg gaaaaagat ttagataag ataagttgg tggcggtttg         720 cttggcggtt taagtggcct cttaaatagt ttaaaatcag aaaaaggtct tctaggtctt     780
ttgaataaga atcaaattga gttattaatt cctttaatca gtgagataaa aagaaaaat      840 atagattta atctcttcga ttctgttgat tctgtcgaaa gaaatttaga cttgaaactt       900
ttcacaagtt ctgtttcaaa agttactgaa ttattaaata aggaatcga tattcaaaca       960 attttgaatg cgaaaatgg agatgaattc gatttaagcg gcaaagaatt gaaaacgtc       1020 aaagggatat ttggtttgat tggaagtttg aaacgctcat taggattaga aaatatattg     1080
aacttaccgt ttaaacgtat acctctgctt aaatta                              1116

<210> SEQ ID NO 21
<211> LENGTH: 1660
<212> TYPE: DNA
<213> ORGANISM: Apis mellifera

<400> SEQUENCE: 21
```

| | | | | | |
|---|---|---|---|---|---|
| atgaaataca | tgctcttgtt | gctatctata | ttcatctgtg | cacatattgt | atgcgcaggc | 60 |
| gtaaatacag | aattaaaaaa | agatggtgaa | ctaaaggaag | agtcttatga | gaaaagcgag | 120 |
| tcaaagagtt | taaagaaat | taaagaagaa | cgtgcttcaa | aatcaaaaag | tgaacgtttg | 180 |
| aagattcgtg | aaggtaattc | gtgagattca | agattcaaat | caattaaatt | tgaaaattat | 240 |
| gaaagtagta | ttgttaaatt | ataagataga | agattttatc | taaaaaataa | taaattaagc | 300 |
| tttttgtatt | tttggatatt | gtagatattt | ttaatataga | attcttataa | agttaaaaaa | 360 |
| tattttataa | attaaacaac | tttttattat | ttttatgatc | taaaaattaa | aaatttcaag | 420 |
| ttaaagttca | aattaaaaat | ttgtaaaaaa | tatggaaaaa | acataaaaat | tgaatttgtt | 480 |
| gtaatttaaa | aaggattttt | attatttatt | gattaattat | gaatataagt | tcgaaaaatc | 540 |
| ctaaatatta | atgtttaaaa | ttttaattct | taacaaaata | tatttaattt | aattcttaac | 600 |
| aaagatacat | ttaaagaatt | tcgcaaattt | aaaaattagg | ttttaatttt | taagaatcaa | 660 |
| atggtaaaaa | acattttaaa | tttgaaatat | ataaagtaa | atcttttaat | cgacaaacgg | 720 |
| atgaatttat | tgattagaaa | aacgcgaaga | ggaagaaaaa | tccaagagtc | tgaatctggt | 780 |
| cgtggtcaga | gaaagagatta | ccaaactttc | ttcatggctc | aaagaagaga | aagatatcag | 840 |
| tcctcttttg | gaagaaaaaa | atggcaaagg | tctattgggt | ttggaagatg | tcacggacga | 900 |
| gttaaatatc | gctcttaaat | cgttgaagga | gggcaaaaag | tttgatactt | ggaaattcga | 960 |
| gaaggtagc | gaagacgttc | gttctttgga | gaacttgat | acgagcgtcg | ttgaactttt | 1020 |
| aaaattaata | aaggaaggaa | aaactgacca | tggtgctata | gatttggaga | agaatggtaa | 1080 |
| ggtacttgta | gatttggaaa | aaatctcaga | aaacatactt | gaaacttgtg | gatcacaaaa | 1140 |
| gaagactgtg | gaagttgtag | atgataaaga | caaaaaatgg | aataaagaat | caggttggaa | 1200 |
| aaaaaatcta | aatgatctag | attggaaaaa | agatttagat | aaagataaag | ttggtggcgg | 1260 |
| tttgcttggc | ggtttaagtg | gcctcttaaa | tagtttaaaa | tcagaaaaag | gtcttctagg | 1320 |
| tcttttgaat | aagaatcaaa | ttgagttatt | aattccttta | atcagtgaga | taaaaaagaa | 1380 |
| aaatatagat | tttaatctct | tcgattctgt | tgattctgtc | gaaagaaatt | tagacttgaa | 1440 |
| acttttcaca | agttctgttt | caaaagttac | tgaattatta | aataaaggaa | tcgatattca | 1500 |
| aacaattttg | aatgcgaaaa | atggagatga | attcgattta | agcggcaaag | aattgaaaaa | 1560 |
| cgtcaaaggg | atatttggtt | tgattggaag | tttgaaacgc | tcattaggat | tagaaaatat | 1620 |
| attgaactta | ccgtttaaac | gtatacctct | gcttaaatta | | | 1660 |

<210> SEQ ID NO 22
<211> LENGTH: 308
<212> TYPE: PRT
<213> ORGANISM: Bombus terrestris

<400> SEQUENCE: 22

Gly Gln Ser Ser Pro Leu Leu Glu Ile Val Gln Gly Ser Ala Ser Ala
1               5                   10                  15

Thr Ala Ser Thr Ala Val Thr Ala Arg Ser Gly Leu Arg Ala Gly Gln
                20                  25                  30

Val Ala Val Ala Ser Gln Lys Asp Ala Thr Leu Gln Ala Asp Ala Ser
            35                  40                  45

Ala Ala Ala Ala Ala Ala Ala Arg Ser Ala Asp Gln Ser Ala Ser
        50                  55                  60

Leu Ala Gln Gln Ser Ala Ser Leu Gln Ser Lys Ala Ala Ala Arg Ala
65                  70                  75                  80

```
Lys Ser Ala Glu Glu Ser Ala Ala Thr Ala Lys Ala Glu Leu Gln
                85                  90                  95

Ala Glu Ser Ile Ala Ala Ser Ala Ser Ser Asn Ala Arg Glu Ala Ala
            100                 105                 110

Ala Ser Ala Lys Ala Ser Ala Ser Ala Met Ser Ser Ala Ala Val Gln
            115                 120                 125

Ala Lys Leu Ala Glu Lys Thr Ala Lys Asn Gln Ala Leu Ala Ser Glu
            130                 135                 140

Glu Ala Lys Leu Lys Ala Ala Ala Ala Ser Ala Ala Ala Ala
145             150                 155                 160

Ser Ala Ala Ala Glu Ala Ala Leu Lys Ala Glu Arg Ile Ala Glu Glu
            165                 170                 175

Ala Ile Ala Lys Ala Ala Ala Lys Ala Ala Ala Arg Ala Ala Ala
            180                 185                 190

Ala Leu Asn Ser Ala Lys Glu Ala Ala Thr Ser Ser Ala Arg Ser
            195                 200                 205

Ala Ala Glu Ala Glu Ala Lys Ser Glu Val Ala Ile Leu Ile Ser Glu
            210                 215                 220

Leu Asp Lys Lys Ser Arg Glu Val Ala Ala Ser Ala Ser Ala Lys Ala
225             230                 235                 240

Arg Ala Ala Ala Ala Ser Ser Arg Asn Ala Glu Thr Ala Val Ile
            245                 250                 255

Gly Ala Asn Ile Asn Val Ala Lys Glu Val Leu Ala Ile Pro Ile Glu
            260                 265                 270

Pro Lys Lys Leu Pro Glu Pro Glu Leu Ala Leu Lys Glu Glu Asn Val
            275                 280                 285

Ala Val Ala Ser Ser Glu Ser Glu Val Lys Val Glu Thr Ser Ser Glu
            290                 295                 300

Ala Trp Ser Ile
305

<210> SEQ ID NO 23
<211> LENGTH: 327
<212> TYPE: PRT
<213> ORGANISM: Bombus terrestris

<400> SEQUENCE: 23

Met Lys Ile Pro Ala Leu Leu Val Thr Cys Leu Tyr Leu Trp Gly Phe
1               5                   10                  15

Ala Ser Ala Gly Gln Ser Ser Pro Leu Leu Glu Ile Val Gln Gly Ser
            20                  25                  30

Ala Ser Ala Thr Ala Ser Thr Ala Val Thr Ala Arg Ser Gly Leu Arg
            35                  40                  45

Ala Gly Gln Val Ala Val Ala Ser Gln Lys Asp Ala Thr Leu Gln Ala
            50                  55                  60

Asp Ala Ser Ala Ala Ala Ala Ala Arg Ala Ser Ala Asp Gln
65                  70                  75                  80

Ser Ala Ser Leu Ala Gln Gln Ser Ala Ser Leu Gln Ser Lys Ala Ala
            85                  90                  95

Ala Arg Ala Lys Ser Ala Glu Glu Ser Ala Ala Ala Thr Ala Lys Ala
            100                 105                 110

Glu Leu Gln Ala Glu Ser Ile Ala Ala Ser Ser Asn Ala Arg
            115                 120                 125

Glu Ala Ala Ala Ser Ala Lys Ala Ser Ala Ser Ala Met Ser Ser Ala
            130                 135                 140
```

```
Ala Val Gln Ala Lys Leu Ala Glu Lys Thr Ala Lys Asn Gln Ala Leu
145                 150                 155                 160

Ala Ser Glu Glu Ala Lys Leu Lys Ala Ala Ala Ala Ser Ala Ala
        165                 170                 175

Ala Ala Ala Ser Ala Ala Ala Glu Ala Ala Leu Lys Ala Glu Arg Ile
        180                 185                 190

Ala Glu Glu Ala Ile Ala Lys Ala Ala Ala Lys Ala Ala Ala Arg
        195                 200                 205

Ala Ala Ala Ala Leu Asn Ser Ala Lys Glu Ala Ala Thr Ser Ser
210                 215                 220

Ala Arg Ser Ala Ala Glu Ala Lys Ser Glu Val Ala Ile Leu
225                 230                 235                 240

Ile Ser Glu Leu Asp Lys Lys Ser Arg Glu Val Ala Ala Ser Ala Ser
                245                 250                 255

Ala Lys Ala Arg Ala Ala Ala Ala Ser Ser Arg Asn Ala Glu Thr
        260                 265                 270

Ala Val Ile Gly Ala Asn Ile Asn Val Ala Lys Glu Val Leu Ala Ile
        275                 280                 285

Pro Ile Glu Pro Lys Lys Leu Pro Glu Pro Glu Leu Ala Leu Lys Glu
        290                 295                 300

Glu Asn Val Ala Val Ala Ser Ser Gly Ser Glu Val Lys Val Glu Thr
305                 310                 315                 320

Ser Ser Glu Ala Trp Ser Ile
                325

<210> SEQ ID NO 24
<211> LENGTH: 293
<212> TYPE: PRT
<213> ORGANISM: Bombus terrestris

<400> SEQUENCE: 24

His Val Val Lys Arg Asp Lys Glu Leu Lys Ala Pro Ala Leu Pro Glu
1               5                   10                  15

Leu Leu Gly Asp Gly Ser Asp Thr Leu Gly Ala Ser Met Glu Asn Gly
            20                  25                  30

Ile Lys Val Ala Arg Ala Ser Gln Asn Val Gly Leu Arg Thr Glu Leu
        35                  40                  45

Asn Ala Ala Ala Arg Ala Ala Ala Ala Ala Thr Lys Gln Ala Lys
50                  55                  60

Asp Thr Glu Ala Ala Glu Ala Gly Ala Ala Ala Ile Ala Ile Ala
65                  70                  75                  80

Ile Ala Lys Arg Glu Glu Ala Ile Lys Ala Ser Glu Leu Ala Ser Lys
                85                  90                  95

Leu Leu Thr Ala Ala Ala Gly Ser Ser Glu Ala Ala Val Ser Ala Thr
            100                 105                 110

Val Arg Ala Ala Gln Leu Thr Ala Ala Ser Ala Ala Ala Lys Ala
        115                 120                 125

Ser Ala Ser Ala Ser Glu Ala Ser Ala Glu Ala Gln Val Arg Ala Asn
130                 135                 140

Ala Glu Ala Asn Ile Ala Lys Lys Ala Ser Ala Glu Ala Lys Ala
145                 150                 155                 160

Ala Ala Glu Ala Gln Val Lys Ala Glu Leu Ala Lys Lys Ala Ala Ala
                165                 170                 175

Gly Phe Leu Ala Lys Ala Arg Leu Ala Ala Ser Ala Glu Ser Glu Ala
```

```
                    180             185             190
Thr Lys Leu Ala Ala Glu Ala Glu Val Ala Leu Ala Lys Ala Arg Val
            195                 200             205
Ala Val Asp Gln Ser Gln Ser Ala Gln Ala Thr Ala Thr Ala Gln Ala
        210                 215                 220
Ala Thr Ala Val Gln Leu Gln Ser Gln Ala Ala Asn Ala Glu Ala Ser
225                 230                 235                 240
Ala Val Ala Gln Ala Glu Thr Leu Leu Val Thr Ala Glu Ala Val Ser
                245                 250                 255
Ala Ala Glu Ala Glu Ala Ala Thr Lys Ala Thr Ser Trp Gly Glu Glu
                260                 265                 270
Cys His Gln Arg Glu Lys Val Thr Phe Ser Glu Asp Arg Leu Asn Glu
            275                 280                 285
Arg Gln Asp Asn Trp
        290

<210> SEQ ID NO 25
<211> LENGTH: 313
<212> TYPE: PRT
<213> ORGANISM: Bombus terrestris

<400> SEQUENCE: 25

Met Lys Ile Pro Ala Ile Leu Val Thr Ser Leu Leu Val Trp Gly Gly
1               5                   10                  15
Leu Ala Glu Gly His Val Val Lys Arg Asp Lys Glu Leu Lys Ala Pro
                20                  25                  30
Ala Leu Pro Glu Leu Leu Gly Asp Gly Ser Asp Thr Leu Gly Ala Ser
            35                  40                  45
Met Glu Asn Gly Ile Lys Val Ala Arg Ala Ser Gln Asn Val Gly Leu
        50                  55                  60
Arg Thr Glu Leu Asn Ala Ala Arg Ala Ala Ala Ala Ala Ala Ala Thr
65                  70                  75                  80
Lys Gln Ala Lys Asp Thr Glu Ala Ala Glu Ala Gly Ala Ala Ala Ala
                85                  90                  95
Ile Ala Ile Ala Ile Ala Lys Arg Glu Glu Ala Ile Lys Ala Ser Glu
                100                 105                 110
Leu Ala Ser Lys Leu Leu Thr Ala Ala Ala Gly Ser Ser Glu Ala Ala
            115                 120                 125
Val Ser Ala Thr Val Arg Ala Ala Gln Leu Thr Ala Ala Ser Ala
        130                 135                 140
Ala Ala Lys Ala Ser Ala Ser Ala Ser Glu Ala Ser Ala Glu Ala Gln
145                 150                 155                 160
Val Arg Ala Asn Ala Glu Ala Asn Ile Ala Lys Lys Ala Ser Ala Ala
                165                 170                 175
Glu Ala Lys Ala Ala Glu Ala Gln Val Lys Ala Glu Leu Ala Lys
            180                 185                 190
Lys Ala Ala Ala Gly Phe Leu Ala Leu Ala Arg Leu Ala Ser Ala
        195                 200                 205
Glu Ser Glu Ala Thr Lys Leu Ala Ala Glu Ala Glu Val Ala Leu Ala
        210                 215                 220
Lys Ala Arg Val Ala Val Asp Gln Ser Gln Ser Ala Gln Ala Thr Ala
225                 230                 235                 240
Thr Ala Gln Ala Ala Thr Ala Val Gln Leu Gln Ser Gln Ala Ala Asn
                245                 250                 255
```

```
Ala Glu Ala Ser Ala Val Ala Gln Ala Glu Thr Leu Leu Val Thr Ala
            260                 265                 270

Glu Ala Val Ser Ala Ala Glu Ala Glu Ala Ala Thr Lys Ala Thr Ser
        275                 280                 285

Trp Gly Glu Glu Cys His Gln Arg Glu Lys Val Thr Phe Ser Glu Asp
290                 295                 300

Arg Leu Asn Glu Arg Gln Asp Asn Trp
305                 310

<210> SEQ ID NO 26
<211> LENGTH: 313
<212> TYPE: PRT
<213> ORGANISM: Bombus terrestris

<400> SEQUENCE: 26

Gly Ser Val Glu Leu Gly Ala Pro Lys Gln Glu Ser Val Leu Val Glu
1               5                   10                  15

Gln Leu Leu Leu Lys Asn Val Glu Thr Ser Ala Lys Arg Lys Glu Asn
            20                  25                  30

Gly Ala Pro Lys Leu Gly Glu Ser Thr Ala Ala Leu Ala Ser Thr
        35                  40                  45

Lys Ala Thr Ala Ala Ala Glu Ala Lys Ala Ser Ala Lys Val Lys Ala
50                  55                  60

Ser Ala Leu Ala Leu Ala Glu Ala Phe Leu Arg Ala Ser Ala Ala Phe
65                  70                  75                  80

Ala Ala Ala Ser Ala Lys Ala Ala Ala Val Lys Glu Ala Thr Gln
            85                  90                  95

Ala Gln Leu Leu Ala Gln Glu Lys Ala Leu Ile Ala Leu Lys Thr Gln
            100                 105                 110

Ser Glu Gln Gln Ala Ala Ser Ala Arg Ala Asp Ala Ala Ala Ala Ala
            115                 120                 125

Ala Val Ser Ala Leu Glu Arg Ala Gln Ala Ser Ser Arg Ala Ala Thr
130                 135                 140

Thr Ala Gln Asp Ile Ser Ser Asp Leu Glu Lys Arg Val Ala Thr Ser
145                 150                 155                 160

Ala Ala Ala Glu Ala Gly Ala Thr Leu Arg Ala Glu Gln Ser Ala Ala
                165                 170                 175

Gln Ser Lys Trp Ser Ala Ala Leu Ala Ala Gln Thr Ala Ala Ala Ala
            180                 185                 190

Ala Ala Ile Glu Ala Lys Ala Thr Ala Ser Ser Glu Ser Thr Ala Ala
        195                 200                 205

Ala Thr Ser Lys Ala Ala Val Leu Thr Ala Asp Thr Ser Ser Ala Glu
210                 215                 220

Ala Ala Ala Ala Ala Glu Gln Ser Ala Ser Arg Ile Ala Gly Thr
225                 230                 235                 240

Ala Ala Thr Glu Gly Ser Ala Asn Trp Ala Ser Glu Asn Ser Arg Thr
                245                 250                 255

Ala Gln Leu Glu Ala Ser Ala Ser Ala Lys Ala Thr Ala Ala Ala
            260                 265                 270

Val Gly Asp Gly Ala Ile Ile Gly Leu Ala Arg Asp Ala Ser Ala Ala
        275                 280                 285

Ala Gln Ala Ala Ala Glu Val Lys Leu Ala Glu Ala Ser Ala Ser
            290                 295                 300

Leu Gly Ala Ser Glu Lys Asp Lys Lys
305                 310
```

<210> SEQ ID NO 27
<211> LENGTH: 332
<212> TYPE: PRT
<213> ORGANISM: Bombus terrestris

<400> SEQUENCE: 27

Met Gln Ile Pro Ala Ile Phe Val Thr Cys Leu Leu Thr Trp Gly Leu
1               5                   10                  15

Val His Ala Gly Ser Val Glu Leu Gly Ala Pro Lys Gln Glu Ser Val
            20                  25                  30

Leu Val Glu Gln Leu Leu Leu Lys Asn Val Glu Thr Ser Ala Lys Arg
        35                  40                  45

Lys Glu Asn Gly Ala Pro Lys Leu Gly Glu Ser Thr Ala Ala Ala Leu
    50                  55                  60

Ala Ser Thr Lys Ala Thr Ala Ala Glu Ala Lys Ala Ser Ala Lys
65                  70                  75                  80

Val Lys Ala Ser Ala Leu Ala Leu Ala Glu Ala Phe Leu Arg Ala Ser
                85                  90                  95

Ala Ala Phe Ala Ala Ala Ser Ala Lys Ala Ala Ala Val Lys Glu
            100                 105                 110

Ala Thr Gln Ala Gln Leu Leu Ala Gln Glu Lys Ala Leu Ile Ala Leu
        115                 120                 125

Lys Thr Gln Ser Glu Gln Gln Ala Ala Ser Ala Arg Ala Asp Ala Ala
    130                 135                 140

Ala Ala Ala Ala Val Ser Ala Leu Glu Arg Ala Gln Ala Ser Ser Arg
145                 150                 155                 160

Ala Ala Thr Thr Ala Gln Asp Ile Ser Ser Asp Leu Glu Lys Arg Val
                165                 170                 175

Ala Thr Ser Ala Ala Ala Glu Ala Gly Ala Thr Leu Arg Ala Glu Gln
            180                 185                 190

Ser Ala Ala Gln Ser Lys Trp Ser Ala Ala Leu Ala Ala Gln Thr Ala
        195                 200                 205

Ala Ala Ala Ala Ala Ile Glu Ala Lys Ala Thr Ala Ser Ser Glu Ser
    210                 215                 220

Thr Ala Ala Ala Thr Ser Lys Ala Ala Val Leu Thr Ala Asp Thr Ser
225                 230                 235                 240

Ser Ala Glu Ala Ala Ala Ala Glu Ala Gln Ser Ala Ser Arg Ile
                245                 250                 255

Ala Gly Thr Ala Ala Thr Glu Gly Ser Ala Asn Trp Ala Ser Glu Asn
            260                 265                 270

Ser Arg Thr Ala Gln Leu Glu Ala Ser Ala Ser Ala Lys Ala Thr Ala
        275                 280                 285

Ala Ala Ala Val Gly Asp Gly Ala Ile Ile Gly Leu Ala Arg Asp Ala
    290                 295                 300

Ser Ala Ala Ala Gln Ala Ala Glu Val Lys Ala Leu Ala Glu Ala
305                 310                 315                 320

Ser Ala Ser Leu Gly Ala Ser Glu Lys Asp Lys Lys
                325                 330

<210> SEQ ID NO 28
<211> LENGTH: 338
<212> TYPE: PRT
<213> ORGANISM: Bombus terrestris

<400> SEQUENCE: 28

Gly Lys Pro Leu Ile Ala Asn Ala Gln Ile Gly Lys Val Lys Thr Glu
1               5                   10                  15

Thr Ser Ser Ser Ser Glu Ile Glu Thr Leu Val Ser Gly Ser Gln Thr
            20                  25                  30

Leu Val Ala Gly Ser Glu Thr Leu Ala Ser Glu Ser Ala Leu Ala
            35                  40                  45

Ser Lys Ser Glu Ala Leu Thr Ser Glu Ala Glu Ile Ala Ser Val Thr
50                  55                  60

Thr Lys Asp Glu Leu Ile Leu Lys Gly Glu Ala Ile Thr Gly Lys Lys
65                  70                  75                  80

Leu Gly Thr Gly Ala Ser Glu Val Ala Ala Ser Gly Glu Ala Ile
            85                  90                  95

Ala Thr Thr Leu Gly Ala Gly Gln Ala Ala Glu Ala Gln Ala Ala
            100                 105                 110

Ala Ala Ala Gln Ala Lys Ser Ala Ala Ala Ala Ala Asn Ala Gly
            115                 120                 125

Glu Ser Ser Asn Ser Ala Ala Ala Leu Val Ala Ala Ala Ala Ala
            130                 135                 140

Gln Gly Lys Ala Ala Ala Ala Ala Ala Ala Thr Lys Ala Ser Leu
145                 150                 155                 160

Glu Ala Ala Asp Ala Ala Glu Glu Ala Glu Ser Ala Val Ala Leu Ala
                165                 170                 175

Arg Ala Ala Ser Ala Lys Ala Glu Ala Leu Ser Thr Ala Ala Ala
            180                 185                 190

Ala Asn Thr Arg Ala Ala Leu Gln Ala Glu Lys Ser Asn Glu Leu Ala
            195                 200                 205

Gln Ala Glu Ala Ala Ala Ala Glu Ala Gln Ala Lys Ala Ala
210                 215                 220

Ala Ala Lys Ala Thr Gln Leu Ala Leu Lys Val Ala Glu Thr Ala Val
225                 230                 235                 240

Lys Thr Glu Ala Asp Ala Ala Ala Ala Val Ala Ala Ala Lys Ala
                245                 250                 255

Arg Ala Val Ala Asp Ala Ala Ser Arg Ala Thr Ala Val Asn Ala
            260                 265                 270

Ile Ala Glu Ala Glu Glu Arg Asp Ser Ala Gln Ala Glu Asn Thr Ala
            275                 280                 285

Gly Val Ala Gln Ala Ala Leu Ala Ala Ala Glu Ala Gln Asp Ser Cys
            290                 295                 300

Ile Gly Ala Ala Ala Thr Pro Arg His Ser Ser Ser Tyr Ala Trp Trp
305                 310                 315                 320

Lys Leu Arg Ile Thr Ser Leu Ile Val Ile Leu Ser Pro Arg Asn Arg
                325                 330                 335

Arg Thr

<210> SEQ ID NO 29
<211> LENGTH: 357
<212> TYPE: PRT
<213> ORGANISM: Bombus terrestris

<400> SEQUENCE: 29

Met Lys Ile Pro Ser Ile Leu Ala Val Ser Leu Leu Val Trp Gly Leu
1               5                   10                  15

Ala Ser Ala Gly Lys Pro Leu Ile Ala Asn Ala Gln Ile Gly Lys Val
            20                  25                  30

Lys Thr Glu Thr Ser Ser Ser Glu Ile Glu Thr Leu Val Ser Gly
            35                  40                  45

Ser Gln Thr Leu Val Ala Gly Ser Glu Thr Leu Ala Ser Glu Ser Glu
    50                  55                  60

Ala Leu Ala Ser Lys Ser Glu Ala Leu Thr Ser Glu Ala Glu Ile Ala
65                  70                  75                  80

Ser Val Thr Thr Lys Asp Glu Leu Ile Leu Lys Gly Glu Ala Ile Thr
                85                  90                  95

Gly Lys Lys Leu Gly Thr Gly Ala Ser Glu Val Ala Ala Ala Ser Gly
                100                 105                 110

Glu Ala Ile Ala Thr Thr Leu Gly Ala Gly Gln Ala Ala Ala Glu Ala
                115                 120                 125

Gln Ala Ala Ala Ala Gln Ala Lys Ser Ala Ala Ala Ala Ala Ala Ala
            130                 135                 140

Asn Ala Gly Glu Ser Ser Asn Ser Ala Ala Leu Val Ala Ala Ala
145                 150                 155                 160

Ala Ala Ala Gln Gly Lys Ala Ala Ala Ala Ala Ala Thr Lys
                165                 170                 175

Ala Ser Leu Glu Ala Ala Asp Ala Ala Glu Glu Ala Glu Ser Ala Val
                180                 185                 190

Ala Leu Ala Arg Ala Ala Ser Ala Lys Ala Glu Ala Leu Ala Ser Thr
                195                 200                 205

Ala Ala Ala Ala Asn Thr Arg Ala Ala Leu Gln Ala Glu Lys Ser Asn
            210                 215                 220

Glu Leu Ala Gln Ala Glu Ala Ala Ala Glu Ala Gln Ala Lys
225                 230                 235                 240

Ala Ala Ala Ala Ala Lys Ala Thr Gln Leu Ala Leu Lys Val Ala Glu
                245                 250                 255

Thr Ala Val Lys Thr Glu Ala Asp Ala Ala Ala Ala Val Ala Ala
                260                 265                 270

Ala Lys Ala Arg Ala Val Ala Asp Ala Ala Ser Arg Ala Thr Ala
            275                 280                 285

Val Asn Ala Ile Ala Glu Ala Glu Glu Arg Asp Ser Ala Gln Ala Glu
                290                 295                 300

Asn Thr Ala Gly Val Ala Gln Ala Ala Leu Ala Ala Ala Glu Ala Gln
305                 310                 315                 320

Asp Ser Cys Ile Gly Ala Ala Ala Thr Pro Arg His Ser Ser Tyr
                325                 330                 335

Ala Trp Trp Lys Leu Arg Ile Thr Ser Leu Ile Val Ile Leu Ser Pro
                340                 345                 350

Arg Asn Arg Arg Thr
            355

<210> SEQ ID NO 30
<211> LENGTH: 422
<212> TYPE: PRT
<213> ORGANISM: Bombus terrestris

<400> SEQUENCE: 30

Gly Asn Ser Glu Ser Gly Glu Asn Trp Lys Asn Gly Glu Ser Ser Glu
1               5                   10                  15

Ser Gly Lys Asn Trp Arg Asn Ser Gly Ser Ser Glu Ser Gly Lys Asn
                20                  25                  30

Trp Lys Asn Gly Gly Ser Ser Glu Ser Asn Lys His Trp Lys Asn Gly

```
                35                  40                  45
Gly Ser Ser Glu Ser Gly Glu Lys Trp Lys Asn Ser Glu Ser Glu
 50                  55                  60

Ser Gly Lys Asn Trp Lys Asn Ser Gly Ser Ser Glu Ser Gly Lys Asn
 65                  70                  75                  80

Trp Lys Asn Gly Gly Ser Glu Ser Asn Lys His Trp Lys Ser Gly
                 85                  90                  95

Gly Ser Ser Glu Ser Gly Glu Lys Trp Lys Asn Ser Glu Ser Gly Asn
                100                 105                 110

Lys Gly Lys Ser Ser Lys Ser Glu Ser Trp Lys Ser Asn Glu Asn
                115                 120                 125

Ser Lys Asn Asp Gly Ser Trp Lys Ser Glu Glu Ser Glu Lys Trp
            130                 135                 140

Lys Asp Gly Lys Ala Val Ala Glu Asp Ser Val Ser Ile Asn Trp Ala
145                 150                 155                 160

Asp Val Lys Glu Gln Ile Ser Asn Ile Ala Thr Ser Leu Glu Lys Gly
                165                 170                 175

Gly Asn Leu Glu Ala Val Leu Lys Ile Lys Gly Glu Lys Lys Ile
                180                 185                 190

Ser Ser Leu Glu Glu Ile Lys Glu Lys Ile Ser Val Leu Leu Lys Trp
            195                 200                 205

Ile Gln Glu Gly Lys Asp Thr Ser Ser Leu Leu Asp Leu Lys Glu Gly
210                 215                 220

Ser Lys Asp Ile Ala Ser Leu Lys Glu Ile Lys Gly Lys Ile Leu Leu
225                 230                 235                 240

Ile Val Lys Leu Val Asn Glu Gly Lys Asp Thr Ser Gly Leu Leu Asp
                245                 250                 255

Leu Glu Ala Ser Gly Lys Val Ile Leu Glu Leu Gln Ser Ala Ile Glu
                260                 265                 270

Lys Val Leu Val Lys Ser Glu Lys Val Thr Lys Val Ser Glu Val Ser
            275                 280                 285

Gly Leu Val Lys Ser Lys Thr Val Ser Asp Ile Lys Pro Leu Gln Ala
290                 295                 300

Val Ile Pro Leu Ile Leu Glu Leu Gln Lys Thr Asp Ile Asn Leu Ser
305                 310                 315                 320

Thr Leu Asn Lys Trp Ser Thr Val Asn Val Asn Ser Ile Asp Lys Glu
                325                 330                 335

Arg Val Thr Lys Thr Val Pro Val Leu Leu Gln Ser Met Lys Gly Gly
            340                 345                 350

Glu Asp Ile Gln Asn Leu Leu Ser Ala Lys Gly Ala Lys Lys Leu Gly
            355                 360                 365

Ile Ser Ala Leu Asp Leu Gln Ala Val Gln Gly Leu Gly Val Val
370                 375                 380

Gly Lys Leu Ser Ser Gly Gly Ala Leu Asn Ser Lys Gly Leu Leu Asn
385                 390                 395                 400

Leu Lys Asp Gly Ala Ser Val Leu Gly Ala Gly Lys Ile Gly Gly Leu
                405                 410                 415

Ile Pro Leu Pro Lys Leu
            420

<210> SEQ ID NO 31
<211> LENGTH: 927
<212> TYPE: DNA
<213> ORGANISM: Bombus terrestris
```

<400> SEQUENCE: 31

```
ggccagagct cacctctgct cgagatcgtg cagggtagcg cgtcggccac cgcatccacc      60
gctgtgaccg ctagatccgg acttcgtgcc ggtcaggtag ccgtggcctc gcagaaggat     120
gccacacttc aggcagatgc ctcagcggcc gccgcgccg ctgcacgcgc ttccgccgac      180
cagtcggcca gtctagccca acagtcggcg tctttgcagt ccaaagctgc cgccagagca     240
aaatcagccg aggagtcagc ggcagctacg gccaaagccg agttgcaggc agaatccatt     300
gctgcatctg ccagttccaa tgccagagag gctgcagcgt ccgcaaaagc ctccgcatcc     360
gcgatgtcat cggctgccgt gcaggcgaaa ctcgctgaaa agacggccaa gaatcaagct     420
ctggcttccg aagaagccaa actcaaggct gccgccgctg ccagcgcagc agcagcagcc     480
agcgccgccg ccgaggcagc cctgaaagct gagagaatag cggaagaagc catcgccaag     540
gcggccgctg ccaaagcagc cgccagagcc gctgcagccg cgttaaactc cgcgaaggaa     600
gccgccacga gcagcaag gagcgccgcc gaagccgaag ctaagagcga agtcgctata      660
ctgatcagcg aactcgacaa gaagagcagg gaagtcgccg cttccgcgtc cgccaaggca     720
cgcgctgctg ctgcggctag ctccagaaac gcagaaacgg ctgttatcgg agctaacatc     780
aatgtggcca agaggtcttt ggcgattccc atcgagccaa gaaacttcc ggagccagag      840
ctggcgttga agaagagaa tgtcgcggtc gcgagctcag agagtgaagt gaaggtagaa     900
acgagcagcg aagcatggtc aatttaa                                         927
```

<210> SEQ ID NO 32
<211> LENGTH: 984
<212> TYPE: DNA
<213> ORGANISM: Bombus terrestris

<400> SEQUENCE: 32

```
atgaagattc cagcactgct cgtaacgtgc ctctacccttt ggggcttcgc gtccgccggc     60
cagagctcac ctctgctcga gatcgtgcag ggtagcgcgt cggccaccgc atccaccgct    120
gtgaccgcta gatccggact tcgtgccggt caggtagccg tggcctcgca gaaggatgcc    180
acacttcagg cagatgcctc agcggccgcc gcggccgctg cacgcgcttc cgccgaccag    240
tcggccagtc tagcccaaca gtcggcgtct ttgcagtcca agctgccgc cagagcaaaa     300
tcagccgagg agtcagcggc agctacggcc aaagccgagt tgcaggcaga atccattgct    360
gcatctgcca gttccaatgc cagagaggct gcagcgtccg caaaagcctc cgcatccgcg    420
atgtcatcgg ctgccgtgca ggcgaaactc gctgaaaaga cggccaagaa tcaagctctg    480
gcttccgaag aagccaaact caaggctgcc gccgctgcca gcgcagcagc agcagccagc    540
gccgccgccg aggcagccct gaaagctgag agaatagcgg aagaagccat cgccaaggcg    600
gccgctgcca aagcagccgc cagagccgct gcagccgcgt taaactccgc gaaggaagcc    660
gccacgagca gcgcaaggag cgccgccgaa gccgaagcta agagcgaagt cgctatactg    720
atcagcgaac tcgacaagaa gagcagggaa gtcgccgctt ccgcgtccgc caaggcacgc    780
gctgctgctg cggctagctc cagaaacgca gaaacggctg ttatcggagc taacatcaat    840
gtggccaaag aggtcttggc gattcccatc gagccaagaa acttccgga gccagagctg     900
gcgttgaaag aagagaatgt cgcggtcgcg agctcagaga gtgaagtgaa ggtagaaacg    960
agcagcgaag catggtcaat ttaa                                            984
```

<210> SEQ ID NO 33

<211> LENGTH: 882
<212> TYPE: DNA
<213> ORGANISM: Bombus terrestris

<400> SEQUENCE: 33

```
cacgtggtga agcgcgacaa ggagctcaag gccccggctt taccggaact actcggtgat       60
gggtctgaca cgctcggtgc ctcgatggag aacgggatca aagtcgccag agcatcgcag      120
aatgtgggtc tgagaacaga gttgaatgca gccgcgcggg ctgcagccgc tgctgcgacc      180
aagcaggcca aagacacaga ggccgcggaa gctggagcgg ccgctgcgat tgccatcgct      240
atcgccaagc gtgaagaagc tatcaaagca agcgaattag ccagcaagtt gttgacagcc      300
gcggctgggt ccagcgaagc tgccgtgtca gcgacggtga gggcggcgca attgacggcc      360
gcagctagcg cagctgccaa agcttctgca tccgcctctg aggcttctgc cgaagcccag      420
gtgagggcca acgccgaagc aaacatcgcc aagaaagctt cggcagctga agcaaaagcc      480
gcagccgaag cccaggttaa ggcggaactc gccaagaaag cggccgccgg tttcttagct      540
aaggctagac tagcggccag cgccgaatcc gaggccacta aactcgcagc cgaagctgaa      600
gtagcactgg ctaaggccag agtcgccgtc gaccagtcgc agagcgcaca ggcaaccgct      660
accgctcaag ctgccacagc cgttcagctg cagtctcaag cagctaacgc ggaagcctcc      720
gctgtagcac aggctgaaac tctgctggtc acggcggaag ccgtctctgc cgcggaagcc      780
gaagccgcga ccaaagctac cagttggggc gaagaatgtc atcaacgaga aaaagttacg      840
tttagcgaag atcgattaaa cgagagacaa gacaattggt ag                         882
```

<210> SEQ ID NO 34
<211> LENGTH: 942
<212> TYPE: DNA
<213> ORGANISM: Bombus terrestris

<400> SEQUENCE: 34

```
atgaagattc cagcaatact ggttacgtct ctgctggtct ggggtggtct ggccgagggc       60
cacgtggtga agcgcgacaa ggagctcaag gccccggctt taccggaact actcggtgat      120
gggtctgaca cgctcggtgc ctcgatggag aacgggatca aagtcgccag agcatcgcag      180
aatgtgggtc tgagaacaga gttgaatgca gccgcgcggg ctgcagccgc tgctgcgacc      240
aagcaggcca aagacacaga ggccgcggaa gctggagcgg ccgctgcgat tgccatcgct      300
atcgccaagc gtgaagaagc tatcaaagca agcgaattag ccagcaagtt gttgacagcc      360
gcggctgggt ccagcgaagc tgccgtgtca gcgacggtga gggcggcgca attgacggcc      420
gcagctagcg cagctgccaa agcttctgca tccgcctctg aggcttctgc cgaagcccag      480
gtgagggcca acgccgaagc aaacatcgcc aagaaagctt cggcagctga agcaaaagcc      540
gcagccgaag cccaggttaa ggcggaactc gccaagaaag cggccgccgg tttcttagct      600
aaggctagac tagcggccag cgccgaatcc gaggccacta aactcgcagc cgaagctgaa      660
gtagcactgg ctaaggccag agtcgccgtc gaccagtcgc agagcgcaca ggcaaccgct      720
accgctcaag ctgccacagc cgttcagctg cagtctcaag cagctaacgc ggaagcctcc      780
gctgtagcac aggctgaaac tctgctggtc acggcggaag ccgtctctgc cgcggaagcc      840
gaagccgcga ccaaagctac cagttggggc gaagaatgtc atcaacgaga aaaagttacg      900
tttagcgaag atcgattaaa cgagagacaa gacaattggt ag                         942
```

<210> SEQ ID NO 35
<211> LENGTH: 942

```
<212> TYPE: DNA
<213> ORGANISM: Bombus terrestris

<400> SEQUENCE: 35
ggtagcgtgg aactcggtgc ccccaagcag gagtctgtcc tcgtggagca gctcctattg      60
aagaacgtgg agactagtgc gaagcgaaag gagaacggcg caccgaaact cggcgagagc     120
acagctgcgg ctctggctag taccaaggca actgcagccg cagaggctaa ggcatccgcc     180
aaagtgaaag cttctgcctt ggccctcgct gaggctttct tgcgtgcgtc ggcagcgttt     240
gctgctgctt cagccaaagc tgctgccgct gtaaaggaag caacgcaggc acagttgctg     300
gcacaggaga aggctttgat agcgttgaaa actcaatctg agcaacaagc tgcctctgct     360
cgcgcggacg ccgcggctgc cgcagccgta tccgcgctag aacgcgccca ggcctcctcc     420
agagcagcca cgaccgccca agacatctcc agcgatctgg agaaacgtgt cgccacctca     480
gccgctgctg aagcaggtgc caccctcaga gcggaacaat ccgccgcgca atcgaaatgg     540
tccgccgcac tggccgccca aaccgccgct gctgcagccg ctatagaagc aaaggccacc     600
gcttcctcag aaagcaccgc tgccgctact agtaaggccg ccgtgttgac cgctgacact     660
agcagcgcag aagctgccgc tgcagcggag gcacaatccg cttcgcggat cgcaggtaca     720
gcagccaccg agggatccgc caactgggct agcgagaact cgcgtaccgc acaactggaa     780
gcttccgcct cagcgaaggc caccgcagcc gcagctgtcg gagatggagc tattatagga     840
cttgcacggg acgctagtgc cgcagctcag gcagccgcag aagttaaagc cttagctgaa     900
gctagtgcca gcttaggtgc ttcagaaaag gacaagaaat ga                        942

<210> SEQ ID NO 36
<211> LENGTH: 999
<212> TYPE: DNA
<213> ORGANISM: Bombus terrestris

<400> SEQUENCE: 36
atgcagatcc cagcgatttt cgtcacgtgc ctgctcacat ggggcctggt gcacgcaggt      60
agcgtggaac tcggtgcccc caagcaggag tctgtcctcg tggagcagct cctattgaag     120
aacgtggaga ctagtgcgaa gcgaaaggag aacggcgcac cgaaactcgg cgagagcaca     180
gctgcggctc tggctagtac caaggcaact gcagccgcag aggctaaggc atccgccaaa     240
gtgaaagctt ctgccttggc cctcgctgag gctttcttgc gtgcgtcggc agcgtttgct     300
gctgcttcag ccaaagctgc tgccgctgta aaggaagcaa cgcaggcaca gttgctggca     360
caggagaagg ctttgatagc gttgaaaact caatctgagc aacaagctgc ctctgctcgc     420
gcggacgccg cggctgccgc agccgtatcc gcgctagaac gcgcccaggc ctcctccaga     480
gcagccacga ccgcccaaga catctccagc gatctggaga acgtgtcgc cacctcagcc     540 gctgctgaag caggtgccac cctcagagcg gaacaatccg ccgcgcaatc gaaatggtcc     600
gccgcactgg ccgcccaaac cgccgctgct gcagccgcta tagaagcaaa ggccaccgct     660
tcctcagaaa gcaccgctgc cgctactagt aaggccgccg tgttgaccgc tgacactagc     720
agcgcagaag ctgccgctgc agcggaggca caatccgctt cgcggatcgc aggtacagca     780
gccaccgagg gatccgccaa ctgggctagc gagaactcgc gtaccgcaca actggaagct     840
tccgcctcag cgaaggccac cgcagccgca gctgtcggag atggagctat tataggactt     900
gcacgggacg ctagtgccgc agctcaggca gccgcagaag ttaaagcctt agctgaagct     960
agtgccagct taggtgcttc agaaaaggac aagaaatga                            999
```

<210> SEQ ID NO 37
<211> LENGTH: 1017
<212> TYPE: DNA
<213> ORGANISM: Bombus terrestris

<400> SEQUENCE: 37

| | | | | | |
|---|---|---|---|---|---|
| ggcaaaccac | tcattgccaa | tgcgcaaata | gggaaggtca | agaccgaaac | gtcatcgtct | 60 |
| tcagagattg | agacgttggt | atcaggaagc | cagacattgg | tggcaggaag | tgagacattg | 120 |
| gcttcagaaa | gcgaggcatt | ggcgtcaaaa | agcgaggcat | tgacgtcaga | agccgagata | 180 |
| gcgagcgtga | caacgaagga | cgagctcata | ctaaagggcg | aagctatcac | tggaaagaaa | 240 |
| ctaggaaccg | gggcgtcgga | agtagcggcg | gcctctgggg | aggctatcgc | aactacccct | 300 |
| ggcgcgggac | aagctgcagc | agaggcacaa | gcagccgccg | ccgcgcaagc | aaaatcagca | 360 |
| gcggcagctg | ccgcgaatgc | aggtgaatcc | agcaacagtg | ctgctgcgtt | ggttgctgct | 420 |
| gcagctgcag | cacaaggaaa | agcggctgcc | gccgcagcag | ccgcgacgaa | ggctagctta | 480 |
| gaggccgcag | acgctgctga | ggaagctgag | tcggccgtgg | ccttggctag | ggctgcctcc | 540 |
| gcaaaggcgg | aagcgctcgc | atcgaccgcc | gctgctgcga | atacccgtgc | tgctctccaa | 600 |
| gcggaaaaat | cgaacgagct | ggcgcaagct | gaggctgcag | ccgccgccga | agcccaggct | 660 |
| aaagccgccg | ctgctgccaa | ggcaacacaa | ctcgccctta | agttgccga | aactgcggtg | 720 |
| aaaacggaag | cagatgcagc | agctgccgcc | gttgcggccg | caaaagccag | agcagtcgca | 780 |
| gacgcagccg | cgtctcgtgc | gaccgcagtg | aacgccattg | ctgaagcgga | agaaagagac | 840 |
| tctgcacagg | cggagaacac | cgctggtgta | gcacaagcag | cgctcgctgc | tgcggaagca | 900 |
| caagactcct | gcatcggcgc | tgccgcgact | cctaggcatt | cgtcgagcta | gcatggtgg | 960 |
| aagcttagga | taacatcctt | gatcgtcatt | ctatcgccac | gcaatcgacg | tacttaa | 1017 |

<210> SEQ ID NO 38
<211> LENGTH: 1074
<212> TYPE: DNA
<213> ORGANISM: Bombus terrestris

<400> SEQUENCE: 38

| | | | | | |
|---|---|---|---|---|---|
| atgaagattc | catcgatact | cgcggtgtcc | ctgctggttt | ggggtctggc | cagcgcaggc | 60 |
| aaaccactca | ttgccaatgc | gcaaataggg | aaggtcaaga | ccgaaacgtc | atcgtcttca | 120 |
| gagattgaga | cgttggtatc | aggaagccag | acattggtgg | caggaagtga | gacattggct | 180 |
| tcagaaagcg | aggcattggc | gtcaaaaagc | gaggcattga | cgtcagaagc | cgagatagcg | 240 |
| agcgtgacaa | cgaaggacga | gctcatacta | aagggcgaag | ctatcactgg | aaagaaacta | 300 |
| ggaaccgggg | cgtcggaagt | agcggcggcc | tctggggagg | ctatcgcaac | tacccttggc | 360 |
| gcgggacaag | ctgcagcaga | ggcacaagca | gccgccgccg | cgcaagcaaa | atcagcagcg | 420 |
| gcagctgccg | cgaatgcagg | tgaatccagc | aacagtgctg | ctgcgttggt | tgctgctgca | 480 |
| gctgcagcac | aaggaaaagc | ggctgccgcc | gcagcagccg | cgacgaaggc | tagcttagag | 540 |
| gccgcagacg | ctgctgagga | agctgagtcg | gccgtggcct | tggctagggc | tgcctccgca | 600 |
| aaggcggaag | cgctcgcatc | gaccgccgct | gctgcgaata | cccgtgctgc | tctccaagcg | 660 |
| gaaaaatcga | acgagctggc | gcaagctgag | gctgcagccg | ccgccgaagc | ccaggctaaa | 720 |
| gccgccgctg | ctgccaaggc | aacacaactc | gcccttaaag | ttgccgaaac | tgcggtgaaa | 780 |
| acggaagcag | atgcagcagc | tgccgccgtt | gcggccgcaa | aagccagagc | agtcgcagac | 840 |
| gcagccgcgt | ctcgtgcgac | cgcagtgaac | gccattgctg | aagcggaaga | aagagactct | 900 |

```
gcacaggcgg agaacaccgc tggtgtagca caagcagcgc tcgctgctgc ggaagcacaa    960
gactcctgca tcggcgctgc cgcgactcct aggcattcgt cgagctatgc atggtggaag   1020
cttaggataa catccttgat cgtcattcta tcgccacgca atcgacgtac ttaa         1074
```

<210> SEQ ID NO 39
<211> LENGTH: 1411
<212> TYPE: DNA
<213> ORGANISM: Bombus terrestris

<400> SEQUENCE: 39

```
ggaaattcgg aaagcggcga aaattggaag aacggtgaaa gctccgaaag cggcaaaaat     60
tggaggaaca gcggaagctc cgaaagcggc aaaaattgga agaatggcgg aagctcagaa    120
agcaacaaac attggaagaa cggtggaagc tcggaaagcg gcgagaaatg aaaaacagt     180 gaaagctccg aaagcggcaa aattggaag aacagcggaa gctccgaaag cggcaaaaat    240
tggaaaaacg gcggaagctc ggaaagcaac aaacattgga gagcggtgg aagctcggaa    300 agtggcgaga atggaaaaa cagtgaaagc ggaaataaag gcaaaagctc aaaaagcagc    360
gaaagttgga gagcaacga aaactcgaag aacgacggca gctggaagag cagtgaagaa    420
tcagaaaagt ggaaagatgg taaagcagtg gcggaagaca gcgttagtat aaactgggca    480
gatgtcaaag agcagattag caacattgct acatccttag aaaagggtgg taacctcgag    540
gctgtattga aaataaagaa aggagaaaag aaaatttcaa gtttggagga aatcaaggag    600
aaaatctctg tcctactgaa atggattcaa gaaggcaaag atactagcag cctattagat    660
ttgaaagagg gtagcaagga tattgcgtcg ttgaaagaaa tcaaaggaaa gatccttttg    720
attgttaaat tagtgaacga agggaaagac actagtggtc ttttagattt agaagcgagt    780
ggcaaagtaa ttttagaatt gcaaagcgcc atagaaaagg ttctcgtaaa gtcagaaaag    840
gtaaccaaag tatctgaagt ttccggttta gtaaaaagca aaactgtctc ggacataaaa    900
ccgcttcaag cagtaattcc tttaatcctt gaattgcaaa aacagacat taaccttagt    960 accttaaaca gtggtccac tgttaacgta aattctatag ataaagaacg cgtcacgaaa   1020
acggttccag tgctccttca atccatgaaa ggaggcgaag atattcagaa ccttttgagt   1080
gcgaaaggtg caaagaaact tggcattagt gctttggact tacaggcagt caaggagct    1140 cttggcgtgg ttgaaaagct aagttcaggt ggtgcgttga actcaaaagg cttgttgaac   1200
ttgaaagacg gcgctagtgt gttaggtgca ggaaaaatcg gaggattaat tccttttaccg   1260 aaactttaag agatagaccg ataaaggcag atatactctc ggaagatttt tttggaagtt   1320
gaatagtccg caaaaaaatt atctctgatt attataattt agcctaaaat attaaataaa   1380
atggagaaat aacgttgaaa tatataaata a                                    1411
```

<210> SEQ ID NO 40
<211> LENGTH: 403
<212> TYPE: PRT
<213> ORGANISM: Myrmecia forficata

<400> SEQUENCE: 40

```
Ser Gly Pro Arg Leu Leu Gly Gly Arg Ser Ala Ala Ser Ala Ser Ala
1               5                   10                  15

Ser Ala Ser Ala Glu Ala Ser Ala Gly Gly Trp Arg Lys Ser Gly Ala
            20                  25                  30

Ser Ala Ser Ala Ser Ala Lys Ala Gly Ser Ser Asn Ile Leu Ser Arg
        35                  40                  45
```

Val Gly Ala Ser Arg Ala Ala Thr Leu Val Ala Ser Ala Ala Val
    50                  55                  60

Glu Ala Lys Ala Gly Leu Arg Ala Gly Lys Ala Thr Ala Glu Glu Gln
65                  70                  75                  80

Arg Glu Ala Leu Glu Met Leu Thr Leu Ser Ala Asp Lys Asn Ala Glu
                85                  90                  95

Ala Arg Ile Leu Ala Asp Asp Thr Ala Val Leu Val Gln Gly Ser Ala
            100                 105                 110

Glu Ala Gln Ser Val Ala Ala Lys Thr Val Ala Glu Glu Glu
            115                 120                 125

Ser Ala Ser Leu Asp Ala Ala Val Glu Ala Val Ala Ala Ala
    130                 135                 140

Thr Ser Lys Ser Ser Ala Gly Gln Ala Leu Gln Ser Ala Gln Thr Ala
145                 150                 155                 160

Ala Ser Ala Leu Arg Thr Ser Ala Arg Ser Ala Leu Thr Ala Leu Lys
                165                 170                 175

Leu Ala Arg Leu Gln Gly Ala Ala Ser Ser Asn Ala Ala Arg Met Met
            180                 185                 190

Glu Lys Ala Leu Ala Ala Thr Gln Asp Ala Asn Ala Ala Ala Gln Gln
    195                 200                 205

Ala Met Ala Ala Glu Ser Ala Ala Ala Glu Ala Ala Ile Ala Ala
210                 215                 220

Ala Lys Gln Ser Glu Ala Arg Asp Ala Gly Ala Glu Ala Lys Ala Ala
225                 230                 235                 240

Met Ala Ala Leu Ile Thr Ala Gln Arg Asn Leu Val Gln Ala Asn Ala
                245                 250                 255

Arg Ala Glu Met Ala Ser Glu Ala Glu Leu Asp Ser Lys Ser Arg
            260                 265                 270

Ala Ser Asp Ala Lys Val Asn Ala Val Ala Arg Ala Ala Ser Lys Ser
    275                 280                 285

Ser Ile Arg Arg Asp Glu Leu Ile Glu Ile Gly Ala Glu Phe Gly Lys
290                 295                 300

Ala Ser Gly Glu Val Ile Ser Thr Gly Thr Arg Ser Asn Gly Gly Gln
305                 310                 315                 320

Asp Ala Ile Ala Thr Ala Glu Ala Ser Ser Ala Ser Ala Val Gly
                325                 330                 335

Ile Lys Lys Thr Ser Gly His Trp Gly Ser Gly Lys Trp Ser Arg Val
            340                 345                 350

Ser Lys Gly Lys Gly Trp Ala Ser Ser Asn Ala Asp Ala Asp Ala Ser
    355                 360                 365

Ser Ser Ser Ile Ile Gly Gly Leu Lys Arg Gly Gly Leu Gly Ser
370                 375                 380

Glu Ala Ser Ala Ala Ser Ala Glu Ala Glu Ala Ser Ala Gly Thr
385                 390                 395                 400

Leu Leu Leu

<210> SEQ ID NO 41
<211> LENGTH: 422
<212> TYPE: PRT
<213> ORGANISM: Myrmecia forficata

<400> SEQUENCE: 41

Met Lys Ile Pro Ala Ile Ile Ala Thr Ser Leu Leu Leu Trp Gly Phe
1               5                   10                  15

```
Ala Ser Ala Ser Gly Pro Arg Leu Leu Gly Gly Arg Ser Ala Ala Ser
            20                  25                  30

Ala Ser Ala Ser Ala Ser Ala Glu Ala Ser Ala Gly Gly Trp Arg Lys
        35                  40                  45

Ser Gly Ala Ser Ala Ser Ala Ser Ala Lys Ala Gly Ser Ser Asn Ile
50                  55                  60

Leu Ser Arg Val Gly Ala Ser Arg Ala Ala Thr Leu Val Ala Ser
65                  70                  75                  80

Ala Ala Val Glu Ala Lys Ala Gly Leu Arg Ala Gly Lys Ala Thr Ala
            85                  90                  95

Glu Glu Gln Arg Glu Ala Leu Glu Met Leu Thr Leu Ser Ala Asp Lys
            100                 105                 110

Asn Ala Glu Ala Arg Ile Leu Ala Asp Asp Thr Ala Val Leu Val Gln
            115                 120                 125

Gly Ser Ala Glu Ala Gln Ser Val Ala Ala Lys Thr Val Ala Val
    130                 135                 140

Glu Glu Glu Ser Ala Ser Leu Asp Ala Ala Val Glu Ala Glu Val
145                 150                 155                 160

Ala Ala Ala Thr Ser Lys Ser Ser Ala Gly Gln Ala Leu Gln Ser Ala
                165                 170                 175

Gln Thr Ala Ala Ser Ala Leu Arg Thr Ser Ala Arg Ser Ala Leu Thr
            180                 185                 190

Ala Leu Lys Leu Ala Arg Leu Gln Gly Ala Ala Ser Ser Asn Ala Ala
            195                 200                 205

Arg Met Met Glu Lys Ala Leu Ala Ala Thr Gln Asp Ala Asn Ala Ala
            210                 215                 220

Ala Gln Gln Ala Met Ala Ala Glu Ser Ala Ala Ala Glu Ala Ala Ala
225                 230                 235                 240

Ile Ala Ala Ala Lys Gln Ser Glu Ala Arg Asp Ala Gly Ala Glu Ala
                245                 250                 255

Lys Ala Ala Met Ala Ala Leu Ile Thr Ala Gln Arg Asn Leu Val Gln
            260                 265                 270

Ala Asn Ala Arg Ala Glu Met Ala Ser Glu Gly Ala Glu Leu Asp Ser
            275                 280                 285

Lys Ser Arg Ala Ser Asp Ala Lys Val Asn Ala Val Ala Arg Ala Ala
290                 295                 300

Ser Lys Ser Ser Ile Arg Arg Asp Glu Leu Ile Glu Ile Gly Ala Glu
305                 310                 315                 320

Phe Gly Lys Ala Ser Gly Glu Val Ile Ser Thr Gly Thr Arg Ser Asn
                325                 330                 335

Gly Gly Gln Asp Ala Ile Ala Thr Ala Glu Ala Ser Ser Ser Ala Ser
            340                 345                 350

Ala Val Gly Ile Lys Lys Thr Ser Gly His Trp Gly Ser Gly Lys Trp
            355                 360                 365

Ser Arg Val Ser Lys Gly Lys Gly Trp Ala Ser Ser Asn Ala Asp Ala
            370                 375                 380

Asp Ala Ser Ser Ser Ile Ile Ile Gly Gly Leu Lys Arg Gly Gly
385                 390                 395                 400

Leu Gly Ser Glu Ala Ser Ala Ala Ala Ser Ala Glu Ala Glu Ala Ser
                405                 410                 415

Ala Gly Thr Leu Leu Leu
            420
```

<210> SEQ ID NO 42
<211> LENGTH: 392
<212> TYPE: PRT
<213> ORGANISM: Myrmecia forficata

<400> SEQUENCE: 42

```
Arg Val Ile Glu Ser Ser Ser Ala Ser Ala Gln Ala Ser Ala Ser
1               5                   10                  15

Ala Gly Ser Arg Gly Leu Leu Gly Lys Arg Pro Ile Gly Lys Leu Glu
            20                  25                  30

Trp Gly Lys Glu Glu Lys Lys Leu Glu Glu Leu Asp Glu Glu Ser Leu
        35                  40                  45

Asn Glu Ala Ala Leu Lys Val Gly Ile Lys Asn Gly Gly Leu Asp Val
    50                  55                  60

Ala Lys Gly Ala Ala Val Leu Glu Ala Ala Met Ser Asp Val Ala Thr
65                  70                  75                  80

Leu Thr Asp Gln Arg Ser Leu Val Asp Leu Gly Leu Gly Pro Val Ala
                85                  90                  95

Asn Glu Ala Glu Ile Leu Ala Glu Ala Gln Ala Ala Thr Ser Ala Gln
                100                 105                 110

Ala Gly Ala Val Ala Asn Ser Ala Ala Glu Arg Ala Ile Ala Ala Met
            115                 120                 125

Glu Met Ala Asp Arg Thr Glu Tyr Ile Ala Ala Leu Val Thr Thr Lys
130                 135                 140

Ala Ala Lys Ala Ala Glu Ala Thr Met Ala Ala Thr Ala Arg Ala Thr
145                 150                 155                 160

Ala Ala Ala Ser Ala Ser Lys Ile Ser Ser Gln Glu Ser Ala Ala Ser
                165                 170                 175

Ala Ala Asn Ala Ala Asn Ala Glu Ala Lys Ala Asn Ala Ala Ser Ile
            180                 185                 190

Ile Ala Asn Lys Ala Asn Ala Val Leu Ala Glu Ala Ala Ala Val Leu
        195                 200                 205

Ala Ala Thr Ala Ala Lys Ala Lys Glu Ser Ala Met Lys Ser Leu Ser
210                 215                 220

Ala Ala Gln Ala Ala Lys Ala Gln Ala Arg Asn Ala Glu Ala Ser
225                 230                 235                 240

Ala Glu Ala Gln Ile Lys Leu Ser Gln Ala Arg Ala Ala Val Ala Arg
                245                 250                 255

Ala Ala Ala Asp Gln Ala Val Cys Ser Ser Gln Ala Gln Ala Ala Ser
            260                 265                 270

Gln Ile Gln Ser Arg Ala Ser Ala Ser Glu Ser Ala Ala Ser Ala Gln
        275                 280                 285

Ser Glu Thr Asn Thr Ala Ala Glu Ala Val Ala Thr Ala Asp Ala
290                 295                 300

Glu Ala Ala Ala Gln Ala Glu Ala Trp Val Met Ser Leu Lys Asn Asp
305                 310                 315                 320

Leu Trp Leu His Leu Asn Met Lys Gly Glu Ala Lys Ala Glu Gly Glu
                325                 330                 335

Ala Val Ser Ile Ser Lys Gly His Arg Gly Ile Arg Ser Gly Ser
            340                 345                 350

Ile Ser Glu Ala Ser Ala Glu Ala Ser Ser Asn Val Ser Met Gly Gly
        355                 360                 365

Arg His Gly Arg Lys Asp Leu Val Ser Glu Ala Leu Ala Gly Ala Ser
370                 375                 380
```

Ala Gly Ser Ser Ala Asp Ser Leu
385                390

<210> SEQ ID NO 43
<211> LENGTH: 411
<212> TYPE: PRT
<213> ORGANISM: Myrmecia forficata

<400> SEQUENCE: 43

Met Lys Ile Pro Ala Ile Leu Val Thr Ser Leu Leu Ala Trp Gly Leu
1               5                   10                  15

Ala Ser Gly Arg Val Ile Glu Ser Ser Ser Ala Ser Ala Gln Ala
            20                  25                  30

Ser Ala Ser Ala Gly Ser Arg Gly Leu Leu Gly Lys Arg Pro Ile Gly
        35                  40                  45

Lys Leu Glu Trp Gly Lys Glu Glu Lys Lys Leu Glu Glu Leu Asp Glu
    50                  55                  60

Glu Ser Leu Asn Glu Ala Ala Leu Lys Val Gly Ile Lys Asn Gly Gly
65                  70                  75                  80

Leu Asp Val Ala Lys Gly Ala Ala Val Leu Glu Ala Ala Met Ser Asp
                85                  90                  95

Val Ala Thr Leu Thr Asp Gln Arg Ser Leu Val Asp Leu Gly Leu Gly
            100                 105                 110

Pro Val Ala Asn Glu Ala Glu Ile Leu Ala Glu Ala Gln Ala Ala Thr
        115                 120                 125

Ser Ala Gln Ala Gly Ala Val Ala Asn Ser Ala Ala Glu Arg Ala Ile
    130                 135                 140

Ala Ala Met Glu Met Ala Asp Arg Thr Glu Tyr Ile Ala Ala Leu Val
145                 150                 155                 160

Thr Thr Lys Ala Ala Lys Ala Ala Glu Ala Thr Met Ala Ala Thr Ala
                165                 170                 175

Arg Ala Thr Ala Ala Ala Ser Ala Ser Lys Ile Ser Ser Gln Glu Ser
            180                 185                 190

Ala Ala Ser Ala Ala Asn Ala Ala Asn Ala Glu Ala Lys Ala Asn Ala
        195                 200                 205

Ala Ser Ile Ile Ala Asn Lys Ala Asn Ala Val Leu Ala Glu Ala Ala
    210                 215                 220

Ala Val Leu Ala Ala Thr Ala Ala Lys Ala Lys Glu Ser Ala Met Lys
225                 230                 235                 240

Ser Leu Ser Ala Ala Gln Ala Ala Lys Ala Gln Ala Arg Asn Ala
                245                 250                 255

Glu Ala Ser Ala Glu Ala Gln Ile Lys Leu Ser Gln Ala Arg Ala Ala
            260                 265                 270

Val Ala Arg Ala Ala Ala Asp Gln Ala Val Cys Ser Ser Gln Ala Gln
        275                 280                 285

Ala Ala Ser Gln Ile Gln Ser Arg Ala Ser Ala Ser Glu Ser Ala Ala
    290                 295                 300

Ser Ala Gln Ser Glu Thr Asn Thr Ala Ala Glu Ala Val Ala Thr
305                 310                 315                 320

Ala Asp Ala Glu Ala Ala Gln Ala Glu Ala Trp Val Met Ser Leu
                325                 330                 335

Lys Asn Asp Leu Trp Leu His Leu Asn Met Lys Gly Glu Ala Lys Ala
            340                 345                 350

Glu Gly Glu Ala Val Ser Ile Ser Lys Gly His Arg Gly Gly Ile Arg

```
                       355                 360                 365
Ser Gly Ser Ile Ser Glu Ala Ser Ala Glu Ala Ser Ser Asn Val Ser
            370                 375                 380

Met Gly Gly Arg His Gly Arg Lys Asp Leu Val Ser Glu Ala Leu Ala
385                 390                 395                 400

Gly Ala Ser Ala Gly Ser Ser Ala Asp Ser Leu
                405                 410

<210> SEQ ID NO 44
<211> LENGTH: 375
<212> TYPE: PRT
<213> ORGANISM: Myrmecia forficata

<400> SEQUENCE: 44

Asn Leu Leu Lys Glu Ser Lys Ala Ser Ala Ser Ala Ser Ala Ser Ala
1               5                   10                  15

Ser Ala Arg Ala Ser Gly Lys Lys Asn Leu His Val Leu Pro Leu Pro
            20                  25                  30

Lys Lys Ser Glu His Gly Ile Val Ile Asp Lys Ser Val Phe Asp Ile
        35                  40                  45

Lys Asp Val Val Leu Ser Ala Val Asp Glu Ile Asn Gly Ala Pro Lys
    50                  55                  60

Leu Gly Leu Gly Trp Lys Lys Val Ser Met Gly Val Glu Arg Ala Glu
65                  70                  75                  80

Ala Asn Ala Ala Ala Ala Glu Ala Leu Ala Met Ile Lys Lys Ile
                85                  90                  95

Ala Met Ala Arg Ser Ser Ala Tyr Val Gln Ala Ala Trp Ala Ser Ala
                100                 105                 110

Gln Ala Ser Ala Asp Ala Leu Ala Ser Ala Arg Val Ala Gln Ala Ser
            115                 120                 125

Gln Glu Ala Ala Glu Ala Lys Gly Arg Ala Ala Ser Glu Ala Leu Ser
        130                 135                 140

Arg Ala Ile Glu Ala Ser Ser Arg Ala Asp Ala Ala Ala Ala Thr
145                 150                 155                 160

Leu Asp Ala Met Asp Arg Thr Met Glu Asn Ala Arg Ala Ala Asn Ala
                165                 170                 175

Ala Gln Thr Gln Ala Ser Gly Gln Ala Glu Asn Ala Asn Arg Ser Ala
            180                 185                 190

Ala Ala Ile Leu Ala Ala Leu Leu Arg Ile Ala Glu Ala Ser Ala Leu
        195                 200                 205

Asn Asn Glu Ala Ala Val Asn Ala Ala Ala Ala Ala Ala Ala Ser
    210                 215                 220

Ala Leu Gln Ala Lys Ala Asn Ala Ala Ser Gln Ala Thr Ala Arg Ala
225                 230                 235                 240

Ala Gly Gln Ala Ser Thr Ala Ala Glu Glu Ala Gln Ser Ala Gln Glu
                245                 250                 255

Ala Ala Asp Lys Asn Ala Glu Leu Thr Thr Val Met Leu Glu Lys Ala
            260                 265                 270

Ser Ala Asp Gln Gln Ala Ala Ser Ala Arg Ala Asp Tyr Tyr Thr Ala
        275                 280                 285

Ser Thr Glu Ala Glu Ala Ala Gln Ala Ser Ala Ile Asn Ala Leu
    290                 295                 300

Arg Asp Gly Ile Val Val Gly Met Gly Asn Asp Ala Gly Ala Ser Ala
305                 310                 315                 320
```

-continued

```
Gln Ala Met Ala Gln Val Glu Ala Leu Ala Arg Ala Ser Glu His Lys
            325                 330                 335

Ala Leu Gly Glu Lys Lys Gly Leu Val Trp Gly Tyr Gly Ser Lys
        340                 345                 350

Gly Ser Ser Ser Ala Ser Ala Ser Ala Ser Ala Glu Ala Ser
        355                 360                 365

Ser Arg Leu Gly Lys Asp Trp
        370             375

<210> SEQ ID NO 45
<211> LENGTH: 394
<212> TYPE: PRT
<213> ORGANISM: Myrmecia forficata

<400> SEQUENCE: 45

Met Lys Ile Pro Ala Ile Leu Val Thr Ser Phe Leu Ala Trp Gly Leu
1               5                   10                  15

Ala Ser Gly Asn Leu Leu Lys Glu Ser Lys Ala Ser Ala Ser Ala Ser
            20                  25                  30

Ala Ser Ala Ser Ala Arg Ala Ser Gly Lys Lys Asn Leu His Val Leu
        35                  40                  45

Pro Leu Pro Lys Lys Ser Glu His Gly Ile Val Ile Asp Lys Ser Val
    50                  55                  60

Phe Asp Ile Lys Asp Val Val Leu Ser Ala Val Asp Glu Ile Asn Gly
65                  70                  75                  80

Ala Pro Lys Leu Gly Leu Gly Trp Lys Lys Val Ser Met Gly Val Glu
                85                  90                  95

Arg Ala Glu Ala Asn Ala Ala Ala Ala Glu Ala Leu Ala Met Ile
            100                 105                 110

Lys Lys Ile Ala Met Ala Arg Ser Ser Ala Tyr Val Gln Ala Ala Trp
        115                 120                 125

Ala Ser Ala Gln Ala Ser Ala Asp Ala Leu Ala Ser Ala Arg Val Ala
    130                 135                 140

Gln Ala Ser Gln Glu Ala Ala Glu Ala Lys Gly Arg Ala Ala Ser Glu
145                 150                 155                 160

Ala Leu Ser Arg Ala Ile Glu Ala Ser Ser Arg Ala Asp Ala Ala
                165                 170                 175

Ala Ala Thr Leu Asp Ala Met Asp Arg Thr Met Glu Asn Ala Arg Ala
            180                 185                 190

Ala Asn Ala Ala Gln Thr Gln Ala Ser Gly Gln Ala Glu Asn Ala Asn
        195                 200                 205

Arg Ser Ala Ala Ala Ile Leu Ala Ala Leu Leu Arg Ile Ala Glu Ala
    210                 215                 220

Ser Ala Leu Asn Asn Glu Ala Ala Val Asn Ala Ala Ala Ala Ala
225                 230                 235                 240

Ala Ala Ser Ala Leu Gln Ala Lys Ala Asn Ala Ala Ser Gln Ala Thr
                245                 250                 255

Ala Arg Ala Ala Gly Gln Ala Ser Thr Ala Ala Glu Glu Ala Gln Ser
            260                 265                 270

Ala Gln Glu Ala Ala Asp Lys Asn Ala Glu Leu Thr Thr Val Met Leu
        275                 280                 285

Glu Lys Ala Ser Ala Asp Gln Gln Ala Ser Ala Arg Ala Asp Tyr
    290                 295                 300

Tyr Thr Ala Ser Thr Glu Ala Glu Ala Ala Ala Gln Ala Ser Ala Ile
305                 310                 315                 320
```

Asn Ala Leu Arg Asp Gly Ile Val Val Gly Met Gly Asn Asp Ala Gly
            325                 330                 335

Ala Ser Ala Gln Ala Met Ala Gln Val Glu Ala Leu Ala Arg Ala Ser
            340                 345                 350

Glu His Lys Ala Leu Gly Glu Lys Lys Gly Leu Val Trp Gly Tyr
            355                 360                 365

Gly Ser Lys Gly Ser Ser Ser Ala Ser Ala Ser Ala Ser Ala
    370                 375                 380

Glu Ala Ser Ser Arg Leu Gly Lys Asp Trp
385                 390

<210> SEQ ID NO 46
<211> LENGTH: 422
<212> TYPE: PRT
<213> ORGANISM: Myrmecia forficata

<400> SEQUENCE: 46

Ser Glu Leu Glu Ser Glu Ala Ser Ala Ala Ser Ala Gln Ala Glu
1               5                   10                  15

Ala Ser Ser Ser Gly Arg Ser Gly Lys Leu Ser Ala Ser Gln Ala Ser
            20                  25                  30

Ala Ser Ala Ser Ala Ser Ala Gly Ser Arg Gly Gly Ser Lys
            35                  40                  45

Gly Gly Trp Gly Gln Leu Arg Arg Gly Asp Val Lys Ser Glu Ala Lys
    50                  55                  60

Ser Ala Ala Ala Ile Ala Val Glu Gly Ala Lys Ile Gly Thr Gly Ile
65                  70                  75                  80

Gly Asn Thr Ala Ser Ser Ala Glu Ala Leu Ser Arg Gly Leu Gly
            85                  90                  95

Ile Gly Gln Ala Ala Ala Glu Ala Gln Ala Ala Ala Gly Gln Ala
            100                 105                 110

Glu Val Ala Ala Lys Ser Cys Glu Leu Ala Asp Lys Thr Thr Ala Lys
            115                 120                 125

Ala Val Ala Met Val Glu Ala Ala Ala Glu Ala Glu Ile Glu Val Ala
            130                 135                 140

Asn Gln Glu Val Ala Ala Val Lys Leu Ser Thr Trp Ala Ala Lys Ala
145                 150                 155                 160

Ala Arg Ile Val Glu Glu Asp Ser Ala Ala Val Arg Ala Ala Ala Gly
            165                 170                 175

Lys Leu Leu Leu Ala Ala Arg Ala Ala Ala Ala Glu Arg Arg Ala
            180                 185                 190

Asn Glu Glu Ser Glu Ala Ala Asn Glu Leu Ala Gln Ala Ser Ser Ala
            195                 200                 205

Ala Ala Ala Glu Ala Glu Ala Lys Ala Asn Ala Gly Arg Glu Ala Ala
            210                 215                 220

Ala Ala Ala Leu Ala Ile Ala Glu Ala Val Ala Ile Glu Gln Glu
225                 230                 235                 240

Ala Val Ile Leu Ala Arg Lys Ala Gln Asp Ala Arg Leu Asn Ala Glu
            245                 250                 255

Ala Ala Ala Ala Ala Met Asn Ala Arg Val Ile Ala Ser Ala Glu
            260                 265                 270

Ser Glu Ala Ser Glu Asp Leu Glu Asn Arg Ala Ser Val Ala Arg Ala
            275                 280                 285

Ser Ala Ala Gly Ala Ala Glu Ala Lys Ala Ile Ala Thr Asp Ala Gly

```
            290                 295                 300
Ala Thr Ala Glu Ile Ala Ala Tyr Ser Trp Ala Lys Lys Gly Glu Leu
305                 310                 315                 320

Ile Asn Pro Gly Pro Leu Pro Lys Ile Ile Ser Val Asn Ala Asp Leu
                325                 330                 335

Ser Lys Ser Glu Val Glu Ala Met Lys Ile Thr Arg Gly Gln Val Gln
            340                 345                 350

Glu Val Lys Lys Ile Ser Thr His Lys Gly Gly Trp Gly Trp Gly Lys
        355                 360                 365

Glu Gly Arg Ser Lys Val Ser Ser Asn Ala Ser Arg Ala Ser Ala
    370                 375                 380

Ser Ala Asn Ala Ala Gly Ser Leu Gly Ser Lys Trp Gly Arg Gln
385                 390                 395                 400

Leu Ser Ala Ser Ser Ala Ser Ala Asp Ala Asn Ala Glu Ala Asp Ser
            405                 410                 415

Gln Leu Leu Lys Val Trp
            420

<210> SEQ ID NO 47
<211> LENGTH: 441
<212> TYPE: PRT
<213> ORGANISM: Myrmecia forficata

<400> SEQUENCE: 47

Met Lys Ile Pro Ala Ile Leu Ala Thr Ser Leu Leu Ile Trp Gly Leu
1               5                   10                  15

Val Gly Ala Ser Glu Leu Glu Ser Glu Ala Ser Ala Ala Ser Ala
            20                  25                  30

Gln Ala Glu Ala Ser Ser Ser Gly Arg Ser Gly Lys Leu Ser Ala Ser
        35                  40                  45

Gln Ala Ser Ala Ser Ala Ser Ala Ser Ala Gly Ser Arg Gly
    50                  55                  60

Gly Ser Lys Gly Gly Trp Gly Gln Leu Arg Arg Gly Asp Val Lys Ser
65                  70                  75                  80

Glu Ala Lys Ser Ala Ala Ile Ala Val Glu Gly Ala Lys Ile Gly
                85                  90                  95

Thr Gly Ile Gly Asn Thr Ala Ser Ala Ser Ala Glu Ala Leu Ser Arg
                100                 105                 110

Gly Leu Gly Ile Gly Gln Ala Ala Glu Ala Gln Ala Ala Ala
        115                 120                 125

Gly Gln Ala Glu Val Ala Ala Lys Ser Cys Glu Leu Ala Asp Lys Thr
    130                 135                 140

Thr Ala Lys Ala Val Ala Met Val Glu Ala Ala Glu Ala Glu Ile
145                 150                 155                 160

Glu Val Ala Asn Gln Glu Val Ala Ala Val Lys Leu Ser Thr Trp Ala
                165                 170                 175

Ala Lys Ala Ala Arg Ile Val Glu Glu Asp Ser Ala Ala Val Arg Ala
            180                 185                 190

Ala Ala Gly Lys Leu Leu Leu Ala Ala Arg Ala Ala Ala Ala Glu
        195                 200                 205

Arg Arg Ala Asn Glu Glu Ser Glu Ala Ala Asn Glu Leu Ala Gln Ala
    210                 215                 220

Ser Ser Ala Ala Ala Glu Ala Glu Ala Lys Ala Asn Ala Gly Arg
225                 230                 235                 240
```

Glu Ala Ala Ala Ala Leu Ala Ile Ala Glu Ala Val Ala Ile
             245                 250                 255

Glu Gln Glu Ala Val Ile Leu Ala Arg Lys Ala Gln Asp Ala Arg Leu
        260                 265                 270

Asn Ala Glu Ala Ala Ala Ala Ala Met Asn Ala Arg Val Ile Ala
    275                 280                 285

Ser Ala Glu Ser Glu Ala Ser Glu Asp Leu Glu Asn Arg Ala Ser Val
    290                 295                 300

Ala Arg Ala Ser Ala Ala Gly Ala Ala Glu Ala Lys Ala Ile Ala Thr
305                 310                 315                 320

Asp Ala Gly Ala Thr Ala Glu Ile Ala Ala Tyr Ser Trp Ala Lys Lys
                325                 330                 335

Gly Glu Leu Ile Asn Pro Gly Pro Leu Pro Lys Ile Ile Ser Val Asn
                340                 345                 350

Ala Asp Leu Ser Lys Ser Glu Val Glu Ala Met Lys Ile Thr Arg Gly
            355                 360                 365

Gln Val Gln Glu Val Lys Lys Ile Ser Thr His Lys Gly Gly Trp Gly
    370                 375                 380

Trp Gly Lys Glu Gly Arg Ser Lys Val Ser Ser Asn Ala Ser Ala Arg
385                 390                 395                 400

Ala Ser Ala Ser Ala Asn Ala Ala Gly Ser Leu Gly Ser Lys Trp
                405                 410                 415

Gly Arg Gln Leu Ser Ala Ser Ser Ala Ser Ala Asp Ala Asn Ala Glu
            420                 425                 430

Ala Asp Ser Gln Leu Leu Lys Val Trp
        435                 440

<210> SEQ ID NO 48
<211> LENGTH: 1212
<212> TYPE: DNA
<213> ORGANISM: Myrmecia forficata

<400> SEQUENCE: 48
agcgggccgc gcttactcgg cggcagatcg gccgcgtccg cgtcggcttc cgcttcggct      60
gaggcgtcgg cgggcggttg gaggaaaagc ggcgcatccg cttccgcttc cgctaaggct     120
ggtagcagca acatcctcag ccgcgtggga gcttcgaggg cggccgcgac gttggtcgct     180
tccgccgcgg tggaggccaa ggcgggtctc cgtgccggca aggcaaccgc cgaggagcag     240
agggaggctt tggaaatgct caccttgtcc gccgacaaga atgccgaggc gcgtatcctg     300
gccgacgaca cggccgttct ggttcaaggc agcgccgagg cacagtcggt cgccgccgcg     360
aagaccgtcg cggtcgagga agagtccgct tccttggatg cggccgcagt tgaagcggag     420
gtcgcagccg ccacgtcgaa atcgtcggct ggccaagcac tccagtccgc acagaccgcc     480
gcatctgctc tcagaacttc cgccaggagc gccttgacgg ccctcaagct ggcacgcctc     540
caaggcgcgg cttctagcaa cgctgccagg atgatggaaa aggcgctggc cgccacccag     600
gacgcaaatg ccgccgccca gcaagctatg gcggccgaga gtgcagccgc agaagcagcg     660
gctatcgcgg cagcgaaaca atcggaggcg agagacgccg gcgccgaggc caaggccgcc     720
atggcagcac tcatcaccgc ccagaggaat ctcgtgcagg ccaatgccag gcggaaatg     780 gcaagcgagg aagccgaatt ggattcgaag tctagagcgt ccgacgccaa ggtgaacgcc     840
gttgctcgtg cggcctccaa gtccagcata cgcagagatg aacttatcga gatcggcgct     900
gagttcggca aggccagcgg cgaggtgatt tccaccggca cgcgttccaa cggcggtcaa     960

| | |
|---|---:|
| gacgccatcg ccaccgccga ggcatcgagt agcgcgtccg ccgtcggcat caagaaaaca | 1020 |
| agcggacact gggggagcgg aaaatggagt cgtgtctcca agggtaaagg atgggcttcc | 1080 |
| tcgaatgcgg acgctgacgc cagcagcagc agcatcatca tcggcggtct caaacgcggc | 1140 |
| ggcctcggtt cggaagcctc tgcggcagct tccgcagaag cggaagcttc cgccggcaca | 1200 |
| ctcctgctgt aa | 1212 |

<210> SEQ ID NO 49
<211> LENGTH: 1269
<212> TYPE: DNA
<213> ORGANISM: Myrmecia forficata

<400> SEQUENCE: 49

| | |
|---|---:|
| atgaagatcc cagcgataat cgcaacgtcc cttctcctct ggggtttcgc cagcgccagc | 60 |
| gggccgcgct tactcggcgg cagatcggcc gcgtccgcgt cggcttccgc ttcggctgag | 120 |
| gcgtcggcgg gcggttggag gaaaagcggc gcatccgctt ccgcttccgc taaggctggt | 180 |
| agcagcaaca tcctcagccg cgtgggagct tcgaggcgg ccgcgacgtt ggtcgcttcc | 240 |
| gccgcggtgg aggccaaggc gggtctccgt gccggcaagg caaccgccga ggagcagagg | 300 |
| gaggctttgg aaatgctcac cttgtccgcc gacaagaatg ccgaggcgcg tatcctggcc | 360 |
| gacgacacgg ccgttctggt tcaaggcagc gccgaggcac agtcggtcgc cgccgcgaag | 420 |
| accgtcgcgc tcgaggaaga gtccgcttcc ttggatgcgg ccgcagttga agcggaggtc | 480 |
| gcagccgcca cgtcgaaatc gtcggctggc caagcactcc agtccgcaca gaccgccgca | 540 |
| tctgctctca gaacttccgc caggagcgcc ttgacgcccc tcaagctggc acgcctccaa | 600 |
| ggcgcggctt ctagcaacgc tgccaggatg atggaaaagg cgctggccgc cacccaggac | 660 |
| gcaaatgccg ccgcccagca agctatggcg gccgagagtg cagccgcaga agcagcggct | 720 |
| atcgcggcag cgaaacaatc ggaggcgaga gacgccggcg ccgaggccaa ggccgccatg | 780 |
| gcagcactca tcaccgccca gaggaatctc gtgcaggcca atgccagggc ggaaatggca | 840 |
| agcgaggaag ccgaattgga ttcgaagtct agagcgtccg acgccaaggt gaacgccgtt | 900 |
| gctcgtgcgg cctccaagtc cagcatacgc agagatgaac ttatcgagat cggcgctgag | 960 |
| ttcggcaagg ccagcggcga ggtgatttcc accggcacgc gttccaacgg cggtcaagac | 1020 |
| gccatcgcca ccgccgaggc atcgagtagc gcgtccgccg tcggcatcaa gaaaacaagc | 1080 |
| ggacactggg ggagcggaaa atggagtcgt gtctccaagg gtaaaggatg gcttcctcg | 1140 |
| aatgcggacg ctgacgccag cagcagcagc atcatcatcg gcgtctcaa acgcggcggc | 1200 |
| ctcggttcgg aagcctctgc ggcagcttcc gcagaagcgg aagcttccgc cggcacactc | 1260 |
| ctgctgtaa | 1269 |

<210> SEQ ID NO 50
<211> LENGTH: 1179
<212> TYPE: DNA
<213> ORGANISM: Myrmecia forficata

<400> SEQUENCE: 50

| | |
|---|---:|
| cgggtcatcg agtccagctc gtcggcttcc gcacaggcgt cggcatcggc cggctcgaga | 60 |
| ggcctgctcg gtaaacggcc gattggcaag ctcgagtggg gcaaggagga gaagaaactc | 120 |
| gaagaactcg acgaggaatc gctcaatgag gccgctctga aggtcggcat caagaacggc | 180 |
| ggattggatg tcgcgaaggg cgcggcagtc ctcgaggcag cgatgagcga cgtcgcgacc | 240 |
| cttacggatc agcgttctct tgtggatctc ggtctcggcc cggtcgcgaa cgaggccgag | 300 |

```
atcctggcgg aggcgcaggc cgccacgagc gcccaagctg gcgctgtcgc taatagcgcc    360
gcggagcgtg cgatcgcggc gatggagatg gccgacagaa ccgaatatat tgcggcactt    420
gtcaccacca agccgccaa agctgccgag gccactatgg ccgctactgc ccgtgccacc     480
gccgccgcct cagcctccaa gatatccagt caggaatcag ccgcatcggc cgctaacgcc    540
gccaacgccg aagccaaggc caacgccgct tccataatcg ctaacaaggc gaacgccgtc    600
ctggctgagg ccgccgccgt actcgcagcc actgctgcca aggccaagga atcggcgatg    660
aaatcgctta gcgccgctca ggccgccgcc aaggcacaag ccaggaacgc cgaggcctcc    720
gccgaagctc agatcaaact tcccaggcc agggccgccg tggcacgcgc tgcagccgat     780
caggccgtct gttcctccca ggctcaggcc gcaagtcaga tacaatcgag ggcatccgca    840
tccgaatccg cggcatcggc acaatcagag accaacaccg ccgcggccga agcggtcgcc    900
accgctgacg ccgaagcggc cgcgcaagct gaagcgtggg tcatgtcgct gaagaacgat    960
ctgtggctgc atctcaacat gaaggtgag gccaaggccg aaggcgaggc cgtttcgatc      1020
agcaaaggac atcgcggcgg tatcaggtcg ggcagcatct cggaagccag cgccgaggca    1080
agcagcaacg tttccatggg cggacgtcat ggacggaagg acctcgtctc tgaagcgtta    1140
gcgggagcat cagcgggcag cagtgccgac tcctttga                            1179
```

```
<210> SEQ ID NO 51
<211> LENGTH: 1236
<212> TYPE: DNA
<213> ORGANISM: Myrmecia forficata
<400> SEQUENCE: 51
atgaagattc cagcgatact cgtgacgtct ctcctcgcct ggggattagc cagcggccgg     60
gtcatcgagt ccagctcgtc ggcttccgca caggcgtcgg catcggccgg ctcgagaggc    120
ctgctcggta acggccgat tggcaagctc gagtggggca aggaggagaa gaaactcgaa     180
gaactcgacg aggaatcgct caatgaggcc gctctgaagg tcggcatcaa gaacggcgga    240
ttggatgtcg cgaagggcgc ggcagtcctc gaggcagcga tgagcgacgt cgcgaccctt    300
acggatcagc gttctcttgt ggatctcggt ctcggcccgg tcgcgaacga ggccgagatc    360
ctggcggagg cgcaggccgc cacgagcgcc caagctggcg ctgtcgctaa tagcgccgcg    420
gagcgtgcga tcgcggcgat ggagatggcc gacagaaccg aatatattgc ggcacttgtc    480
accaccaaag ccgccaaagc tgccgaggcc actatggccg ctactgcccg tgccaccgcc    540
gccgcctcag cctccaagat atccagtcag gaatcagccg catcggccgc taacgccgcc    600
aacgccgaag ccaaggccaa cgccgcttcc ataatcgcta acaaggcgaa cgccgtcctg    660
gctgaggccg ccgccgtact cgcagccact gctgccaagg ccaaggaatc ggcgatgaaa    720
tcgcttagcg ccgctcaggc cgccgccaag gcacaagcca ggaacgccga ggcctccgcc    780
gaagctcaga tcaaactttc ccaggccagg ccgccgtgg cacgcgctgc agccgatcag     840
gccgtctgtt cctcccaggc tcaggccgca agtcagatac aatcgagggc atccgcatcc    900
gaatccgcgg catcggcaca atcagagacc aacaccgccg cggccgaagc ggtcgccacc    960
gctgacgccg aagcggccgc gcaagctgaa gcgtgggtca tgtcgctgaa gaacgatctg    1020
tggctgcatc tcaacatgaa gggtgaggcc aaggccgaag gcgaggccgt ttcgatcagc    1080
aaaggacatc gcggcggtat caggtcgggc agcatctcgg aagccagcgc cgaggcaagc    1140
agcaacgttt ccatgggcgg acgtcatgga cggaaggacc tcgtctctga agcgttagcg    1200
```

```
ggagcatcag cgggcagcag tgccgactcc ctttga                              1236
```

<210> SEQ ID NO 52
<211> LENGTH: 1128
<212> TYPE: DNA
<213> ORGANISM: Myrmecia forficata

<400> SEQUENCE: 52

```
aatctcctta aggagtcgaa agcttccgcg tccgcgtccg cgtccgcttc cgcgagggcc     60
agcggcaaga agaatcttca cgtgttgcca ttaccgaaga aaagcgagca tggcatcgtg    120
atcgacaagt cggtgttcga catcaaggat gtagtgctga gcgcggtcga cgagatcaac    180
ggcgccccga aactcggcct gggatggaag aaggtcagca tgggggtgga gcgcgccgag    240
gcgaacgcag ccgctgccgc cgaggcattg gcgatgatca agaagattgc catggcccgc    300
agcagtgcat acgtccaggc ggcctgggca tcggcccagg catcagctga cgcattggct    360
agcgccaggg tggcacaggc gtctcaggag gctgcggagg caagggtag agcggcttcc    420
gaggcgctct ccagagccat cgaagcatcc tcgcgagccg atgcggcagc cgctgcgacg    480
ctggacgcga tggaccgcac catggagaac gcgagggcgg caaatgccgc gcaaacgcag    540
gccagcggcc aagctgagaa cgcaaatcgc agcgctgctg ccatcctcgc agctctgcta    600
cgtatcgcgg aggcatccgc gttgaacaac gaggccgcgg tcaacgcggc cgcggccgca    660
gccgcagcgt ctgcccttca ggccaaggct aacgcggctt ctcaagcaac cgccagagcc    720
gcaggacagg cgtcgacggc cgccgaagag gcgcaatccg cccaagaagc cgccgataag    780
aacgcggagc tgaccacggt catgctcgaa aaggctagtg ctgatcaaca ggcggcatcc    840
gctagggctg actactacac cgcctcaacc gaggccgaag ccgctgcaca ggcgtctgct    900
atcaacgcac tcagggacgg aatagttgtc ggaatgggaa atgacgctgg cgcatcggcc    960
caagcgatgg cacaggtaga agctctcgct cgcgccagcg agcacaaggc gttaggcgag   1020
aagaagaagg gcctggtttg gggctacgga agcaagggca gtagctccgc cagcgcatcc   1080
gccagcgcct ccgccgaagc atcctcgaga ctcggaaagg actggtag               1128
```

<210> SEQ ID NO 53
<211> LENGTH: 1185
<212> TYPE: DNA
<213> ORGANISM: Myrmecia forficata

<400> SEQUENCE: 53

```
atgaagatac cagcgatact cgtgacgtcc ttcctcgcct ggggactggc cagcgggaat     60
ctccttaagg agtcgaaagc ttccgcgtcc gcgtccgcgt ccgcttccgc gagggccagc    120
ggcaagaaga atcttcacgt gttgccatta ccgaagaaaa gcgagcatgg catcgtgatc    180
gacaagtcgg tgttcgacat caaggatgta gtgctgagcg cggtcgacga gatcaacggc    240
gccccgaaac tcggcctggg atggaagaag gtcagcatgg gggtggagcg cgccgaggcg    300
aacgcagccg ctgccgccga ggcattggcg atgatcaaga gattgccat ggcccgcagc    360
agtgcatacg tccaggcggc ctgggcatcg gcccaggcat cagctgacgc attggctagc    420
gccagggtgg cacaggcgtc tcaggaggct gcggaggcaa agggtagagc ggcttccgag    480
gcgctctcca gagccatcga agcatcctcg cgagccgatg cggcagccgc tgcgacgctg    540
gacgcgatgg accgcaccat ggagaacgcg agggcggcaa atgccgcgca aacgcaggcc    600
agcggccaag ctgagaacgc aaatcgcagc gctgctgcca tcctcgcagc tctgctacgt    660
atcgcggagg catccgcgtt gaacaacgag gccgcggtca acgcggccgc ggccgcagcc    720
```

```
gcagcgtctg cccttcaggc caaggctaac gcggcttctc aagcaaccgc cagagccgca    780
ggacaggcgt cgacggccgc cgaagaggcg caatccgccc aagaagccgc cgataagaac    840
gcggagctga ccacggtcat gctcgaaaag gctagtgctg atcaacaggc ggcatccgct    900
agggctgact actacaccgc ctcaaccgag gccgaagccg ctgcacaggc gtctgctatc    960
aacgcactca gggacggaat agttgtcgga atgggaaatg acgctggcgc atcggcccaa   1020
gcgatggcac aggtagaagc tctcgctcgc gccagcgagc acaaggcgtt aggcgagaag   1080
aagaagggcc tggtttgggg ctacggaagc aagggcagta gctccgccag cgcatccgcc   1140
agcgcctccg ccgaagcatc ctcgagactc ggaaaggact ggtag                   1185
```

<210> SEQ ID NO 54
<211> LENGTH: 1269
<212> TYPE: DNA
<213> ORGANISM: Myrmecia forficata

<400> SEQUENCE: 54

```
agcgagctcg aatcggaagc gagtgcggcg gcgtctgcgc aagcggaagc gtcctcgtct     60
ggtcgctccg gcaaactgtc cgcgtctcag gcttccgcca gcgcgtccgc cagcgcgtca    120
gccggcagca gaggtggcag caaaggtggc tggggccagc tccgccgtgg tgatgttaag    180
agcgaggcga gagcgccgc cgcgatcgcg gtcgaaggag ctaaaatcgg caccggaatc    240
ggaaataccg cgtccgcatc cgcggaggcg ctctcacgag gactcggcat cggacaggcg    300
gccgcggagg cgcaagccgc agccgcaggt caggcagagg tcgccgcgaa atcgtgcgaa    360
cttgccgaca agaccaccgc caaagcggtc gccatggtcg aagcggcagc cgaggccgaa    420
atcgaggtgg ccaatcagga ggtcgcagcc gtcaaattat cgacttgggc cgctaaagca    480
gcaaggatag tcgaggaaga cagcgccgcc gtgagggcgg ctgccggcaa attgcttttg    540
gccgcgagag ctgccgccgc cgccgagaga cgcgccaacg aggaatccga gcggccaac    600 gaacttgctc aagcgtcatc tgccgctgcc gccgaggccg aagccaaagc gaacgccggc    660
cgtgaggccg ctgccgctgc cttggctatc gccgaggccg ccgtcgccat cgaacaagaa    720
gccgtcattt tggctcgcaa ggcacaagat gcccgtttga atgctgaagc cgcagccgcc    780
gctgcgatga acgcccgtgt catcgcttcc gccgaatccg aggccagtga agatctggag    840
aatcgcgcta gtgtggcgcg tgccagtgcg gccggtgccg ctgaggcaaa ggctatcgcc    900
accgatgccg gcgccactgc cgagatcgcg gcctacagtt gggccaagaa gggcgaactg    960
atcaaccccg gcccgttgcc gaagatcatc agcgtcaacg ccgatctgtc caagagcgag   1020
gtcgaggcca tgaagatcac ccggggtcaa gtacaggaag tcaagaaaat cagcactcac   1080
aaaggtggct ggggatgggg aaaggaagga aggtcgaagg tatcttccaa cgctagtgcc   1140
agagctagtg ccagcgccaa tgcagccgcc ggtagcctcg gcagcaaatg gggaagacaa   1200
ctatccgcat catccgcgtc ggctgacgcc aacgccgaag ccgacagcca gttgctgaaa   1260
gtgtggtga                                                           1269
```

<210> SEQ ID NO 55
<211> LENGTH: 1326
<212> TYPE: DNA
<213> ORGANISM: Myrmecia forficata

<400> SEQUENCE: 55

```
atgaagattc cagcgatact tgcgacgtcc ctcctcatct ggggtcttgt cggcgccagc     60
```

-continued

```
gagctcgaat cggaagcgag tgcggcggcg tctgcgcaag cggaagcgtc ctcgtctggt    120
cgctccggca aactgtccgc gtctcaggct tccgccagcg cgtccgccag cgcgtcagcc    180
ggcagcagag gtggcagcaa aggtggctgg ggccagctcc gccgtggtga tgttaagagc    240
gaggcgaaga gcgccgccgc gatcgcggtc gaaggagcta aaatcggcac cggaatcgga    300
aataccgcgt ccgcatccgc ggaggcgctc tcacgaggac tcggcatcgg acaggcggcc    360
gcggaggcgc aagccgcagc cgcaggtcag gcagaggtcg ccgcgaaatc gtgcgaactt    420
gccgacaaga ccaccgccaa agcggtcgcc atggtcgaag cggcagccga ggccgaaatc    480
gaggtggcca atcaggaggt cgcagccgtc aaattatcga cttgggccgc taaagcagca    540
aggatagtcg aggaagacag cgccgccgtg agggcggctg ccggcaaatt gcttttggcc    600
gcgagagctg ccgccgccgc cgagagacgc gccaacgagg aatccgaggc ggccaacgaa    660
cttgctcaag cgtcatctgc cgctgccgcc gaggccgaag ccaaagcgaa cgccggccgt    720
gaggccgctg ccgctgcctt ggctatcgcc gaggccgccg tcgccatcga acaagaagcc    780
gtcattttgg ctcgcaaggc acaagatgcc cgtttgaatg ctgaagccgc agccgccgct    840
gcgatgaacg cccgtgtcat cgcttccgcc gaatccgagg ccagtgaaga tctggagaat    900
cgcgctagtg tggcgcgtgc cagtgcggcc ggtgccgctg aggcaaaggc tatcgccacc    960
gatgccggcg ccactgccga gatcgcggcc tacagttggg ccaagaaggg cgaactgatc   1020
aaccccggcc cgttgccgaa gatcatcagc gtcaacgccg atctgtccaa gagcgaggtc   1080
gaggccatga agatcacccg gggtcaagta caggaagtca agaaaatcag cactcacaaa   1140
ggtggctggg gatggggaaa ggaaggaagg tcgaaggtat cttccaacgc tagtgccaga   1200
gctagtgcca gcgccaatgc agccgccggt agcctcggca gcaaatgggg aagacaacta   1260
tccgcatcat ccgcgtcggc tgacgccaac gccgaagccg acagccagtt gctgaaagtg   1320
tggtga                                                               1326
```

<210> SEQ ID NO 56
<211> LENGTH: 372
<212> TYPE: PRT
<213> ORGANISM: Oecophylla smaragdina

<400> SEQUENCE: 56

```
Ser Lys Ser Tyr Leu Leu Gly Ser Ser Ala Ser Ala Ser Ala Ser Ala
1               5                   10                  15

Ser Ala Ser Ala Ser Ala Gly Gly Ser Thr Gly Gly Val Gly Val Gly
            20                  25                  30

Ser Val Ile Ser Gly Gly Asn Asn Ile Ile Arg Gly Ala Ser Thr Thr
        35                  40                  45

Ser Val Thr Leu Ala Ala Ala Ala Glu Ala Lys Ala Ala Leu Asn
    50                  55                  60

Ala Gly Lys Ala Thr Val Glu Glu Gln Arg Glu Ala Leu Gln Leu Leu
65                  70                  75                  80

Thr Ala Ser Ala Glu Lys Asn Ala Glu Ala Arg Ser Leu Ala Asp Asp
                85                  90                  95

Ala Ala Val Leu Val Gln Gly Ala Ala Glu Ala Gln Ser Val Ala Ala
            100                 105                 110

Ala Lys Thr Val Ala Val Glu Gln Gly Ser Asn Ser Leu Asp Ala Ala
        115                 120                 125

Ala Ala Glu Ala Glu Ala Ala Ala Ala Ser Arg Val Ser Ala Gln
    130                 135                 140
```

Gln Ala Leu Gln Ala Ala Gln Thr Ser Ala Ala Ile Gln Thr Ala
145                 150                 155                 160

Ala Gly Ser Ala Leu Thr Ala Leu Lys Leu Ala Arg Lys Gln Glu Ala
            165                 170                 175

Glu Ser Asn Asn Ala Ala Glu Gln Ala Asn Lys Ala Leu Ala Leu Ser
            180                 185                 190

Arg Ala Ala Ser Ala Ala Thr Gln Arg Ala Val Ala Ala Gln Asn Ala
        195                 200                 205

Ala Ala Ala Ser Ala Ala Ser Ala Gly Ala Ala Gln Ala Glu Ala Arg
    210                 215                 220

Asn Ala Tyr Ala Lys Ala Lys Ala Ala Ile Ala Ala Leu Thr Ala Ala
225                 230                 235                 240

Gln Arg Asn Tyr Ala Ala Ala Lys Ala Ser Ala Ser Ala Gly Ser Val
                245                 250                 255

Val Ala Glu Gln Asp Ala Gln Ser Arg Ala Ala Asp Ala Glu Val Asn
            260                 265                 270

Ala Val Ala Gln Ala Ala Arg Ala Ser Val Arg Asn Gln Glu Ile
        275                 280                 285

Val Glu Ile Gly Ala Glu Phe Gly Asn Ala Ser Gly Gly Val Ile Ser
290                 295                 300

Thr Gly Thr Arg Ser Ser Gly Gly Lys Gly Val Ser Val Thr Ala Gly
305                 310                 315                 320

Ala Gln Ala Ser Ala Ser Ala Ser Ala Thr Ser Ser Ser Ser Ser Ser
                325                 330                 335

Ser Gly Ile Asn Lys Gly His Pro Arg Trp Gly His Asn Trp Gly Leu
            340                 345                 350

Gly Ser Ser Glu Ala Ser Ala Asn Ala Glu Ala Glu Ser Ser Ala Ser
            355                 360                 365

Ser Tyr Ser Ser
        370

<210> SEQ ID NO 57
<211> LENGTH: 391
<212> TYPE: PRT
<213> ORGANISM: Oecophylla smaragdina

<400> SEQUENCE: 57

Met Lys Ile Pro Ala Ile Ile Ala Thr Thr Leu Leu Leu Trp Gly Phe
1               5                   10                  15

Ala Asp Ala Ser Lys Ser Tyr Leu Leu Gly Ser Ser Ala Ser Ala Ser
            20                  25                  30

Ala Ser Ala Ser Ala Ser Ala Ser Ala Gly Gly Ser Thr Gly Gly Val
        35                  40                  45

Gly Val Gly Ser Val Ile Ser Gly Gly Asn Asn Ile Ile Arg Gly Ala
    50                  55                  60

Ser Thr Thr Ser Val Thr Leu Ala Ala Ala Ala Glu Ala Lys Ala
65                  70                  75                  80

Ala Leu Asn Ala Gly Lys Ala Thr Val Glu Glu Gln Arg Glu Ala Leu
                85                  90                  95

Gln Leu Leu Thr Ala Ser Ala Glu Lys Asn Ala Glu Ala Arg Ser Leu
            100                 105                 110

Ala Asp Asp Ala Ala Val Leu Val Gln Gly Ala Ala Glu Ala Gln Ser
        115                 120                 125

Val Ala Ala Ala Lys Thr Val Ala Val Glu Gln Gly Ser Asn Ser Leu
    130                 135                 140

```
Asp Ala Ala Ala Glu Ala Glu Ala Ala Ala Ser Arg Val
145                 150                 155                 160

Ser Ala Gln Gln Ala Leu Gln Ala Ala Gln Thr Ser Ala Ala Ala Ile
            165                 170                 175

Gln Thr Ala Ala Gly Ser Ala Leu Thr Ala Leu Lys Leu Ala Arg Lys
            180                 185                 190

Gln Glu Ala Glu Ser Asn Asn Ala Ala Glu Gln Ala Asn Lys Ala Leu
            195                 200                 205

Ala Leu Ser Arg Ala Ala Ser Ala Ala Thr Gln Arg Ala Val Ala Ala
            210                 215                 220

Gln Asn Ala Ala Ala Ser Ala Ala Ser Ala Gly Ala Ala Gln Ala
225                 230                 235                 240

Glu Ala Arg Asn Ala Tyr Ala Lys Ala Lys Ala Ala Ile Ala Ala Leu
            245                 250                 255

Thr Ala Ala Gln Arg Asn Tyr Ala Ala Ala Lys Ala Ser Ala Ser Ala
            260                 265                 270

Gly Ser Val Val Ala Glu Gln Asp Ala Gln Ser Arg Ala Ala Asp Ala
            275                 280                 285

Glu Val Asn Ala Val Ala Gln Ala Ala Arg Ala Ser Val Arg Asn
290                 295                 300

Gln Glu Ile Val Glu Ile Gly Ala Glu Phe Gly Asn Ala Ser Gly Gly
305                 310                 315                 320

Val Ile Ser Thr Gly Thr Arg Ser Ser Gly Gly Lys Gly Val Ser Val
            325                 330                 335

Thr Ala Gly Ala Gln Ala Ser Ala Ser Ala Ser Ala Thr Ser Ser Ser
            340                 345                 350

Ser Ser Ser Ser Gly Ile Asn Lys Gly His Pro Arg Trp Gly His Asn
            355                 360                 365

Trp Gly Leu Gly Ser Ser Glu Ala Ser Ala Asn Ala Glu Ala Glu Ser
            370                 375                 380

Ser Ala Ser Ser Tyr Ser Ser
385                 390

<210> SEQ ID NO 58
<211> LENGTH: 381
<212> TYPE: PRT
<213> ORGANISM: Oecophylla smaragdina

<400> SEQUENCE: 58

Gly Val Ile Gly Pro Asp Thr Ser Ser Ser Gln Ala Ser Ala Ser
1               5                   10                  15

Ala Ser Ala Ser Ala Ser Ala Ser Ala Ser Ser Ala Ser Ile Gly
            20                  25                  30

Tyr Asn Glu Leu His Lys Ser Ile Asn Ala Pro Ala Leu Ala Val Gly
            35                  40                  45

Val Lys Asn Gly Gly Val Asp Val Ala Lys Gly Ala Ala Val Val Glu
            50                  55                  60

Ser Ala Ile Ser Asp Val Ser Thr Leu Thr Asp Asp Arg Thr Leu Asn
65                  70                  75                  80

Gly Leu Ala Ile Ile Gly Asn Ser Ala Glu Ser Leu Ala Arg Ala Gln
            85                  90                  95

Ala Ser Ser Ser Ala Ser Ala Gly Ala Lys Ala Asn Ala Leu Ile Lys
            100                 105                 110

Gln Ser Ile Ala Ala Ile Glu Ile Thr Glu Lys Ala Glu Tyr Leu Ala
```

```
            115                 120                 125
Ser Ile Val Ala Thr Lys Ala Lys Ala Ala Glu Ala Thr Ala Ala
    130                 135                 140

Ala Thr Ala Arg Ala Thr Ala Val Ala Glu Ala Ala Lys Val Ser Ser
145                 150                 155                 160

Glu Gln Phe Ala Ala Glu Ala Arg Ala Ala Ala Asp Ala Glu Ala Lys
                165                 170                 175

Ala Asn Ala Ala Ser Ile Ile Ala Asn Lys Ala Asn Ala Val Leu Ala
            180                 185                 190

Glu Ala Ala Thr Gly Leu Ser Ala Ser Ala Gly Lys Ala Gln Gln Ser
        195                 200                 205

Ala Thr Arg Ala Leu Gln Ala Ala Arg Ala Ala Lys Ala Gln Ala
    210                 215                 220

Glu Leu Thr Gln Lys Ala Ala Gln Ile Leu Val Leu Ile Ala Glu Ala
225                 230                 235                 240

Lys Ala Ala Val Ser Arg Ala Ser Ala Asp Gln Ser Val Cys Thr Ser
                245                 250                 255

Gln Ala Gln Ala Ala Ser Gln Ile Gln Ser Arg Ala Ser Ala Ala Glu
            260                 265                 270

Ser Ala Ala Ser Ala Gln Ser Glu Ala Asn Thr Ile Ala Ala Glu Ala
        275                 280                 285

Val Ala Arg Ala Asp Ala Glu Ala Ala Ser Gln Ala Gln Ala Trp Ala
    290                 295                 300

Glu Ser Phe Lys Arg Glu Leu Ser Ser Val Val Leu Glu Ala Glu Ala
305                 310                 315                 320

Asn Ala Ser Ala Ser Ala Ser Ala Gly Ala Leu Ala Ser Gly Ser Ser
                325                 330                 335

Ser Ser Gly Ala Ser Ser Ala Asp Ala Ser Ala Gly Ala Ser Ser
            340                 345                 350

Tyr Gly Ser Leu Gly Gly Tyr Arg His Gly Gly Ser Phe Ser Glu Ala
        355                 360                 365

Ser Ala Ala Ala Ser Ala Ala Ser Arg Ala Glu Ala Ala
    370                 375                 380

<210> SEQ ID NO 59
<211> LENGTH: 400
<212> TYPE: PRT
<213> ORGANISM: Oecophylla smaragdina

<400> SEQUENCE: 59

Met Lys Ile Pro Ala Ile Phe Val Thr Ser Leu Leu Ala Trp Gly Leu
1               5                   10                  15

Ala Ser Gly Gly Val Ile Gly Pro Asp Thr Ser Ser Ser Ser Gln Ala
            20                  25                  30

Ser Ala Ser Ala Ser Ala Ser Ala Ser Ala Ser Ala Ser Ser Ser Ala
        35                  40                  45

Ser Ile Gly Tyr Asn Glu Leu His Lys Ser Ile Asn Ala Pro Ala Leu
    50                  55                  60

Ala Val Gly Val Lys Asn Gly Val Asp Val Ala Lys Gly Ala Ala
65                  70                  75                  80

Val Val Glu Ser Ala Ile Ser Asp Val Ser Thr Leu Thr Asp Asp Arg
                85                  90                  95

Thr Leu Asn Gly Leu Ala Ile Ile Gly Asn Ser Ala Glu Ser Leu Ala
            100                 105                 110
```

```
Arg Ala Gln Ala Ser Ser Ala Ser Ala Gly Ala Lys Ala Asn Ala
        115                 120                 125

Leu Ile Lys Gln Ser Ile Ala Ala Ile Glu Ile Thr Glu Lys Ala Glu
130                 135                 140

Tyr Leu Ala Ser Ile Val Ala Thr Lys Ala Ala Lys Ala Ala Glu Ala
145                 150                 155                 160

Thr Ala Ala Ala Thr Ala Arg Ala Thr Ala Val Ala Glu Ala Ala Lys
            165                 170                 175

Val Ser Ser Glu Gln Phe Ala Ala Glu Ala Arg Ala Ala Ala Asp Ala
        180                 185                 190

Glu Ala Lys Ala Asn Ala Ala Ser Ile Ile Ala Asn Lys Ala Asn Ala
    195                 200                 205

Val Leu Ala Glu Ala Ala Thr Gly Leu Ser Ala Ser Ala Gly Lys Ala
210                 215                 220

Gln Gln Ser Ala Thr Arg Ala Leu Gln Ala Ala Arg Ala Ala Ala Lys
225                 230                 235                 240

Ala Gln Ala Glu Leu Thr Gln Lys Ala Ala Gln Ile Leu Val Leu Ile
            245                 250                 255

Ala Glu Ala Lys Ala Ala Val Ser Arg Ala Ser Ala Asp Gln Ser Val
        260                 265                 270

Cys Thr Ser Gln Ala Gln Ala Ser Gln Ile Gln Ser Arg Ala Ser
    275                 280                 285

Ala Ala Glu Ser Ala Ala Ser Ala Gln Ser Glu Ala Asn Thr Ile Ala
    290                 295                 300

Ala Glu Ala Val Ala Arg Ala Asp Ala Glu Ala Ala Ser Gln Ala Gln
305                 310                 315                 320

Ala Trp Ala Glu Ser Phe Lys Arg Glu Leu Ser Ser Val Val Leu Glu
            325                 330                 335

Ala Glu Ala Asn Ala Ser Ala Ser Ala Ser Gly Ala Leu Ala Ser
        340                 345                 350

Gly Ser Ser Ser Gly Ala Ser Ser Ala Asp Ala Ser Ala Gly
    355                 360                 365

Ala Ser Ser Tyr Gly Ser Leu Gly Gly Tyr Arg His Gly Gly Ser Phe
    370                 375                 380

Ser Glu Ala Ser Ala Ala Ser Ala Ala Ser Arg Ala Glu Ala Ala
385                 390                 395                 400

<210> SEQ ID NO 60
<211> LENGTH: 376
<212> TYPE: PRT
<213> ORGANISM: Oecophylla smaragdina

<400> SEQUENCE: 60

Gly Val Pro Lys Glu Leu Gly Thr Ser Ile Ser Ser Ala Ser Ala Ser
1               5                   10                  15

Ala Ser Ala Ser Ala Ser Ala Thr Ala Ser Ser Ser Lys Asn Val
            20                  25                  30

His Leu Leu Pro Leu Lys Ser Glu His Gly Ile Val Ile Asp Lys Ser
        35                  40                  45

Lys Phe Asn Ile Arg Lys Val Val Leu Ser Ala Ile Asp Glu Ile Asn
    50                  55                  60

Gly Ala Pro Asn Ile Gly Leu Gly Leu Lys Gln Val Ser Leu Ala Leu
65                  70                  75                  80

Ala Lys Ala Gln Ala Ser Ala Gln Ser Ser Ala Glu Ala Leu Ala Ile
            85                  90                  95
```

```
Ile Lys Lys Ile Val Ala Leu Leu Ile Ser Ala Tyr Val Arg Ala Ala
            100                 105                 110

Glu Ala Ala Ala Arg Ala Ser Ala Glu Ala Leu Ala Thr Val Arg Ala
            115                 120                 125

Ala Glu Gln Ala Gln Lys Ile Ala Glu Ala Lys Gly Arg Ala Ala Ala
            130                 135                 140

Glu Ala Leu Ser Glu Leu Val Glu Ala Ser Gln Lys Ala Asp Ala Ala
145                 150                 155                 160

Ala Ala Gly Thr Thr Asp Ala Ile Glu Arg Thr Tyr Gln Asp Ala Arg
                165                 170                 175

Ala Ala Thr Ser Ala Gln Thr Lys Ala Ser Gly Glu Ala Glu Asn Ala
            180                 185                 190

Asn Arg Asn Ala Ala Ala Thr Leu Ala Ala Val Leu Ser Ile Ala Lys
                195                 200                 205

Ala Ala Ser Gly Gln Gly Gly Thr Arg Ala Ala Val Asp Ala Ala Ala
            210                 215                 220

Ala Ala Ala Ala Ala Ala Leu His Ala Lys Ala Asn Ala Val Ser
225                 230                 235                 240

Gln Ala Thr Ser Lys Ala Ala Glu Ala Arg Val Ala Ala Glu Glu
            245                 250                 255

Ala Ala Ser Ala Gln Ser Ala Ser Ala Ser Ala Gln Leu Thr Ala
            260                 265                 270

Gln Leu Glu Glu Lys Val Ser Ala Asp Gln Gln Ala Ala Ser Ala Ser
            275                 280                 285

Thr Asp Thr Ser Ala Ala Ile Ala Glu Ala Glu Ala Ala Leu Ala
            290                 295                 300

Ser Thr Val Asn Ala Ile Asn Asp Gly Val Val Ile Gly Leu Gly Asn
305                 310                 315                 320

Thr Ala Ser Ser Ser Ala Gln Ala Ser Ala Gln Ala Ser Ala Leu Ala
                325                 330                 335

Arg Ala Lys Asn Ala Arg Pro Lys Ile Lys Gly Trp Tyr Lys Ile Gly
            340                 345                 350

Gly Ala Thr Ser Ala Ser Ala Ser Ala Ser Ala Ser Ala Gln
            355                 360                 365

Ser Ser Ser Gln Gly Leu Val Tyr
    370                 375

<210> SEQ ID NO 61
<211> LENGTH: 395
<212> TYPE: PRT
<213> ORGANISM: Oecophylla smaragdina

<400> SEQUENCE: 61

Met Lys Ile Pro Ala Ile Leu Val Thr Ser Phe Leu Ala Trp Gly Leu
1               5                   10                  15

Ala Ser Gly Gly Val Pro Lys Glu Leu Gly Thr Ser Ile Ser Ser Ala
            20                  25                  30

Ser Ala Ser Ala Ser Ala Ser Ala Thr Ala Ser Ser Ser
        35                  40                  45

Lys Asn Val His Leu Leu Pro Leu Lys Ser Glu His Gly Ile Val Ile
        50                  55                  60

Asp Lys Ser Lys Phe Asn Ile Arg Lys Val Val Leu Ser Ala Ile Asp
65              70                  75                  80

Glu Ile Asn Gly Ala Pro Asn Ile Gly Leu Gly Leu Lys Gln Val Ser
```

```
                        85                  90                  95
Leu Ala Leu Ala Lys Ala Gln Ala Ser Ala Gln Ser Ser Ala Glu Ala
                100                 105                 110

Leu Ala Ile Ile Lys Lys Ile Val Ala Leu Leu Ile Ser Ala Tyr Val
            115                 120                 125

Arg Ala Ala Glu Ala Ala Ala Arg Ala Ser Ala Glu Ala Leu Ala Thr
        130                 135                 140

Val Arg Ala Ala Glu Gln Ala Gln Lys Ile Ala Glu Ala Lys Gly Arg
145                 150                 155                 160

Ala Ala Ala Glu Ala Leu Ser Glu Leu Val Glu Ala Ser Gln Lys Ala
                165                 170                 175

Asp Ala Ala Ala Gly Thr Thr Asp Ala Ile Glu Arg Thr Tyr Gln
                180                 185                 190

Asp Ala Arg Ala Ala Thr Ser Ala Gln Thr Lys Ala Ser Gly Glu Ala
            195                 200                 205

Glu Asn Ala Asn Arg Asn Ala Ala Thr Leu Ala Ala Val Leu Ser
        210                 215                 220

Ile Ala Lys Ala Ala Ser Gly Gln Gly Gly Thr Arg Ala Ala Val Asp
225                 230                 235                 240

Ala Ala Ala Ala Ala Ala Ala Ala Leu His Ala Lys Ala Asn
                245                 250                 255

Ala Val Ser Gln Ala Thr Ser Lys Ala Ala Glu Ala Arg Val Ala
            260                 265                 270

Ala Glu Glu Ala Ala Ser Ala Gln Ala Ser Ser Ala Ser Ala Gln
        275                 280                 285

Leu Thr Ala Gln Leu Glu Glu Lys Val Ser Ala Asp Gln Gln Ala Ala
            290                 295                 300

Ser Ala Ser Thr Asp Thr Ser Ala Ala Ile Ala Glu Ala Glu Ala Ala
305                 310                 315                 320

Ala Leu Ala Ser Thr Val Asn Ala Ile Asn Asp Gly Val Val Ile Gly
                325                 330                 335

Leu Gly Asn Thr Ala Ser Ser Ala Gln Ala Ser Ala Gln Ala Ser
            340                 345                 350

Ala Leu Ala Arg Ala Lys Asn Ala Arg Pro Lys Ile Lys Gly Trp Tyr
        355                 360                 365

Lys Ile Gly Gly Ala Thr Ser Ala Ser Ala Ser Ala Ser Ala
            370                 375                 380

Ser Ala Gln Ser Ser Ser Gln Gly Leu Val Tyr
385                 390                 395

<210> SEQ ID NO 62
<211> LENGTH: 424
<212> TYPE: PRT
<213> ORGANISM: Oecophylla smaragdina

<400> SEQUENCE: 62

Ser Glu Leu Val Gly Ser Asp Ala Ser Ala Thr Ala Ser Ala Glu Ala
1               5                   10                  15

Ser Ala Ser Ser Ser Ala Tyr Gly Ser Lys Tyr Gly Ile Gly Ser Gly
            20                  25                  30

Ala Val Ser Gly Ala Ser Ala Ser Ala Ser Ala Ser Ala Ser
        35                  40                  45

Ala Ser Ala Ser Ser Ala Pro Ala Ile Glu Gly Val Asn Val Gly Thr
50                  55                  60
```

Gly Val Ser Asn Thr Ala Ser Ala Ser Ala Glu Leu Ser Arg Gly
65                  70                  75                  80

Leu Gly Ile Gly Gln Ala Ala Ala Glu Ala Gln Ala Ala Ala Gly
            85                  90                  95

Gln Ala Ala Ile Ala Ala Lys Ser Cys Ala Leu Ala Ala Lys Ser Thr
        100                 105                 110

Ala Gln Ala Val Ala Leu Val Glu Lys Val Ala Arg Ala Glu Val Asp
        115                 120                 125

Leu Ala Glu Ser Ala Arg Lys Ala Thr Arg Leu Ser Ala Glu Ala Ala
        130                 135                 140

Lys Ala Ala Ala Glu Val Glu Lys Asp Leu Val Gly Leu Arg Gly Ala
145                 150                 155                 160

Ala Gly Lys Leu Asn Leu Ala Ala Arg Ala Gly Ser Lys Ala Gln Glu
            165                 170                 175

Arg Ala Asn Glu Asp Ser Ile Glu Ala Asn Glu Leu Ala Gln Ala Thr
        180                 185                 190

Ala Ala Ala Gly Ala Glu Ala Gly Ala Lys Ala Asn Ala Ala Gln Glu
        195                 200                 205

Ala Gly Ala Ser Ala Leu Ala Ile Ala Gln Ala Ala Leu Asn Ile Glu
        210                 215                 220

Gln Glu Thr Val Lys Leu Thr Arg Gln Ala Gln Asn Thr Arg Leu Arg
225                 230                 235                 240

Ser Glu Asn Ile Leu Ala Ala Ser Asn Ala Arg Ala Ile Ala Ser
            245                 250                 255

Ala Glu Ala Glu Ala Ser Ser Asp Leu Asn Asn Arg Ala Asn Ala Ala
        260                 265                 270

Arg Ser Asn Ala Arg Ala Ala Glu Thr Arg Ala Val Ala Thr Glu
        275                 280                 285

Ala Ala Ser Thr Ala Glu Ile Ala Ala Tyr Ser Ser Ser Glu Lys Gly
        290                 295                 300

Glu Ile Thr Asn Pro Gly Pro Leu Pro Lys Ile Val Ser Val Thr Ala
305                 310                 315                 320

Gly Leu Thr Gln Asn Glu Ile Ala Gly Ser Gly Ala Ala Ala Ser Ala
            325                 330                 335

Ser Ala Ser Ala Leu Ala Ser Ala Ser Ala Gly Ala Gly Ala Gly Ala
        340                 345                 350

Gly Ala Gly Ala Gly Ala Ser Ala Gly Ala Gly Ala Val Ala Gly Ala
        355                 360                 365

Gly Ala Gly Ala Gly Ala Gly Ser Ala Gly Ala Ser Ala Gly Ala
        370                 375                 380

Asn Ala Gly Ala Gly Ala Ser Ser Leu Leu Pro Gln Ser Lys Leu
385                 390                 395                 400

His Pro Ile Ser Arg Ser Ser Ala Ser Ala Ser Ala Glu Ala
            405                 410                 415

Glu Ala Asn Ser Ser Ala Tyr Ala
            420

<210> SEQ ID NO 63
<211> LENGTH: 443
<212> TYPE: PRT
<213> ORGANISM: Oecophylla smaragdina

<400> SEQUENCE: 63

Met Lys Ile Pro Ala Ile Leu Ala Thr Ser Leu Phe Val Trp Gly Leu
1               5                   10                  15

```
Val Gly Ala Ser Glu Leu Val Gly Ser Asp Ala Ser Ala Thr Ala Ser
             20                  25                  30

Ala Glu Ala Ser Ala Ser Ser Ala Tyr Gly Ser Lys Tyr Gly Ile
         35                  40                  45

Gly Ser Gly Ala Val Ser Gly Ala Ser Ala Ser Ala Ser Ala
 50                  55                  60

Ser Ala Ser Ala Ser Ala Ser Ala Pro Ala Ile Glu Gly Val Asn
 65                  70                  75                  80

Val Gly Thr Gly Val Ser Asn Thr Ala Ser Ala Ser Ala Glu Ala Leu
                 85                  90                  95

Ser Arg Gly Leu Gly Ile Gly Gln Ala Ala Glu Ala Gln Ala Ala
             100                 105                 110

Ala Ala Gly Gln Ala Ala Ile Ala Ala Lys Ser Cys Ala Leu Ala Ala
             115                 120                 125

Lys Ser Thr Ala Gln Ala Val Ala Leu Val Glu Lys Val Ala Arg Ala
130                 135                 140

Glu Val Asp Leu Ala Glu Ser Ala Arg Lys Ala Thr Arg Leu Ser Ala
145                 150                 155                 160

Glu Ala Ala Lys Ala Ala Ala Glu Val Glu Lys Asp Leu Val Gly Leu
                 165                 170                 175

Arg Gly Ala Ala Gly Lys Leu Asn Leu Ala Arg Ala Gly Ser Lys
             180                 185                 190

Ala Gln Glu Arg Ala Asn Glu Asp Ser Ile Glu Ala Asn Glu Leu Ala
             195                 200                 205

Gln Ala Thr Ala Ala Ala Gly Ala Ala Glu Ala Lys Ala Asn Ala
             210                 215                 220

Ala Gln Glu Ala Gly Ala Ser Ala Leu Ala Ile Ala Gln Ala Ala Leu
225                 230                 235                 240

Asn Ile Glu Gln Glu Thr Val Lys Leu Thr Arg Gln Ala Gln Asn Thr
                 245                 250                 255

Arg Leu Arg Ser Glu Asn Ile Leu Ala Ala Ala Ser Asn Ala Arg Ala
             260                 265                 270

Ile Ala Ser Ala Glu Ala Glu Ala Ser Ser Asp Leu Asn Asn Arg Ala
             275                 280                 285

Asn Ala Ala Arg Ser Asn Ala Arg Ala Ala Ala Glu Thr Arg Ala Val
             290                 295                 300

Ala Thr Glu Ala Ala Ser Thr Ala Glu Ile Ala Ala Tyr Ser Ser Ser
305                 310                 315                 320

Glu Lys Gly Glu Ile Thr Asn Pro Gly Pro Leu Pro Lys Ile Val Ser
                 325                 330                 335

Val Thr Ala Gly Leu Thr Gln Asn Glu Ile Ala Gly Ser Gly Ala Ala
                 340                 345                 350

Ala Ser Ala Ser Ala Ser Ala Leu Ala Ser Ser Ala Gly Ala Gly
             355                 360                 365

Ala Gly Ala Gly Ala Gly Ala Gly Ser Ala Gly Ala Val
             370                 375                 380

Ala Gly Ala Gly Ala Gly Ala Gly Ala Ser Ala Gly Ala Ser
385                 390                 395                 400

Ala Gly Ala Asn Ala Gly Ala Gly Ala Ser Ser Leu Leu Pro Gln
             405                 410                 415

Ser Lys Leu His Pro Ile Ser Arg Ser Ser Ala Ser Ala Ser Ala Ser
             420                 425                 430
```

Ala Glu Ala Glu Ala Asn Ser Ser Ala Tyr Ala
         435                 440

<210> SEQ ID NO 64
<211> LENGTH: 1119
<212> TYPE: DNA
<213> ORGANISM: Oecophylla smaragdina

<400> SEQUENCE: 64

| | | | | |
|---|---|---|---|---|
| agcaagtcgt | acctcttagg | ctcatccgcg | tctgcttccg | cttccgcttc cgcctcggca | 60 |
| tcagcgggag | gaagcaccgg | cggcgtcggc | gtcggatctg | taatatccgg tggcaacaac | 120 |
| atcatcagag | gagcttcgac | cacatccgtg | acattggcag | ccgccgcagc ggaggccaag | 180 |
| gcagctctga | atgctggaaa | agcgactgtc | gaagagcaaa | gggaagcgtt acagttgctc | 240 |
| accgcgtccg | ctgaaaaaaa | cgccgaggcg | cgttccttgg | ccgacgatgc ggccgttcta | 300 |
| gttcagggtg | ccgctgaggc | gcaatcggtc | gccgccgcga | gacggtcgc ggtcgagcaa | 360 |
| ggatccaact | ctctggatgc | agctgcagcc | gaagcggaag | ccgccgccgc cgcatccagg | 420 |
| gtatcggccc | agcaggcact | ccaggccgcg | cagacctccg | ccgccgctat tcaaaccgct | 480 |
| gccggtagcg | ccctgacggc | tctcaaattg | cacgcaaac | aggaagcgga atccaataat | 540 |
| gccgccgaac | aggcaaataa | agcattggcc | ttaagtcgcg | cagccagcgc tgccactcaa | 600 |
| cgagccgtgg | cagctcagaa | cgcggctgcc | gcatcagcgg | cttcggctgg agccgcacaa | 660 |
| gctgaggcaa | ggaacgccta | cgccaaagcc | aaagcagcga | tagctgctct tacggccgcc | 720 |
| caaagaaatt | acgccgcggc | caaggctagc | gcaagcgcgg | gtagcgtggt ggccgaacaa | 780 |
| gatgctcaat | ctagagcggc | cgatgccgag | gtgaacgccg | ttgcccaagc cgctgcccga | 840 |
| gccagcgttc | gcaatcagga | gatcgttgaa | atcggcgcgg | aattcggcaa cgccagcggc | 900 |
| ggagtgatct | cgaccggcac | acgttcttcc | ggaggcaagg | gtgtctccgt taccgctgga | 960 |
| gctcaggcta | gcgcgtccgc | ttccgcgacc | tcctcctcct | cctcctcctc cggcatcaac | 1020 |
| aaaggacatc | ccagatgggg | gcacaattgg | ggtttaggtt | cttcggaagc gtcagcaaac | 1080 |
| gctgaagccg | aaagcagcgc | ttcctcttat | tcatcttaa | | 1119 |

<210> SEQ ID NO 65
<211> LENGTH: 1176
<212> TYPE: DNA
<213> ORGANISM: Oecophylla smaragdina

<400> SEQUENCE: 65

| | | | | |
|---|---|---|---|---|
| atgaagatcc | cagcgataat | cgcaacgacc | ctccttctct | ggggtttcgc cgacgccagc | 60 |
| aagtcgtacc | tcttaggctc | atccgcgtct | gcttccgctt | ccgcttccgc ctcggcatca | 120 |
| gcgggaggaa | gcaccggcgg | cgtcggcgtc | ggatctgtaa | tatccggtgg caacaacatc | 180 |
| atcagaggag | cttcgaccac | atccgtgaca | ttggcagccg | ccgcagcgga ggccaaggca | 240 |
| gctctgaatg | ctggaaaagc | gactgtcgaa | gagcaaaggg | aagcgttaca gttgctcacc | 300 |
| gcgtccgctg | aaaaaaacgc | cgaggcgcgt | tccttggccg | acgatgcggc cgttctagtt | 360 |
| cagggtgccg | ctgaggcgca | atcggtcgcc | gccgcgaaga | cggtcgcggt cgagcaagga | 420 |
| tccaactctc | tggatgcagc | tgcagccgaa | gcggaagccg | ccgccgccgc atccagggta | 480 |
| tcggcccagc | aggcactcca | ggccgcgcag | acctccgccg | ccgctattca aaccgctgcc | 540 |
| ggtagcgccc | tgacggctct | caaattggca | cgcaaacagg | aagcggaatc caataatgcc | 600 |
| gccgaacagg | caaataaagc | attggcctta | agtcgcgcag | ccagcgctgc cactcaacga | 660 |

```
gccgtggcag ctcagaacgc ggctgccgca tcagcggctt cggctggagc cgcacaagct    720
gaggcaagga acgcctacgc caaagccaaa gcagcgatag ctgctcttac ggccgcccaa    780
agaaattacg ccgcggccaa ggctagcgca agcgcgggta gcgtggtggc cgaacaagat    840
gctcaatcta gcggccga tgccgaggtg aacgccgttg cccaagccgc tgcccgagcc     900
agcgttcgca atcaggagat cgttgaaatc ggcgcggaat tcggcaacgc cagcggcgga    960
gtgatctcga ccggcacacg ttcttccgga ggcaagggtg tctccgttac cgctggagct   1020
caggctagcg cgtccgcttc cgcgacctcc tcctcctcct cctcctccgg catcaacaaa   1080
ggacatccca gatgggggca caattggggt ttaggttctt cggaagcgtc agcaaacgct   1140
gaagccgaaa gcagcgcttc ctcttattca tcttaa                            1176
```

<210> SEQ ID NO 66
<211> LENGTH: 1146
<212> TYPE: DNA
<213> ORGANISM: Oecophylla smaragdina

<400> SEQUENCE: 66

```
ggagtcatag gtcccgacac gtcctcatcg tcccaggcat cggcatcggc atcggcgtca     60
gcatcggcgt cggcatcatc gtcggcatcg atcggttaca cgaactccta taaatcgatc    120
aatgcgcccg ccttggcggt cggcgtcaag aacggcggag tggatgtcgc caagggcgcg    180
gccgttgtcg aatcagcgat atccgacgta tcgactctaa ccgatgatcg tacgttgaac    240
ggtctcgcta tcatcgggaa tagcgccgag agtctggcaa gagcacaggc ttcctcgagc    300
gccagcgccg gcgcaaaagc caatgctctc atcaaacaat cgatagcggc tatagagatc    360
accgaaaagg cagagtacct tgcgtcgatc gtcgccacca aggcagcgaa ggccgccgag    420
gccacagcgc ccgcgaccgc tcgcgccact gccgtcgccg aggctgccaa ggtttccagc    480
gagcaattcg cggccgaggc acgcgcggcc gccgacgccg aagccaaggc caacgccgct    540
tccatcatcg ccaacaaagc gaacgccgtc tcgcgcagg cagccaccgg acttagcgcc    600
agcgctggca agcccaaca tcggcgacc agggcgttgc aagccgcacg agctgccgct    660
aaggctcaag ccgaacttac ccagaaagcc gctcaaatct tagtcctcat tgctgaagcc    720
aaagccgccg tgagccgagc aagcgccgat caatccgtct gtacgtccca ggcacaagcc    780
gccagtcaga ttcaatcgag agcctccgcg gccgaatccg cggcatcggc tcaatcggaa    840
gccaacacca ttgcggccga ggcggtcgct agagctgacg ccgaggcggc cagtcaagct    900
caagcgtggg ccgaatcctt caaacgcgaa ctctcgagtg tcgttttgga ggccgaggcc    960
aatgcctcgg ctagtgcctc ggctggtgcc ctggccagtg gtagcagcag ctcgggcgcg   1020
agttccagcg cggatgccag cgccggagcg agcagctatg gatccttggg cggatatcga   1080
cacggcggaa gcttcagcga ggcatcggca gccgcgtcag cggccagtcg cgccgaggct   1140
gcgtaa                                                             1146
```

<210> SEQ ID NO 67
<211> LENGTH: 1203
<212> TYPE: DNA
<213> ORGANISM: Oecophylla smaragdina

<400> SEQUENCE: 67

```
atgaagattc cagcgatatt cgtgacgtct ctgctcgcct ggggactcgc cagcggcgga     60
gtcataggtc ccgacacgtc ctcatcgtcc caggcatcgg catcggcatc ggcgtcagca    120
tcggcgtcgg catcatcgtc ggcatcgatc ggttacaacg aactccataa atcgatcaat    180
```

```
gcgcccgcct tggcggtcgg cgtcaagaac ggcggagtgg atgtcgccaa gggcgcggcc      240
gttgtcgaat cagcgatatc cgacgtatcg actctaaccg atgatcgtac gttgaacggt      300
ctcgctatca tcgggaatag cgccgagagt ctggcaagag cacaggcttc ctcgagcgcc      360
agcgccggcg caaaagccaa tgctctcatc aaacaatcga tagcggctat agagatcacc      420
gaaaaggcag agtaccttgc gtcgatcgtc gccaccaagg cagcgaaggc cgccgaggcc      480
acagcggccg cgaccgctcg cgccactgcc gtcgccgagg ctgccaaggt ttccagcgag      540
caattcgcgg ccgaggcacg cgcggccgcc gacgccgaag ccaaggccaa cgccgcttcc      600
atcatcgcca caaagcgaa cgccgtcctc gcggaggcag ccaccggact tagcgccagc       660
gctggcaaag cccaacaatc ggcgaccagg gcgttgcaag ccgcacgagc tgccgctaag      720
gctcaagccg aacttaccca gaaagccgct caaatcttag tcctcattgc tgaagccaaa      780
gccgccgtga gccgagcaag cgccgatcaa tccgtctgta cgtcccaggc acaagccgcc      840
agtcagattc aatcgagagc ctccgcggcc gaatccgcgg catcggctca atcggaagcc      900
aacaccattg cggccgaggc ggtcgctaga gctgacgccg aggcggccag tcaagctcaa      960
gcgtgggccg aatccttcaa acgcgaactc tcgagtgtcg ttttggaggc cgaggccaat     1020
gcctcggcta gtgcctcggc tggtgccctg gccagtggta gcagcagctc gggcgcgagt     1080
tccagcgcgg atgccagcgc cggagcgagc agctatggat ccttgggcgg atatcgacac     1140
ggcggaagct tcagcgaggc atcggcagcc gcgtcagcgg ccagtcgcgc cgaggctgcg     1200
taa                                                                    1203

<210> SEQ ID NO 68
<211> LENGTH: 1131
<212> TYPE: DNA
<213> ORGANISM: Oecophylla smargdina

<400> SEQUENCE: 68
ggtgtcccta aagagttggg aacttccatt tcttccgcgt ccgcatccgc atccgcatcc       60
gcatccgcga ccgcgtcctc cagtagcaag aatgttcact tattaccatt gaaaagcgag      120
catggcatcg taattgacaa gtcaaaattc aacatcagaa aggtagtgtt gagcgcaatc      180
gatgagatca acggcgcgcc caacatcggt ctgggattga acaggtcag tttggcgctc       240 gcaaaagccc aggctagtgc tcaatcgagc gccgaggcat ggcaatcat caagaaaatc       300 gtcgcgctcc tcatctcggc ctacgtcaga gcagccgagg ccgcggctcg agcatccgcc      360
gaagctttag ctaccgttag ggctgcggaa caagcgcaaa aaattgctga agcgaagggt      420
agagcggctg ctgaggcgct ctccgagtta gtcgaggcgt cccagaaggc cgatgcggcg      480
gccgcgggaa cgacggacgc gatcgaacgc acctaccagg atgccagagc ggccacttcc      540
gcacagacca aggccagcgg cgaagccgag aatgctaatc gcaatgctgc cgccaccctc      600
gcggcggtct tgagcatcgc taaggccgcc tccggtcaag gaggcactcg agccgctgtc      660
gatgcagctg ctgccgctgc cgccgcagcc gctctgcatg ctaaagctaa cgcggtttcg      720
caagctacca gcaaagcagc cgctgaagct agagtcgcgg ctgaggaggc agcatccgcc      780
caggcatccg cctcagcaag cgcacagctg accgcacaat tagaggagaa agtcagcgcc      840
gatcaacaag cagcctccgc cagtactgat acctccgctg ctatagccga ggctgaagct      900
gccgcgttag cgtccaccgt caacgcgatc aacgacggag tggtcatcgg attaggaaat      960
accgccagtt cttctgccca agcttccgca caggccagtg ctctcgctcg cgcaaaaaat     1020
```

```
gcgcgcccta aaataaaggg ctggtacaaa atcggaggcg cgacttccgc ttctgcaagc     1080
gcatcggcca gcgcttccgc ccagtcatcc tcgcaaggac tggtatacta g             1131

<210> SEQ ID NO 69
<211> LENGTH: 1188
<212> TYPE: DNA
<213> ORGANISM: Oecophylla smaragdina

<400> SEQUENCE: 69
atgaagattc cagcgatact cgtgacgtcc ttcctcgcct ggggactggc cagcggggt      60 gtccctaaag agttgggaac ttccatttct tccgcgtccg catccgcatc cgcatccgca    120
tccgcgaccg cgtcctccag tagcaagaat gttcacttat taccattgaa aagcgagcat    180
ggcatcgtaa ttgacaagtc aaaattcaac atcagaaagg tagtgttgag cgcaatcgat    240
gagatcaacg gcgcgcccaa catcggtctg ggattgaaac aggtcagttt ggcgctcgca    300
aaagcccagg ctagtgctca atcgagcgcg gaggcattgg caatcatcaa gaaaatcgtc    360
gcgctcctca tctcggccta cgtcagagca gccgaggccg cggctcgagc atccgccgaa    420
gctttagcta ccgttagggc tgcggaacaa gcgcaaaaaa ttgctgaagc gaagggtaga    480
gcggctgctg aggcgctctc cgagttagtc gaggcgtccc agaaggccga tgcggcggcc    540
gcgggaacga cggacgcgat cgaacgcacc taccaggatg ccagagcggc cacttccgca    600
cagaccaagg ccagcggcga agccgagaat gctaatcgca atgctgccgc caccctcgcg    660
gcggtcttga gcatcgctaa ggccgcctcc ggtcaaggag gcactcgagc cgctgtcgat    720
gcagctgctg ccgctgccgc cgcagccgct ctgcatgcta aagctaacgc ggtttcgcaa    780
gctaccagca aagcagccgc tgaagctaga gtcgcggctg aggaggcagc atccgcccag    840
gcatccgcct cagcaagcgc acagctgacc gcacaattag aggagaaagt cagcgccgat    900
caacaagcag cctccgccag tactgatacc tccgctgcta tagccgaggc tgaagctgcc    960
gcgttagcgt ccaccgtcaa cgcgatcaac gacgagtgg tcatcggatt aggaaatacc    1020
gccagttctt ctgcccaagc ttccgcacag gccagtgctc tcgctcgcgc aaaaaatgcg    1080 cgcccctaaaa taagggctg gtacaaaatc ggaggcgcga cttccgcttc tgcaagcgca    1140
tcggccagcg cttccgccca gtcatcctcg caaggactgg tatactag                 1188

<210> SEQ ID NO 70
<211> LENGTH: 1275
<212> TYPE: DNA
<213> ORGANISM: Oecophylla smaragdina

<400> SEQUENCE: 70
agcgaactcg tcggatcgga cgcgagcgcg acggcatctg ctgaagcgtc agcatcgtca     60
tccgcatacg gtagcaagta tggtattggt agtggtgctg tctccggtgc atcagccagc    120
gcctctgcca gcgcgtctgc tagcgcatca gccagcagtg ctcccgcgat cgaaggagta    180
aacgttggca ccggagtcag taacaccgct tccgcgtccg cagaagctct ctcccgtgga    240
ctcggcatcg acaagcggc tgccgaagcg caagccgctg ccgctggcca gcggcgatc     300 gctgcgaaat cgtgcgcgct agcggccaag agcaccgctc aagcggttgc cctggttgag    360
aaagtggccc gcgccgaggt agatctggcc gaaagcgcga gaaaggctac aagattatcg    420
gcagaagcag ccaaggcagc ggcggaagtc gagaaggacc tcgtcggtct gagaggggct    480
gccggtaaac tgaatctggc tgcgagagcc ggttctaaag cccaagaacg cgccaacgaa    540
gactctatag aggctaacga acttgcccaa gcaacggccg ccgccggtgc cgaggctgaa    600
```

| gccaaggcga atgccgccca ggaggcaggc gcctccgctt tggccatcgc ccaagccgcc | 660 |
| cttaacatcg agcaagagac tgttaaattg acccgccagg cccagaatac tcgtctcaga | 720 |
| tctgaaaata ttctcgccgc ggccagcaat gcccgcgcca tcgcttccgc tgaggccgag | 780 |
| gccagtagtg atttgaataa tcgtgcgaat gcagcgcgtt ccaatgcccg agctgctgcc | 840 |
| gagaccagag ccgtagctac cgaagccgct tctaccgccg agatcgcagc ttatagttca | 900 |
| tccgagaaag gcgagatcac caatcccggt cctctgccca agatcgtcag tgttaccgca | 960 |
| ggtctgaccc agaacgaaat agcgggatca ggagcggccg ctagtgctag tgccagtgct | 1020 |
| cttgccagtg ccagtgccgg tgccggtgcc ggtgcaggtg caggagccgg tgcaagtgca | 1080 |
| ggagccggtg cagttgcagg tgcaggagcc ggtgcaggag ccggtgctag tgccggagcg | 1140 |
| agtgccggag cgaatgccgg tgccggtgcc agcagtttac tcttgccgca gagtaaactc | 1200 |
| catccaatct ccaggtcttc cgcctctgcc tccgcttccg ccgaggccga agctaacagt | 1260 |
| tcggcgtatg cgtaa | 1275 |

<210> SEQ ID NO 71
<211> LENGTH: 1332
<212> TYPE: DNA
<213> ORGANISM: Oecophylla smaragdina

<400> SEQUENCE: 71

| atgaagattc cagcgatact tgcgacgtcc cttttcgtct ggggtcttgt cggcgccagc | 60 |
| gaactcgtcg gatcggacgc gagcgcgacg gcatctgctg aagcgtcagc atcgtcatcc | 120 |
| gcatacggta gcaagtatgg tattggtagt ggtgctgtct ccggtgcatc agccagcgcc | 180 |
| tctgccagcg cgtctgctag cgcatcagcc agcagtgctc ccgcgatcga aggagtaaac | 240 |
| gttggcaccg gagtcagtaa caccgcttcc gcgtccgcag aagctctctc ccgtggactc | 300 |
| ggcatcggac aagcggctgc cgaagcgcaa gccgctgccg ctggccaagc ggcgatcgct | 360 |
| gcgaaatcgt gcgcgctagc ggccaagagc accgctcaag cggttgccct ggttgagaaa | 420 |
| gtggcccgcg ccgaggtaga tctggccgaa agcgcgagaa aggctacaag attatcggca | 480 |
| gaagcagcca aggcagcggc ggaagtcgag aaggacctcg tcggtctgag aggggctgcc | 540 |
| ggtaaactga atctggctgc gagagccggt tctaaagccc aagaacgcgc caacgaagac | 600 |
| tctatagagg ctaacgaact tgcccaagca acggccgccg ccgtgccgga ggctgaagcc | 660 |
| aaggcgaatg ccgcccagga ggcaggcgcc tccgctttgg ccatcgccca agccgccctt | 720 |
| aacatcgagc aagagactgt taaattgacc cgccaggccc agaatactcg tctcagatct | 780 |
| gaaaatattc tcgccgcggc cagcaatgcc cgcgccatcg cttccgctga ggccgaggcc | 840 |
| agtagtgatt tgaataatcg tgcgaatgca gcgcgttcca atgcccgagc tgctgccgag | 900 |
| accagagccg tagctaccga agccgcttct accgccgaga tcgcagctta tagttcatcc | 960 |
| gagaaaggcg agatcaccaa tcccggtcct ctgcccaaga tcgtcagtgt taccgcaggt | 1020 |
| ctgacccaga acgaaatagc gggatcagga gcggccgcta gtgctagtgc cagtgctctt | 1080 |
| gccagtgcca gtgccggtgc cggtgccggt gcaggtgcag gagccggtgc aagtgcagga | 1140 |
| gccggtgcag ttgcaggtgc aggagccggt gcaggagccg gtgctagtgc cggagcgagt | 1200 |
| gccggagcga atgccggtgc cggtgccagc agtttactct tgccgcagag taaactccat | 1260 |
| ccaatctcca ggtcttccgc ctctgcctcc gcttccgccg aggccgaagc taacagttcg | 1320 |
| gcgtatgcgt aa | 1332 |

<210> SEQ ID NO 72
<211> LENGTH: 562
<212> TYPE: PRT
<213> ORGANISM: Mallada signata

<400> SEQUENCE: 72

```
Ala Val Leu Ile Ser Gly Ser Ala Gly Ala Ser Ser His Asn Ala
 1               5                  10                  15

Ala Gly Ala Ala Ala Ala Arg Ala Ala Leu Gly Ala Ser Gly Ala
                20                  25                  30

Ala Gly Leu Gly Ala Ala Ser Gly Ala Ala Arg Arg Asn Val Ala Val
                35                  40                  45

Gly Ala Asn Gly Ala Ala Ala Ser Ala Ala Ala Ala Ala Arg
         50                  55                  60

Arg Ala Gly Ala Ile Gly Leu Asn Gly Ala Ala Gly Ala Asn Val Ala
 65                  70                  75                  80

Val Ala Gly Gly Lys Lys Gly Gly Ala Ala Gly Leu Asn Ala Gly Ala
                85                  90                  95

Gly Ala Ser Leu Val Ser Ala Ala Arg Arg Asn Gly Ala Leu Gly
                100                 105                 110

Leu Asn Gly Ala Ala Gly Ala Asn Leu Ala Ala Ala Gly Gly Lys Lys
                115                 120                 125

Gly Gly Ala Ile Gly Leu Asn Ala Gly Ala Ser Ala Asn Val Gly Ala
 130                 135                 140

Ala Ala Ala Lys Lys Asn Gly Ala Ile Gly Leu Asn Ser Ala Ala Ser
145                 150                 155                 160

Ala Asn Ala Ala Ala Ala Ala Lys Lys Gly Gly Ala Ile Gly Leu
                165                 170                 175

Asn Ala Gly Ala Ser Ala Asn Ala Ala Ala Ala Ala Lys Lys Ser
                180                 185                 190

Gly Ala Val Gly Leu Asn Ala Gly Ala Ser Ala Asn Ala Ala Ala Ala
                195                 200                 205

Ala Ala Lys Lys Ser Gly Ala Val Ala Ala Asn Ser Ala Ala Ser Ala
 210                 215                 220

Asn Ala Ala Ala Ala Gln Lys Lys Ala Ala Ala Asp Ala Ala Asn
225                 230                 235                 240

Ala Ala Ala Ser Glu Ser Ala Ala Ala Ala Lys Lys Ala Ala
                245                 250                 255

Ala Val Ala Glu Asn Ala Ala Ala Thr Ala Asn Ala Ala Ser Ala Leu
                260                 265                 270

Arg Lys Asn Ala Leu Ala Ile Ala Ser Asp Ala Ala Ala Val Arg Ala
                275                 280                 285

Asp Ala Ala Ala Ala Asp Asp Ala Ala Lys Ala Asn Asn Ala
 290                 295                 300

Ala Ser Arg Gly Ser Asp Gly Leu Thr Ala Arg Ala Asn Ala Ala Thr
305                 310                 315                 320

Leu Ala Ser Asp Ala Ala Arg Arg Ala Ser Asn Ala Ala Thr Ala Ala
                325                 330                 335

Ser Asp Ala Ala Thr Asp Arg Leu Asn Ala Ala Thr Ala Ala Ser Asn
                340                 345                 350

Ala Ala Thr Ala Arg Ala Asn Ala Ala Thr Arg Ala Asp Asp Ala Ala
                355                 360                 365

Thr Asp Ala Asp Asn Ala Ala Ser Lys Ala Ser Asp Val Ser Ala Ile
                370                 375                 380
```

```
Glu Ala Asp Asn Ala Ala Arg Ala Asp Asp Ala Ile Ala Thr
385                 390                 395                 400

Asn Arg Ala Ala Glu Ala Ser Asp Ala Ala Ile Ala Ala Asp Ala
            405                 410                 415

Ala Ala Asn Ala Ala Asp Ala Ala Gln Cys Asn Asn Lys Val Ala
        420                 425                 430

Arg Val Ser Asp Ala Leu Ala Leu Ala Ala Asn Ala Ala Arg Gly
            435                 440                 445

Ser Asp Ala Ala Ala Glu Ala Gln Asp Ala Val Ala Arg Ala Ser Asp
    450                 455                 460

Ala Ala Ala Ala Gln Ala Asp Gly Val Ala Ile Ala Val Asn Gly Ala
465                 470                 475                 480

Thr Ala Arg Asp Ser Ala Ile Glu Ala Ala Thr Ala Gly Ala Ala
            485                 490                 495

Gln Ala Lys Ala Ala Gly Arg Ala Gly Ala Ala Ala Gly Leu Arg
            500                 505                 510

Ala Gly Ala Ala Arg Gly Ala Ala Gly Ser Ala Arg Gly Leu Ala
            515                 520                 525

Gly Gly Leu Ala Ala Gly Ser Asn Ala Gly Ile Ala Ala Gly Ala Ala
530                 535                 540

Ser Gly Leu Ala Arg Gly Ala Ala Ala Glu Val Cys Ala Ala Arg Ile
545                 550                 555                 560

Ala Leu

<210> SEQ ID NO 73
<211> LENGTH: 588
<212> TYPE: PRT
<213> ORGANISM: Mallada signata

<400> SEQUENCE: 73

Met Ala Ala Ser Asn Lys Ile Ile Phe Ser Phe Leu Ala Ile Val Leu
1               5                   10                  15

Leu Gln Leu Ala Thr His Cys Ser Ser Thr Ala Val Leu Ile Ser Gly
            20                  25                  30

Ser Ala Ala Gly Ala Ser Ser His Asn Ala Ala Gly Ala Ala Ala Ala
        35                  40                  45

Ala Arg Ala Ala Leu Gly Ala Ser Gly Ala Ala Gly Leu Gly Ala Ala
    50                  55                  60

Ser Gly Ala Ala Arg Arg Asn Val Ala Val Gly Ala Asn Gly Ala Ala
65                  70                  75                  80

Ala Ala Ser Ala Ala Ala Ala Ala Arg Arg Ala Gly Ala Ile Gly
                85                  90                  95

Leu Asn Gly Ala Ala Gly Ala Asn Val Ala Val Ala Gly Gly Lys Lys
            100                 105                 110

Gly Gly Ala Ala Gly Leu Asn Ala Gly Ala Gly Ala Ser Leu Val Ser
        115                 120                 125

Ala Ala Ala Arg Arg Asn Gly Ala Leu Gly Leu Asn Gly Ala Ala Gly
    130                 135                 140

Ala Asn Leu Ala Ala Ala Gly Gly Lys Lys Gly Gly Ala Ile Gly Leu
145                 150                 155                 160

Asn Ala Gly Ala Ser Ala Asn Val Gly Ala Ala Ala Lys Lys Asn
                165                 170                 175

Gly Ala Ile Gly Leu Asn Ser Ala Ala Ser Ala Asn Ala Ala Ala Ala
            180                 185                 190
```

```
Ala Ala Lys Lys Gly Gly Ala Ile Gly Leu Asn Ala Gly Ala Ser Ala
            195                 200                 205

Asn Ala Ala Ala Ala Ala Lys Lys Ser Gly Ala Val Gly Leu Asn
    210                 215                 220

Ala Gly Ala Ser Ala Asn Ala Ala Ala Ala Lys Lys Ser Gly
225                 230                 235                 240

Ala Val Ala Ala Asn Ser Ala Ser Ala Asn Ala Ala Ala Ala
            245                 250                 255

Gln Lys Lys Ala Ala Ala Asp Ala Ala Asn Ala Ala Ala Ser Glu Ser
            260                 265                 270

Ala Ala Ala Ala Ala Lys Lys Ala Ala Ala Val Ala Glu Asn Ala
            275                 280                 285

Ala Ala Thr Ala Asn Ala Ala Ser Ala Leu Arg Lys Asn Ala Leu Ala
            290                 295                 300

Ile Ala Ser Asp Ala Ala Val Arg Ala Asp Ala Ala Ala Ala
305                 310                 315                 320

Ala Asp Asp Ala Ala Lys Ala Asn Asn Ala Ala Ser Arg Gly Ser Asp
                325                 330                 335

Gly Leu Thr Ala Arg Ala Asn Ala Ala Thr Leu Ala Ser Asp Ala Ala
            340                 345                 350

Arg Arg Ala Ser Asn Ala Ala Thr Ala Ala Ser Asp Ala Ala Thr Asp
            355                 360                 365

Arg Leu Asn Ala Ala Thr Ala Ala Ser Asn Ala Ala Thr Ala Arg Ala
            370                 375                 380

Asn Ala Ala Thr Arg Ala Asp Asp Ala Ala Thr Asp Ala Asp Asn Ala
385                 390                 395                 400

Ala Ser Lys Ala Ser Asp Val Ser Ala Ile Glu Ala Asp Asn Ala Ala
                405                 410                 415

Arg Ala Ala Asp Ala Asp Ala Ile Ala Thr Asn Arg Ala Ala Glu Ala
                420                 425                 430

Ser Asp Ala Ala Ala Ile Ala Ala Asp Ala Ala Asn Ala Ala Asp
            435                 440                 445

Ala Ala Ala Gln Cys Asn Asn Lys Val Ala Arg Val Ser Asp Ala Leu
            450                 455                 460

Ala Leu Ala Ala Asn Ala Ala Arg Gly Ser Asp Ala Ala Ala Glu
465                 470                 475                 480

Ala Gln Asp Ala Val Ala Arg Ala Ser Asp Ala Ala Ala Gln Ala
            485                 490                 495

Asp Gly Val Ala Ile Ala Val Asn Gly Ala Thr Ala Arg Asp Ser Ala
            500                 505                 510

Ile Glu Ala Ala Ala Thr Ala Gly Ala Ala Gln Ala Lys Ala Ala Gly
            515                 520                 525

Arg Ala Gly Ala Ala Ala Gly Leu Arg Ala Gly Ala Ala Arg Gly
            530                 535                 540

Ala Ala Ala Gly Ser Ala Arg Gly Leu Ala Gly Gly Leu Ala Ala Gly
545                 550                 555                 560

Ser Asn Ala Gly Ile Ala Ala Gly Ala Ala Ser Gly Leu Ala Arg Gly
                565                 570                 575

Ala Ala Ala Glu Val Cys Ala Ala Arg Ile Ala Leu
            580                 585
```

<210> SEQ ID NO 74
<211> LENGTH: 1689

```
<212> TYPE: DNA
<213> ORGANISM: Mallada signata

<400> SEQUENCE: 74
gctgtattga tttctggttc ggctgctggt gcttcctcac acaatgctgc tggtgcagct    60
gcagcagcca gagctgcctt aggcgcttct ggggctgcag gtttaggtgc tgcatctggt   120
gctgcaagaa gaaacgtagc agttggtgct aacggtgccg ccgccgctag tgctgcagct   180
gcagctgcca gacgagctgg cgctattggc ctaaatggag cagctggagc taatgtagct   240
gtcgctggtg gcaaaaaagg aggtgctgct ggattaaatg ctggcgctgg tgcttctttta  300
gtatctgcag ctgcaagacg aaatggagcc cttggactta acgtgcagc tggagcaaat   360
ctcgcagcag ctggtggcaa aaaggaggt gctattggat taaacgctgg agcatcagcc   420
aatgttggtg ccgctgctgc caagaaaaat ggagccatag gacttaactc agctgcttca   480
gctaatgctg ccgctgccgc tgctaaaaaa ggtggagcca ttggattgaa tgctggagct   540
tcagcaaatg ctgctgctgc cgctgccaag aagagtggag ctgttggatt aaatgctgga   600
gcttctgcta acgctgctgc tgctgctgcc aagaaaagtg gagctgttgc tgccaattcc   660
gctgcttcag caaatgcagc tgctgctgca caaaagaaag ccgctgctga tgccgcaaat   720
gctgctgctt ctgaaagtgc tgctgctgct gcagccaaga aagccgccgc tgttgctgaa   780
aatgcagctc caccgccaa tgccgcttca gctttacgta aaaatgcatt agccattgcc   840
agtgatgcag cagctgtccg tgctgatgcc gctgccgccg ccgctgacga tgctgctaaa   900
gctaacaacg ctgcttcccg tggaagtgat ggtttaactg cccgcgccaa tgccgccact   960
ttagccagtg atgctgcccg tagagctagc aatgcagcaa cagctgccag cgatgctgcc  1020
actgaccgat tgaacgccgc caccgctgct agcaacgctg ccactgctcg tgcaaatgcc  1080
gccacacgtg ccgatgatgc cgccactgat gccgacaatg ctgcttcaaa ggccagtgat  1140
gtatcagcta ttgaagccga caacgctgca cgagctgctg atgctgatgc tatcgctacc  1200
aaccgtgccg ctgaagcaag cgatgctgct gctattgccg ctgatgccgc tgccaatgct  1260
gctgatgccg ctgcccaatg taataacaaa gttgcccgag taagtgatgc cttagctctc  1320
gccgctaatg ctgctgcccg aggatctgat gccgccgctg aagctcaaga tgctgttgcc  1380
agagcaagtg acgctgccgc tgcccaagct gatggtgttg ccattgccgt aaatggagct  1440
actgcgagag actcagcaat tgaagccgct gctactgctg gagctgccca agctaaagcc  1500
gctggacgtg ctggagctgc tgcagctggt ttaagagctg gtgccgctag aggtgctgcc  1560
gctggtagtg cccgcggtct agctggagga ttagctgcag gttccaatgc tggaatcgcg  1620
gctggtgcag cttctggatt agcaagaggc gcagctgctg aagtttgcgc agctagaata  1680
gcattgtaa                                                         1689

<210> SEQ ID NO 75
<211> LENGTH: 1767
<212> TYPE: DNA
<213> ORGANISM: Mallada signata

<400> SEQUENCE: 75
atggcagcgt cgaacaaaat catcttcagc ttttagcta ttgttctatt acaacttgcc     60
acacactgtt catcaacagc tgtattgatt tctggttcgg ctgctggtgc ttcctcacac   120
aatgctgctg gtcagctgc agcagccaga gctgccttag gcgcttctgg ggctgcaggt   180
ttaggtgctg catctggtgc tgcaagaaga aacgtagcag ttggtgctaa cggtgccgcc   240
```

-continued

```
gccgctagtg ctgcagctgc agctgccaga cgagctggcg ctattggcct aaatggagca    300
gctggagcta atgtagctgt cgctggtggc aaaaaaggag gtgctgctgg attaaatgct    360
ggcgctggtg cttctttagt atctgcagct gcaagacgaa atggagccct ggacttaac     420 ggtgcagctg gagcaaatct cgcagcagct ggtggcaaaa aaggaggtgc tattggatta    480
aacgctggag catcagccaa tgttggtgcc gctgctgcca agaaaatgg agccatagga     540 cttaactcag ctgcttcagc taatgctgcc gctgccgctg ctaaaaaagg tggagccatt    600
ggattgaatg ctggagcttc agcaaatgct gctgctgccg ctgccaagaa gagtggagct    660
gttggattaa atgctggagc ttctgctaac gctgctgctg ctgctgccaa gaaaagtgga    720
gctgttgctg ccaattccgc tgcttcagca aatgcagctg ctgctgcaca aagaaagcc     780 gctgctgatg ccgcaaatgc tgctgcttct gaaagtgctg ctgctgctgc agccaagaaa    840
gccgccgctg ttgctgaaaa tgcagctgcc accgccaatg ccgcttcagc tttacgtaaa    900
aatgcattag ccattgccag tgatgcagca gctgtccgtg ctgatgccgc tgccgccgcc    960
gctgacgatg ctgctaaagc taacaacgct gcttcccgtg aagtgatgg tttaactgcc     1020 cgcgccaatg ccgccacttt agccagtgat gctgcccgta gagctagcaa tgcagcaaca    1080
gctgccagcg atgctgccac tgaccgattg aacgccgcca ccgctgctag caacgctgcc    1140
actgctcgtg caaatgccgc cacacgtgcc gatgatgccg ccactgatgc cgacaatgct    1200
gcttcaaagg ccagtgatgt atcagctatt gaagccgaca cgctgcacg agctgctgat     1260 gctgatgcta tcgctaccaa ccgtgccgct gaagcaagcg atgctgctgc tattgccgct    1320
gatgccgctc caatgctgct gatgccgct gcccaatgta ataacaaagt tgcccgagta     1380
agtgatgcct agctctcgc cgctaatgct gctgcccgag atctgatgc cgccgctgaa      1440 gctcaagatg ctgttgccag agcaagtgac gctgccgctg cccaagctga tggtgttgcc    1500
attgccgtaa atggagctac tgcgagagac tcagcaattg aagccgctgc tactgctgga    1560
gctgcccaag ctaaagccgc tggacgtgct ggagctgctg cagctggttt aagagctggt    1620
gccgctagag gtgctgccgc tggtagtgcc cgcggtctag ctggaggatt agctgcaggt    1680
tccaatgctg gaatcgcggc tggtgcagct tctggattag caagaggcgc agctgctgaa    1740
gtttgcgcag ctagaatagc attgtaa                                        1767
```

<210> SEQ ID NO 76
<211> LENGTH: 975
<212> TYPE: DNA
<213> ORGANISM: Artificial
<220> FEATURE:
<223> OTHER INFORMATION: Honeybee silk protein (Xenospira4) open reading frame optimized for plant expression (before sub-cloned into pET14b and pVEC8)

<400> SEQUENCE: 76

```
atggctagag aagaggttga gactagggat aagactaaga cttctactgt ggtgaagtct     60
gagaaggttg aagttgtggc tccagctaag gatgagctta gttgacttc tgagccaatt     120 ttcggaagaa gagtgggaac tggagcttct gaagtggctt cttctagtgg agaggctatt    180
gctatttctc ttggagctgg acaatcagca gcagagtctc aagctcttgc tgcttctcag    240
tctaagactg ctgctaacgc tgctattggt gcttctgagc ttactaacaa ggtggcagct    300
cttgttgctg gtgctactgg tgctcaagct agagctactg ctgcttcttc ttctgctctt    360
aaggcttctc ttgctactga gaggctgct gaagaagctg aagctgctgt tgcagatgct     420
aaagcagctg ctgagaaggc tgagtctctt gctaagaacc ttgcttctgc tagtgctaga    480
```

-continued

```
gctgctcttt cttctgagag ggctaatgag cttgctcagg ctgaaagtgc tgcagctgct    540
gaagctcaag ctaagaccgc tgctgctgcc aaagcagctg agattgctct taaggtggca    600
gagattgctg taaaagctga ggcagatgct gccgccgcag ccgtggcagc tgcaaaagct    660
agagctgtgg ctgatgcagc agccgccagg gctgctgctg ttaacgctat tgctaaggct    720
gaagaagagg cttcagctca agctgagaac gcagctggtg ttcttcaagc agctgcaagt    780
gctgctgctg agtcaagagc agcagcagcc gctgccgcag ctacttctga gcagcagct    840 gaagcaggac cacttgctgg tgaaatgaag ccaccacatt ggaagtggga gaggattcca    900
gtgaagaaag aagagtggaa aacttctaca aaagaggaat ggaaaactac taacgaagag    960
tgggaggtga agtga                                                    975
```

<210> SEQ ID NO 77
<211> LENGTH: 324
<212> TYPE: PRT
<213> ORGANISM: Artificial
<220> FEATURE:
<223> OTHER INFORMATION: Honeybee silk protein (Xenospira4) encoded by open reading frame optimized for plant expression (without translational fusion)

<400> SEQUENCE: 77

```
Met Ala Arg Glu Glu Val Glu Thr Arg Asp Lys Thr Lys Thr Ser Thr
1               5                   10                  15

Val Val Lys Ser Glu Lys Val Glu Val Ala Pro Ala Lys Asp Glu
            20                  25                  30

Leu Lys Leu Thr Ser Glu Pro Ile Phe Gly Arg Arg Val Gly Thr Gly
        35                  40                  45

Ala Ser Glu Val Ala Ser Ser Ser Gly Glu Ala Ile Ala Ile Ser Leu
    50                  55                  60

Gly Ala Gly Gln Ser Ala Ala Glu Ser Gln Ala Leu Ala Ala Ser Gln
65                  70                  75                  80

Ser Lys Thr Ala Ala Asn Ala Ala Ile Gly Ala Ser Glu Leu Thr Asn
                85                  90                  95

Lys Val Ala Ala Leu Val Ala Gly Ala Thr Gly Ala Gln Ala Arg Ala
            100                 105                 110

Thr Ala Ala Ser Ser Ser Ala Leu Lys Ala Ser Leu Ala Thr Glu Glu
        115                 120                 125

Ala Ala Glu Glu Ala Glu Ala Ala Val Ala Asp Ala Lys Ala Ala Ala
    130                 135                 140

Glu Lys Ala Glu Ser Leu Ala Lys Asn Leu Ala Ser Ala Ser Ala Arg
145                 150                 155                 160

Ala Ala Leu Ser Ser Glu Arg Ala Asn Glu Leu Ala Gln Ala Glu Ser
                165                 170                 175

Ala Ala Ala Ala Glu Ala Gln Ala Lys Thr Ala Ala Ala Ala Lys Ala
            180                 185                 190

Ala Glu Ile Ala Leu Lys Val Ala Glu Ile Ala Val Lys Ala Glu Ala
        195                 200                 205

Asp Ala Ala Ala Ala Val Ala Ala Ala Lys Ala Arg Ala Val Ala
    210                 215                 220

Asp Ala Ala Ala Ala Arg Ala Ala Ala Val Asn Ala Ile Ala Lys Ala
225                 230                 235                 240

Glu Glu Glu Ala Ser Ala Gln Ala Glu Asn Ala Ala Gly Val Leu Gln
                245                 250                 255
```

```
Ala Ala Ala Ser Ala Ala Ala Glu Ser Arg Ala Ala Ala Ala Ala Ala
            260             265             270

Ala Ala Thr Ser Glu Ala Ala Glu Ala Gly Pro Leu Ala Gly Glu
        275             280             285

Met Lys Pro Pro His Trp Lys Trp Glu Arg Ile Pro Val Lys Lys Glu
    290             295             300

Glu Trp Lys Thr Ser Thr Lys Glu Glu Trp Lys Thr Thr Asn Glu Glu
305             310             315             320

Trp Glu Val Lys
```